United States Patent
Fernandez Rodriguez et al.

(10) Patent No.: US 11,939,598 B2
(45) Date of Patent: *Mar. 26, 2024

(54) PRODUCTION BACTERIAL CELLS AND USE THEREOF IN PRODUCTION METHODS

(71) Applicant: Eligo Bioscience, Paris (FR)

(72) Inventors: Jesus Fernandez Rodriguez, Paris (FR); Antoine Decrulle, Paris (FR); Aymeric Leveau, Paris (FR); Ines Canadas Blasco, Paris (FR); Aurélie Mathieu, Paris (FR); Thibault Carlier, Paris (FR)

(73) Assignee: Eligo Bioscience, Paris (FR)

( * ) Notice: Subject to any disclaimer, the term of this patent is extended or adjusted under 35 U.S.C. 154(b) by 0 days.

This patent is subject to a terminal disclaimer.

(21) Appl. No.: 18/319,918

(22) Filed: May 18, 2023

(65) Prior Publication Data
US 2023/0279364 A1    Sep. 7, 2023

Related U.S. Application Data

(62) Division of application No. 17/742,671, filed on May 12, 2022, now Pat. No. 11,697,802.
(Continued)

(51) Int. Cl.
*C12N 7/00* (2006.01)
*C12N 1/20* (2006.01)
(Continued)

(52) U.S. Cl.
CPC ............... *C12N 7/00* (2013.01); *C12N 1/20* (2013.01); *C12N 15/70* (2013.01); *C12N 15/74* (2013.01);
(Continued)

(58) Field of Classification Search
None
See application file for complete search history.

(56) References Cited

U.S. PATENT DOCUMENTS

| 4,920,048 A | 4/1990 | Diderichsen |
| 5,691,185 A | 11/1997 | Dickely et al. |

(Continued)

FOREIGN PATENT DOCUMENTS

| WO | 94/17201 A1 | 8/1994 |
| WO | 2014/124226 A1 | 8/2014 |

(Continued)

OTHER PUBLICATIONS

U.S. Appl. No. 18/348,910, filed May 2021, Fernandez.*
(Continued)

*Primary Examiner* — Michelle S Horning
(74) *Attorney, Agent, or Firm* — Arrigo, Lee, Guttman & Mouta-Bellum LLP

(57) ABSTRACT

The present invention concerns a production bacterial cell for producing phage particles or phage-derived delivery vehicles, said production bacterial cell stably comprising at least one phage structural gene(s) and at least one phage DNA packaging gene(s), said phage structural gene(s) and phage DNA packaging gene(s) being derived from a first type of bacteriophage,
wherein the expression of at least one of said phage structural gene(s) and/or at least one of said phage DNA packaging gene(s) in said production bacterial cell is controlled by at least one induction mechanism, and
wherein said production bacterial cell is from a bacterial species or strain different from the bacterial species or
(Continued)

strain from which said first type of bacteriophage comes and/or that said first type of bacteriophage targets.

16 Claims, 11 Drawing Sheets

Specification includes a Sequence Listing.

Related U.S. Application Data

(60) Provisional application No. 63/187,531, filed on May 12, 2021, provisional application No. 63/187,532, filed on May 12, 2021.

(51) Int. Cl.
 *C12N 15/70* (2006.01)
 *C12N 15/74* (2006.01)

(52) U.S. Cl.
 CPC .............. *C12N 2795/10322* (2013.01); *C12N 2795/10352* (2013.01); *C12N 2800/101* (2013.01); *C12N 2800/40* (2013.01)

(56) References Cited

U.S. PATENT DOCUMENTS

| | | |
|---|---|---|
| 6,291,245 B1 | 9/2001 | Kopetzki et al. |
| 6,413,768 B1 | 7/2002 | Galen |
| 6,752,994 B2 | 6/2004 | Jacobs, Jr. et al. |
| 10,113,163 B2 | 10/2018 | Liu et al. |
| 11,739,304 B2 * | 8/2023 | Fernandez Rodriguez .................. C12N 7/00 |
| 2005/0186666 A1 | 8/2005 | Schneider et al. |
| 2015/0064138 A1 | 3/2015 | Lu et al. |
| 2015/0166980 A1 | 6/2015 | Liu et al. |
| 2019/0160120 A1 | 5/2019 | Haaber |
| 2022/0135986 A1 | 5/2022 | Leveau et al. |
| 2022/0135987 A1 | 5/2022 | Leveau et al. |

FOREIGN PATENT DOCUMENTS

| | | |
|---|---|---|
| WO | 2017/141173 A2 | 8/2017 |
| WO | 2018/236548 A1 | 12/2018 |
| WO | 2020/181178 A1 | 9/2020 |
| WO | 2020/181180 A1 | 9/2020 |
| WO | 2020/181193 A1 | 9/2020 |
| WO | 2020/181195 A1 | 9/2020 |
| WO | 2020/181202 A1 | 9/2020 |

OTHER PUBLICATIONS

Rajagopala et al. The protein interaction map of bacteriophage lambda. BMC Microbiology 2011, 11:213, 1-15.

Ravin et al. The anti-immunity system of phage-plasmid N15: identification of the antirepressor gene and its control by a small processed RNA. Molecular Microbiology (1999) 34(5), 980-994.

Rees and Liu. Base editing: precision chemistry on the genome and transcriptome of living cells. Nat Rev Genet. Dec. 2018 ; 19(12): 770-788. doi:10.1038/s41576-018-0059-1.

Russel and Model. Genetic Analysis of the Filamentous Bacteriophage Packaging Signal and of the Proteins That Interact with It. Journal of Virology, Aug. 1989, 63 (8), 3284-3295.

Sharon et al. Functional genetic variants revealed by massively parallel precise genome editing. Cell. Oct. 4, 2018; 175(2): 544-557.e16. doi: 10.1016/j.cell.2018.08.057.

Simon et al. Retrons and their applications in genome engineering. Nucleic Acids Research, 2019, vol. 47, No. 21 11007-11019 doi: 10.1093/nar/gkz86.

Sorensen et al. A Food-Grade Cloning System for Industrial Strains of Lactococcus lactis. Applied and Environmental Microbiology, Apr. 2000, 66(4), 1253-1258.

Stanton et al. Genomic Mining of Prokaryotic Repressors for Orthogonal Logic Gates. Nat Chem Biol. Feb. 2014 ; 10(2): 99-105. doi: 10.1038/nchembio.1411.

Struhl et al. Functional genetic expression of eukaryotic DNA in *Escherichia coli*. Proc. Natl. Acad. Sci. May 1976. 73 (5), 1471-1475.

Tomida et al. Pan-Genome and Comparative Genome Analyses of Propionibacterium acnes Reveal Its Genomic Diversity in the Healthy and Diseased Human Skin Microbiome. mBio. 4(3), e00003-13, 1-11. doi: 10.1128/mBio.00003-13.

Vo et al. CRISPR RNA-guided integrases for high-efficiency, multiplexed bacterial genome engineering. Nature Biotechnology, 2021, 39, 480-489. https://doi.org/10.1038/s41587-020-00745-y.

Wanneir et al. Improved bacterial recombineering by parallelized protein discovery. PNAS, 2020, 117(24), 13689-13698.

Wannier et al. Recombineering and MAGE. Nat Rev Methods Primers. 2021, 1-51. doi: 10.1038/s43586-020-00006-x.

Weigele and Raleigh. Biosynthesis and Function of Modified Bases in Bacteria and Their Viruses. Chemical Reviews. 2016, 12655-12687.

Wu et al. The DNA site utilized by bacteriophage P22 for initiation of DNA packaging. Molecular Microbiology (2002) 45(6), 1631-1646.

Yan et al. Cas13d is a compact RNA-targeting type VI CRISPR effector positively modulated by a WYL domain- containing accessory protein. Mol Cell. Apr. 19, 2018; 70(2): 327-339.e5. doi: 10.1016/j.molcel.2018.02.028.

Zhao et al. New base editors change C to A in bacteria and C to G in mammalian cells. Nat Biotechnol 2021, 39, 35-40. https://doi.org/10.1038/s41587-020-0592-2.

Abudayyeh et al RNA targeting with CRISPR-Cas13a. Nature. Oct. 12, 2017; 550(7675): 280-284. doi: 10.1038/nature24049.

Anne et al. Protein Secretion in Gram-Positive Bacteria: From Multiple Pathways to Biotechnology. Current Topics in Microbiology and Immunology. Nov. 25, 2016. 267-308. DOI 10.1007/82_2016_49.

Anzalone et al. Search-and-replace genome editing without double-strand breaks or donor DNA. Nature. Dec. 2019 ; 576(7785): 149-157. doi: 10.1038/s41586-019-1711-4.

Brede et al. Heterologous Production of Antimicrobial Peptides in Propionibacterium freudenreichii. Applied and Environmental Microbiology, Dec. 2005, 8077-8084. doi:10.1128/AEM.71.12.8077-8084.2005.

Brüggemann H, et al. A Janus-Faced Bacterium: Host-Beneficial and -Detrimental Roles of Cutibacterium acnes. Front. Microbiol. (2021)12:673845. 1-22. doi: 10.3389/fmicb.2021.673845.

Cambray G et al. Measurement and modeling of intrinsic transcription terminator. Nucleic Acids Research, 2013, vol. 41, No. 9 5139-5148 doi:10.1093/nar/gkt163.

Casjens et al. The pKO2 Linear Plasmid Prophage of Klebsiella oxytoca. Journal of Bacteriology, Mar. 2004, vol. 186, No. 6, 1818-1832 DOI: 10.1128/JB.186.6.1818-1832.2004.

Chen et al. Characterization of 582 natural and synthetic terminators and quantification of their design constraints. 2013. Nature Methods, vol. 10, No. 7, 659-666.

Chen et al. Precise and programmable C:G to G:C base editing in genomic DNA.2020. 1-19. https://doi.org/10.1101/2020.07.21.213827.

Chen et al. Programmable C:G to G:C genome editing with CRISPR-Cas9-directed base excision repair proteins. Nature Communications, (2021) 12:1384. 1-7. https://doi.org/10.1038/s41467-021-21559-9.

Cheng et al. Complete genomic sequences of Propionibacterium freudenreichii phages from Swiss cheese reveal greater diversity than Cutibacterium (formerly Propionibacterium) acnes phages. BMC Microbiology (2018) 18:19, 1-13 https://doi.org/10.1186/s12866-018-1159-y.

(56) References Cited

OTHER PUBLICATIONS

Chung and Hinkle. Bacteriophage T7 DNA Packaging II. Analysis of the DNA Sequences Required for Packaging Using a Plasmid Transduction Assay. Journal of Molecular Biology. 1990, 216, 927-938.

Costa et al. Secretion systems in Gram-negative bacteria: structural and mechanistic insights. 2015. Nature Reviews Microbiology. vol. 13, 343-359.

Cotter et al. Bacteriocins—a viable alternative to antibiotics. 2013. Nature Reviews Microbiology. vol. 11, 95-105.

Cox et al. RNA Editing with CRISPR-Cas13. Science. Nov. 24, 2017; 358(6366): 1019-1027. doi:10.1126/science.aaq0180.

Del Solar et al. Replication and Control of Circular Bacterial Plasmids. Microbiology and Molecular Biology Reviews. 1998. vol. 62, No. 2, 434-4.

Dickely et al. Isolation of Lactococcus lactis nonsense suppressors and construction of a food-grade cloning vector. Molecular Microbiology (1992), 15 (5), 839-847.

Farzadfard and Lu. Genomically Encoded Analog Memory with Precise In vivo DNA Writing in Living Cell Population. Science. Nov. 14, 2014; 346(6211): 1256272. doi:10.1126/science.1256272.

Fiedler and Skerra. proBA complementation of an auxotrophic E. coli strain improves plasmid stability and expression yield during fermenter production of a recombinant antibody fragment. 2001. Gene. 274, 111-118.

Fillol-Salom et al. Phage-inducible chromosomal islands are ubiquitous within the bacterial universe. The ISME Journal (2018) 12:2114-2128.

Fonfara et al. Phylogeny of Cas9 determines functional exchangeability of dual-RNA and Cas9 among orthologous type II CRISPR-Cas systems. Nucleic Acids Research, 2014, vol. 42, No. 4 2577-2590.

Gaudelli et al. Programmable base editing of A•T to G•C in genomic DNA without DNA cleavage. Nature. Nov. 23, 2017; 551(7681): 464-471. doi:10.1038/nature24644.

Gautier et al. Bacteriophages infecting dairy propionibacteria. Lait (1995) 75, 427-434.

Gautier et al. Occurrence of Propionibacterium freudenreichii Bacteriophages in Swiss Cheese. Applied and Environmental Microbiology, Jul. 1995, vol. 61, No. 7. p. 2572-2576.

Groenen and Van de Putte. Mapping of a Site for Packaging of Bacteriophage Mu DNA. Virology. 1985, 144, 520-522.

Grunewald et al. A dual-deaminase CRISPR base editor enables concurrent adenine and cytosine editing. Nat Biotechnol. Jul. 2020 ; 38(7): 861-864. doi: 10.1038/s41587-020-0535-y.

Hashimoto and Fujisawa. DNA Sequences Necessary for Packaging Bacteriophage T3 DNA. Virology 1992, 187, 7,788-795.

Henkel et al. Toxins from Bacteria. EXS. 2010 ; 100: 1-29.

Hohn. DNA sequences necessary for packaging of bacteriophage A DNA (cosmid/in vivo packaging/in vitro packaging of restriction fragments). Dec. 1983. Proc. Nati. Acad. Sci. USA vol. 80, pp. 7456-7460.

Ioannidi et al. Drag-and-drop genome insertion without DNA cleavage with CRISPR directed integrases. 2021. bioRxiv 2021.11. 01.466786; doi: https://doi.org/10.1101/2021.11.01.466786.

Jinek et al. A Programmable Dual-RNA-Guided DNA Endonuclease in Adaptive Bacterial Immunity. Science. Aug. 17, 2012. vol. 337, 6096, 816-821.

Kabashima et al. The immunological anatomy of the skin. Nature Reviews Immunology. 2019. vol. 19, 19-30.

Kala et al. HNH proteins are a widespread component of phage DNA packaging machines. PNAS 2014. 111, 16, 6022-6027.

Karberg et al. Group II introns as controllable gene targeting vectors for genetic manipulation of bacteria. Nature Biotechnology. 2001, 19, 1162-1167.

Kashaf et al. Integrating cultivation and metagenomics for a multi-kingdom view of skin microbiome diversity and functions. Nature Microbiology. 2022. 7, 169-191.

Komor et al. Programmable editing of a target base in genomic DNA without double-stranded DNA cleavage. Nature. 2016. 533(7603): 420-424. doi:10.1038/nature17946.

Koonin et al. Diversity, classification and evolution of CRISPR-Cas systems. 2018. Curr Opin Microbiol. Jun. 2017 ; 37: 67-78. doi:10.1016/j.mib.2017.05.008.

Krupovic et al. A classification system for virophages and satellite viruses. 2016. Arch Virology. 161:233-247.

Kues and Stahl. Replication of Plasmids in Gram-Negative Bacteria. Microbiological Reviews, Dec. 1989, 53, 4, 491-516.

Kurt et al. CRISPR C-to-G base editors for inducing targeted DNA transversions in human cells. Nat Biotechnol. Jan. 2021 ; 39(1): 41-46. doi:10.1038/s41587-020-0609-x.

Li et al. Targeted, random mutagenesis of plant genes with dual cytosine and adenine base editors. Nature Biotechnology. 2020. 38, 875-882.

Ma et al. Transposon-Associated CRISPR-Cas System: A Powerful DNA Insertion Tool. Trends in Microbiology. 2021. 29, 7, 565-586.

MacCormick et al. Construction of a food-grade host/vector system for Lactococcus lactis based on the lactose operon. FEMS Microbiology Letters 127 (1995) 105-109.

Marinelli et al. Propionibacterium acnes Bacteriophages Display Limited Genetic Diversity and Broad Killing Activity against Bacterial Skin Isolates. mBio 2012, 3(5), 1-13.

Miwa and Matsubara. Identification of sequences necessary for packaging DNA into lambda phage heads (Recombinant DNA; cosmid; MI3 dideoxynucleotide sequencing; h cohesive end; plasmid vector). Gene, 20(1982) 261-279.

Moodley et al. The protein gp74 from the bacteriophage HK97 functions as a HNH endonuclease. Protein Science. 2012. 21, 809-818.

Mutalik et al. Precise and reliable gene expression via standard transcription and translation initiation elements. Nature Methods. 2013, 10, 4, 354-368.

Nakayama et al. The R-type pyocin of Pseudomonas aeruginosa is related to P2 phage, and the F-type is related to lambda phage. Molecular Microbiology (2000) 38(2), 213-231.

Petri and Schmieger. Isolation of fragments with pac function for phage P22 from phage LP7 DNA and comparison of packaging gene 3 sequences. Gene, 88 (1990) 47-55.

Quiles-Puchalt et al. Staphylococcal pathogenicity island DNA packaging system involving cos-site packaging and phage-encoded HNH endonucleases. PNAS. 2014. 111 (16), 6016-6021.

\* cited by examiner

PCR ORF3 with expected size ~ 1329bp based on reference BW phage genome KX620751

PCR ORF5 with expected size ~ 1036bp based on reference BW phage genome KX620751

Production from Pf1s22904
colonies 1-8

SLST PCR
Expected size 612bp pAN594 specific PCR
Expected size 769bp

PRODUCTION BACTERIAL CELLS AND USE THEREOF IN PRODUCTION METHODS

CROSS REFERENCE TO RELATED APPLICATIONS

This application is a divisional of U.S. application Ser. No. 17/742,671 filed on May 12, 2022, which claims the benefit of U.S. application 63/187,531 filed May 12, 2021, and U.S. application 63/187,532 filed May 12, 2021, which are incorporated herein by reference in their entirety.

REFERENCE TO SEQUENCE LISTING SUBMITTED ELECTRONICALLY

The instant application contains a Sequence Listing which has been filed electronically in ST.26 format and is hereby incorporated by reference in its entirety. Said ST.26 copy, created on May 16, 2023, is named EB2021-04a_USDiv.xml and is 172,032 bytes bytes in size.

FIELD OF THE INVENTION

The present invention concerns bacterial cells for producing phage particles and methods using such bacterial cells.

BACKGROUND

Most current phage or phage-derived delivery vehicle production methods imply the use, as production cell, of the bacterial species or strain which is the natural host of said phages. Such methods can turn out to be dangerous when such bacterial cells are pathogenic, for example when they produce toxins. Moreover, many bacterial species cannot be easily manipulated, for instance because of their growth conditions or because there is no efficient genetic tool for those bacteria. It can also be difficult to identify a bacterial strain that only contains a prophage, since in many cases, a same bacterial strain contains several prophages, which can give rise to unwanted particles being produced or unwanted recombination events, etc., and/or to induce and/or stably maintain a prophage/phage in a given species or strain, for example.

There is thus a need for a method enabling the safe, easier and efficient production of any phage or phage-derived particle.

The present invention meets this need.

The present inventors considered that phages can be viewed as more or less large genetic circuits, the final output of which is the generation of more phage particles. To do this, no matter if the phage is lytic, temperate or chronic (for instance filamentous phages such as M13), the present inventors considered that the information encoded in their genomes can be roughly categorized depending on the function it performs:

Genes devoted to insertion/excision (for temperate phages).

Genes devoted to DNA replication, RNA transcription, etc. Indeed, some lytic phages encode their own RNA or DNA polymerases, for instance. Some genes modify the host's RNA polymerases to be able to work past terminators, and some other genes are involved in the segregation of the prophage sequence if it exists in a plasmid or linear plasmid form.

Genes devoted to packaging of the newly synthesized phage genome into the newly synthesized phage capsids: terminases and accessory proteins, ligases, etc.

Structural genes devoted to building a protein capsid for the DNA: apart from strictly structural genes, such as capsid genes, tape measure, fibers, baseplate etc, many other genes are needed to assemble the components (chaperones, proteases) as well as proteins that can be packaged inside the capsid, be it as scaffold or as pilot proteins injected into the cell (for instance, the RNA polymerase of phage N4 or some minor pilot proteins in other phages).

Genes related to defense from host's anti-phage mechanisms, degradation/modification of host's elements to complete the lytic cycle, super-exclusion mechanisms or genes that are advantageous for the host.

The DNA packaging and structural genes categories are deeply connected, since the packaging machinery recognizes the pre-assembled capsid heads and the DNA to be packaged in these heads, initiates and terminates DNA packaging.

The present inventors hypothesized that by abstracting and differentiating all the modules defined above, a system could be built that contains all excision/insertion, replication and regulation elements from one phage and encodes the packaging/structural elements for another one, since, as considered by the inventors, they could be viewed as independent genetic modules.

Treating them as independent genetic modules could also allow for the construction of a system that contains only the desired structural and/or regulatory elements of the phage to be produced under the control of a master regulatory element (an inducible repressor, for example) that may not be derived from a phage, as opposed to wild-type phages where gene expression is tightly regulated by phage elements. For instance, only the structural operon and the DNA packaging machinery of a phage could be placed under the control of a repressor that responds to a small molecule or a physical/chemical signal (LacI, AraC, PhIF, Lambda cI, etc.), triggering the production of all the elements necessary to generate pure mature phage delivery particles (phages or packaged phagemids). This "trimmed down" version of a phage genome could be stably maintained in a bacterial production strain.

SUMMARY OF THE INVENTION

The present invention arises from the unexpected finding by the inventors that it is possible, by exchanging the structural operon of an *Escherichia coli* production strain encoding a system to generate pure Lambda packaged phagemids with the structural operon of a prophage coming from a different species (such as *Klebsiella pneumoniae*), to drive the assembly and packaging of pure heterologous phagemid particles when supplemented with a plasmid containing the correct packaging signals (cos site for the *Klebsiella pneumoniae* phage). The present inventors thus here showed that phagemids can be produced structurally based on a *K. pneumoniae* prophage, but regulated and maintained in the lysogenic state by the Lambda prophage machinery in an *Escherichia coli* production strain.

The inventors also showed that the structural operon of a *P. freudenreichii* prophage can be exchanged with the structural operon of a phage of a *C. acnes* strain. With this approach, the inventors showed that it is possible, by exchanging the structural operon of a *P. freudenreichii* prophage with the structural operon of a phage of a *C. acnes* strain, to drive the assembly and packaging of pure *C. acnes* phagemids.

This approach represents a novel avenue for easier and/or safer generation of phage particles and/or phage-derived delivery vehicles, targeting bacterial cells known to be pathogenic and/or difficult to manipulate and/or inefficient to use in phage particles and/or phage-derived delivery vehicles production for any reason.

The present invention thus concerns a production bacterial cell for producing phage particles or phage-derived delivery vehicles, said production bacterial cell stably comprising at least one phage structural gene(s) and at least one phage DNA packaging gene(s), said phage structural gene(s) and phage DNA packaging gene(s) being derived from a first type of bacteriophage, wherein the expression of at least one of said phage structural gene(s) and/or at least one of said phage DNA packaging gene(s) in said production bacterial cell is controlled by at least one induction mechanism, and wherein said production bacterial cell is from a bacterial species or strain different from the bacterial species or strain from which said first type of bacteriophage comes and/or that said first type of bacteriophage targets.

The present invention also concerns a method for producing phage particles or phage-derived delivery vehicles, comprising:
(a) providing the production bacterial cell of the invention, and
(b) inducing, in said production bacterial cell, expression of said at least one of said phage structural gene(s) and phage DNA packaging gene(s), and assembly of the products expressed by said at least one phage structural gene(s) and said at least one phage DNA packaging gene(s), thereby producing phage particles or phage-derived delivery vehicles.

Another object of the invention concerns a hybrid helper phage system comprising:
(i) at least one phage DNA packaging gene(s) derived from a first type of bacteriophage,
(i') at least one phage structural gene(s) derived from said first type of bacteriophage, and
(ii) at least one gene, derived from a second type of bacteriophage, involved in phage excision/insertion, phage DNA replication, and/or phage regulation, wherein said genes (i), (i') and (ii) are comprised in a unique nucleic acid molecule or in separate nucleic acid molecules, wherein said first type of bacteriophage comes from and/or target bacterial species or strain different from the bacterial species or strain from which said second type of bacteriophage comes and/or that said second type of bacteriophage targets, and wherein said hybrid helper phage system does not comprise any expressed phage structural gene derived from said second type of bacteriophage.

DETAILED DESCRIPTION OF THE INVENTION

Production Bacterial Cell

The present invention concerns a production bacterial cell for producing phage particles or phage-derived delivery vehicles, said production bacterial cell stably comprising at least one phage structural gene(s) and at least one phage DNA packaging gene(s) derived from a first type of bacteriophage, wherein the expression of at least one of said phage structural gene(s) and at least one of said phage DNA packaging gene(s) in said production bacterial cell is controlled by an induction mechanism, and wherein said production bacterial cell is from a bacterial species or strain different from the bacterial species or strain from which said first type of bacteriophage comes and/or that said first type of bacteriophage targets.

As used herein, the term "phage particle" refers to a functional or non-functional (for example non-reproductive and/or replicative) virion.

As used herein, the term "phage-derived delivery vehicle" refers to any means that allows the transfer of a payload into a bacterium and which is derived from a bacteriophage. In the context of the invention, the term "phage-derived delivery vehicle" further encompasses bacteriophage-derived particles which do not comprise any payload but are able to target bacterial cells.

The phage-derived delivery vehicle can refer to a bacteriophage derived scaffold and can be obtained from a natural, evolved or engineered bacteriophage.

Bacterial Cell

The production bacterial cell of the invention may be of any bacterial species or strain, in particular defined below under the section "Targeted bacteria", provided that said bacterial species or strain is different from the bacterial species or strain from which said first type of bacteriophage comes and/or that said first type of bacteriophage targets.

However, the production bacterial cell is preferably a non-pathogenic bacterial cell. Still preferably, the production bacterial cell is a bacterial cell which can be easily manipulated.

By "easily manipulated" is meant herein that the bacterial cell can be cultured and/or modified using well-known techniques.

In a particular preferred embodiment, said production bacterial cell is an *E. coli* bacterial cell. Alternatively, said production bacterial cell may be a *Bacteroides* bacterial cell, more particularly a *Bacteroides* thetaiotaomicron bacterial cell, a *P. freudenreichii* bacterial cell, a *Fusobacterium* bacterial cell, or a *Streptococcus* bacterial cell. In a particular embodiment, said production bacterial cell is a *P. freudenreichii* bacterial cell.

The production bacterial cell of the invention can be obtained by any technique well-known from the skilled person, in particular by introducing into a bacterial cell, said phage structural gene(s) and phage DNA packaging gene(s) derived from a first type of bacteriophage, by any technique well-known in the art.

The production bacterial cell of the invention can typically be obtained by homologous recombination or recombineering including for example MAGE (Wannier et al. Recombineering and MAGE. *Nat Rev Methods Primers* 1, 7 (2021)), using CRISPR, TALEN, meganucleases and/or Zn-finger technologies for instance or using site specific recombination with phage integrase, PASTE (Ioannidi et al. Drag-and-drop genome insertion without DNA cleavage with CRISPR-directed integrases. Biorxiv 2021.11.01.466786 (2021) doi:10.1101/2021.11.01.466786) or Transposon-Associated CRISPR-Cas System (Ma et al. *Trends Microbiol* 29, 565-568 (2021)).

Phage DNA Packaging Genes and Phage Structural Genes

The production bacterial cell of the invention stably comprises at least one phage structural gene(s) and at least one phage DNA packaging gene(s) derived from a first type of bacteriophage.

By "stably comprise" or "stably comprising" is meant herein that the production bacterial cell retains said phage structural gene(s) and phage DNA packaging gene(s) either incorporated into its chromosome, or on an episome that is maintained in the cell typically through selection (e.g., with a nutritional, auxotrophic, or drug resistance marker). Each gene stably comprised by the production bacterial cell can independently be on a plasmid, on a helper phage, or is integrated into the production bacterial cell chromosome.

In a particular embodiment, said production bacterial cell stably comprises at least two, 3, 4, or all phage structural genes derived from said first type of bacteriophage, and at least one phage DNA packaging gene(s) derived from said first type of bacteriophage.

In a particular embodiment, said production bacterial cell stably comprises at least one phage structural gene(s) derived from said first type of bacteriophage, and at least two or all phage DNA packaging genes derived from said first type of bacteriophage.

In a particular embodiment, said production bacterial cell stably comprises at least two, 3, 4, or all phage structural genes derived from said first type of bacteriophage, and at least two or all phage DNA packaging genes derived from said first type of bacteriophage.

In a particular embodiment, said production bacterial cell stably comprises all phage structural genes derived from said first type of bacteriophage, and all phage DNA packaging genes derived from said first type of bacteriophage.

By "phage structural genes" is meant herein genes from a bacteriophage which are involved in the building of the bacteriophage protein capsid. Phage structural genes include genes encoding phage structural elements; genes encoding phage proteins involved in the assembly of the phage structural elements; and genes encoding phage proteins packaged inside the capsid as scaffold or as pilot proteins to be injected into a targeted bacterial cell.

Phage structural elements are well-known from the skilled person and depend on the type of bacteriophage from which they are derived. Phage structural elements can be proteins but also RNAs (for example some phages like phi29 from *Bacillus subtilis* encode a structural scaffold made of RNA). Phage structural elements typically include capsid proteins, tape measure proteins, fibers, baseplate proteins, tail sheath proteins, whisker proteins, decoration proteins, etc. . . .

Phage proteins involved in the assembly of the structural elements are well-known from the skilled person and depend on the type of bacteriophage from which they are derived, and optionally on the structural elements encoded by the other phage structural genes. Phage proteins involved in the assembly of the structural elements typically include phage chaperone proteins and phage proteases.

Phage proteins packaged inside the capsid as scaffold or as pilot proteins to be injected into a target host cell are well-known from the skilled person and depend on the type of bacteriophage from which they are derived. Examples of such phage proteins are RNA polymerase from phage N4 or minor pilot proteins.

As will be understood by the skilled person, the presence of a particular phage structural gene in the production bacterial cell of the invention will depend on the bacteriophage from which said phage structural genes are derived.

By "phage DNA packaging genes" is meant herein genes from a bacteriophage which are involved in the packaging of the bacteriophage genome into the bacteriophage capsid. Phage DNA packaging genes are well-known from the skilled person and include genes encoding phage terminases, genes encoding phage accessory proteins, genes encoding phage ligases, genes encoding phage exonucleases involved in DNA packaging and genes encoding phage endonucleases involved in DNA packaging.

In a particular embodiment, said production bacterial cell further stably comprises at least one gene involved in phage regulation derived from said first type of bacteriophage.

By "gene involved in phage regulation" is meant herein phage genes involved in the interaction of the phage with the host. Examples of genes involved in phage regulation include phage genes encoding master repressors, phage genes encoding anti-termination proteins, phage genes involved in super-exclusion mechanisms, phage genes involved in defense against host's anti-phage mechanisms, phage genes involved in degradation and/or modification of host's elements for example to complete the lytic cycle, and phage genes advantageous for the host.

In a particular embodiment, said production bacterial cell stably comprises phage gene(s) involved in defense against host's anti-phage mechanisms derived from said first type of bacteriophage.

In a particular embodiment, said phage structural gene(s) and phage DNA packaging gene(s) derived from said first type of bacteriophage, and optionally said gene(s) involved in phage regulation derived from said first type of bacteriophage are comprised in at least one plasmid, chromosome and/or helper phage. In a particular embodiment, said phage structural gene(s) and phage DNA packaging gene(s) derived from said first type of bacteriophage, and optionally said gene(s) involved in phage regulation derived from said first type of bacteriophage are comprised in at least two separate nucleic acid molecules, in particular at least two plasmids, chromosomes, helper phages or combinations thereof.

In a particular embodiment, said phage structural gene(s) and phage DNA packaging gene(s) derived from said first type of bacteriophage, and optionally said gene(s) involved in phage regulation derived from said first type of bacteriophage are comprised in a hybrid helper phage system as defined below.

In a particular embodiment, said phage structural gene(s) and phage DNA packaging gene(s) derived from said first type of bacteriophage, and optionally said gene(s) involved in phage regulation derived from said first type of bacteriophage are comprised in a helper phage.

Induction Mechanism

In the context of the invention, the expression of at least one of said phage structural gene(s) and/or at least one of said phage DNA packaging genes, as defined in the section "*Phage DNA packaging genes, and phage structural genes*" above, in said production bacterial cell is controlled by at least one induction mechanism.

In a particular embodiment, the expression of at least one of said phage structural gene(s), in particular at least two, at least three, or all said phage structural genes, in said production bacterial cell is(are) controlled by at least one induction mechanism, in particular by one induction mechanism.

In a particular embodiment, the expression of at least one of said phage DNA packaging gene(s), in particular at least two, at least three, or all said phage DNA packaging genes, in said production bacterial cell is(are) controlled by at least one induction mechanism, in particular by one induction mechanism.

In a particular embodiment, the same induction mechanism controls the expression of the at least one of said phage structural gene(s) and the at least one of said phage DNA packaging gene(s).

In an alternative embodiment, the expression of the at least one of said phage structural gene(s) and the expression of the at least one of said phage DNA packaging gene(s) are controlled by different induction mechanisms.

By "induction mechanism" is meant herein a mechanism, encoded by a gene or group of genes comprised, in particular stably comprised, in said production bacterial cell, able to induce the expression of the genes they control, in response to a given trigger.

In a particular embodiment, said induction mechanism further controls the copy number of said at least one of said phage structural gene(s) and/or said at least one of said phage DNA packaging gene(s). In other words, in a particular embodiment, said induction mechanism further controls the replication of said at least one of said phage structural gene(s) and/or of said at least one of said phage DNA packaging gene(s), in particular the replication of the nucleic acid molecule(s) carrying said at least one of said phage structural gene(s) and/or said at least one of said phage DNA packaging gene(s).

In a particular embodiment, said induction mechanism further controls the assembly of the products expressed by said at least one of said phage structural gene(s) and at least one of said phage DNA packaging gene(s).

Examples of such induction mechanism include:

Protein repressor or activator-based induction systems responding to small molecules (for example sugars, quorum-sensing molecules, gases, synthetic molecules, peptides, amino acids, metabolites, etc), physical signals (temperature, pressure, etc.), chemical signals (osmolarity, pH, etc.), biological signals (cell density, DNA damage, etc.); these systems may be activated by a secondary protein such as an orthogonal RNA polymerase or sigma factor.

Protein degradation systems to activate or repress transcription from a promoter.

RNA-based induction systems such as aptamers responding to the signals stated above, such as RNAi, CRISPRi, toehold systems, riboswitches, etc.

One or more nucleic acids comprising at least one gene, derived from a second type of bacteriophage, involved in phage excision/insertion, phage DNA replication, and/or phage regulation.

In a particular embodiment, said induction mechanism comprises at least one gene, derived from a second type of bacteriophage, involved in phage excision/insertion, phage DNA replication, and/or phage regulation.

Therefore, in particular embodiment, said production bacterial cell further comprises at least one gene, derived from a second type of bacteriophage, involved in phage excision/insertion, phage DNA replication, and/or phage regulation.

Genes Involved in Phage Excision/Insertion, Phage DNA Replication, and/or Phage Regulation By "gene involved in phage excision/insertion" is meant herein genes from lysogenic phages involved in the excision of the phage, present as a prophage, from the genome or episome of a bacterial cell and/or the insertion of the phage, as a prophage, in the genome or episome of a bacterial cell.

By "gene involved in phage DNA replication" is meant herein genes from lysogenic or lytic phages, involved in the mechanism of replication of the phage DNA. Examples of genes involved in phage DNA replication include genes encoding DNA polymerase and genes involved in the segregation of the prophage sequence if it exists in a plasmid or linear plasmid form.

By "gene involved in phage regulation" is meant herein phage genes involved in the interaction of the phage with the host. Examples of genes involved in phage regulation include phage genes encoding master repressors, phage genes encoding anti-termination proteins, phage genes involved in super-exclusion mechanisms, phage genes involved in defense against host's anti-phage mechanisms, phage genes involved in degradation and/or modification of host's elements for example to complete the lytic cycle, and phage genes advantageous for the host.

In the context of the invention, said gene(s) involved in phage excision/insertion, phage DNA replication, and/or phage regulation, is(are) not DNA packaging gene(s) nor structural gene(s), as defined above.

In a preferred embodiment, the production bacterial cell of the invention comprises at least one gene, preferably all the genes, involved in phage excision/insertion derived from a second type of bacteriophage; at least one gene, preferably all the genes, involved in phage DNA replication derived from a second type of bacteriophage; and/or at least one gene, preferably all the genes, involved in phage regulation derived from a second bacteriophage.

In the context of the invention, said production bacterial cell does not comprise genes derived from the first type of bacteriophage which are involved in phage excision/insertion and/or phage DNA replication.

In a particular embodiment, said gene(s) involved in phage excision/insertion, phage DNA replication, and/or phage regulation derived from said second type of bacteriophage, are comprised in at least one plasmid, chromosome and/or helper phage. In a particular embodiment, said gene(s) involved in phage excision/insertion, phage DNA replication, and/or phage regulation derived from said second type of bacteriophage are comprised in at least two separate nucleic acid molecules, in particular at least two plasmids, chromosomes, helper phages or combinations thereof.

In a particular embodiment, said gene(s) involved in phage excision/insertion, phage DNA replication, and/or phage regulation derived from said second type of bacteriophage are comprised in a hybrid helper phage system as defined below.

In a particular embodiment, said gene(s) involved in phage excision/insertion, phage DNA replication, and/or phage regulation derived from said second type of bacteriophage, are comprised in a helper phage system, more particularly on the same helper phage system as said phage structural gene(s) and phage DNA packaging gene(s) derived from said first type of bacteriophage, and optionally said gene(s) involved in phage regulation derived from said first type of bacteriophage.

In the context of the invention, said second type of bacteriophage comes from and/or targets bacterial species or strain different from the bacterial species or strain from which said first type of bacteriophage comes and/or that said first type of bacteriophage targets.

In a particular embodiment, said production bacterial cell is from the same bacterial species or strain as the bacterial species or strain from which said second type of bacteriophage comes and/or that said second type of bacteriophage targets.

In a more particular embodiment, said production bacterial cell is an *E. coli* bacterial cell. In another particular embodiment, said production bacterial cell is a *P. freudenreichii* bacterial cell.

Other Elements

In a particular embodiment, the production bacterial cell of the invention further comprises at least one gene involved in phage RNA transcription.

By "gene involved in phage RNA transcription" is meant genes from temperate or lytic phages, involved in the mechanism of transcription of the phage RNA. Examples of such genes include genes encoding phage RNA polymerase and phage genes encoding proteins modifying the host's RNA polymerases, typically to be able to work past terminators.

Bacteriophage and Gene Derived from a Bacteriophage

By "gene derived from a bacteriophage" is meant herein that the sequence of the gene is obtained from a bacteriophage, said sequence being optionally modified, recoded and/or optimized compared to the sequence initially present in the bacteriophage. For example, said sequence may be recoded for codon exchange or optimization (for example some proteins of the Kappa prophage contain an amber TAG stop codon, which is not recognized by *E. coli*, and which is preferably changed to TAA or TGA) or preventing recombination.

Bacteriophages are obligate intracellular parasites that multiply inside bacteria by co-opting some or all of the host biosynthetic machinery. Bacteriophage can be found inside bacteria as a prophage whose genome is integrated in the bacterial chromosome or as a phage-plasmid whose genome is part of an extrachromosomal plasmid (such phage-plasmids are for example disclosed in Ravin et al. (1999) Molecular Microbiology 34(5):980-994). Examples of bacteriophage which can be in the form of a phage-plasmid include phages P1, N15, SSU5, P7, D6, pMCR-1-P3, IEBH, phiGILI6c, Bam35c, pBClin15, VP882, KS-14, P88, pLP39, F116, D3, phiSG1. Phage genomes come in a variety of sizes and shapes (e.g., linear or circular). Most phages range in size from 24-200 nm in diameter. Phages contain nucleic acid (i.e., genome) and proteins, and may be enveloped by a lipid membrane. Depending upon the phage, the nucleic acid genome can be either DNA or RNA, and can exist in either circular or linear forms. The size of the phage genome varies depending upon the phage. The simplest phages have genomes that are only a few thousand nucleotides in size, while the more complex phages may contain more than 100,000 nucleotides in their genome, and in rare instances more than 1,000,000. The number and amount of individual types of protein in phage particles will vary depending upon the phage.

In a particular embodiment, the first type of bacteriophage is selected from the Order Caudovirales consisting of, based on the taxonomy of Krupovic et al. (Krupovic et al. Arch Virol. 2016 January; 161(1):233-47):

family Myoviridae (such as, without limitation, genus Cp220virus, Cp8virus, Ea214virus, Felixo1virus, Mooglevirus, Suspvirus, Hp1virus, P2virus, Kayvirus, P100virus, Silviavirus, Spo1virus, Tsarbombavirus, Twortvirus, Cc31virus, Jd18virus, Js98virus, Kp15virus, Moonvirus, Rb49virus, Rb69virus, S16virus, Schizot4virus, Sp18virus, T4virus, Cr3virus, Se1virus, V5virus, Abouovirus, Agatevirus, Agrican357virus, Ap22virus, Arv1virus, B4virus, Bastillevirus, Bc431virus, Bcep78virus, Bcepmuvirus, Biquartavirus, Bxz1virus, Cd119virus, Cp51virus, Cvm10virus, Eah2virus, Elvirus, Hapunavirus, Jimmervirus, Kpp10virus, M12virus, Machinavirus, Marthavirus, Msw3virus, Muvirus, Myohalovirus, Nit1virus, P1virus, Pakpunavirus, Pbunavirus, Phikzvirus, Rheph4virus, Rsl2virus, Rslunavirus, Secunda5virus, Sep1virus, Spn3virus, Svunavirus, Tg1virus, Vhmlvirus and Wphvirus)

family Podoviridae (such as, without limitation, genus Fri1virus, Kp32virus, Kp34virus, Phikmvvirus, Pradovirus, Sp6virus, T7virus, Cp1virus, P68virus, Phi29virus, Nona33virus, Pocjvirus, Tl2011virus, Bcep22virus, Bpp1virus, Cba41virus, Dfl12virus, Ea92virus, Epsilon15virus, F116virus, G7cvirus, Jwalphavirus, Kfl1virus, Kpp25virus, Lit1virus, Luz24virus, Luz7virus, N4virus, Nonanavirus, P22virus, Pagevirus, Phieco32virus, Prtbvirus, Sp58virus, Una961virus and Vp5virus)

family Siphoviridae (such as, without limitation, genus Camvirus, Likavirus, R4virus, Acadianvirus, Coopervirus, Pg1virus, Pipefishvirus, Rosebushvirus, Brujitavirus, Che9cvirus, Hawkeyevirus, Plotvirus, Jerseyvirus, K1gvirus, Sp31virus, Lmd1virus, Una4virus, Bongovirus, Reyvirus, Buttersvirus, Charlievirus, Redivirus, Baxtervirus, Nymphadoravirus, Bignuzvirus, Fishburnevirus, Phayoncevirus, Kp36virus, Rogue1virus, Rtpvirus, T1virus, Tlsvirus, Ab18virus, Amigovirus, Anatolevirus, Andromedavirus, Attisvirus, Barnyardvirus, Bernal13virus, Biseptimavirus, Bronvirus, C2virus, C5virus, Cba181virus, Cbastvirus, Cecivirus, Che8virus, Chivirus, Cjw1virus, Corndogvirus, Cronusvirus, D3112virus, D3virus, Decurrovirus, Demosthenesvirus, Doucettevirus, E125virus, Eiauvirus, Ff47virus, Gaiavirus, Gilesvirus, Gordonvirus, Gordtnkvirus, Harrisonvirus, Hk578virus, Hk97virus, Jenstvirus, Jwxvirus, Kelleziovirus, Korravirus, L5virus, Lambdavirus, Laroyevirus, Liefievirus, Marvinvirus, Mudcatvirus, N15virus, Nonagvirus, Np1virus, Omegavirus, P12002virus, P12024virus, P23virus, P70virus, Pa6virus, Pamx74virus, Patiencevirus, Pbi1virus, Pepy6virus, Pfr1virus, Phic31virus, Phicbkvirus, Phietavirus, Phifelvirus, Phijl1virus, Pis4avirus, Psavirus, Psimunavirus, Rdjlvirus, Rer2virus, Sap6virus, Send513virus, Septima3virus, Seuratvirus, Sextaecvirus, Sfi11virus, Sfi21dt1virus, Sitaravirus, Sk1virus, Slashvirus, Smoothievirus, Soupsvirus, Spbetavirus, Ssp2virus, T5virus, Tankvirus, Tin2virus, Titanvirus, Tm4virus, Tp21virus, Tp84virus, Triavirus, Trigintaduovirus, Vegasvirus, Vendettavirus, Wbetavirus, Wildcatvirus, Wizardvirus, Woesvirus, Xp10virus, Ydn12virus and Yuavirus)

family Ackermannviridae (such as, without limitation, genus Ag3virus, Limestonevirus, Cba120virus and Vi1virus)

In a particular embodiment, the first type of bacteriophage is not part of the Order Caudovirales but from families with Unassigned order such as, without limitation, family Tectiviridae (such as genus Alphatectivirus, Betatectivirus), family Corticoviridae (such as genus Corticovirus), family Inoviridae (such as genus Fibrovirus, Habenivirus, Inovirus, Lineavirus, Plectrovirus, Saetivirus, Vespertiliovirus), family Cystoviridae (such as genus Cystovirus), family Leviviridae (such as genus Allolevivirus, Levivirus), family Microviridae (such as genus Alpha3microvirus, G4microvirus, Phix174microvirus, Bdellomicrovirus, Chlamydiamicrovirus, Spiromicrovirus) and family Plasmaviridae (such as genus Plasmavirus).

In a particular embodiment, the first type of bacteriophage is targeting Archea not part of the Order Caudovirales but from families with Unassigned order such as, without limitation, Ampullaviridae, FuselloViridae, Globuloviridae, Guttaviridae, Lipothrixviridae, Pleolipoviridae, Rudiviridae, Salterprovirus and Bicaudaviridae.

In a particular embodiment, the second type of bacteriophage is selected from the bacteriophages defined above, provided that said second type of bacteriophage is different from said first type of bacteriophage.

In a particular embodiment, said first type of bacteriophage comes from a first bacterial species or strain, and said second type of bacteriophage comes from a second bacterial species or strain, wherein said first and second bacterial species or strains are different.

By "bacteriophage coming from a particular bacterial species or strain" is meant herein a bacteriophage specifically targeting a particular bacterial species or strain and/or a bacteriophage hosted by a particular bacterial species or strain.

A non-exhaustive listing of bacterial genera and their known host-specific bacteria viruses is presented in the following paragraphs. Synonyms and spelling variants are indicated in parentheses. Homonyms are repeated as often as they occur (e.g., D, D, d). Unnamed phages are indicated by "NN" beside their genus and their numbers are given in parentheses.

Bacteria of the genus *Actinomyces* can be infected by the following phages: Av-I, Av-2, Av-3, BF307, CTI, CT2, CT3, CT4, CT6, CT7, CT8 and 1281.

Bacteria of the genus *Aeromonas* can be infected by the following phages: AA-I, Aeh2, N, PMI, TP446, 3, 4, 11, 13, 29, 31, 32, 37, 43, 43-10T, 51, 54, 55R.1, 56, 56RR2, 57, 58, 59.1, 60, 63, Aehl, F, PM2, 1, 25, 31, 40RR2.8t, (syn=44R), (syn=44RR2.8t), 65, PM3, PM4, PM5 and PM6.

Bacteria of the genus *Bacillus* can be infected by the following phages: A, aizl, AI-K-I, B, BCJAI, BCI, BC2, BLLI, BLI, BP142, BSLI, BSL2, BSI, BS3, BS8, BS15, BS18, BS22, BS26, BS28, BS31, BS104, BS105, BS106, BTB, B1715V1, C, CK-I, Coll, Corl, CP-53, CS-I, CSi, D, D, D, D5, entl, FP8, FP9, FSi, FS2, FS3, FS5, FS8, FS9, G, GH8, GT8, GV-I, GV-2, GT-4, g3, gl2, gl3, gl4, gl6, gl7, g21, g23, g24, g29, H2, kenl, KK-88, Kuml, Kyul, J7W-1, LP52, (syn=LP-52), L7, MexI, MJ-I, mor2, MP-7, MPIO, MP12, MP14, MP15, Neol, N°2, N5, N6P, PBCI, PBLA, PBPI, P2, S-a, SF2, SF6, Shal, Sill, SP02, (syn=ΦSPP1), SPβ, STI, STi, SU-II, t, TbI, Tb2, Tb5, TbIO, Tb26, Tb51, Tb53, Tb55, Tb77, Tb97, Tb99, Tb560, Tb595, Td8, Td6, TdI5, TgI, Tg4, Tg6, Tg7, Tg9, TgIO, TgII, TgI3, TgI5, Tg21, TinI, Tin7, Tin8, TinI3, Tm3, Tocl, Togl, toll, TP-I, TP-10 vir, TP-15c, TP-16c, TP-17c, TP-19, TP35, TP51, TP-84, Tt4, Tt6, type A, type B, type C, type D, type E, Tφ3, VA-9, W, wx23, wx26, Yunl, α, γ, pl I, φmed-2, φT, φμ-4, φ3T, φ75, φIO5, (syn=φIO5), IA, IB, 1-97A, 1-97B, 2, 2, 3, 3, 3, 5, 12, 14, 20, 30, 35, 36, 37, 38, 41C, 51, 63, 64, 138D, I, II, IV, NN-*Bacillus* (13), alel, ARI, AR2, AR3, AR7, AR9, Bace-11, (syn=11), Bastille, BLI, BL2, BL3, BL4, BL5, BL6, BL8, BL9, BP124, BS28, BS80, Ch, CP-51, CP-54, D-5, darl, denl, DP-7, entl, FoSi, FoS2, FS4, FS6, FS7, G, gall, gamma, GEI, GF-2, GSi, GT-I, GT-2, GT-3, GT-4, GT-5, GT-6, GT-7, GV-6, g15, 19, 110, ISi, K, MP9, MP13, MP21, MP23, MP24, MP28, MP29, MP30, MP32, MP34, MP36, MP37, MP39, MP40, MP41, MP43, MP44, MP45, MP47, MP50, NLP-I, No.I, N17, N19, PBSI, PKI, PMBI, PMB12, PMJI, S, SPOI, SP3, SP5, SP6, SP7, SP8, SP9, SPIO, SP-15, SP50, (syn=SP-50), SP82, SST, subl, SW, Tg8, TgI2, TgI3, TgI4, thul, thuΛ, thuS, Tin4, Tin23, TP-13, TP33, TP50, TSP-I, type V, type VI, V, Vx, β22, φe, φNR2, φ25, φ63, 1, 1, 2, 2C, 3NT, 4, 5, 6, 7, 8, 9, 10, 12, 12, 17, 18, 19, 21, 138, III, 4 (*B. megaterium*), 4 (*B. sphaericus*), AR13, BPP-IO, BS32, BS107, BI, B2, GA-I, GP-IO, GV-3, GV-5, g8, MP20, MP27, MP49, Nf, PP5, PP6, SF5, TgI8, TP-1, Versailles, (φI5, φ29, 1-97, 837/IV, mi-*Bacillus* (1), BatIO, BSLIO, BSLI I, BS6, BSI I, BS16, BS23, BSIOI, BS102, gl8, morl, PBLI, SN45, thu2, thu3, TmI, Tm2, TP-20, TP21, TP52, type F, type G, type IV, HN-BacMus (3), BLE, (syn=θc), BS2, BS4, BS5, BS7, BIO, B12, BS20, BS21, F, MJ-4, PBA12, AP50, AP50-04, AP50-11, AP50-23, AP50-26, AP50-27 and Bam35. The following *Bacillus*-specific phages are defective: DLP10716, DLP-11946, DPB5, DPB12, DPB21, DPB22, DPB23, GA-2, M, No. IM, PBLB, PBSH, PBSV, PBSW, PBSX, PBSY, PBSZ, phi, SPa, type 1 and μ.

Bacteria of the genus *Bacteroides* can be infected by the following phages: crAss-phage, ad I2, Baf-44, Baf-48E, Baf-64, Bf-I, Bf-52, B40-8, FI, β1, φAI, φBrOI, φBrO2, 11, 67.1, 67.3, 68.1, mt-*Bacteroides* (3), Bf42, Bf71, HN-*Bdellovibrio* (1) and BF-41.

Bacteria of the genus *Bordetella* can be infected by the following phages: 134 and NN-*Bordetella* (3).

Bacteria of the genus *Borrelia* can be infected by the following phages: NN-*Borrelia* (1) and NN-*Borrelia* (2).

Bacteria of the genus *Brucella* can be infected by the following phages: A422, Bk, (syn=Berkeley), BM29, FOi, (syn=FOI), (syn=FOI), D, FP2, (syn=FP2), (syn=FD2), Fz, (syn=Fz75/13), (syn=Firenze 75/13), (syn=Fi), Fi, (syn=FI), Fim, (syn=Flm), (syn=Fim), FiU, (syn=FIU), (syn=FiU), F2, (syn=F2), F3, (syn=F3), F4, (syn=F4), F5, (syn=F5), F6, F7, (syn=F7), F25, (syn=F25), (syn=£25), F25U, (syn=F25u), (syn=F25U), (syn=F25V), F44, (syn-F44), F45, (syn=F45), F48, (syn=F48), I, Im, M, MC/75, M51, (syn=M85), P, (syn=D), S708, R, Tb, (syn=TB), (syn=Tbilisi), W, (syn=Wb), (syn=Weybridge), X, 3, 6, 7, 10/1, (syn=10), (syn=F8), (syn=F8), 12 m, 24/11, (syn=24), (syn=F9), (syn=F9), 45/111, (syn=45), 75, 84, 212/XV, (syn=212), (syn=Fi0), (syn=FIO), 371/XXIX, (syn=371), (syn=Fn), (syn=FI I) and 513.

Bacteria of the genus *Burkholderia* can be infected by the following phages: CP75, NN-*Burkholderia* (1) and 42.

Bacteria of the genus *Campylobacter* can be infected by the following phages: C type, NTCC12669, NTCC12670, NTCC12671, NTCC12672, NTCC12673, NTCC12674, NTCC12675, NTCC12676, NTCC12677, NTCC12678, NTCC12679, NTCC12680, NTCC12681, NTCC12682, NTCC12683, NTCC12684, 32f, 111c, 191, NN-*Campylobacter* (2), Vfi-6, (syn=V19), VfV-3, V2, V3, V8, V16, (syn=Vfi-1), V19, V20 (V45), V45, (syn=V-45) and NN-*Campylobacter* (1).

Bacteria of the genus *Chlamydia* can be infected by the following phage: ChpI.

Bacteria of the genus *Clostridium* can be infected by the following phages: CAKI, CA5, Ca7, CEβ, (syn=1C), CEγ, Cldl, c-n71, c-203 Tox-, DEβ, (syn=ID), (syn=IDt0X+), HM3, KMI, KT, Ms, NAI, (syn=Naltox+), PA135Oe, Pfó, PL73, PL78, PL81, PI, P50, P5771, P19402, ICt0X+, 2CtOX\2D3 (syn=2Dt0X+), 3C, (syn=3 Ctox+), 4C, (syn=4Ct0X+), 56, III-I, NN-*Clostridium* (61), NBIt0X+, αI, CAI, HMT, HM2, PFI5 P-23, P-46, Q-05, Q-oe, Q-16, Q-21, Q-26, Q-40, Q-46, S111, SA02, WA01, WA03, Wm, W523, 80, C, CA2, CA3, CPTI, CPT4, cI, c4, c5, HM7, H11/A1, H18/Ax, FWS23, Hi58ZA1, K2ZA1, K21ZS23, ML, NA2tOX; Pf2, Pf3, Pf4, S9ZS3, S41ZA1, S44ZS23, α2, 41, 112ZS23, 214/S23, 233/Ai, 234/S23, 235/S23, II-I, II-2, II-3, NN-*Clostridium* (12), CAI, FI, K, S2, 1, 5 and NN-*Clostridium* (8).

Bacteria of the genus *Corynebacterium* can be infected by the following phages: CGKI (defective), A, A2, A3, AIOI, A128, A133, A137, A139, A155, A182, B, BF, B17, B18, B51, B271, B275, B276, B277, B279, B282, C, capi, CCI, CGI, CG2, CG33, CL31, Cog, (syn=CG5), D, E, F, H, H-I, hqi, hq2, 11ZH33, Ii/31, J, K, K, (syn=Ktox"), L, L, (syn=Ltox+), M, MC-I, MC-2, MC-3, MC-4, MLMa, N, O, ovi, ov2, ov3, P, P, R, RP6, RS29, S, T, U, UB1, ub2, UH1, UH3, uh3, uh5, uh6, β, (syn=βtox+), βhv64, βvir, γ, (syn=γtoχ-), γI9, δ, (syn=δ'ox+), p, (syn=ptoχ-), Φ9, φ984, ω, IA, 1/1180, 2, 2/1180, 5/1180, 5ad/9717, 7/4465, 8/4465, 8ad/10269, 10/9253, 13Z9253, 15/3148, 21/9253, 28, 29, 55, 2747, 2893, 4498 and 5848.

Bacteria of the genus *Enterococcus* are infected by the following phage: DF78, FI, F2, 1, 2, 4, 14, 41, 867, DI, SB24, 2BV, 182, 225, C2, C2F, E3, E62, DS96, H24, M35, P3, P9, SBIOI, S2, 2 BII, 5, 182a, 705, 873, 881, 940, 1051, 1057, 21096C, NN-*Enterococcus* (1), PEI, FI, F3, F4, VD13, 1, 200, 235 and 341.

Bacteria of the genus *Erysipelothrix* can be infected by the following phage: NN-Eiysipelothrix (1).

Bacteria of the genus *Escherichia* can be infected by the following phages: BW73, B278, D6, D108, E, EI, E24, E41, FI-2, FI-4, FI-5, HI8A, Ffl8B, i, MM, Mu, (syn=mu), (syn=MuI), (syn=Mu-I), (syn=MU-I), (syn=MuI), (syn=μ), 025, PhI-5, Pk, PSP3, PI, PID, P2, P4 (defective), SI, Wφ, φK13, φR73 (defective), φI, φ2, φ7, φ92, ψ (defective), 7 A, 8φ, 9φ, 15 (defective), 18, 28-1, 186, 299, HH-*Escherichia* (2), AB48, CM, C4, C16, DD-VI, (syn=Dd-Vi), (syn=DDVI), (syn=DDVi), E4, E7, E28, FII, FI3, H, HI, H3, H8, K3, M, N, ND-2, ND-3, ND4, ND-5, ND6, ND-7, Ox-I (syn=OXI), (syn=HF), Ox-2 (syn=0x2), (syn=0X2), Ox-3, Ox-4, Ox-5, (syn=0X5), Ox-6, (syn=66F), (syn=φ66t), (syn=φ66t-)5 0111, PhI-I, RB42, RB43, RB49, RB69, S, SaI-I, SaI-2, SaI-3, SaI-4, SaI-5, SaI-6, TC23, TC45, TuII*-6, (syn=TuII*), TuIP-24, TuII*46, TuIP-60, T2, (syn=ganuTia), (syn=γ), (syn=PC), (syn=P.C.), (syn=T-2), (syn=T2), (syn=P4), T4, (syn=T-4), (syn=T4), T6, T35, αI, 1, IA, 3, (syn=Ac3), 3A, 3T+, (syn=3), (syn=MI), 5φ, (syn=φ5), 9266Q, CFO103, HK620, J, K, KIF, m59, no. A, no. E, no. 3, no. 9, N4, sd, (syn=Sd), (syn=SD), (syn=Sa)3 (syn=sd), (syn=SD), (syn=CD), T3, (syn=T-3), (syn=T3), T7, (syn=T-7), (syn=T7), WPK, W31, ΔH, φC3888, φK3, φK7, φK12, φV-1, Φ04-CF, Φ05, Φ06, Φ07, φI, φI.2, φ20, φ95, φ263, φIO92, φI, φII, (syn=φW), Ω8, 1, 3, 7, 8, 26, 27, 28-2, 29, 30, 31, 32, 38, 39, 42, 933W, NN-*Escherichia* (1), Esc-7-11, AC30, CVX-5, CI, DDUP, ECI, EC2, E21, E29, FI, F26S, F27S, Hi, HK022, HK97, (syn=ΦHK97), HK139, HK253, HK256, K7, ND-I, no.D, PA-2, q, S2, TI, (syn=α), (syn=P28), (syn=T-I), (syn=Tx), T3C, T5, (syn=T-5), (syn=T5), UC-I, w, β4, γ2, λ (syn=lambda), (syn=Φλ), ΦD326, φγ, Φ06, Φ7, Φ10, φ80, χ, (syn=χi), (syn=φχ), (syn=φχi), 2, 4, 4A, 6, 8A, 102, 150, 168, 174, 3000, AC6, AC7, AC28, AC43, AC50, AC57, AC81, AC95, HK243, KIO, ZG/3A, 5, 5A, 21EL, H19-J, 933H, O157 typing phages 1 to 16, JES-2013, 121Q, 172-1, 1720a-02, ADB-2, AKFV33, av-05, bV_EcoS_AHP42, bV_EcoS_AHP24, bC_EcoS_AHS24, bV_EcoS_AKS96, CBA120.

Bacteria of the genus *Fusobacterium* are infected by the following phage: NN-*Fusobacterium* (2), fv83-554/3, fv88-531/2, 227, fv2377, fv2527 and fv8501.

Bacteria of the genus *Haemophilus* are infected by the following phage: HPI, S2 and N3.

Bacteria of the genus *Helicobacter* are infected by the following phage: HPI and ^^-*Helicobacter* (1).

Bacteria of the genus *Klebsiella* are infected by the following phage: AIO-2, KI4B, KI6B, KI9, (syn=K19), KI14, KI15, KI21, KI28, KI29, KI32, KI33, KI35, KI106B, KI171B, KI181B, KI832B, AIO-I, AO-I, AO-2, AO-3, FC3-10, K, KI1, (syn=KII), KI2, (syn=K12), KI3, (syn=K13), (syn=KI 70/11), KI4, (syn=K14), KI5, (syn=K15), KI6, (syn=K16), KI7, (syn=K17), KI8, (syn=K18), KI9, (syn=K19), KI27, (syn=K127), KI31, (syn=K131), KI35, KI171B, II, VI, IX, CI-I, KI4B, KI8, KI11, KI12, KI13, KI16, KI17, KI18, KI20, KI22, KI23, KI24, KI26, KI30, KI34, KI106B, KIi65B, KI328B, KLXI, K328, P5046, 11, 380, III, IV, VII, VIII, FC3-11, KI2B, (syn=K12B), KI25, (syn=K125), KI42B, (syn=K142), (syn=K142B), KI181B, (syn=KII 81), (syn=K1181B), KI765/!, (syn=K1765/1), KI842B, (syn=K1832B), KI937B, (syn=K1937B), LI, φ28, 7, 231, 483, 490, 632 and 864/100.

Bacteria of the genus *Leptospira* are infected by the following phage: LEI, LE3, LE4 and ~NN-*Leptospira* (1).

Bacteria of the genus *Listeria* are infected by the following phage: A511, 01761, 4211, 4286, (syn=BO54), A005, A006, A020, A500, A502, A511, AI 18, A620, A640, B012, B021, B024, B025, B035, B051, B053, B054, B055, B056, BIOI, BI IO, B545, B604, B653, C707, D441, HSO47, HIOG, H8/73, H19, H21, H43, H46, H107, H108, HI IO, H163/84, H312, H340, H387, H391/73, H684/74, H924A, PSA, U153, φMLUP5, (syn=P35), 00241, 00611, 02971A, 02971C, 5/476, 5/911, 5/939, 5/11302, 5/11605, 5/11704, 184, 575, 633, 699/694, 744, 900, 1090, 1317, 1444, 1652, 1806, 1807, 1921/959, 1921/11367, 1921/11500, 1921/11566, 1921/12460, 1921/12582, 1967, 2389, 2425, 2671, 2685, 3274, 3550, 3551, 3552, 4276, 4277, 4292, 4477, 5337, 5348/11363, 5348/11646, 5348/12430, 5348/12434, 10072, 11355C, 11711A, 12029, 12981, 13441, 90666, 90816, 93253, 907515, 910716 and NN-*Listeria* (15).

Bacteria of the genus *Morganella* are infected by the following phage: 47.

Bacteria of the genus *Mycobacterium* are infected by the following phage: 13, AGI, ALi, ATCC 11759, A2, B.C3, BG2, BKI, BK5, butyricum, B-I, B5, B7, B30, B35, Clark, CI, C2, DNAIII, DSP1, D4, D29, GS4E, (syn=GS4E), GS7, (syn=GS-7), (syn=GS7), IPa, Iacticola, Legendre, Leo, L5, (syn=ΦL-5), MC-I, MC-3, MC-4, minetti, MTPHI I, Mx4, MyF3P/59a, phlei, (syn=phlei 1), phlei 4, Polonus II, rabinovitschi, smegmatis, TM4, TM9, TMIO, TM20, Y7, YIO, φ630, IB, IF, IH, 1/1, 67, 106, 1430, BI, (syn=BoI), B24, D, D29, F-K, F-S, HP, Polonus I, Roy, RI, (syn=RI-Myb), (syn=Ri), 11, 31, 40, 50, 103a, 103b, 128, 3111-D, 3215-D and NN-*Mycobacterium* (1).

Bacteria of the genus *Neisseria* are infected by the following phage: Group I, group II and NPI.

Bacteria of the genus *Nocardia* are infected by the following phage: MNP8, NJ-L, NS-8, N5 and TtiN-*Nocardia*.

Bacteria of the genus *Proteus* are infected by the following phage: Pm5, 13 vir, 2/44, 4/545, 6/1004, 13/807, 20/826, 57, 67b, 78, 107/69, 121, 9/0, 22/608, 30/680, PmI, Pm3, Pm4, Pm6, Pm7, Pm9, PmIO, PmI I, Pv2, πI, φm, 7/549, 9B/2, 10A/31, 12/55, 14, 15, 16/789, 17/971, 19A/653, 23/532, 25/909, 26/219, 27/953, 32A/909, 33/971, 34/13, 65, 5006M, 7480b, VI, 13/3a, Clichy 12, π2600, φχ7, 1/1004, 5/742, 9, 12, 14, 22, 24/860, 2600/D52, Pm8 and 24/2514.

Bacteria of the genus *Providencia* are infected by the following phage: PL25, PL26, PL37, 9211/9295, 9213/921 Ib, 9248, 7/R49, 7476/322, 7478/325, 7479, 7480, 9000/9402 and 9213/921 Ia.

Bacteria of the genus *Pseudomonas* are infected by the following phage: PfI, (syn=Pf-I), Pf2, Pf3, PP7, PRRI, 7s, im-*Pseudomonas* (1), AI-I, AI-2, B 17, B89, CB3, CoI 2, CoI 11, CoI 18, CoI 21, C154, C163, C167, C2121, E79, F8, ga, gb, H22, K1, M4, N2, Nu, PB-I, (syn=PBI), pfI6, PMN17, PPI, PP8, PsaI, PsPI, PsP2, PsP3, PsP4, PsP5, PS3, PS17, PTB80, PX4, PX7, PYOI, PYO2, PYO5, PYO6, PYO9, PYOIO, PYO13, PYO14, PYO16, PYO18, PYO19, PYO20, PYO29, PYO32, PYO33, PYO35, PYO36, PYO37, PYO38, PYO39, PYO41, PYO42, PYO45, PYO47, PYO48, PYO64, PYO69, PYO103, PIK, SLPI, SL2, S2, UNL-I, wy, Yai, Ya4, Yan, φBE, φCTX, φC17, φKZ, (syn=ΦKZ), φ-LT, Φmu78, φNZ, φPLS-1, φST-1, φW-14, φ-2, 1/72, 2/79, 3, 3/DO, 4/237, 5/406, 6C, 6/6660, 7, 7v, 7/184, 8/280, 9/95, 10/502, 11/DE, 12/100, 12S, 16, 21, 24, 25F, 27, 31, 44, 68, 71, 95, 109, 188, 337, 352, 1214, HN-*Pseudomonas* (23), A856, B26, CI-I, CI-2, C5, D, gh-1, FI 16, HF, H90, K5, K6, KI 04, K109, K166, K267, N4, N5, O6N-25P, PE69, Pf, PPN25, PPN35, PPN89, PPN91, PP2, PP3, PP4, PP6, PP7, PP8, PP56, PP87, PPI 14, PP206, PP207, PP306, PP651, Psp231a, Pssy401, Pssy9220, psi, PTB2, PTB20, PTB42, PXI, PX3, PXIO, PX12, PX14, PYO70, PYO71, R, SH6, SH133, tf, Ya5, Ya7, φBS, ΦKf77, φ-MC, ΦmnF82, φPLS27, φPLS743, φS-1, 1, 2, 2, 3, 4, 5, 6, 7, 7, 8, 9, 10, 11, 12, 12B, 13, 14, φ15, 14, 15, 16, 17, 18, 19, 20, 20, 21, 21, 22, 23, 23, 24, 25, 31, 53, 73, 119x, 145, 147, 170, 267, 284, 308, 525, NN-*Pseudomonas* (5), af, A7, B3, B33, B39, BI-I, C22, D3, D37, D40, D62, D3112, F7, FIO, g, gd, ge, gξ HwI2, Jb 19, KFI, L°, OXN-32P, O6N-52P, PCH-I, PC13-1, PC35-1, PH2, PH51, PH93, PH132, PMW, PM13, PM57, PM61, PM62, PM63, PM69, PM105, PMI 13, PM681, PM682, PO4, PPI, PP4, PP5, PP64, PP65, PP66, PP71, PP86, PP88, PP92, PP401, PP711, PP891, Pssy41, Pssy42, Pssy403, Pssy404, Pssy420, Pssy923, PS4, PS-IO, Pz, SDI, SLI, SL3, SL5, SM, φC5, φCI I, φCI I-1, φC13, φC15, φMO, φX, φO4, φI I, φ240, 2, 2F, 5, 7 m, 11, 13, 13/441, 14, 20, 24, 40, 45, 49, 61, 73, 148, 160, 198, 218, 222, 236, 242, 246, 249, 258, 269, 295, 297, 309, 318, 342, 350, 351, 357-1, 400-1, HN-*Pseudomonas* (6), GIOI, M6, M6a, LI, PB2, PssyI5, Pssy4210, Pssy4220, PYO12, PYO34, PYO49, PYO50, PYO51, PYO52, PYO53, PYO57, PYO59, PYO200, PX2, PX5, SL4, φO3, φO6 and 1214.

Bacteria of the genus *Rickettsia* are infected by the following phage: NN-*Rickettsia*.

Bacteria of the genus *Salmonella* are infected by the following phage: b, Beccles, CT, d, Dundee, f, FeIs 2, GI, GUI, GVI, GVIII, k, K, i, j, L, 01, (syn=0-1), (syn=O1), (syn=O-I), (syn=7), 02, 03, P3, P9a, PIO, Sab3, Sab5, SanIS, SanI7, SI, Taunton, ViI, (syn=ViI), 9, imSalmonella (1), N-I, N-5, N-IO, N-17, N-22, 11, 12, 16-19, 20.2, 36, 449C/C178, 966A/C259, a, B.A.O.R., e, G4, GUI, L, LP7, M, MG40, N-18, PSA68, P4, P9c, P22, (syn=P22), (syn=PLT22), (syn=PLT22), P22aI, P22-4, P22-7, P22-11, SNT-I, SNT-2, SP6, ViIIi, ViIV, ViV, ViVI, ViVII, Worksop, Sj5, ε34, 1, 37, 1(40), (syn=φI[40]), 1, 422, 2, 2.5, 3b, 4, 5, 6, 14(18), 8, 14(6,7), 10, 27, 28B, 30, 31, 32, 33, 34, 36, 37, 39, 1412, SNT-3, 7-11, 40.3, c, C236, C557, C625, C966N, g, GV, G5, GI 73, h, IRA, Jersey, MB78, P22-1, P22-3, P22-12, SabI, Sab2, Sab2, Sab4, SanI, San2, San3, San4, San6, San7, San8, San9, San13, SanI4, San16, San18, San19, San20, San21, San22, San23, San24, San25, San26, SasLI, SasL2, SasL3, SasL4, SasL5, SIBL, SII, ViII, φI, 1, 2, 3a, 3aI, 1010, Ym-*Salmonella* (1), N-4, SasL6 and 27.

Bacteria of the genus *Serratia* are infected by the following phage: A2P, PS20, SMB3, SMP, SMP5, SM2, V40, V56, ic, ΦCP-3, ΦCP-6, 3M, 10/Ia, 20A, 34CC, 34H, 38T, 345G, 345P, 501B, SMB2, SMP2, BC, BT, CW2, CW3, CW4, CW5, Lt232, L2232, L34, L.228, SLP, SMPA, V.43, σ, φCWI, ΦCP-1, ΦCP6-2, ΦCP6-5, 3T, 5, 8, 9F, 10/1, 2OE, 32/6, 34B, 34CT, 34P, 37, 41, 56, 56D, 56P, 6OP, 61/6, 74/6, 76/4, 101/8900, 226, 227, 228, 229F, 286, 289, 290F, 512, 764a, 2847/10, 2847/1Oa, L.359 and SMBI.

Bacteria of the genus *Shigella* are infected by the following phage: Fsa, (syn=a), FSD2d, (syn=D2d), (syn=W2d), FSD2E, (syn=W2e), fv, F6, f7.8, H-Sh, PE5, P90, SfII, Sh, SHm, SHrv, (syn=HIV), SHvi, (syn=HVI), SHVvm, (syn=HVIII), SKγ66, (syn=gamma 66), (syn=γββ), (syn=γ66b), SKm, (syn=SIIIb)5 (syn=UI), SKw, (syn=Siva), (syn=IV), SIC™, (syn=SIVA), (syn=IVA), SKvi, (syn=KVI), (syn=Svi), (syn=VI), SKvm, (syn=Svm), (syn=VIII), SKVIIIA, (syn=SvmA), (syn=VIIIA), STvi, STK, STx1, STxn, S66, W2, (syn=D2c), (syn=D20), φI, φIVb 3-SO-R, 8368-SO-R, F7, (syn=FS7), (syn=K29), FIO, (syn=FSIO), (syn=K31), I1, (syn=alfa), (syn=FSa), (syn=KI 8), (syn=α), I2, (syn=a), (syn=K19), SG33, (syn=G35), (syn=SO-35/G), SG35, (syn=SO-55/G), SG3201, (syn=SO-3201/G), SHn, (syn=HII), SHv, (syn=SHV), SHx, SHX, SKn, (syn=K2), (syn=KII), (syn=Sn), (syn=SsII), (syn=II), SKrv, (syn=Sm), (syn=SsIV), (syn=IV), SK1Va, (syn=Swab), (syn=SsIVa), (syn=IVa), SKV, (syn=K4), (syn=KV), (syn=SV), (syn=SsV), (syn=V), SKx, (syn=K9), (syn=KX), (syn=SX), (syn=SsX), (syn=X), STV, (syn=T35), (syn=35-50-R), STvm, (syn=T8345), (syn=8345-SO—S-R), W1, (syn=D8), (syn=FSD8), W2a, (syn=D2A), (syn=FS2a), DD-2, Sf6, FSi, (syn=FI), SF6, (syn=F6), SG42, (syn=SO-42/G), SG3203, (syn=SO-3203/G), SKF12, (syn=SsF12), (syn=F12), (syn=F12), STn, (syn=1881-SO-R), γ66, (syn=gamma 66a), (syn=Ssγ66), φ2, BII, DDVII, (syn=DD7), FSD2b, (syn=W2B), FS2, (syn=F2), (syn=F2), FS4, (syn=F4), (syn=F4), FS5, (syn=F5), (syn=F5), FS9, (syn=F9), (syn=F9), FI I, P2-S0-S, SG36, (syn=SO-36/G), (syn=G36), SG3204, (syn=SO-3204/G), SG3244, (syn=SO-3244/G), SHi, (syn=HI), SHvπ, (syn=HVII), SHK, (syn=HIX), SHx1, SHxπ, (syn=HXn), SKI, KI, (syn=S1), (syn=SsI), SKVII, (syn=KVII), (syn=Svπ), (syn=SsVII), SKIX, (syn=KIX), (syn=S1x), (syn=SsIX), SKXII, (syn=KXII), (syn=Sxn), (syn=SsXII), STi, STffI, STrv, STVi, STvπ, S70, S206, U2-SO-S, 3210-SO-S, 3859-SO-S, 4020-SO-S, φ3, φ5, φ7, φ8, φ9, φIO, φI I, φI3, φI4, φI8, SHm, (syn=Hπi), SHχi, (syn=HXt) and SKxI, (syn=KXI), (syn=Sχi), (syn=SsXI), (syn=XI).

Bacteria of the genus *Staphylococcus* are infected by the following phage: A, EW, K, Ph5, Ph9, PhIO, PhI3, PI, P2, P3, P4, P8, P9, PIO, RG, SB-i, (syn=Sb-I), S3K, Twort, ΦSK311, φ812, 06, 40, 58, 119, 130, 131, 200, 1623, STCI, (syn=stcI), STC2, (syn=stc2), 44 AHJD, 68, ACI, AC2, A6"C", A9"C", b581, CA-I, CA-2, CA-3, CA-4, CA-5, DI I, L39×35, L54a, M42, NI, N2, N3, N4, N5, N7, N8, NIO, Ni I, N12, N13, N14, N16, Ph6, PhI2, PhI4, UC-18, U4, U15, SI, S2, S3, S4, S5, X2, Z1, φB5-2, φD, ω, 11, (syn=φI I), (syn=P11-M15), 15, 28, 28A, 29, 31, 31B, 37, 42D, (syn=P42D), 44A, 48, 51, 52, 52A, (syn=P52A), 52B, 53, 55, 69, 71, (syn=P71), 71A, 72, 75, 76, 77, 79, 80, 80α, 82, 82A, 83 A, 84, 85, 86, 88, 88A, 89, 90, 92, 95, 96, 102, 107, 108, 111, 129-26, 130, 130A, 155, 157, 157A, 165, 187, 275, 275A, 275B, 356, 456, 459, 471, 471A, 489, 581, 676, 898, 1139, 1154A, 1259, 1314, 1380, 1405, 1563, 2148, 2638A, 2638B, 2638C, 2731, 2792A, 2792B, 2818, 2835, 2848A, 3619, 5841, 12100, AC3, A8, AIO, A13, b594n, D, HK2, N9, N15, P52, P87, SI, S6, Z4, φRE, 3A, 3B, 3C, 6, 7, 16, 21, 42B, 42C, 42E, 44, 47, 47A5 47C, 51, 54, 54×1, 70, 73, 75, 78, 81, 82, 88, 93, 94, 101, 105, 110, 115, 129/16, 174, 594n, 1363/14, 2460 and mS-*Staphylococcus* (1).

Bacteria of the genus *Streptococcus* are infected by the following phage: EJ-I, NN-Streptococais (1), a, CI, FL0 Ths, H39, Cp-I, Cp-5, Cp-7, Cp-9, Cp-IO, AT298, A5, aIO/JI, aIO/J2, aIO/J5, aIO/J9, A25, BTI I, b6, CAI, c20-1, c20-2, DP-I, Dp-4, DTI, ET42, eIO, FA101, FETHs, F$_K$, FKKIOI, FKLIO, FKP74, FKH, FLOTHs, FyIOI, fI, F10, F20140/76, g, GT-234, HB3, (syn=HB-3), HB-623, HB-746, M102, O1205, φO1205, PST, PO, PI, P2, P3, P5, P6, P8, P9, P9, P12, P13, P14, P49, P50, P51, P52, P53, P54, P55, P56, P57, P58, P59, P64, P67, P69, P71, P73, P75, P76, P77, P82, P83, P88, sc, sch, sf, SfII 1, (syn=SFiI I), (syn=φSFII), (syn=ΦSfiI I), (syn=φSfiI 1), sfiI9, (syn=SFiI9), (syn=φSfiI9), Sfi21, (syn=SFi21), (syn=φSFi21), (syn=φSfi21), ST0, STX, st2, ST2, ST4, S3, (syn=φS3), s265, Φ17, φ42, Φ57, φ80, φ81, φ82, φ83, φ84, φ85, φ86, φ87, φ88, φ89, φ90, φ91, φ92, φ93, φ94, φ95, φ96, φ97, φ98, φ99, φIOO, φIOI, φIO2, φ227, Φ7201, ωI, ω2, ω3, ω4, ω5, ω6, ω8, ωIO, 1, 6, 9, 1OF, 12/12, 14, 17SR, 19S, 24, 50/33, 50/34, 55/14, 55/15, 70/35, 70/36, 71/ST15, 71/45, 71/46, 74F, 79/37, 79/38, 80/J4, 80/J9, 80/ST16, 80/15, 80/47, 80/48, 101, 103/39, 103/40, 121/41, 121/42, 123/43, 123/44, 124/44, 337/ST17 and mStreptococcus (34).

Bacteria of the genus *Treponema* are infected by the following phage: NN-*Treponema* (1).

Bacteria of the genus *Vibrio* are infected by the following phage: CTXΦ, fs, (syn=si), fs2, Ivpf5, VfI2, Vf33, VPIΦ, VSK, v6, 493, CP-TI, ET25, kappa, K139, Labol, )XN-69P, OXN-86, O6N-21P, PB-I, P147, rp-1, SE3, VA-I, (syn=VcA-I), VcA-2, VPI, VP2, VP4, VP7, VP8, VP9, VPIO, VP17, VP18, VP19, X29, (syn=29 d'Herelle), t, ΦHAWI-1, ΦHAWI-2, ΦHAWI-3, ΦHAWI-4, ΦHAWI-5, ΦHAWI-6, ΦHAWI-7, ΦHAWI-8, ΦHAWI-9, ΦHAWI-10, ΦHC1-1, ΦHC1-2, ΦHC1-3, ΦHC1-4, ΦHC2-1, ΦHC2-2, ΦHC2-3, ΦHC2-4, ΦHC3-1, ΦHC3-2, ΦHC3-3, ΦHD1S-1, ΦHD1S-2, ΦHD2S-1, ΦHD2S-2, ΦHD2S-3, ΦHD2S-4, ΦHD2S-5, ΦHDO-1, ΦHDO-2, ΦHDO-3, ΦHDO-4, ΦHDO-5, ΦHDO-6, ΦKL-33, ΦKL-34, ΦKL-35, ΦKL-36, ΦKWH-2, ΦKWH-3, ΦKWH-4, ΦMARQ-1, ΦMARQ-2, ΦMARQ-3, ΦMOAT-1, ΦO139, ΦPEL1A-1, ΦPEL1A-2, ΦPEL8A-1, ΦPEL8A-2, ΦPEL8A-3, ΦPEL8C-1, ΦPEL8C-2, ΦPEL13A-1, ΦPEL13B-1, ΦPEL13B-2, ΦPEL13B-3, ΦPEL13B-4, ΦPEL13B-5, ΦPEL13B-6, ΦPEL13B-7, ΦPEL13B-8, ΦPEL13B-9, ΦPEL13B-10, φVP143, φVP253, Φ16, φI38, 1-II, 5, 13, 14, 16, 24, 32, 493, 6214, 7050, 7227, II, (syn=group II), (syn=φ2), V, VIII, ~m-*Vibrio* (13), KVP20, KVP40, nt-1, O6N-22P, P68, eI, e2, e3, e4, e5, FK, G, I, K, nt-6, NI, N2, N3, N4, N5, O6N-34P, OXN-72P, OXN-85P, OXN-100P, P, Ph-I, PL163/10, Q, S, T, φ92, 1-9, 37, 51, 57, 70A-8, 72A-4, 72A-10, 110A-4, 333, 4996, I (syn=group I), III (syn=group III), VI, (syn=A-Saratov), VII, IX, X, HN-*Vibrio* (6), pAI, 7, 7-8, 70A-2, 71A-6, 72A-5, 72A-8, 108A-10, 109A-6, 109A-8, I IOA-1, 110A-5, 110A-7, hv-1, OXN-52P, P13, P38, P53, P65, P108, PiII, TPI3 VP3, VP6, VP12, VPI3, 70A-3, 70A-4, 70A-10, 72A-1, 108A-3, 109-B1, 110A-2, 149, (syn=T149), IV, (syn=group IV), NN-*Vibrio* (22), VP5, VPII, VP15, VP16, α1, α2, α3a, α3b, 353B and HN-*Vibrio* (7).

Bacteria of the genus *Yersinia* are infected by the following phage: H, H-I, H-2, H-3, H-4, Lucas 110, Lucas 303, Lucas 404, YerA3, YerA7, YerA20, YerA41, 3/M64-76, 5/G394-76, 6/C753-76, 8/C239-76, 9/F18167, 1701, 1710, PST, 1/F2852-76, D'Herelle, EV, H, Kotljarova, PTB, R, Y, YerA41, φYerO3-12, 3, 4/C1324-76, 7/F783-76, 903, 1/M6176 and Yer2AT.

In a particular embodiment, the first type of bacteriophage is selected from the group consisting of the bacteriophages listed above, and the second type of bacteriophage is selected from the group consisting of the bacteriophages listed above, said second type of bacteriophage being a type of bacteriophage different from the first type of bacteriophage.

In a particular embodiment, the first and/or the second type of bacteriophage is selected in the group consisting of Salmonella virus SKML39, Shigella virus AG3, Dickeya virus Limestone, Dickeya virus RC2014, Escherichia virus CBA120, Escherichia virus PhaxI, Salmonella virus 38, Salmonella virus Det7, Salmonella virus GG32, Salmonella virus PM10, Salmonella virus SFP10, Salmonella virus SH19, Salmonella virus SJ3, Escherichia virus ECML4, Salmonella virus Marshall, Salmonella virus Maynard, Salmonella virus SJ2, Salmonella virus STML131, Salmonella virus ViI, Erwinia virus Ea2809, Klebsiella virus 0507KN21, Serratia virus IME250, Serratia virus MAM1, Campylobacter virus CP21, Campylobacter virus CP220, Campylobacter virus CPt10, Campylobacter virus IBB35, Campylobacter virus CP81, Campylobacter virus CP30A, Campylobacter virus CPX, Campylobacter virus NCTC12673, Erwinia virus Ea214, Erwinia virus M7, Escherichia virus AYO145A, Escherichia virus EC6, Escherichia virus HY02, Escherichia virus JH2, Escherichia virus TP1, Escherichia virus VpaE1, Escherichia virus wV8, Salmonella virus FelixO1, Salmonella virus HB2014, Salmonella virus Mushroom, Salmonella virus UAB87, Citrobacter virus Moogle, Citrobacter virus Mordin, Escherichia virus SUSP1, Escherichia virus SUSP2, Aeromonas virus phiO18P, Haemophilus virus HP1, Haemophilus virus HP2, Pasteurella virus F108, Vibrio virus K139, Vibrio virus Kappa, Burkholderia virus phi52237, Burkholderia virus phiE122, Burkholderia virus phiE202, Escherichia virus 186, Escherichia virus P4, Escherichia virus P2, Escherichia virus Wphi, Mannheimia virus PHL101, Pseudomonas virus phiCTX, Ralstonia virus RSA1, Salmonella virus FeIs2, Salmonella virus PsP3, Salmonella virus SopEphi, Yersinia virus L413C, Staphylococcus virus G1, Staphylococcus virus G15, Staphylococcus virus JD7, Staphylococcus virus K, Staphylococcus virus MCE2014, Staphylococcus virus P108, Staphylococcus virus Rodi, Staphylococcus virus S253, Staphylococcus virus S25-4, Staphylococcus virus SA12, Listeria virus A511, Listeria virus P100, Staphylococcus virus Remus, Staphylococcus virus SA11, Staphylococcus virus Stau2, Bacillus virus Camphawk, Bacillus virus SPO1, Bacillus virus BCP78, Bacillus virus TsarBomba, Staphylococcus virus Twort, Enterococcus virus phiEC24C, Lactobacillus virus Lb338-1, Lactobacillus virus LP65, Enterobacter virus PG7, Escherichia virus CC31, Klebsiella virus JD18, Klebsiella virus PKO111, Escherichia virus Bp7, Escherichia virus IME08, Escherichia virus JS10, Escherichia virus JS98, Escherichia virus QL01, Escherichia virus VR5, Enterobacter virus Eap3, Klebsiella virus KP15, Klebsiella virus KP27, Klebsiella virus Matisse, Klebsiella virus Miro, Citrobacter virus Merlin, Citrobacter virus Moon, Escherichia virus JSE, Escherichia virus phi1, Escherichia virus RB49, Escherichia virus HX01, Escherichia virus JS09, Escherichia virus RB69, Shigella virus UTAM, Salmonella virus S16, Salmonella virus STML198, Vibrio virus KVP40, Vibrio virus nt1, Vibrio virus ValKK3, Escherichia virus VR7, Escherichia virus VR20, Escherichia virus VR25, Escherichia virus VR26, Shigella virus SP18, Escherichia virus AR1, Escherichia virus C40, Escherichia virus E112, Escherichia virus ECML134, Escherichia virus HY01, Escherichia virus Ime09, Escherichia virus RB3, Escherichia virus RB14, Escherichia virus T4, Shigella virus Pss1, Shigella virus ShfI2, Yersinia virus D1, Yersinia virus PST, Acinetobacter virus 133, Aeromonas virus 65, Aeromonas virus Aeh1, Escherichia virus RB16, Escherichia virus RB32, Escherichia virus RB43, Pseudomonas virus 42, Cronobacter virus CR3, Cronobacter virus CR8, Cronobacter virus CR9, Cronobacter virus PBES02, Pectobacterium virus phiTE, Cronobacter virus GAP31, Escherichia virus 4MG, Salmonella virus SE1, Salmonella virus SSE121, Escherichia virus FFH2, Escherichia virus FV3, Escherichia virus JES2013, Escherichia virus V5, Brevibacillus virus Abouo, Brevibacillus virus Davies, Bacillus virus Agate, Bacillus virus Bobb, Bacillus virus Bp8pC, Erwinia virus Deimos, Erwinia virus Ea35-70, Erwinia virus RAY, Erwinia virus Simmy50, Erwinia virus SpecialG, Acinetobacter virus AB1, Acinetobacter virus AB2, Acinetobacter virus AbC62, Acinetobacter virus AP22, Arthrobacter virus ArV1, Arthrobacter virus Trina, Bacillus virus AvesoBmore, Bacillus virus B4, Bacillus virus Bigbertha, Bacillus virus Riley, Bacillus virus Spock, Bacillus virus Troll, Bacillus virus Bastille, Bacillus virus CAM003, Bacillus virus Bc431, Bacillus virus Bcp1, Bacillus virus BCP82, Bacillus virus BM15, Bacillus virus Deepblue, Bacillus virus JBP901, Burkholderia virus Bcep1, Burkholderia virus Bcep43, Burkholderia virus Bcep781, Burkholderia virus BcepNY3, Xanthomonas virus OP2, Burkholderia virus BcepMu, Burkholderia virus phiE255, Aeromonas virus 44RR2, Mycobacterium virus Alice, Mycobacterium virus Bxz1, Mycobacterium virus Dandelion, Mycobacterium virus HyRo, Mycobacterium virus 13, Mycobacterium virus Nappy, Mycobacterium virus Sebata, Clostridium virus phiC2, Clostridium virus phiCD27, Clostridium virus phiCD119, Bacillus virus CP51, Bacillus virus JL, Bacillus virus Shanette, Escherichia virus CVM10, Escherichia virus ep3, Erwinia virus Asesino, Erwinia virus EaH2, Pseudomonas virus EL, Halomonas virus HAP1, Vibrio virus VP882, Brevibacillus virus Jimmer, Brevibacillus virus Osiris, Pseudomonas virus Ab03, Pseudomonas virus KPP10, Pseudomonas virus PAKP3, Sinorhizobium virus M7, Sinorhizobium virus M12, Sinorhizobium virus N3, Erwinia virus Machina, Arthrobacter virus Brent, Arthrobacter virus Jawnski, Arthrobacter virus Martha, Arthrobacter virus Sonny, Edwardsiella virus MSW3, Edwardsiella virus PEi21, Escherichia virus Mu, Shigella virus SfMu, Halobacterium virus phiH, Bacillus virus Grass, Bacillus virus NIT1, Bacillus virus SPG24, Aeromonas virus 43, Escherichia virus P1, Pseudomonas virus CAb1, Pseudomonas virus CAb02, Pseudomonas virus JG004, Pseudomonas virus PAKP1, Pseudomonas virus PAKP4, Pseudomonas virus PaP1, Burkholderia virus BcepF1, Pseudomonas virus 141, Pseudomonas virus Ab28, Pseudomonas virus DL60, Pseudomonas virus DL68, Pseudomonas virus F8, Pseudomonas virus JG024, Pseudomonas virus KPP12, Pseudomonas virus LBL3, Pseudomonas virus LMA2, Pseudomonas virus PB1, Pseudomonas virus SN, Pseudomonas virus PA7, Pseudomonas virus phiKZ, Rhizobium virus RHEph4, Ralstonia virus RSF1, Ralstonia virus RSL2, Ralstonia virus RSL1, Aeromonas virus 25, Aeromonas virus 31, Aeromonas virus Aes12, Aeromonas virus Aes508, Aeromonas virus AS4, Stenotrophomonas virus IME13, Staphylococcus virus IPLAC1C, Staphylococcus virus SEP1, Salmonella virus SPN3US, Bacillus virus 1, Geobacillus virus GBSV1, Yersinia virus R1RT, Yersinia virus TG1, Bacillus virus G, Bacillus virus PBS1, Microcystis virus Ma-LMM01, Vibrio virus MAR, Vibrio virus VHML, Vibrio virus VP585, Bacillus virus BPS13, Bacillus virus Hakuna, Bacillus virus Megatron, Bacillus virus WPh, Acinetobacter virus AB3, Acinetobacter virus Abp1, Acinetobacter virus Fri1, Acinetobacter virus IME200, Acinetobacter virus PD6A3, Acinetobacter virus PDAB9, Acinetobacter virus phiAB1, Escherichia virus K30, Klebsiella virus K5, Klebsiella virus K11, Klebsiella virus Kp1, Klebsiella virus KP32, Klebsiella virus KpV289, Klebsiella virus F19, Klebsiella virus K244, Klebsiella virus Kp2, Klebsiella virus KP34, Klebsiella virus KpV41, Klebsiella virus KpV71, Klebsiella virus KpV475, Klebsiella virus SU503, Klebsiella virus SU552A, Pantoea virus Limelight, Pantoea virus Limezero, Pseudomonas virus LKA1, Pseudomonas virus phiKMV, Xanthomonas virus f20, Xanthomonas virus f30, Xylella virus Prado, Erwinia virus Era103, Escherichia virus K5, Escherichia virus K1-5, Escherichia virus K1E, Salmonella virus SP6, Escherichia virus T7, Kluyvera virus Kvp1, Pseudomonas virus gh1, Prochlorococcus virus PSSP7, Synechococcus virus P60, Synechococcus virus Syn5, Streptococcus virus Cp1, Streptococcus virus Cp7, Staphylococcus virus 44 AHJD, Streptococcus virus C1, Bacillus virus B103, Bacillus virus GA1, Bacillus virus phi29, *Kurthia* virus 6, Actinomyces virus Av1, Mycoplasma virus P1, Escherichia virus 24B, Escherichia virus 933W, Escherichia virus Min27, Escherichia virus PA28, Escherichia virus Stx2 II, Shigella virus 7502 Stx, Shigella virus POCJ13, Escherichia virus 191, Escherichia virus PA2, Escherichia virus TL2011, Shigella virus VASD, Burkholderia virus Bcep22, Burkholderia virus BcepiI02, Burkholderia virus Bcepmigl, Burkholderia virus DC1, Bordetella virus BPP1, Burkholderia virus BcepC6B, Cellulophaga virus Cba41, *Cellulophaga* virus Cba172, *Dinoroseobacter* virus DFL12, Erwinia virus Ea9-2, Erwinia virus Frozen, Escherichia virus phiV10, Salmonella virus Epsilon15, Salmonella virus SPN1S, Pseudomonas virus F116, Pseudomonas virus H66, Escherichia virus APEC5, Escherichia virus APEC7, Escherichia virus Bp4, Escherichia virus EC1 UPM, Escherichia virus ECBP1, Escherichia virus G7C, Escherichia virus IME11, Shigella virus Sb1, Achromobacter virus Axp3, Achromobacter virus JWAlpha, Edwardsiella virus KF1, Pseudomonas virus KPP25, Pseudomonas virus R18, Pseudomonas virus Ab09, Pseudomonas virus LIT1, Pseudomonas virus PA26, Pseudomonas virus Ab22, Pseudomonas virus CHU, Pseudomonas virus LUZ24, Pseudomonas virus PAA2, Pseudomonas virus PaP3, Pseudomonas virus PaP4, Pseudomonas virus TL, Pseudomonas virus KPP21, Pseudomonas virus LUZ7, Escherichia virus N4, Salmonella virus 9NA, Salmonella virus SP069, Salmonella virus BTP1, Salmonella virus HK620, Salmonella virus P22, Salmonella virus ST64T, Shigella virus Sf6, Bacillus virus Page, Bacillus virus Palmer, Bacillus virus Pascal, Bacillus virus Pony, Bacillus virus Pookie, Escherichia virus 172-1, Escherichia virus ECB2, Escherichia virus NJ01, Escherichia virus phiEco32, Escherichia virus Septima11, Escherichia virus SU10, Brucella virus Pr, Brucella virus Tb, Escherichia virus Pollock, Salmonella virus FSL SP-058, Salmonella virus FSL SP-076, Helicobacter virus 1961P, Helicobacter virus KHP30, Helicobacter virus KHP40, Hamiltonella virus APSE1, Lactococcus virus KSY1, *Phormidium* virus WMP3, *Phormidium* virus WMP4, Pseudomonas virus 119X, Roseobacter virus SIO1, Vibrio virus VpV262, Vibrio virus VC8, Vibrio virus VP2, Vibrio virus VP5, Streptomyces virus Amela, Streptomyces virus phiCAM, Streptomyces virus Aaronocolus, Streptomyces virus Caliburn, Streptomyces virus Danzina, Streptomyces virus Hydra, Streptomyces virus Izzy, Streptomyces virus Lannister, Streptomyces virus Lika, Streptomyces virus Sujidade, Streptomyces virus Zemlya, Streptomyces virus ELB20, Streptomyces virus R4, Streptomyces virus phiHau3, Mycobacterium virus Acadian, Mycobacterium virus Baee, Mycobacterium virus Reprobate, Mycobacterium virus Adawi, Mycobacterium virus Bane1, Mycobacterium virus BrownCNA, Mycobacterium virus Chrisnmich, Mycobacterium virus Cooper, Mycobacterium virus JAMaL, Mycobacterium virus Nigel, Mycobacterium virus Stinger, Mycobacterium virus Vincenzo, Mycobacterium virus Zemanar, Mycobacterium virus Apizium, Mycobacterium virus Manad, Mycobacterium virus Oline, Mycobacterium virus Osmaximus, Mycobacterium virus Pg1, Mycobacterium virus Soto, Mycobacterium virus Suffolk, Mycobacterium virus Athena, Mycobacterium virus Bernardo, Mycobacterium virus Gadjet, Mycobacterium virus Pipefish, Mycobacterium virus Godines, Mycobacterium virus Rosebush, Mycobacterium virus Babsiella, Mycobacterium virus Brujita, Mycobacterium virus Che9c, Mycobacterium virus Sbash, Mycobacterium virus Hawkeye, Mycobacterium virus Plot, Salmonella virus AG11, Salmonella virus Ent1, Salmonella virus f18SE, Salmonella virus Jersey, Salmonella virus L13, Salmonella virus LSPA1, Salmonella virus SE2, Salmonella virus SETP3, Salmonella virus SETP7, Salmonella virus SETP13, Salmonella virus SP101, Salmonella virus SS3e, Salmonella virus wksI3, Escherichia virus K1G, Escherichia virus K1H, Escherichia virus K1 ind1, Escherichia virus K1 ind2, Salmonella virus SP31, Leuconostoc virus Lmd1, Leuconostoc virus LNO3, Leuconostoc virus LN04, Leuconostoc virus LN12, Leuconostoc virus LN6B, Leuconostoc virus P793, Leuconostoc virus 1A4, Leuconostoc virus Ln8, Leuconostoc virus Ln9, Leuconostoc virus LN25, Leuconostoc virus LN34, Leuconostoc virus LNTR3, Mycobacterium virus Bongo, Mycobacterium virus Rey, Mycobacterium virus Butters, Mycobacterium virus Michelle, Mycobacterium virus Charlie, Mycobacterium virus Pipsqueaks, Mycobacterium virus Xeno, Mycobacterium virus Panchino, Mycobacterium virus Phrann, Mycobacterium virus Redi, Mycobacterium virus Skinnyp, Gordonia virus BaxterFox, Gordonia virus Yeezy, Gordonia virus Kita, Gordonia virus Zirinka, Gordonia virus Nymphadora, Mycobacterium virus Bignuz, Mycobacterium virus Brusacoram, Mycobacterium virus Donovan, Mycobacterium virus Fishburne, Mycobacterium virus Jebeks, Mycobacterium virus Malithi, Mycobacterium virus Phayonce, Enterobacter virus F20, Klebsiella virus 1513, Klebsiella virus KLPN1, Klebsiella virus KP36, Klebsiella virus PKP126, Klebsiella virus Sushi, Escherichia virus AHP42, Escherichia virus AHS24, Escherichia virus AKS96, Escherichia virus C119, Escherichia virus E41c, Escherichia virus Eb49, Escherichia virus Jk06, Escherichia virus KP26, Escherichia virus Rogue1, Escherichia virus ACGM12, Escherichia virus Rtp, Escherichia virus ADB2, Escherichia virus JMPW1, Escherichia virus JMPW2, Escherichia virus T1, Shigella virus PSf2, Shigella virus ShfI1, Citrobacter virus Stevie, Escherichia virus TLS, Salmonella virus SP126, *Cronobacter* virus Esp2949-1, Pseudomonas virus Ab18, Pseudomonas virus Ab19, Pseudomonas virus PaMx11, Arthrobacter virus Amigo, Propionibacterium virus Anatole, Propionibacterium virus B3, Bacillus virus *Andromeda*, Bacillus virus Blastoid, Bacillus virus Curly, Bacillus virus Eoghan, Bacillus virus Finn, Bacillus virus Glittering, Bacillus virus Riggi, Bacillus virus Taylor, Gordonia virus Attis, Mycobacterium virus Barnyard, Mycobacterium virus Konstantine, Mycobacterium virus Predator, Mycobacterium virus Bernal13, Staphylococcus virus 13, Staphylococcus virus 77, Staphylococcus virus 108 PVL, Mycobacterium virus Bron, Mycobacterium virus Faith1, ycobacterium virus Joedirt, Mycobacterium virus Rumpelstiltskin, Lactococcus virus bIL67, actococcus virus c2, Lactobacillus virus c5, Lactobacillus virus Ld3, Lactobacillus virus Ld17, actobacillus virus Ld25A, Lactobacillus virus LLKu, Lactobacillus virus phiLdb, Cellulophaga virus Cba121, *Cellulophaga* virus Cba171, *Cellulophaga* virus Cba181, *Cellulophaga* virus ST, Bacillus virus 250, Bacillus virus IEBH, Mycobacterium virus Ardmore, Mycobacterium virus Avani, Mycobacterium virus Boomer, Mycobacterium virus Che8, Mycobacterium virus Che9d, Mycobacterium virus Deadp, Mycobacterium virus Dlane, Mycobacterium virus Dorothy, Mycobacterium virus Dotproduct, Mycobacterium virus Drago, Mycobacterium virus Fruitloop, Mycobacterium virus Gumbie, Mycobacterium virus Ibhubesi, Mycobacterium virus Llij, Mycobacterium virus Mozy, Mycobacterium virus Mutaforma13, Mycobacterium virus Pacc40, ycobacterium virus PMC, Mycobacterium virus Ramsey, Mycobacterium virus Rockyhorror, Mycobacterium virus SG4, Mycobacterium virus Shauna1, Mycobacterium virus Shilan, Mycobacterium virus Spartacus, Mycobacterium virus Taj, Mycobacterium virus Tweety, Mycobacterium virus Wee, Mycobacterium virus Yoshi, Salmonella virus Chi, Salmonella virus FSLSP030, Salmonella virus FSLSP088, Salmonella virus iEPS5, Salmonella virus SPN19, ycobacterium virus 244, Mycobacterium virus Bask21, Mycobacterium virus CJW1, ycobacterium virus Eureka, Mycobacterium virus Kostya, Mycobacterium virus Porky, Mycobacterium virus Pumpkin, Mycobacterium virus Sirduracell, Mycobacterium virus Toto, Mycobacterium virus Corndog, Mycobacterium virus Firecracker, Rhodobacter virus RcCronus, Pseudomonas virus D3112, Pseudomonas virus DMS3, Pseudomonas virus FHA0480, seudomonas virus LPB1, Pseudomonas virus MP22, Pseudomonas virus MP29, Pseudomonas virus MP38, Pseudomonas virus PA1 KOR, Pseudomonas virus D3, Pseudomonas virus PMG1, rthrobacter virus Decurro, Gordonia virus Demosthenes, Gordonia virus Katyusha, Gordonia virus Kvothe, Propionibacterium virus B22, Propionibacterium virus Doucette, Propionibacterium virus E6, Propionibacterium virus G4, Burkholderia virus phi6442, Burkholderia virus phil026b, Burkholderia virus phiE125, *Edwardsiella* virus eiAU, Mycobacterium virus Ff47, Mycobacterium virus Muddy, Mycobacterium virus Gaia, Mycobacterium virus Giles, Arthrobacter virus Captnmurica, Arthrobacter virus Gordon, Gordonia virus GordTnk2, Paenibacillus virus Harrison, Escherichia virus EK99P1, Escherichia virus HK578, Escherichia virus JL1, Escherichia virus SSL2009a, Escherichia virus YD2008s, Shigella virus EP23, *Sodalis* virus SO1, Escherichia virus HK022, Escherichia virus HK75, Escherichia virus HK97, Escherichia virus HK106, Escherichia virus HK446, Escherichia virus HK542, Escherichia virus HK544, Escherichia virus HK633, scherichia virus mEp234, Escherichia virus mEp235, Escherichia virus mEpX1, Escherichia virus mEpX2, Escherichia virus mEp043, Escherichia virus mEp213, Escherichia virus mEp237, scherichia virus mEp390, Escherichia virus mEp460, Escherichia virus mEp505, Escherichia virus mEp506, Brevibacillus virus Jenst, Achromobacter virus 83-24, Achromobacter virus JWX, Arthrobacter virus Kellezzio, Arthrobacter virus Kitkat, Arthrobacter virus Bennie, Arthrobacter virus DrRobert, Arthrobacter virus Glenn, Arthrobacter virus HunterDalle, Arthrobacter virus Joann, Arthrobacter virus Korra, Arthrobacter virus Preamble, Arthrobacter virus Pumancara, Arthrobacter virus Wayne, Mycobacterium virus Alma, Mycobacterium virus Arturo, Mycobacterium virus Astro, Mycobacterium virus Backyardigan, Mycobacterium virus BBPiebs31, Mycobacterium virus Benedict, Mycobacterium virus Bethlehem, Mycobacterium virus Billknuckles, Mycobacterium virus Bruns, Mycobacterium virus Bxb1, Mycobacterium virus Bxz2, Mycobacterium virus Che12, Mycobacterium virus Cuco, Mycobacterium virus D29, ycobacterium virus Doom, Mycobacterium virus Ericb, Mycobacterium virus Euphoria, Mycobacterium virus George, Mycobacterium virus Gladiator, Mycobacterium virus Goose, Mycobacterium virus Hammer, Mycobacterium virus Heldan, Mycobacterium virus Jasper, Mycobacterium virus JC27, Mycobacterium virus Jeffabunny, Mycobacterium virus JHC117, ycobacterium virus KBG, Mycobacterium virus Kssjeb, Mycobacterium virus Kugel, Mycobacterium virus L5, Mycobacterium virus Lesedi, Mycobacterium virus LHTSCC, Mycobacterium virus lockley, Mycobacterium virus Marcell, Mycobacterium virus Microwolf, Mycobacterium virus Mrgordo, Mycobacterium virus Museum, Mycobacterium virus Nepal, Mycobacterium virus Packman, Mycobacterium virus Peaches, Mycobacterium virus Perseus, Mycobacterium virus Pukovnik, Mycobacterium virus Rebeuca, Mycobacterium virus Redrock, Mycobacterium virus Ridgecb, Mycobacterium virus Rockstar, Mycobacterium virus Saintus, Mycobacterium virus Skipole, Mycobacterium virus Solon, Mycobacterium virus Switzer, Mycobacterium virus SWU1, Mycobacterium virus Ta17a, Mycobacterium virus Tiger, Mycobacterium virus Timshel, Mycobacterium virus Trixie, Mycobacterium virus Turbido, Mycobacterium virus Twister, Mycobacterium virus U2, Mycobacterium virus Violet, Mycobacterium virus Wonder, Escherichia virus DE3, Escherichia virus HK629, Escherichia virus HK630, Escherichia virus Lambda, Arthrobacter virus Laroye, Mycobacterium virus Halo, Mycobacterium virus Liefie, Mycobacterium virus Marvin, Mycobacterium virus Mosmoris, Arthrobacter virus Circum, Arthrobacter virus Mudcat, Escherichia virus N15, Escherichia virus 9 g, Escherichia virus JenK1, Escherichia virus JenP1, Escherichia virus JenP2, Pseudomonas virus NP1, Pseudomonas virus PaMx25, Mycobacterium virus Baka, Mycobacterium virus Courthouse, Mycobacterium virus Littleo, Mycobacterium virus Omega, Mycobacterium virus Optimus, Mycobacterium virus Thibault, Polaribacter virus P12002L, Polaribacter virus P12002S, Nonlabens virus P12024L, Nonlabens virus P12024S, Thermus virus P23-45, Thermus virus P74-26, Listeria virus LP26, Listeria virus LP37, Listeria virus LP110, Listeria virus LP114, isteria virus P70, Propionibacterium virus ATCC29399BC, Propionibacterium virus ATCC29399BT, Propionibacterium virus Attacne, Propionibacterium virus Keiki, Propionibacterium virus Kubed, Propionibacterium virus Lauchelly, Propionibacterium virus MrAK, Propionibacterium virus Ouroboros, Propionibacterium virus P91, Propionibacterium virus P105, Propionibacterium virus P144, Propionibacterium virus P1001, Propionibacterium virus P1.1, Propionibacterium virus P100A, Propionibacterium virus P100D, Propionibacterium virus P101A, Propionibacterium virus P104A, Propionibacterium virus PA6, Propionibacterium virus Pacnes201215, Propionibacterium virus PAD20, Propionibacterium virus PAS50, Propionibacterium virus PHL009M11, Propionibacterium virus PHL025M00, Propionibacterium virus PHL037M02, Propionibacterium virus PHL041M10, Propionibacterium virus PHL060L00, ropionibacterium virus PHL067M01, Propionibacterium virus PHL070N00, Propionibacterium virus PHL071N05, Propionibacterium virus PHL082M03, Propionibacterium virus PHL092M00, ropionibacterium virus PHL095N00, Propionibacterium virus PHL111M01, Propionibacterium virus PHL112N00, Propionibacterium virus PHL113M01, Propionibacterium virus PHL114L00, ropionibacterium virus PHL116M00, Propionibacterium virus PHL117M00, Propionibacterium virus PHL117M01, Propionibacterium virus PHL132N00, Propionibacterium virus PHL141N00, ropionibacterium virus PHL151M00, Propionibacterium virus PHL151N00, Propionibacterium virus PHL152M00, Propionibacterium virus PHL163M00, Propionibacterium virus PHL171M01, ropionibacterium virus PHL179M00, Propionibacterium virus PHL194M00, Propionibacterium virus PHL199M00, Propionibacterium virus PHL301M00, Propionibacterium virus PHL308M00, ropionibacterium virus Pirate, Propionibacterium virus Procrass1, Propionibacterium virus SKKY, Propionibacterium virus Solid, Propionibacterium virus Stormborn, Propionibacterium virus Wizzo, Pseudomonas virus PaMx28, Pseudomonas virus PaMx74, Mycobacterium virus Patience, Mycobacterium virus P11, Rhodococcus virus Pepy6, Rhodococcus virus Poco6, ropionibacterium virus PFR1, Streptomyces virus phiBT1, Streptomyces virus phiC31, treptomyces virus TG1, Caulobacter virus Karma, Caulobacter virus Magneto, Caulobacter virus phiCbK, Caulobacter virus Rogue, Caulobacter virus Swift, Staphylococcus virus 11, taphylococcus virus 29, Staphylococcus virus 37, Staphylococcus virus 53, Staphylococcus virus 55, Staphylococcus virus 69, Staphylococcus virus 71, Staphylococcus virus 80, taphylococcus virus 85, Staphylococcus virus 88, Staphylococcus virus 92, Staphylococcus virus 96, Staphylococcus virus 187, Staphylococcus virus 52a, Staphylococcus virus 80 alpha, Staphylococcus virus CNPH82, Staphylococcus virus EW, Staphylococcus virus IPLA5, taphylococcus virus IPLA7, Staphylococcus virus IPLA88, Staphylococcus virus PH15, taphylococcus virus phiETA, Staphylococcus virus phiETA2, Staphylococcus virus phiETA3, taphylococcus virus phiMR11, Staphylococcus virus phiMR25, Staphylococcus virus phiNM1, taphylococcus virus phiNM2, Staphylococcus virus phiNM4, Staphylococcus virus SAP26, taphylococcus virus X2, Enterococcus virus FL1, Enterococcus virus FL2, Enterococcus virus FL3, Lactobacillus virus ATCC8014, Lactobacillus virus phiJL1, Pediococcus virus cP1, eromonas virus plS4A, Listeria virus LP302, Listeria virus PSA, Methanobacterium virus psiM1, *Roseobacter* virus RDJL1, *Roseobacter* virus RDJL2, Rhodococcus virus RER2, Enterococcus virus BC611, Enterococcus virus IMEEF1, Enterococcus virus SAP6, Enterococcus virus VD13, treptococcus virus SPQS1, Mycobacterium virus *Papyrus, Mycobacterium* virus Send513, urkholderia virus KL1, Pseudomonas virus 73, Pseudomonas virus Ab26, Pseudomonas virus Kakheti25, Escherichia virus Cajan, Escherichia virus Seurat, Staphylococcus virus SEP9, Staphylococcus virus Sextaec, Streptococcus virus 858, Streptococcus virus 2972, treptococcus virus ALQ132, Streptococcus virus 01205, Streptococcus virus Sfi11, treptococcus virus 7201, Streptococcus virus DT1, Streptococcus virus phiAbc2, Streptococcus virus Sfi19, Streptococcus virus Sfi21, Paenibacillus virus Diva, Paenibacillus virus Hb10c2, aenibacillus virus Rani, Paenibacillus virus Shelly, Paenibacillus virus Sitara, Paenibacillus virus Willow, Lactococcus virus 712, Lactococcus virus ASCC191, Lactococcus virus ASCC273, actococcus virus ASCC281, Lactococcus virus ASCC465, Lactococcus virus ASCC532, actococcus virus Bibb29, Lactococcus virus bIL170, Lactococcus virus CB13, Lactococcus virus CB14, Lactococcus virus CB19, Lactococcus virus CB20, Lactococcus virus jj50, Lactococcus virus P2, Lactococcus virus P008, Lactococcus virus sk1, Lactococcus virus S14, Bacillus virus Slash, Bacillus virus Stahl, Bacillus virus Staley, Bacillus virus Stills, Gordonia virus Bachita, Gordonia virus ClubL, Gordonia virus OneUp, Gordonia virus Smoothie, Gordonia virus Soups, Bacillus virus SPbeta, Vibrio virus MAR10, Vibrio virus SSP002, Escherichia virus AKFV33, scherichia virus BF23, Escherichia virus DT57C, Escherichia virus EPS7, Escherichia virus FFH1, Escherichia virus H8, Escherichia virus slur09, Escherichia virus T5, Salmonella virus 118970 sal2, Salmonella virus Shivani, Salmonella virus SPC35, Salmonella virus Stitch, Arthrobacter virus Tank, Tsukamurella virus TIN2, Tsukamurella virus TIN3, Tsukamurella virus TIN4, Rhodobacter virus RcSpartan, Rhodobacter virus RcTitan, Mycobacterium virus Anaya, Mycobacterium virus *Angelica, Mycobacterium* virus Crimd, Mycobacterium virus Fionnbarth, Mycobacterium virus Jaws, Mycobacterium virus Larva, Mycobacterium virus Macncheese, Mycobacterium virus Pixie, Mycobacterium virus TM4, Bacillus virus BMBtp2, Bacillus virus TP21, Geobacillus virus Tp84, Staphylococcus virus 47, Staphylococcus virus 3a, Staphylococcus virus 42e, Staphylococcus virus IPLA35, Staphylococcus virus phi12, taphylococcus virus phiSLT, Mycobacterium virus 32HC, Rhodococcus virus RGL3, aenibacillus virus Vegas, Gordonia virus Vendetta, Bacillus virus Wbeta, Mycobacterium virus Wildcat, Gordonia virus Twister6, Gordonia virus Wizard, Gordonia virus Hotorobo, Gordonia virus Monty, Gordonia virus Woes, Xanthomonas virus CP1, Xanthomonas virus OP1, anthomonas virus phil7, Xanthomonas virus Xop411, Xanthomonas virus Xp10, Streptomyces virus TP1604, Streptomyces virus YDN12, Alphaproteobacteria virus phiJI001, Pseudomonas virus LKO4, Pseudomonas virus M6, Pseudomonas virus MP1412, Pseudomonas virus PAE1, seudomonas virus Yua, Pseudoalteromonas virus PM2, Pseudomonas virus phi6, seudomonas virus phi8, Pseudomonas virus phi12, Pseudomonas virus phi13, Pseudomonas virus phi2954, Pseudomonas virus phiNN, Pseudomonas virus phiYY, Vibrio virus fs1, Vibrio virus VGJ, Ralstonia virus RS603, Ralstonia virus RSM1, Ralstonia virus RSM3, Escherichia virus M13, Escherichia virus 122, Salmonella virus IKe, Acholeplasma virus L51, Vibrio virus fs2, ibrio virus VFJ, Escherichia virus If1, Propionibacterium virus B5, Pseudomonas virus Pf1, Pseudomonas virus Pf3, Ralstonia virus PE226, Ralstonia virus RSS1, Spiroplasma virus SVTS2, Stenotrophomonas virus PSH1, Stenotrophomonas virus SMA6, Stenotrophomonas virus SMA7, Stenotrophomonas virus SMA9, Vibrio virus CTXphi, Vibrio virus KSF1, Vibrio virus VCY, Vibrio virus Vf33, Vibrio virus VfO3K6, Xanthomonas virus Cf1c, Spiroplasma virus C74, Spiroplasma virus R8A2B, Spiroplasma virus SkV1CR23x, Escherichia virus FI, Escherichia virus Qbeta, Escherichia virus BZ13, Escherichia virus MS2, Escherichia virus alpha3, scherichia virus ID21, Escherichia virus ID32, Escherichia virus ID62, Escherichia virus NC28, scherichia virus NC29, Escherichia virus NC35, Escherichia virus phiK, Escherichia virus St1, scherichia virus WA45, Escherichia virus G4, Escherichia virus ID52, Escherichia virus Talmos, Escherichia virus phiX174, Bdellovibrio virus MAC1, Bdellovibrio virus MH2K, Chlamydia virus Chp1, Chlamydia virus Chp2, Chlamydia virus CPAR39, Chlamydia virus CPG1, Spiroplasma virus SpV4, Acholeplasma virus L2, Pseudomonas virus PR4, Pseudomonas virus PRD1, acillus virus AP50, Bacillus virus Bam35, Bacillus virus GIL16, Bacillus virus Wip1, Escherichia virus phi80, Escherichia virus RB42, Escherichia virus T2, Escherichia virus T3, Escherichia virus T6, Escherichia virus VT2-Sa, Escherichia virus VT1-Sakai, Escherichia virus VT2-Sakai, Escherichia virus CP-933V, Escherichia virus P27, Escherichia virus Stx2 phi-I, Escherichia virus Stx1 phi, Escherichia virus Stx2 phi-II, Escherichia virus CP-1639, based on the Escherichia virus BP-4795, Escherichia virus 86, Escherichia virus Min27, Escherichia virus 2851, Escherichia virus 1717, Escherichia virus YYZ-2008, Escherichia virus EC026_P06, Escherichia virus ECO103_P15, Escherichia virus ECO103_P12, Escherichia virus ECO111_P16, Escherichia virus ECO111_P11, Escherichia virus VT2 phi_272, Escherichia virus TL-2011c, Escherichia virus P13374, Escherichia virus Sp5; the first bacteriophage being different from the second bacteriophage.

In one embodiment, the first bacteriophage is selected in the group consisting of BW73, B278, D6, D108, E, EI, E24, E41, FI-2, FI-4, FI-5, HI8A, Ffl8B, i, MM, Mu, 025, PhI-5, Pk, PSP3, PI, PID, P2, P4, SI, Wφ, φK13, φ1, φ2, φ7, φ92, 7 A, 8φ, 9φ, 18, 28-1, 186, 299, HH-Escherichia (2), AB48, CM, C4, C16, DD-VI, E4, E7, E28, FII, FI3, H, HI, H3, H8, K3, M, N, ND-2, ND-3, ND4, ND-5, ND6, ND-7, Ox-I, Ox-2, Ox-3, Ox-4, Ox-5, Ox-6, PhI-I, RB42, RB43, RB49, RB69, S, SaI-I, SaI-2, SaI-3, SaI-4, SaI-5, SaI-6, TC23, TC45, TuII*-6, TuIP-24, TuII*46, TuIP-60, T2, T4, T6, T35, αI, 1, IA, 3, 3A, 3T+, 5φ, 9266Q, CFO103, HK620, J, K, KIF, m59, no. A, no. E, no. 3, no. 9, N4, sd, T3, T7, WPK, W31, ΔH, φC3888, φK3, φK7, φK12, φV-1, Φ04-CF, Φ05, Φ06, Φ07, φI, φI.2, φ20, φ95, φ263, φIO92, φI, φII, Ω8, 1, 3, 7, 8, 26, 27, 28-2, 29, 30, 31, 32, 38, 39, 42, 933W, NN-Escherichia (1), Esc-7-11, AC30, CVX-5, CI, DDUP, ECI, EC2, E21, E29, FI, F26S, F27S, Hi, HK022, HK97, HK139, HK253, HK256, K7, ND-I, PA-2, q, S2, TI, ), T3C, T5, UC-I, w, β4, γ2, λ, ΦD326, φγ, Φ06, Φ7, Φ10, φ80, χ, 2, 4, 4A, 6, 8A, 102, 150, 168, 174, 3000, AC6, AC7, AC28, AC43, AC50, AC57, AC81, AC95, HK243, KIO, ZG/3A, 5, 5A, 21EL, H19-J and 933H.

In a particular embodiment, said first type of bacteriophage is a prophage.

In another particular embodiment, said first type of bacteriophage is a temperate bacteriophage, filamentous phage, or pseudo-lysogenic phage.

By "temperate bacteriophage" or "lysogenic bacteriophage" is meant herein a bacteriophage which infects bacteria or achaea, which can be stably maintained in the genome and/or as episomes of/in a strain, and which replicates with cells without, in their lysogenic state, producing virions. It is well-known from the skilled person which bacteriophages, in the bacteriophages listed above, are temperate phages.

By "filamentous phage" is meant herein a bacteriophage characterized by having a single-stranded DNA genome that is encased by a long protein capsid cylinder. Typically, bacteria infected by filamentous phages are not lysed during the life cycle and replication of the phage, but rather experience a reduced rate of growth. It is well-known from the skilled person which bacteriophages, in the bacteriophages listed above, are filamentous phages.

By "pseudo-lysogenic phage" is meant herein a bacteriophage being at a stage of stalled development in a host cell without either multiplication of the phage genome (as in lytic development) or its replication synchronized with the cell cycle and stable maintenance in the cell line (as in lysogenization), which proceeds with no viral genome degradation, thus allowing the subsequent restart of virus development.

In a preferred embodiment, said first type of bacteriophage is a K. pneumoniae prophage. In another preferred embodiment, said first type of bacteriophage is a C. acnes bacteriophage.

In a preferred embodiment, said second type of bacteriophage is lambda bacteriophage. In another preferred embodiment, said second type of bacteriophage is a P. freudenreichii bacteriophage.

In a preferred embodiment, said first type of bacteriophage is a K. pneumoniae prophage and said second type of bacteriophage is lambda bacteriophage. In another preferred embodiment, said first type of bacteriophage is a C. acnes bacteriophage and said second type of bacteriophage is a P. freudenreichii bacteriophage.

Additional Bacterial Gene

As well-known from the skilled person, some phages use products produced by their bacterial host for folding and/or assembly of their structural elements, and/or for proper packaging of their DNA.

Therefore, in a particular embodiment, said production bacterial cell further comprises at least one bacterial gene, derived from a bacterial species or strain from which the first type of bacteriophage comes, involved in folding and/or assembly of phage structural elements and/or involved in DNA packaging.

As will be understood by the skilled person, bacterial genes involved in folding and/or assembly of phage structural elements depend on the particular bacteriophage from which said phage structural elements are obtained. They typically include bacterial genes encoding chaperones.

Similarly, bacterial genes involved in phage DNA packaging depend on the particular bacteriophage from which the phage DNA packaging genes are obtained. Examples of such bacterial genes include genes encoding IHF proteins.

Payload

In a particular embodiment, said production bacterial cell further comprises a payload to be packaged into said phage particles or phage-derived delivery vehicles.

As used herein, the term "payload" refers to any nucleic acid sequence (DNA and/or RNA) or amino acid sequence, or a combination of both (such as, without limitation, peptide nucleic acid or peptide-oligonucleotide conjugate) transferred into a bacterium with a delivery vehicle. In a particular embodiment, the payload is a nucleic acid payload, more particularly a DNA and/or RNA payload, still particularly a DNA payload.

The term "payload" may also refer to a plasmid, a vector or a cargo.

The payload can be a phagemid or phasmid obtained from a natural, evolved or engineered bacteriophage genome. The payload can also be composed only in part of a phagemid or phasmid obtained from a natural, evolved or engineered bacteriophage genome.

As used herein, the term "phagemid" or "phasmid" are equivalent and refer to a recombinant DNA vector comprising at least one sequence of a bacteriophage genome and is able to permit packaging in a capsid, and which is preferably not able of producing progeny, more particularly a vector that derives from both a plasmid and a bacteriophage genome. A phagemid of the disclosure comprises a phage packaging site and optionally an origin of replication (ori), in particular a bacterial and/or phage origin of replication. In one embodiment, the phagemid does not comprise an origin of replication and thus cannot replicate by itself once injected into a bacterium. Alternatively, the phagemid comprises a plasmid origin of replication, in particular a bacterial and/or phage origin of replication.

In a particular embodiment, said payload is to be packaged in the form of a packaged phagemid.

As used herein, the term "packaged phagemid" refers to a phagemid which is encapsidated in a bacteriophage scaffold, phage-derived delivery particle or capsid. Particularly, it refers to a bacteriophage scaffold, phage delivery particle or capsid devoid of a bacteriophage genome. The packaged phagemid may be produced with a helper phage strategy, well known from the man skilled in the art. The helper phage typically comprises all the genes coding for the structural and functional proteins that are indispensable for the phagemid according to the invention to be encapsidated.

In a particular embodiment, said payload is to be delivered into targeted bacterial cells, as defined below.

In a more particular embodiment, said payload is stably maintained in said targeted bacterial cells. In an alternative embodiment, said payload does not replicate in said targeted bacterial cells.

Sequence of Interest Under the Control of a Promoter

In a particular embodiment, the payload comprises a sequence of interest, in particular under the control of a promoter.

As known by the person skilled in the art, a promoter may be classified as strong or weak according to its affinity for RNA polymerase. The strength of a promoter may depend on whether initiation of transcription occurs at that promoter with high or low frequency. Different promoters with different strengths may be used in the present invention leading to different levels of gene/protein expression (e.g. the level of expression initiated from an mRNA originating from a weak promoter is lower than the level of expression initiated from a strong promoter).

It will be appreciated by those of ordinary skill in the art that a promoter sequence may be selected from a large number of known bacterial genes expressed by various bacterial species. Also, methods of prokaryotic promoter prediction exist, and can be based on DNA stability analysis as described in Kanhere and Bansal (BMC Bioinformatics 2005, 6:1). The choice of promoter on the payload used in the context of the present invention can thus be made based on the bacteria to target.

In some embodiments, the nucleic acid of interest may be positioned under the control of a recombinant or heterologous promoter, which refers to a promoter that is not normally associated with the nucleic acid of interest in its natural environment.

Examples of bacterial promoters for use in accordance with the present invention include, without limitation, positively regulated *E. coli* promoters such as positively regulated a 70 promoters (e.g., inducible pBad/araC promoter, Lux cassette right promoter, modified lambda Prm promote, plac Or2-62 (positive), pBad/AraC with extra REN sites, pBad, P(Las) TetO, P(Las) CIO, P(RhI), Pu, FecA, pRE, cadC, hns, pLas, pLux), a "s" promoter (e.g., Pdps), σ 32 promoters (e.g., heat shock) and σ 54 promoters (e.g., glnAp2); negatively regulated *E. coli* promoters such as negatively regulated a 70 promoters (e.g., Promoter (PRM+), modified lambda Prm promoter, TetR-TetR-4C P(Las) TetO, P(Las) CIO, P(Lac) IQ, RecA_DlexO_D-Lac01, dapAp, FecA, Pspac-hy, pel, plux-cl, plux-lac, CinR, CinL, glucose controlled, modified Pr, modified Prm+, FecA, Pcya, rec A (SOS), Rec A (SOS), EmrR_regulated, BetI_regulated, pLac_lux, pTet_Lac, pLac/Mnt, pTet/Mnt, LsrA/cl, pLux/cl, Lacl, LaclQ, pLacIQI, pLas/cl, pLas/Lux, pLux/Las, pRecA with LexA binding site, reverse BBa_R0011, pLacI/ara-1, pLacIq, rrnB PI, cadC, hns, PfhuA, pBad/araC, nhaA, OmpF, RcnR), σ S promoters (e.g., Lutz-Bujard LacO with alternative sigma factor σ 38), σ 32 promoters (e.g., Lutz-Bujard LacO with alternative sigma factor σ 32), σ 54 promoters (e.g., glnAp2); negatively regulated *B. subtilis* promoters such as repressible *B. subtilis* σA promoters (e.g., Gram-positive IPTG-inducible, Xyl, hyper-spank), a promoters, and the BioFAB promoters disclosed in Mutalik V K et al (Nature Methods, 2013, 10: 354-360, see in particular the supplementary data) as well as on the BioFAB website (http://biofab.synberc.org/data). Other inducible microbial promoters and/or bacterial promoters may be used in accordance with the present invention. An inducible promoter for use in accordance with the present disclosure may be induced by (or repressed by) one or more physiological condition(s), such as changes in pH, temperature, radiation, osmotic pressure, saline gradients, cell surface binding, and the concentration of one or more extrinsic or intrinsic inducing agent(s). The extrinsic inducer or inducing agent may comprise, without limitation, amino acids and amino acid analogs, saccharides and polysaccharides, nucleic acids, protein transcriptional activators and repressors, cytokines, toxins, petroleum-based compounds, metal containing compounds, salts, ions, enzyme substrate analogs, hormones or combinations thereof.

Particularly preferred bacterial promoters for use in accordance with the present invention may be selected from constitutive promoters regulated by σ 70 such as the promoters of the Anderson collection (http://parts.igem.org/Promoters/Catalog/Anderson): BBa_J23100, BBa_J23101, BBa_J23102, BBa_J23103, BBa_J23104, BBa_J23105, BBa_J23106, BBa_J23107, BBa_J23108, BBa_J23109, BBa_J23110, BBa_J23111, BBa_J23112, BBa_J23113, BBa_J23114, BBa_J23115, BBa_J23116, BBa_J23117, BBa_J23118, and BBa_J23119.

Other preferred bacterial promoters are the promoters disclosed in Stanton et al. (2014) *Nat. Chem. Biol.* 10:99-105, incorporated herein by reference, including in particular TetR, IcaR(A), AmtR, BetI, SrpR, Orf2, BM3R1, ButR, PhlF, PsrA, HlyIIR, AmeR, LmrA, QacR, ScbR, McbR, LitR, HapR, SmcR, TarA and variants thereof. In a particular embodiment, said promoter is SrpR and/or PhlF, or a variant thereof.

In some embodiments of the present invention, a promoter may or may not be used in conjunction with an "enhancer," which refers to a cis-acting regulatory sequence involved in the transcriptional activation of a nucleic acid sequence downstream of the promoter. The enhancer may be located at any functional location before or after the promoter.

In some embodiments, the payload may comprise a terminator sequence, or terminator. A "terminator," as used herein, is a nucleic acid sequence that causes transcription to stop. A terminator may be unidirectional or bidirectional. It consists of a DNA sequence involved in specific termination of an RNA transcript by an RNA polymerase. A terminator sequence prevents transcriptional activation of downstream nucleic acid sequences by upstream promoters. Thus, in certain embodiments, a terminator that ends the production of an RNA transcript is contemplated. A terminator may be necessary in vivo to achieve desirable gene/protein expression levels.

The most commonly used type of terminator is a forward terminator. When placed downstream of a nucleic acid of interest that is usually transcribed, a forward transcriptional terminator will cause transcription to abort. In some embodiments, bidirectional transcriptional terminators are provided, which usually cause transcription to terminate on both the forward and reverse strand. In some embodiments, reverse transcriptional terminators are provided, which usually terminate transcription on the reverse strand only. In prokaryotic systems, terminators usually fall into two categories (1) rho-independent terminators and (2) rho-dependent terminators. Rho-independent terminators are generally composed of a palindromic sequence that forms a stem loop rich in G-C base pairs followed by a string of uracil bases.

Terminators for use in accordance with the present invention include any terminator of transcription described herein or known to one of ordinary skill in the art. Examples of terminators include, without limitation, the termination sequences of genes such as, for example, the bovine growth hormone terminator, and viral termination sequences such as, for example, the TO terminator, the TE terminator, lambda TI and the T1T2 terminator found in bacterial systems. In some embodiments, the termination signal may be a sequence that cannot be transcribed or translated, such as those resulting from a sequence truncation.

Terminators for use in accordance with the present invention also include terminators disclosed in Chen Y J et al (2013, Nature Methods, 10: 659-664), and the BioFAB terminators disclosed in Cambray G et al (Nucl Acids Res, 2013, 41(9): 5139-5148).

In one embodiment, the sequence of interest is a programmable nuclease circuit to be delivered to the targeted bacteria. This programmable nuclease circuit may be able to mediate in vivo sequence-specific elimination of bacteria that contain a target gene of interest (e.g. a gene that is harmful to humans). Some embodiments of the present disclosure relate to engineered variants of the Type II CRISPR-Cas (Clustered Regularly Interspaced Short Palindromic Repeats-CRISPR-associated) system of *Streptococcus pyogenes*. Other programmable nucleases that can be used include other CRISPR-Cas systems, engineered TALEN (Transcription Activator-Like Effector Nuclease) variants, engineered zinc finger nuclease (ZFN) variants, natural, evolved or engineered meganuclease or recombinase variants, and any combination or hybrids of programmable nucleases. Thus, the engineered autonomously distributed circuits provided herein may be used to selectively cleave DNA encoding a gene of interest such as, for example, a toxin gene, a virulence factor gene, an antibiotic resistance gene, a remodeling gene or a modulatory gene (cf. WO2014124226 and US2015/0064138).

Other sequences of interest, preferably programmable, can be added to the payload so as to be delivered to targeted bacteria. Preferably, the sequence of interest added to the payload leads to cell death of the targeted bacteria. For example, the nucleic acid sequence of interest added to the payload may encode holins, endolysins, restriction enzymes or toxins affecting the targeted bacteria.

Alternatively, the sequence of interest added to the payload does not lead to death of targeted bacteria. For example, the sequence of interest may encode reporter genes leading to a luminescence or fluorescence signal. Alternatively, the sequence of interest may comprise proteins and enzymes achieving a useful function such as modifying the metabolism of the targeted bacteria, the composition of its environment or affecting the host subject. More specifically the sequence of interest can be an antigen triggering a host subject's immune response. The specific antigen can be released in the environment after induction of the lysis of the target cell or can be secreted by the target cell. (Costa et al. Nat Rev Microbiol. 2015 June; 13(6):343-59; Anné et al. Curr Top Microbiol Immunol. 2017; 404:267-308)

In a particular embodiment, the nucleic acid sequence of interest is selected from the group consisting of a Cas nuclease, a Cas9 nuclease, a guide RNA, a single guide RNA (sgRNA), a CRISPR locus, a gene expressing an enzyme such as a nuclease or a kinase, a TALEN, a ZFN, a meganuclease, a recombinase, a transposase, a bacterial receptor, a membrane protein, a structural protein, a secreted protein, a gene expressing resistance to an antibiotic or to a drug in general, a gene expressing a toxic protein or a toxic factor and a gene expressing a virulence protein or a virulence factor, a bacterial secretory protein or transporter, a bacterial pore or any of their combination. These proteins can also be modified or engineered to include extra features, like the addition or removal of a function (e.g. dCas9), the addition of a secretion signal to a protein not normally secreted, the addition of an exogenous peptide in a loop as non-limiting examples.

In a particular embodiment, the nucleic acid sequence of interest encodes a guide RNA-assisted targeting (INTE-GRATE) system, typically as disclosed in Vo et al. Nat Biotechnol. 2021 April; 39(4):480-489, said INTEGRATE system including for example a Type I-F *V. cholerae* CRISPR-transposon or a Type V-K *S. hofmanii* CRISPR-transposon. In a particular embodiment, said nucleic acid sequence of interest includes a nucleic acid encoding a crRNA, a nucleic acid encoding TniQ cascade, cas8, cas7 and cas6 proteins, a nucleic acid encoding tnsA, tnsB and tnsC proteins, and further including a donor DNA, said donor DNA encoding a protein of interest to be added into the targeted bacteria genome. In a particular embodiment, said nucleic acids encoding TniQ cascade, cas8, cas7 and cas6 proteins, and encoding tnsA, tnsB and tnsC proteins, are in the form of a single polycistronic nucleic acid. In another particular embodiment, said nucleic acid sequence of interest includes a nucleic acid encoding a guide RNA, a nucleic acid encoding cas12k protein, tnsB and tnsC proteins and TniQ cascade, and further including a donor DNA, said donor DNA encoding a protein of interest to be added into the targeted bacteria genome.

In a particular embodiment, the payload used in the context of the invention comprises a sequence of interest that encodes a bacteriocin, which can be a proteinaceous toxin produced by bacteria to kill or inhibit growth of other bacteria. Bacteriocins are categorized in several ways, including producing strain, common resistance mechanisms, and mechanism of killing. Such bacteriocins have been described from gram negative bacteria (e.g. microcins, colicin-like bacteriocins and tailocins) and from gram positive bacteria (e.g. Class I, Class II, Class III or Class IV bacteriocins).

In one embodiment, the payload used in the context of the invention further comprises a sequence of interest encoding a toxin selected in the group consisting of microcins, colicin-like bacteriocins, tailocins, Class I, Class II, Class III and Class IV bacteriocins. The circuit may also encode the transporter needed to secrete the toxin to the extracellular space.

In a particular embodiment, the corresponding immunity polypeptide (i.e. anti-toxin) may be used to protect bacterial cells (see review by Cotter et al., Nature Reviews Microbiology 11: 95, 2013) for payload production and encapsidation purpose but is absent in the pharmaceutical composition and in the targeted bacteria in which the payload used in the context of the invention is delivered.

In a particular embodiment, the payload used in the context of the invention comprises a sequence of interest that encodes a CRISPR-Cas system.

The CRISPR system contains two distinct elements, i.e. i) an endonuclease, in this case the CRISPR associated nuclease (Cas or "CRISPR associated protein") and ii) a guide RNA. Depending on the type of CRISPR system, the guide RNA may be in the form of a chimeric RNA which consists of the combination of a CRISPR (crRNA) bacterial RNA and a tracrRNA (trans-activating RNA CRISPR) (Jinek et al. Science. 2012 Aug. 17; 337(6096):816-21). The guide RNA combines the targeting specificity of the crRNA corresponding to the "spacing sequences" that serve as guides to the Cas proteins, and the conformational properties of the tracrRNA in a single transcript. When the guide RNA and the Cas protein are expressed simultaneously in the cell, the target genomic sequence can be permanently interrupted (and causing disappearance of the targeted and surrounding sequences and/or cell death, depending on the location) or modified. The modification may be guided by a repair matrix.

The CRISPR system includes two main classes depending on the nuclease mechanism of action:
Class 1 is made of multi-subunit effector complexes and includes type 1, III and IV;
Class 2 is made of single-unit effector modules, like Cas9 nuclease, and includes type II (II-A,II-B,II-C,II-C variant), V (V-A,V-B,V-C,V-D,V-E,V-U1,V-U2,V-U3,V-U4,V-U5) and VI (VI-A,VI-B1,VI-B2,VI-C,VI-D).

The sequence of interest according to the present invention may comprise a nucleic acid sequence encoding Cas protein. A variety of CRISPR enzymes are available for use as a sequence of interest on the payload used in the context of the present invention. In some embodiments, the CRISPR enzyme is a Type II CRISPR enzyme, a Type II-A or Type II-B CRISPR enzyme. In another embodiment, the CRISPR enzyme is a Type I CRISPR enzyme or a Type III CRISPR enzyme. In some embodiments, the CRISPR enzyme catalyzes DNA cleavage. In some other embodiments, the CRISPR enzyme catalyzes RNA cleavage. In one embodiment, the CRISPR enzymes may be coupled to a guide RNA or single guide RNA (sgRNA). In certain embodiments, the guide RNA or sgRNA targets a gene selected from the group consisting of an antibiotic resistance gene, virulence protein or factor gene, toxin protein or factor gene, a bacterial receptor gene, a membrane protein gene, a structural protein gene, a secreted protein gene, a gene expressing resistance to a drug in general and a gene causing a deleterious effect to the host subject.

The sequence of interest may comprise a nucleic acid sequence encoding a guide RNA or sgRNA to guide the Cas protein endogenous to the targeted bacteria, alone or in combination with a Cas protein and/or a guide RNA encoded by the payload.

Non-limiting examples of Cas proteins as part of a multi-subunit effector or as a single-unit effector include Cas1, Cas1B, Cas2, Cas3, Cas4, Cas5, Cas6, Cas7, Cas8, Cas9 (also known as Csn1 and Csx12), Cas10, Cas11 (SS), Cas12a (Cpf1), Cas12b (C2c1), Cas12c (C2c3), Cas12d (CasY), Cas12e (CasX), C2c4, C2c8, C2c5, C2c10, C2c9, Cas13a (C2c2), Cas13b (C2c6), Cas13c (C2c7), Cas13d, Csa5, Csc1, Csc2, Cse1, Cse2, Csy1, Csy2, Csy3, Csf1, Csf2, Csf3, Csf4, Csm1, Csm2, Csm3, Csm4, Csm5, Csm6, Cmr1, Cmr3, Cmr4, Cmr5, Cmr6, Csn2, Csb1, Csb2, Csb3, Csx17, Csx14, Csx10, Csx16, CsaX, Csx13, Csx1, Csx15, SdCpf1, CmtCpf1, TsCpf1, CmaCpf1, PcCpf1, ErCpf1, FbCpf1, UbcCpf1, AsCpf1, LbCpf1, Mad4, Mad7, Cms1, homologues thereof, orthologues thereof, variants thereof, or modified versions thereof. In some embodiments, the CRISPR enzyme cleaves both strands of the target nucleic acid at the Protospacer Adjacent Motif (PAM) site.

In a particular embodiment, the CRISPR enzyme is any Cas9 protein, for instance any naturally-occurring bacterial Cas9 as well as any variants, homologs or orthologs thereof.

By "Cas9" is meant a protein Cas9 (also called Csn1 or Csx12) or a functional protein, peptide or polypeptide fragment thereof, i.e. capable of interacting with the guide RNA(s) and of exerting the enzymatic activity (nuclease) which allows it to perform the double-strand cleavage of the DNA of the target genome. "Cas9" can thus denote a modified protein, for example truncated to remove domains of the protein that are not essential for the predefined functions of the protein, in particular the domains that are not necessary for interaction with the gRNA(s).

The sequence encoding Cas9 (the entire protein or a fragment thereof) as used in the context of the invention can be obtained from any known Cas9 protein (Fonfara et al. Nucleic Acids Res. 2014 February; 42(4):2577-90; Koonin et al. Curr Opin Microbiol. 2017 June; 37:67-78). Examples of Cas9 proteins useful in the present invention include, but are not limited to, Cas9 proteins of *Streptococcus pyogenes* (SpCas9), *Streptococcus thermophiles* (St1 Cas9, St3 Cas9), *Streptococcus mutans, Staphylococcus aureus* (SaCas9), *Campylobacter jejuni* (CjCas9), *Francisella novicida* (Fn-Cas9) and *Neisseria meningitides* (NmCas9).

The sequence encoding Cpf1 (Cas12a) (the entire protein or a fragment thereof) as used in the context of the invention can be obtained from any known Cpf1 (Cas12a) protein (Koonin et al. Curr Opin Microbiol. 2017 June; 37:67-78). Examples of Cpf1(Cas12a) proteins useful in the present invention include, but are not limited to, Cpf1(Cas12a) proteins of *Acidaminococcus* sp, Lachnospiraceae bacteriu and *Francisella novicida*.

The sequence encoding Cas13a (the entire protein or a fragment thereof) as used in the context of the invention can be obtained from any known Cas13a (C2c2) protein (Abudayyeh et al. Nature. 2017 Oct. 12; 550(7675):280-284). Examples of Cas13a (C2c2) proteins useful in the present invention include, but are not limited to, Cas13a (C2c2) proteins of *Leptotrichia wadei* (LwaCas13a).

The sequence encoding Cas13d (the entire protein or a fragment thereof) as used in the context of the invention can be obtained from any known Cas13d protein (Yan et al. Mol Cell. 2018 Apr. 19; 70(2):327-339.e5). Examples of Cas13d proteins useful in the present invention include, but are not limited to, Cas13d proteins of *Eubacterium* siraeum and *Ruminococcus* sp.

The sequence encoding Mad4 (the entire protein or a fragment thereof) as used in the context of the invention is disclosed in international application WO2018/236548.

The sequence encoding Mad7 (the entire protein or a fragment thereof) as used in the context of the invention is disclosed in international application WO2018/236548.

The sequence encoding Cms1 (the entire protein or a fragment thereof) as used in the context of the invention is disclosed in international patent application WO2017/141173.

In a particular embodiment, the nucleic sequence of interest is a CRISPR/Cas9 system for the reduction of gene expression or inactivation of a gene selected from the group consisting of an antibiotic resistance gene, virulence factor or protein gene, toxin factor or protein gene, a gene expressing a bacterial receptor, a membrane protein, a structural protein, a secreted protein, a gene expressing resistance to a drug in general and a gene causing a deleterious effect to the host subject.

In one embodiment, the CRISPR system is used to target and inactivate a virulence factor. A virulence factor can be any substance produced by a pathogen that alter host subject-pathogen interaction by increasing the degree of damage done to the host subject. Virulence factors are used by pathogens in many ways, including, for example, in cell adhesion or colonization of a niche in the host subject, to evade the host subject's immune response, to facilitate entry to and egress from host subject's cells, to obtain nutrition from the host subject, or to inhibit other physiological processes in the host subject. Virulence factors can include enzymes, endotoxins, adhesion factors, motility factors, factors involved in complement evasion, scavenging factors and factors that promote biofilm formation. For example, such targeted virulence factor gene can be *E. coli* virulence factor gene such as, without limitation, EHEC-HlyA, Stx1 (VT1), Stx2 (VT2), Stx2a (VT2a), Stx2b (VT2b), Stx2c (VT2c), Stx2d (VT2d), Stx2e (VT2e) and Stx2f (VT2f), Stx2h (VT2h), stx2k, fimA, fimF, fimH, neuC, kpsE, sfa, foc, iroN, aer, iha, papC, papGI, papGII, papGIII, hIyC, cnf1, hra, sat, ireA, usp ompT, ibeA, maIX, fyuA, irp2, traT, afaD, ipaH, eltB, estA, bfpA, eaeA, espA, aaiC, aatA, TEM, CTX, SHV, csgA, csgB, csgC, csgD, csgE, csgF, csgG, csgH, T1SS, T2SS, T3SS, T4SS, T5SS, T6SS (secretion systems). For example, such targeted virulence factor gene can be *Shigella dysenteriae* virulence factor gene such as, without limitation, stx1 and stx2. For example, such targeted virulence factor gene can be *Yersinia pestis* virulence factor gene such as, without limitation, yscF (plasmid-borne (pCDI) T3SS external needle subunit). For example, such targeted virulence factor gene can be *Francisella tularensis* virulence factor gene such as, without limitation, fsIA. For example, such targeted virulence factor gene can be *Bacillus anthracis* virulence factor gene such as, without limitation, pag (*Anthrax* toxin, cell-binding protective antigen). For example, such targeted virulence factor gene can be *Vibrio cholera* virulence factor gene such as, without limitation, ctxA and ctxB (cholera toxin), tcpA (toxin co-regulated pilus), and toxT (master virulence regulator). For example, such targeted virulence factor gene can be *Pseudomonas aeruginosa* virulence factor genes such as, without limitation, pyoverdine (e.g., sigma factor pvdS, biosynthetic genes pvdL, pvdI, pvdJ, pvdH, pvdA, pvdF, pvdQ, pvdN, pvdM, pvdO, pvdP, transporter genes pvdE, pvdR, pvdT, opmQ), siderophore pyochelin (e.g., pchD, pchC, pchB, pchA, pchE, pchF and pchG, and toxins (e.g., exoU, exoS and exoT). For example, such targeted virulence factor gene can be *Klebsiella pneumoniae* virulence factor genes such as, without limitation, fimA (adherence, type I fimbriae major subunit), and cps (capsular polysaccharide). For example, such targeted virulence factor gene can be *Acinetobacter baumannii* virulence factor genes such as, without limitation, ptk (capsule polymerization) and epsA (assembly). For example, such targeted virulence factor gene can be *Salmonella enterica* Typhi virulence factor genes such as, without limitation, MIA (invasion, SPI-1 regulator), ssrB (SPI-2 regulator), and those associated with bile tolerance, including efflux pump genes acrA, acrB and tolC. For example, such targeted virulence factor gene can be *Fusobacterium nucleatum* virulence factor genes such as, without limitation, FadA and TIGIT. For example, such targeted virulence factor gene can be *Bacteroides fragilis* virulence factor genes such as, without limitation, bft. For example, such targeted virulence factor gene can be *Cutibacterium acnes* porphyrins genes, CAMP-factors (CAMP1, CAMP2, CAMP3, CAMP4), Hyaluronate lyase (HYL-IB/II, HYL-IA), Lipases (GehA, GehB), Haemolysins, Sialidases, Endoglycoceramidases, Endo-B-N-acetylglucosaminidase, Dermatan sulfate adhesin (DsA1, DsA2), Proline-Threonine Repeats (PTRs) or any virulence factors included on the acne associated genomic loci 1, 2, 3(plasmid), 4 such as a tight adhesion locus (tad), Streptolysin S-associated genes (sag), nonribosomal peptide synthetases (NRPS) as described in Tomida et al. mBio. 2013 Apr. 30; 4(3):e00003-13.

In another embodiment, the CRISPR/Cas system is used to target and inactivate an antibiotic resistance gene such as,', without limitation, GyrB, ParE, ParY, AAC(1), AAC(2'), AAC(3), AAC(6'), ANT(2"), ANT(3"), ANT(4'), ANT(6), ANT(9), APH(2"), APH(3"), APH(3'), APH(4), APH(6), APH(7"), APH(9), ArmA, RmtA, RmtB, RmtC, Sgm, AER, BLA1, CTX-M, KPC, SHV, TEM, BlaB, CcrA, IMP, NDM, VIM, ACT, AmpC, CMY, LAT, PDC, OXA β-lactamase, mecA, Omp36, OmpF, PIB, bla (blaI, blaR1) and mec (mecI, mecR1) operons, Chloramphenicol acetyltransferase (CAT), Chloramphenicol phosphotransferase, Ethambutol-resistant arabinosyltransferase (EmbB), MupA, MupB, Integral membrane protein MprF, Cfr 23S rRNA methyltransferase, Rifampin ADP-ribosyltransferase (Arr), Rifampin glycosyltransferase, Rifampin monooxygenase, Rifampin phosphotransferase, DnaA, RbpA, Rifampin-resistant beta-subunit of RNA polymerase (RpoB), Erm 23S rRNA methyltransferases, Lsa, MsrA, Vga, VgaB, Streptogramin Vgb lyase, Vat acetyltransferase, Fluoroquinolone acetyltransferase, Fluoroquinolone-resistant DNA topoisomerases, Fluoroquinolone-resistant GyrA, GyrB, ParC, Quinolone resistance protein (Qnr), FomA, FomB, FosC, FosA, FosB, FosX, VanA, VanB, VanD, VanR, VanS, Lincosamide nucleotidyltransferase (Lin), EreA, EreB, GimA, Mgt, Ole, Macrolide phosphotransferases (MPH), MefA, MefE, Mel, Streptothricin acetyltransferase (sat), Sul1, Sul2, Sul3, sulfonamide-resistant FoIP, Tetracycline inactivation enzyme TetX, TetA, TetB, TetC, Tet30, Tet31, TetM, TetO, TetQ, Tet32, Tet36, MacAB-ToIC, MsbA, MsrA, VgaB, EmrD, EmrAB-ToIC, NorB, GepA, MepA, AdeABC, AcrD, MexAB-OprM, mtrCDE, EmrE, adeR, acrR, baeSR, mexR, phoPQ, mtrR, or any antibiotic resistance gene described in the Comprehensive Antibiotic Resistance Database (CARD https://card.mcmaster.ca/).

In another embodiment, the CRISPR/Cas system is used to target and inactivate a bacterial toxin gene. Bacterial toxins can be classified as either exotoxins or endotoxins. Exotoxins are generated and actively secreted; endotoxins remain part of the bacteria. The response to a bacterial toxin can involve severe inflammation and can lead to sepsis. Such toxin can be for example Botulinum neurotoxin, Tetanus toxin, *Staphylococcus* toxins, Diptheria toxin, *Anthrax* toxin, *Alpha* toxin, Pertussis toxin, Shiga toxin, Heat-stable enterotoxin (*E. coli* ST), colibactin, BFT (*B. fragilis* toxin) or any toxin described in Henkel et al., (Toxins from Bacteria in EXS. 2010; 100: 1-29).

In a particular embodiment, the payload used in the context of the invention comprises a sequence of interest that encodes a base editing system.

Base editing (BE) refers to the ability to substitute a specific nucleotide base pair on a DNA or RNA molecule by another. Until recently, the only way to perform a specific substitution on DNA in vivo was using recombination of a template DNA, carrying the specific base pair change, with the locus of interest. Base editing technology relies on completely different strategies. There is no exchange of DNA, instead an enzymatic reaction converts a nucleotide to another one leading to a mismatch at the level of dsDNA that is then corrected by the cell machinery.

In some embodiments, the base editing system comprises one or more of the following enzymes and systems:

A) Cytosine base editors (CBE) and Adenosine base editors (ABE), as described in Rees, H. A. & Liu, D. R. *Nat Rev Genet* 19, 770-788 (2018).

So far there are seven types of DNA base editors described:

Cytosine Base Editor (CBE) that convert C:G into T:A (Komor, A et al. Nature 533:420-4. (2016))

Adenine Base Editor (ABE) that convert A:T into G:C (Gaudelli, N. M. et al. Nature 551(7681) 464-471 (2017))

Cytosine Guanine Base Editor (CGBE) that convert C:G into G:C (Chen, L et al. Precise and programmable C:G to G:C base editing in genomic DNA. Biorxiv (2020); Kurt, I et al. CRISPR C-to-G base editors for inducing targeted DNA transversions in human cells. Nature Biotechnology (2020))

Cytosine Adenine Base Editor (CABE) that convert C:G into A:T (Zhao, D et al. New base editors change C to A in bacteria and C to G in mammalian cells. Nature Biotechnology (2020))

Adenine Cytosine Base Editor (ACBE) that convert A:T into C:G (WO2020181180)

Adenine Thymine Base Editor (ATBE) that convert A:T into T:A (WO2020181202)

Thymine Adenine Base Editor (TABE) that convert T:A into A:T (WO2020181193; WO2020181178; WO2020181195)

Base editors differ in the base modification enzymes. CBE rely on ssDNA cytidine deaminase among which: APOBEC1, rAPOBEC1, APOBEC1 mutant or evolved version (evoAPOBEC1), and APOBEC homologs (APOBEC3A (eA3A), Anc689), Cytidine deaminase 1 (CDA1), evoCDA1, FERNY, evoFERNY.

ABE rely on deoxyadenosine deaminase activity of a tandem fusion TadA-TadA* where TadA* is an evolved version of TadA, an *E. coli* tRNA adenosine deaminase enzyme, able to convert adenosine into Inosine on ssDNA. TadA* include TadA-8a-e and TadA-7.10.

Except from base modification enzyme there has been also modifications implemented to base editor to increase editing efficacy, precision and modularity:

the addition of one or two uracil DNA glycosylase inhibitor domain (UGI) to prevent base excision repair mechanism to revert base edition the addition of Mu-GAM that decrease insertion-deletion rate by inhibiting Non-homologous end joining mechanism in the cell (NHEJ)

the use of nickase active Cas9 (nCas9 D10A) that, by creating nicks on the non-edited strand favors its repair and consequently the fixation of the edited base.

the use of diverse Cas proteins from for example different organisms, mutants with different PAM motifs or different fidelity or different family (e.g. Cas12a).

Non-limiting examples of DNA-based editor proteins include BE1, BE2, BE3, BE4, BE4-GAM, HF-BE3, Sniper-BE3, Target-AID, Target-AID-NG, ABE, EE-BE3, YE1-BE3, YE2-BE3, YEE-BE3, BE-PLUS, SaBE3, SaBE4, SaBE4-GAM, Sa(KKH)-BE3, VQR-BE3, VRER-BE3, EQR-BE3, xBE3, Cas12a-BE, Ea3A-BE3, A3A-BE3, TAM, CRISPR-X, ABE7.9, ABE7.10, ABE7.10*, xABE, ABESa, VQR-ABE, VRER-ABE, Sa(KKH)-ABE, ABE8e, SpRY-ABE, SpRY-CBE, SpG-CBE4, SpG-ABE, SpRY-CBE4, SpCas9-NG-ABE, SpCas9-NG-CBE4, enAsBE1.1, enAsBE1.2, enAsBE1.3, enAsBE1.4, AsBE1.1, AsBE1.4, CRISPR-Abest, CRISPR-Cbest, eA3A-BE3, AncBE4.

Cytosine Guanine Base Editors (CGBE) consist of a nickase CRISPR fused to:

A cytosine deaminase (rAPOBEC) and base excision repair proteins (e.g. rXRCC1) (Chen, L et al. Precise and programmable C:G to G:C base editing in genomic DNA. Biorxiv (2020); Chen et al. Nature Communications 12:1384 (2021))

A rat APOBEC1 variant (R33A) protein and an *E. coli*-derived uracil DNA N-glycosylase (eUNG) (Kurt, I et al. CRISPR C-to-G base editors for inducing targeted DNA transversions in human cells. Nature Biotechnology (2020))

Cytosine Adenine Base Editors (CABE) consist of a Cas9 nickase, a cytidine deaminase (e.g. AID), and a uracil-DNA glycosylase (Ung) (Zhao, D et al. New base editors change C to A in bacteria and C to G in mammalian cells. Nature Biotechnology (2020)).

ACBE include a nucleic acid programmable DNA-binding protein and an adenine oxidase (WO2020181180).

ATBE consist of a Cas9 nickase and one or more adenosine deaminase or an oxidase domain (WO2020181202).

TABE consist of a Cas9 nickase and an adenosine methyltransferase, a thymine alkyltransferase, or an adenosine deaminase domain (WO2020181193; WO2020181178; WO2020181195).

Base editor molecules can also consist of two or more of the above listed editor enzymes fused to a Cas protein (e.g. combination of an ABE and CBE). These biomolecules are named dual base editors and enable the editing of two different bases (Grunewald, J et al. A dual-deaminase CRISPR base editor enables concurrent adenine and cytosine editing, Nature Biotechnology (2020); Li, C et al. Targeted, random mutagenesis of plant genes with dual cytosine and adenine base editors, Nature Biotechnology (2020)).

In a particular embodiment, the base editing system comprises a Cytosine base editor (CBE) and/or an Adenosine base editor (ABE) as defined above.

B) Prime editors (PE), as described in Anzalone, A. V. et al. Nature 576, 149-157 (2019), consist of a nCas9 fused to a reverse transcriptase used in combination with a prime editing RNA (pegRNA; a guide RNA that includes a template region for reverse transcription).

Prime Editing allows introduction of insertions, deletions (indels), and 12 base-to-base conversions. Prime editing relies on the ability of a reverse transcriptase (RT), fused to a Cas nickase variant, to convert RNA sequence brought by a prime editing guide RNA (pegRNA) into DNA at the nick site generated by the Cas protein. The DNA flap generated from this process is then included or not in the targeted DNA sequence.

Prime editing systems include:
a Cas nickase variant such as Cas9-H840A fused to a reverse transcriptase domain such as M-MLV RT or its mutant version (M-MLV RT(D200N), M-MLV RT(D200N/L603W), M-MLV RT(D200N/L603W/T330P/T306K/W313F)
a prime editing guide RNA (pegRNA)

To favor editing, the prime editing system can include the expression of an additional sgRNA targeting the Cas nickase activity towards the non-edited DNA strand ideally only after the resolution of the edited strand flap by designing the sgRNA to anneal with the edited strand but not with the original strand.

Non-limiting examples of prime editing systems include PE1, PE1-M1, PE1-M2, PE1-M3, PE1-M6, PE1-M15, PE1-M3 inv, PE2, PE3, PE3b.

Cas9 Retron precISe Parallel Editing via homologY ('CRISPEY'), a retron RNA fused to the sgRNA and expressed together with Cas9 and the retron proteins including at least the reverse transcriptase (Sharon, E. et al. Cell 175, 544-557.e16 (2018)).

The SCRIBE strategy: a retron system expressed in combination with a recombinase promoting the recombination of single stranded DNA, also known as single stranded annealing proteins (SSAPs) (Farzadfard, F. & Lu, T. K. Science 346, 1256272 (2014)). Such recombinases include but are not limited to phage recombinases such as lambda red, recET, Sak, Sak4, and newly described SSAPs described in Wannier, T. M. et al. Improved bacterial recombineering by parallelized protein discovery. Biorxiv 2020.01.14.906594 (2020) doi:10.1101/2020.01.14.906594.

The targetron system based on group II introns described in Karberg, M. et al. *Nat Biotechnol* 19, 1162-7 (2001) which has been adapted to many bacterial species.

Other retron based gene targeting approaches are described in Simon, A. J., Ellington, A. D. & Finkelstein, I. J. *Nucleic Acids Res* 47, 11007-11019 (2019).

C) CRISPR/Cas. In various embodiments, the sequence of interest encodes fusion proteins comprising a Cas9 (e.g., a Cas9 nickase) domain and a deaminase domain. In some embodiments, the fusion protein comprises Cas9 and a cytosine deaminase enzyme, such as APOBEC enzymes, or adenosine deaminase enzymes, such as ADAT enzymes, for example as disclosed in U.S. Patent Publ. 2015/0166980. In one embodiment, the deaminase is an ACF1/ASE deaminase.

In various embodiments, the APOBEC deaminase is selected from the group consisting of APOBEC1 deaminase, APOBEC2 deaminase, APOBEC3A deaminase, APOBEC3B deaminase, APOBEC3C deaminase, APOBEC3D deaminase, APOBEC3F deaminase, APOBEC3G deaminase, and APOBEC3H deaminase. In various embodiments, the fusion protein comprises a Cas9 domain, a cytosine deaminase domain, and a uracil glycosylase inhibitor (UGI) domain.

In one embodiment, the deaminase is an adenosine deaminase that deaminate adenosine in DNA, for example as disclosed in U.S. Pat. No. 10,113,163. In some embodiments, the fusion proteins further comprise an inhibitor of base repair, such as, a nuclease dead inosine specific nuclease (dISN), for example as disclosed in U.S. Pat. No. 10,113,163. In various embodiments, the nucleic acid of interest encodes fusion proteins comprising a catalytically impaired Cas9 endonuclease fused to an engineered reverse transcriptase, programmed with a prime editing guide RNA (pegRNA) that both specifies the target site and encodes the desired edit, for example as described in Anzalone et al.

In some embodiments, other programmable nucleases can be used. These include an engineered TALEN (Transcription Activator-Like Effector Nuclease) and variants, engineered zinc finger nuclease (ZFN) variants, natural, evolved or engineered meganuclease or recombinase variants, and any combination or hybrids of programmable nucleases. Thus, the programmable nucleases provided herein may be used to selectively modify DNA encoding a DNA sequence or gene of interest such as, for example, a toxin gene, a virulence factor gene, an antibiotic resistance gene, a remodeling gene or a modulatory gene (cf. WO2014124226 and US2015/0064138).

In one embodiment, the base editing system or base editor is used to inactivate the expression of a gene by editing one or several nucleotides involved in transcription or translation. More specifically the base editing system or base editor is targeting one or several nucleotides of a promoter, a RBS, a start codon.

In one embodiment, the base editing system or base editor is used to introduce a premature stop codon.

In one embodiment, the base editing system or base editor is used to introduce one or several rare codons.

In another embodiment, the base editing system or base editor is used to modulate the expression of genes by editing one or several nucleotides involved in transcription or translation. More specifically the base editing system or base editor is targeting one or several nucleotides of a promoter, a RBS, a start codon. leading to an increase or decrease of gene expression.

In another embodiment, the base editing system or base editor is used to revert a mutation that leads to the inactivation, decrease or increase in activity of a gene or pathway.

In another embodiment, the base editing system or base editor is used to revert a mutation that leads to an increase of pathogenicity.

In one embodiment, the base editing system or base editor is used to modify the regulation of a gene by editing one or several nucleotides involved in its regulation such as nucleotides of operator sequence, transcription factor binding site, riboswitch, RNAse recognition site, protease cleavage site, methylation site, post translational modification site (phosphorylation, glycosylation, acetylation, pupylation . . . ).

In some embodiments, the sequence of interest encodes a RNA base editing system. RNA base editing is based on the same principle as DNA base editing: an enzyme catalyzing the conversion of a RNA base into another must be brought close to the target base to perform its conversion locally. In one embodiment, the enzyme used for RNA editing is an adenosine deaminase from ADAR family that converts Adenosine into Inosine in dsRNA structure. Several seminal studies used this specificity for dsRNA and fused the ADAR deaminase domain ($ADAR_{DD}$) to an antisense oligo in order to program local RNA base editing. More recently the ability of some CRISPR-Cas systems to bind RNA molecules was repurposed into RNA editing. Using catalytically dead Cas13b enzyme (dPspCas13b) fused to a hyperactive mutant of ADAR2 deaminase domain ($ADAR2_{DD}$-E488Q for REPAIRv1 and $ADAR2_{DD}$-E488Q-T375G for REPAIRv2), Cox et al improved specificity and efficiency compare to previous RNA editing strategies (Cox, D. B. T. et al. *Science* 358, 1019-1027 (2017)).

Non-limiting examples of RNA based editor proteins include REPAIRv1 and REPAIRv2.

In one embodiment, the RNA base editor is used to inactivate the expression of a gene by editing one or several nucleotides involved in translation. More specifically the base editor is targeting one or several nucleotides of a 5'UTR, a RBS, a start codon.

In one embodiment, the RNA base editor is used to introduce a premature stop codon.

In one embodiment, the RNA base editor is used to introduce one or several rare codons.

In another embodiment, the RNA base editor is used to modulate the expression of genes by editing one or several nucleotides involved in translation. More specifically the base editor is targeting one or several nucleotides of a 5'UTR, a RBS, a start codon leading to an increase or decrease of gene expression.

In another embodiment, the RNA base editor is used to revert a mutation that leads to the inactivation or a decrease in activity of a gene or pathway.

In another embodiment, the base editor is used to revert a mutation that leads to an increase of pathogenicity.

In a preferred embodiment, said sequence of interest only generates an effect in said targeted bacterial cells. More preferably, said sequence of interest is only expressed in said targeted bacterial cells.

Origins of Replication

In a particular embodiment, the copy number of said payload is controlled, in said production bacterial cell, by said at least one induction mechanism defined above. In an alternative embodiment, another induction mechanism controls the copy number of said payload in said production bacterial cell.

Origins of replication known in the art have been identified from species-specific plasmid DNAs (e.g. ColE1, RI, pT181, pSC101, pMB1, R6K, RK2, p15a and the like), from bacterial virus (e.g. φX174, M13, F1 and P4) and from bacterial chromosomal origins of replication (e.g. oriC).

In one embodiment, the payload used in the context of the invention comprises a bacterial origin of replication that is functional in the targeted bacteria.

Alternatively, the payload used in the context of the invention does not comprise any functional bacterial origin of replication or contains an origin of replication that is inactive in the targeted bacteria. In such embodiment, the payload used in the context of the invention cannot replicate by itself once it has been introduced into a bacterium by the phage particle or phage-derived delivery particle.

In one embodiment, the origin of replication on the payload to be packaged is inactive in the targeted bacteria, meaning that this origin of replication is not functional in the bacteria targeted by the phage particle or phage-derived delivery vehicle, thus preventing unwanted plasmid replication.

In one embodiment, the payload comprises a bacterial origin of replication that is functional in the production bacterial cell of the invention.

Bacteria-Specific Origins of Replication

Plasmid replication depends on host bacteria enzymes and on plasmid-controlled cis and trans determinants. For example, some plasmids have determinants that are recognized in almost all gram-negative bacteria and act correctly in each host bacteria during replication initiation and regulation. Other plasmids possess this ability only in some bacteria (Kues, U and Stahl, U 1989 Microbiol Rev 53:491-516).

Plasmids are replicated by three general mechanisms, namely theta type, strand displacement, and rolling circle (reviewed by Del Solar et al. 1998 Microbio and Molec Biol. Rev 62:434-464) that start at the origin of replication. These replication origins contain sites that are required for interactions of plasmid and/or host encoded proteins.

Origins of replication used on the payload used in the context of the invention may be moderate copy number, such as ColE1 on from pBR322 (15-20 copies per cell) or the R6K plasmid (15-20 copies per cell) or may be high copy number, e.g. pUC oris (500-700 copies per cell), pGEM oris (300-400 copies per cell), pTZ oris (>1000 copies per cell) or pBluescript oris (300-500 copies per cell).

In one embodiment, the bacterial origin of replication is selected in the group consisting of ColE1, pMB1 and variants (pBR322, pET, pUC, etc), p15a, ColA, ColE2, pOSAK, pSC101, R6K, IncW (pSa etc), IncFII, pT181, P1, F IncP, IncC, IncJ, IncN, IncP1, IncP4, IncQ, IncH11, RSF1010, CloDF13, NTP16, R1, f5, pPS10, pC194, pE194, BBR1, pBC1, pEP2, pWVO1, pLF1311, pAP1, pWKS1, pLS1, pLS11, pUB6060, pJD4, pIJ101, pSN22, pAMbeta1, pIP501, pIP407, ZM6100(Sa), pCU1, RA3, pMOL98, RK2/RP4/RP1/R68, pB10, R300B, pRO1614, pRO1600, pECB2, pCM1, pFA3, RepFIA, RepFIB, RepFIC, pYVE439-80, R387, phasyl, RA1, TF-FC2, pMV158 and pUB113.

More preferably, the bacterial origin of replication is a *E. coli* origin of replication selected in the group consisting of ColE1, pMB1 and variants (pBR322, pET, pUC, etc), p15a, ColA, ColE2, pOSAK, pSC101, R6K, IncW(pSa etc), IncFII, pT181, P1, F IncP, IncC, IncJ, IncN, IncP1, IncP4, IncQ, IncH11, RSF1010, CloDF13, NTP16, R1, f5, pPS10.

More preferably, the bacterial origin of replication is selected in the group consisting of pC194, pE194, BBR1, pBC1, pEP2, pWVO1, pLF1311, pAP1, pWKS1, pLS1, pLS11, pUB6060, pJD4, pIJ101, pSN22, pAMbeta1, pIP501, pIP407, ZM6100(Sa), pCU1, RA3, pMOL98, RK2/

RP4/RP1/R68, pB10, R300B, pRO1614, pRO1600, pECB2, pCM1, pFA3, RepFIA, RepFIB, RepFIC, pYVE439-80, R387, phasyl, RA1, TF-FC2, pMV158 and pUB113.

Even more preferably, the bacterial origin of replication are ColE1 and p15a.

In one embodiment, the bacterial origin of replication is functional in Propionibacterium and Cutibacterium, more specifically in *Propionibacterium freudenreichii* and Cutibacterium *acnes* and is selected from the group consisting of pLME108, pLME106, p545, pRGO1, pZGX01, pPG01, pYS1, FRJS12-3, FRJS25-1, pIMPLE-HL096PA1, A_15_1_R1. In a particular embodiment, the bacterial origin of replication is selected from the bacterial origins of replication disclosed in US applications US2022/135986 and US2022/135987.

Phage Origin of Replication

The payload used in the context of the invention may comprise a phage origin of replication which can initiate, with complementation of a complete phage genome, the replication of the payload for later encapsulation into the different capsids.

A phage origin of replication can also be engineered to act as a bacterial origin of replication without the need to package any phage particles.

A phage origin of replication comprised in the payload used in the context of the invention can be any origin of replication found in a phage.

Preferably, the phage origin of replication can be the wild-type or non-wild type sequence of the M13, f1, φX174, P4, Lambda, P2, 186, Lambda-like, HK022, mEP237, HK97, HK629, HK630, mEP043, mEP213, mEP234, mEP390, mEP460, mEPx1, mEPx2, phi80, mEP234, T2, T4, T5, T7, RB49, phiX174, R17, PRD1 PI-like, P2-like, P22, P22-like, N15 and N15-like bacteriophages.

More preferably, the phage origin of replication is selected in the group consisting of phage origins of replication of M13, f1, φX174, P4, and Lambda.

In a particular embodiment, the phage origin of replication is the P4 origin of replication.

In a particular embodiment, the phage origin of replication is from *Propionibacterium* phages: BW-like phages such as Doucette, B22, E6, G4; BV-like phages such as Anatole, E1, E3; BX-like phages such as PFR1 and PFR2; filamentous B5 phage; BU-like phages (*Cutibacterium acnes* phages). In a particular embodiment, the phage origin of replication is selected from the phage origins of replication disclosed in US applications US2022/135986 and US2022/135987.

Conditional Origin of Replication

In a particular embodiment, the payload comprises a conditional origin of replication which is inactive in the targeted bacteria but is active in the production bacterial cell.

In the context of the invention, a "conditional origin of replication" refers to an origin of replication whose functionality may be controlled by the presence of a specific molecule.

In a particular embodiment, the conditional origin of replication is an origin of replication, the replication of which depends upon the presence of one or more given protein, peptid, RNA, nucleic acid, molecule or any combination thereof.

In a particular embodiment, the replication involving said origin of replication may further depend on a process, such as transcription, to activate said replication.

In the context of the invention, said conditional origin of replication is inactive in the targeted bacteria because of the absence of said given protein, peptid, RNA, nucleic acid, molecule or any combination thereof in said targeted bacteria.

In a particular embodiment, said conditional origin of replication is active in said production bacterial cell because said production bacterial cell expresses said given protein, peptid, RNA, nucleic acid, molecule or any combination thereof. In a particular embodiment, said protein, peptid, RNA nucleic acid, molecule or any combination thereof is expressed in trans in said production bacterial cell.

By "in trans" is meant herein that said protein, peptid, RNA, nucleic acid, molecule or any combination thereof is not encoded on the same nucleic acid molecule as the one comprising the origin of replication. In a particular embodiment, said protein, peptid, RNA, nucleic acid, molecule or any combination thereof is encoded on a chromosome or on a vector, in particular a plasmid. In a particular embodiment, said vector comprises an antibiotic resistance marker. In an alternative embodiment, said vector is devoid of antibiotic resistance marker.

Since said conditional origin of replication is inactive in the targeted bacteria because of the absence of said given protein, peptid, RNA, nucleic acid, molecule or any combination thereof in said targeted bacteria, said conditional origin of replication may be selected depending on the specific bacteria to be targeted.

The conditional origin of replication disclosed herein may originate from plasmids, bacteriophages or PICIs which preferably share the following characteristics: they contain in their origin of replication repeat sequences, or iterons, and they code for at least one protein interacting with said origin of replication (i.e. Rep, protein O, protein P, pri) which is specific to them.

By way of example, mention may be made of the conditional replication systems of the following plasmids and bacteriophages: RK2, R1, pSC101, F, Rts1, RSF1010, P1, P4, lambda, phi82, phi80.

In a particular embodiment, said conditional origin of replication is selected from the group consisting of the R6KA DNA replication origin and derivatives thereof, the IncPα oriV origin of replication and derivatives thereof, ColE1 origins of replication modified to be under an inducible promoter, and origins of replication from phage-inducible chromosomal islands (PICIs) and derivatives thereof.

In a particular embodiment, said conditional origin of replication is an origin of replication present in less than 50%, or less than 40%, less than 30%, less than 20%, less than 10% or less than 5% of the bacteria of the host subject's microbiome.

In another particular embodiment, said conditional origin of replication comprises or consists of a sequence less than 80% identical, in particular less than 70%, less than 60%, less than 50%, less than 40%, less than 30%, less than 20%, less than 10%, less than 5% or less than 1% identical to the sequences of the origins of replication of the bacteria of the host subject's microbiome, in particular of the bacteria representing more than 50%, more particularly more than 60%, more than 70%, more than 80%, more than 90% or more than 95% of the host subject's microbiome.

As used herein, the term "phage-inducible chromosomal islands" or "PICIs" refers to mobile genetic elements having a conserved gene organization, and encode a pair of divergent regulatory genes, including a PICI master repressor. Typically, in Gram-positive bacteria, left of rpr, and transcribed in the same direction, PICIs encode a small set of genes including an integrase (int) gene; right of rpr, and transcribed in the opposite direction, the PICIs encode an excision function (xis), and a replication module consisting of a primase homolog (pri) and optionally a replication initiator (rep), which are sometimes fused, followed by a replication origin (ori), next to these genes, and also transcribed in the same direction, PICIs encode genes involved in phage interference, and optionally, a terminase small subunit homolog (terS).

In a particular embodiment, said conditional origin of replication is an origin of replication derived from phage-inducible chromosomal islands (PICIs).

A particular conditional origin of replication has indeed been derived from PICIs.

It was shown that it is possible to derive novel conditionally replicative vectors, in particular based on the primase-helicase and origin of replication from PICIs. These origins may be relatively rare in target strains, and more advantageously the primase-ori pair may be unique for each PICI, significantly reducing the possibility of undesired recombination or payload spread events. They can further be modified to further limit recombination chances and remove restriction sites to bypass target bacteria defense systems.

In a particular embodiment, said conditional origin of replication is derived from the origin of replication from the PICI of the *Escherichia coli* strain CFT073, disclosed in Fillol-Salom et al. (2018) *The ISME Journal* 12:2114-2128.

In a particular embodiment, said conditional origin of replication is the primase ori from the PICI of the *Escherichia coli* strain CFT073, typically of sequence SEQ ID NO: 1.

In another particular embodiment, said conditional origin of replication is the primase ori from the PICI of the *Escherichia coli* strain CFT073, devoid of at least 1, at least 2, at least 3, at least 4, at least 5, at least 6, at least 7, at least 8, at least 9, at least 10, at least 11, at least 12, at least 13, at least 14, at least 15 or at least 16 restriction site(s) selected from the group consisting of GAAABCC, GCCGGC, RCCGGY, GCNGC, TWCANNNNNNTGG (SEQ ID NO: 2), TGGCCA, ACCYAC, YGGCCR, AGACC, GCWGC, GGGANGC, GKAGATD, GCCGGYYD, GGCYAC, RGCCGGYYD, and VGCCGGYBD.

In a particular embodiment, said conditional origin of replication is the primase on from the PICI of the *Escherichia coli* strain CFT073, devoid of the restriction site GAAABCC. Preferably, said conditional origin of replication is of sequence SEQ ID NO: 3.

In another particular embodiment, said conditional origin of replication is the primase on from the PICI of the *Escherichia coli* strain CFT073 devoid of the restriction sites GAAABCC, GCCGGC, RCCGGY, GCNGC, TWCANNNNNNTGG (SEQ ID NO: 2), TGGCCA, ACCYAC, YGGCCR, AGACC, GCWGC, GGGANGC, GKAGATD, GCCGGYYD, GGCYAC, RGCCGGYYD, and VGCCGGYBD. Preferably, said conditional origin of replication is of sequence SEQ ID NO: 4.

In a particular embodiment, wherein said origin of replication is derived from phage-inducible chromosomal islands (PICIs), said conditional origin of replication is active in said production bacterial cell because said production bacterial cell expresses a rep protein, in particular a primase-helicase, in particular a primase-helicase of sequence SEQ ID NO: 5, typically encoded by a nucleic acid comprising or consisting of the sequence SEQ ID NO: 6.

It was demonstrated that these specific conditional origins of replication were particularly compatible with lambda-based packaging, leading to sufficiently high titers (>10$^{10}$/mL) required for microbiota-related applications.

Preferably, said production bacterial cell stably comprises said payload and is able to replicate said payload.

In a particular embodiment, when the conditional origin of replication of said payload is an origin of replication, the replication of which depends upon the presence of a given protein, peptid, nucleic acid, RNA, molecule or any combination thereof, said donor bacterial cell expresses said protein, peptid, nucleic acid, RNA, molecule or any combination thereof. Preferably, said protein, peptid, nucleic acid, RNA, molecule or any combination thereof is expressed in trans, as defined above.

In a particular embodiment, said production bacterial cell stably comprises a nucleic acid encoding said protein, peptid, nucleic acid, RNA, molecule or any combination thereof.

In a particular embodiment, when said origin of replication is derived from phage-inducible chromosomal islands (PICIs), said conditional origin of replication is active in said donor bacterial cell because said donor bacterial cell expresses a rep protein, in particular a primase-helicase, in particular a primase-helicase of sequence SEQ ID NO: 5.

In a particular embodiment, said production bacterial cell stably comprises a nucleic acid encoding said rep protein, in particular said primase-helicase, said nucleic acid typically comprising or consisting of the sequence SEQ ID NO: 6.

Packaging Site

In a particular embodiment, said payload is a nucleic acid payload comprising a packaging site derived from said first type of bacteriophage.

By "packaging site" is meant herein the DNA sequence on the phage genome that is required for genome packaging into the virion. Host-specific bacteriophages (and their packaging sites) include but are not limited to SPP1 (SPP1 pac site), P1 (P1 pac site), T1 (T1 pac site), T7 (T7 concatamer junction), lambda (cos site), mu (mu pac site), P22 (P22 pac site), φ8 (φ8 pac site), Sf6 (Sf6 pac site), 149 (149 pac site), and A1122 (A1122-concatamer junction). For most bacteriophages, the packaging site is termed the pac site. In some cases, the packaging site is referred to as a concatamer junction (e.g. T7 concatamer junction). In every case, the packaging site is substantially in isolation from sequences naturally occurring adjacent thereto in the bacteriophage genome.

For some bacteriophages, the packaging site may be unknown. In these cases, pac sites can be determined by taking advantage of the property that plasmids containing a functional bacteriophage pac site are packaged. For example, the DNA sequences necessary for packaging of bacteriophage A were determined by incorporating small restriction fragments of the A phage genomic DNA into a plasmid (Hohn 1983 PNAS USA 80:7456-7460). Following introduction into an in vivo packaging strain, the efficiency of packaging/transduction was quantitatively assessed. Using a similar strategy, the pac sites for a number of bacteriophages have been determined: A (Miwa 1982 Gene 20:267-279); Mu (Croenen et al. 1985 Virology 144:520-522); filamentous bacteriophages including f1, fd, M13, and Ike (Russel et al. 1989 J Virol 1989 63:3284-3295); P22 (Petri et al. 1990 Gene 88:47-55; Wu et al. 2002 Molec Microbiol 45:1631-1646); T7 (Chung et al. 1990 J Mol Biol 216:927-938), and T3 (Hashimoto et al. 1992 Virology 187:788-795).

In a particular embodiment, said packaging site is as disclosed in US applications US2022/135986 and US2022/135987, incorporated herein by reference.

Other Components of the Payload

The payload used in the context of the invention is preferably devoid of antibiotic resistance marker.

Antibiotic resistance genes are well known in the art and include but are not limited to ampicillin resistance (Amp), chloramphenicol resistance (Cm), tetracycline resistance (Tet), kanamycin resistance (Kan), hygromycin resistance (Qiyg or hph genes), and zeomycin resistance (Zeo).

In a particular embodiment, the payload used in the context of the invention comprises an auxotrophic marker. Auxotrophic markers in bacteria have previously been described, for example, in U.S. Pat. Nos. 4,920,048, 5,691,185, 6,291,245, 6,413,768, and 6,752,994; U.S. Patent Publication No. 20050186666; Struhl et al. (1976) PNAS USA 73; 1471-1475; MacCormick et al., (1995) FEMS Microbiol. Lett. 127:105-109; Dickely et al. (1995) Mol. Microbiol. 15:839-847; Sorensen et al. (2000) Appl. Environ. Microbiol 66:1253-1258; and Fiedler & Skerra (2001) Gene 274: 111 118, and typically include DapA and ThyA. In a particular embodiment, said auxotrophic marker is ThyA.

In a particular embodiment, said payload does not comprise any restriction site recognized by restriction enzymes which are frequently encoded by said targeted bacterial cell. In another particular embodiment, said payload comprises no more than 40, 30, 20, 10, 9, 8, 7, 6, 5, 4, 3, 2 or 1 restriction site(s) recognized by restriction enzymes which are frequently encoded by said targeted bacterial cell or a population or a group of targeted bacterial cell(s).

As used herein, the terms "restriction site" and "restriction enzyme site" are equivalent and refer to locations on a nucleic acid containing specific sequences of nucleotides, which are recognized by restriction enzymes. In particular, the nucleic acid comprises specific sequences which are bound and cleaved by restriction enzymes. Restriction sites are generally palindromic sequences of 4-8 base pairs in length. More precisely, the restriction site refers to a particular sequence and a modification state, so as to be bound and cleaved by restriction enzymes. In particular, it refers to a particular unmodified sequence, so as to be bound and cleaved by restriction enzymes. Especially the sequence is not methylated, hydroxymethylated and glucosyl-hydroxymethylated. In this context, the restriction enzyme is of type I, II or III. Alternatively, it may refer to a particular modified sequence, so as to be bound and cleaved by restriction enzymes, for instance a methylated, hydroxymethylated and glucosyl-hydroxymethylated DNA. In this context, the restriction enzyme is of type IV.

As used herein, "recognized by" with respect to a restriction site and a restriction enzyme means that the restriction site is cleaved by the restriction enzyme.

In a restriction site sequence N means that the nucleotide can be A, C, G or T; B means that the nucleotide can be C, G or T; Y means that the nucleotide can be C or T; W means that the nucleotide can be A or T; R means that the nucleotide can be A or G; and D means A, G or T.

As used herein, the terms "restriction enzyme" and "restriction endonuclease" are equivalent and refer to an enzyme that cuts nucleic acids at or near restriction sites. Restriction enzymes are commonly classified into four types (types I to type IV). The REBASE database allow to list the restriction sites that a given bacterium can recognize according to the restriction enzymes that it expresses.

By "frequent" or "frequently" in a group of bacteria of interest is meant that at least 10, 20, 30, 40, 50, 60, 70, 75, 80, 85, 90, 95 or 99% of the bacteria of the group encode the restriction enzyme.

The payload according to the invention preferably comprises no more than 100 restriction sites. In a preferred embodiment, the payload according to the invention comprises no more than 10 restriction sites. In a most preferred embodiment, the payload according to the invention does not comprise any restriction site.

Targeted Bacteria

The bacteria targeted by the phage particles or phage-derived delivery particles of the invention can be any bacteria present in a mammal organism, a plant or in the environment. It can be any commensal, symbiotic or pathogenic bacteria of the microbiota or microbiome.

A microbiome may comprise a variety of endogenous bacterial species, any of which may be targeted in accordance with the present disclosure. In some embodiments, the genus and/or species of targeted endogenous bacterial cells may depend on the first type of bacteriophage as defined in the section "Bacteriophage and gene derived from a bacteriophage" above. For example, some bacteriophages exhibit tropism for, or preferentially target, specific host species of bacteria. Other bacteriophages do not exhibit such tropism and may be used to target a number of different genus and/or species of endogenous bacterial cells.

Examples of bacterial cells include, without limitation, cells from bacteria of the genus *Yersinia* spp., *Escherichia* spp., *Klebsiella* spp., *Acinetobacter* spp., *Bordetella* spp., *Neisseria* spp., *Aeromonas* spp., *Francisella* spp., *Corynebacterium* spp., *Citrobacter* spp., *Chlamydia* spp., *Hemophilus* spp., *Brucella* spp., *Mycobacterium* spp., *Legionella* spp., *Rhodococcus* spp., *Pseudomonas* spp., *Helicobacter* spp., *Vibrio* spp., *Bacillus* spp., *Erysipelothrix* spp., *Salmonella* spp., *Streptomyces* spp., *Streptococcus* spp., *Staphylococcus* spp., *Bacteroides* spp., *Prevotella* spp., *Clostridium* spp., *Bifidobacterium* spp., *Clostridium* spp., *Brevibacterium* spp., *Lactococcus* spp., *Leuconostoc* spp., *Actinobacillus* spp., *Selenomonas* spp., *Shigella* spp., *Zymonas* spp., *Mycoplasma* spp., *Treponema* spp., *Leuconostoc* spp., *Corynebacterium* spp., *Enterococcus* spp., *Enterobacter* spp., *Pyrococcus* spp., *Serratia* spp., *Morganella* spp., *Parvimonas* spp., *Fusobacterium* spp., *Actinomyces* spp., *Porphyromonas* spp., *Micrococcus* spp., *Bartonella* spp., *Borrelia* spp., *Brucella* spp., *Campylobacter* spp., *Chlamydophila* spp., *Cutibacterium* spp., *Propionibacterium* spp., *Gardnerella* spp., *Ehrlichia* spp., *Haemophilus* spp., *Leptospira* spp., *Listeria* spp., *Mycoplasma* spp., *Nocardia* spp., *Rickettsia* spp., *Ureaplasma* spp., *Lactobacillus* spp., *Faecalibacterium* spp., *Ruminococcus* spp. and a mixture thereof.

Thus, phage particles, phage delivery particles and/or phages may target (e.g., specifically target) a bacterial cell from any one or more of the foregoing genus of bacteria in particular to specifically deliver the payload according to the invention.

Preferably, the targeted bacteria can be selected from the group consisting of *Yersinia* spp., *Escherichia* spp., *Klebsiella* spp., *Acinetobacter* spp., *Pseudomonas* spp., *Helicobacter* spp., *Vibrio* spp, *Salmonella* spp., *Streptococcus* spp., *Staphylococcus* spp., *Bacteroides* spp., *Clostridium* spp., *Shigella* spp., *Enterococcus* spp., *Enterobacter* spp., *Listeria* spp., *Cutibacterium* spp., *Propionibacterium* spp., *Fusobacterium* spp., *Porphyromonas* spp. and *Gardnerella* spp.

In some embodiments, the targeted bacteria are anaerobic bacterial cells (e.g., cells that do not require oxygen for growth). Anaerobic bacterial cells include facultative anaerobic cells such as but not limited to *Escherichia coli, Shewanella oneidensi, Gardnerella vaginalis* and *Listeria*. Anaerobic bacterial cells also include obligate anaerobic cells such as, for example, *Bacteroides, Clostridium, Cutibacterium, Propionibacterium, Fusobacterium* and *Porphyromonas* species. In humans, anaerobic bacteria are most commonly found in the gastrointestinal tract. In some particular embodiments, the targeted bacteria are thus bacteria most commonly found in the gastrointestinal tract. Bacteriophages used for preparing the hybrid helper phage, and then the phage particles, phage delivery vehicles and/or phages, may target (e.g., to specifically target) anaerobic bacterial cells according to their specific spectra known by the person skilled in the art to specifically deliver the plasmid.

In some embodiments, the targeted bacterial cells are, without limitation, *Bacteroides thetaiotaomicron, Bacteroides fragilis, Bacteroides distasonis, Bacteroides vulgatus, Clostridium leptum, Clostridium coccoides, Staphylococcus aureus, Bacillus subtilis, Clostridium butyricum, Brevibacterium lactofermentum, Streptococcus agalactiae, Lactococcus lactis, Leuconostoc lactis, Actinobacillus actinomycetemcomitans*, cyanobacteria, *Escherichia coli, Helicobacter pylori, Selenomonas ruminantium, Shigella sonnei, Zymomonas mobilis, Mycoplasma mycoides, Treponema denticola, Bacillus thuringiensis, Staphylococcus lugdunensis, Leuconostoc oenos, Corynebacterium xerosis, Lactobacillus plantarum, Lactobacillus rhamnosus, Lactobacillus casei, Lactobacillus acidophilus, Enterococcus faecalis, Bacillus coagulans, Bacillus cereus, Bacillus popillae, Synechocystis* strain PCC6803, *Bacillus liquefaciens, Pyrococcus abyssi, Selenomonas nominantium, Lactobacillus hilgardii, Streptococcus ferus, Lactobacillus pentosus, Bacteroides fragilis, Staphylococcus epidermidis, Streptomyces phaechromogenes, Streptomyces ghanaenis, Klebsiella pneumoniae, Enterobacter cloacae, Enterobacter aerogenes, Serratia marcescens, Morganella morganii, Citrobacter freundii, Propionibacterium freudenreichii, Pseudomonas aeruginosa, Parvimonas micra, Prevotella intermedia, Fusobacterium nucleatum, Prevotella nigrescens, Actinomyces israelii, Porphyromonas endodontalis, Porphyromonas gingivalis Micrococcus luteus, Bacillus megaterium, Aeromonas hydrophila, Aeromonas caviae, Bacillus anthracis, Bartonella henselae, Bartonella Quintana, Bordetella pertussis, Borrelia burgdorferi, Borrelia garinii, Borrelia afzelii, Borrelia recurrentis, Brucella abortus, Brucella canis, Brucella melitensis, Brucella suis, Campylobacter jejuni, Campylobacter coli, Campylobacter fetus, Chlamydia pneumoniae, Chlamydia trachomatis, Chlamydophila psittaci, Clostridium botulinum, Clostridium difficile, Clostridium perfringens, Clostridium tetani, Corynebacterium diphtheria, Cutibacterium acnes* (formerly *Propionibacterium acnes*), *Ehrlichia canis, Ehrlichia chaffeensis, Enterococcus faecium, Francisella tularensis, Haemophilus influenza, Legionella pneumophila, Leptospira interrogans, Leptospira santarosai, Leptospira weilii, Leptospira noguchii, Listeria monocytogenes, Mycobacterium leprae, Mycobacterium tuberculosis, Mycobacterium ulcerans, Mycoplasma pneumonia, Neisseria gonorrhoeae, Neisseria meningitides, Nocardia asteroids, Rickettsia rickettsia, Salmonella enteritidis, Salmonella typhi, Salmonella paratyphi, Salmonella typhimurium, Shigella flexneri, Shigella dysenteriae, Staphylococcus saprophyticus, Streptococcus pneumoniae, Streptococcus pyogenes, Gardnerella vaginalis, Streptococcus viridans, Treponema pallidum, Ureaplasma urealyticum, Vibrio cholera, Vibrio parahaemolyticus, Yersinia pestis, Yersinia enterocolitica, Yersinia pseudotuberculosis, Actinobacter baumanii, Pseudomonas aeruginosa*, and a mixture thereof, preferably the bacteria of interest are selected from the group consisting of *Escherichia coli, Enterococcus faecium, Staphylococcus aureus, Klebsiella pneumoniae, Acinetobacter baumanii, Pseudomonas aeruginosa, Enterobacter cloacae*, and *Enterobacter aerogenes*, and a mixture thereof.

In some embodiments, the targeted bacterial cells are, without limitation, *Anaerotruncus, Acetanaerobacterium, Acetitomaculum, Acetivibrio, Anaerococcus, Anaerofilum, Anaerosinus, Anaerostipes, Anaerovorax, Butyrivibrio, Clostridium, Capracoccus, Dehalobacter, Dialister, Dorea, Enterococcus, Ethanoligenens, Faecalibacterium, Fusobacterium, Gracilibacter, Guggenheimella, Hespellia, Lachnobacterium, Lachnospira, Lactobacillus, Leuconostoc, Megamonas, Moryella, Mitsuokella, Oribacterium, Oxobacter, Papillibacter, Proprionispira, Pseudobutyrivibrio, Pseudoramibacter, Roseburia, Ruminococcus, Sarcina, Seinonella, Shuttleworthia, Sporobacter, Sporobacterium, Streptococcus, Subdoligranulum, Syntrophococcus, Thermobacillus,* Turibacter, *Weissella, Clostridium, Bacteroides, Ruminococcus, Faecalibacterium, Treponema, Phascolarctobacterium, Megasphaera, Faecalibacterium, Bifidobacterium, Lactobacillus, Sutterella*, and/or *Prevotella*.

In other embodiments, the targeted bacteria cells are, without limitation, *Achromobacter xylosoxidans, Acidaminococcus fermentans, Acidaminococcus intestini, Acidaminococcus* sp., *Acinetobacter baumannii, Acinetobacter junii, Acinetobacter lwoffii, Actinobacillus capsulatus, Actinomyces naeslundii, Actinomyces neuii, Actinomyces odontolyticus, Actinomyces radingae, Adlercreutzia equolifaciens, Aeromicrobium massiliense, Aggregatibacter actinomycetemcomitans, Akkermansia muciniphila, Aliagarivorans marinus, Alistipes finegoldii, Alistipes indistinctus, Alistipes inops, Alistipes onderdonkii, Alistipes putredinis, Alistipes senegalensis, Alistipes shahii, Alistipes timonensis, Alloscardovia omnicolens, Anaerobacter polyendosporus, Anaerobaculum hydrogeniformans, Anaerococcus hydrogenalis, Anaerococcus prevotii, Anaerococcus senegalensis, Anaerofustis stercorihominis, Anaerostipes caccae, Anaerostipes hadrus, Anaerotruncus colihominis, Aneurinibacillus aneurinilyticus, Bacillus licheniformis, Bacillus massilioanorexius, Bacillus massiliosenegalensis, Bacillus simplex, Bacillus smithii, Bacillus subtilis, Bacillus thuringiensis, Bacillus timonensis, Bacteroides xylanisolvens, Bacteroides acidifaciens, Bacteroides caccae, Bacteroides capillosus, Bacteroides cellulosilyticus, Bacteroides clarus, Bacteroides coprocola, Bacteroides coprophilus, Bacteroides dorei, Bacteroides eggerthii, Bacteroides faecis, Bacteroides finegoldii, Bacteroides fluxus, Bacteroides fragilis, Bacteroides gallinarum, Bacteroides intestinalis, Bacteroides nordii, Bacteroides oleiciplenus, Bacteroides ovatus, Bacteroides pectinophilus, Bacteroides plebeius, Bacteroides salanitronis, Bacteroides salyersiae, Bacteroides* sp., *Bacteroides stercoris, Bacteroides* thetaiotaomicron, *Bacteroides uniformis, Bacteroides vulgatus, Bacteroides xylanisolvens, Bacteroides pectinophilus* ATCC, *Barnesiella intestinihominis, Bavariicoccus seileri, Bifidobacterium adolescentis, Bifidobacterium angulatum, Bifidobacterium animalis, Bifidobacterium bifidum, Bifidobacterium breve, Bifidobacterium catenulatum, Bifidobacterium dentium, Bifidobacterium gallicum, Bifidobacterium longum, Bifidobacterium pseudocatenulatum, Bifidobacterium stercoris, Bilophila wadsworthia, Blautia faecis, Blautia hansenii,*

*Blautia hydrogenotrophica, Blautia luti, Blautia obeum, Blautia producta, Blautia wexlerae, Brachymonas chironomi, Brevibacterium senegalense, Bryantella formatexigens,* butyrate-producing bacterium, *Butyricicoccus pullicaecorum, Butyricimonas virosa, Butyrivibrio crossotus, Butyrivibrio fibrisolvens, Caldicoprobacter faecalis, Campylobacter concisus, Campylobacter jejuni, Campylobacter upsaliensis, Catenibacterium mitsuokai, Cedecea davisae, Cellulomonas massiliensis, Cetobacterium somerae, Citrobacter braakii, Citrobacter freundii, Citrobacter pasteurii, Citrobacter sp., Citrobacter youngae, Cloacibacillus evryensis,* Clostridiales bacterium, *Clostridioides difficile, Clostridium asparagiforme, Clostridium bartlettii, Clostridium boliviensis, Clostridium bolteae, Clostridium hathewayi, Clostridium hiranonis, Clostridium hylemonae, Clostridium leptum, Clostridium methylpentosum, Clostridium nexile, Clostridium orbiscindens, Clostridium ramosum, Clostridium scindens, Clostridium sp, Clostridium sp., Clostridium spiroforme, Clostridium sporogenes, Clostridium symbiosum, Collinsella aerofaciens, Collinsella intestinalis, Collinsella stercoris, Collinsella tanakaei, Coprobacillus cateniformis,* Coprobacter fastidiosus, *Coprococcus catus, Coprococcus comes, Coprococcus eutactus, Corynebacterium ammoniagenes, Corynebacterium amycolatum, Corynebacterium pseudodiphtheriticum, Cutibacterium acnes, Dermabacter hominis, Desulfitobacterium hafniense, Desulfovibrio fairfieldensis, Desulfovibrio piger, Dialister succinatiphilus,* Dielma fastidiosa, *Dorea formicigenerans, Dorea longicatena, Dysgonomonas capnocytophagoides, Dysgonomonas gadei, Dysgonomonas mossii, Edwardsiella tarda, Eggerthella lenta,* Eisenbergiella tayi, Enorma massiliensis, *Enterobacter aerogenes, Enterobacter asburiae, Enterobacter cancerogenus, Enterobacter cloacae, Enterobacter massiliensis, Enterococcus casseliflavus, Enterococcus durans, Enterococcus faecalis, Enterococcus faecium, Enterococcus flavescens, Enterococcus gallinarum, Enterococcus sp., Enterovibrio nigricans, Erysipelatoclostridium ramosum, Escherichia coli, Escherichia sp., Eubacterium biforme, Eubacterium dolichum, Eubacterium hallii, Eubacterium limosum, Eubacterium ramulus, Eubacterium rectale, Eubacterium siraeum, Eubacterium ventriosum, Exiguobacterium marinum, Exiguobacterium undae, Faecalibacterium cf, Faecalibacterium prausnitzii,* Faecalitalea cylindroides, *Ferrimonas balearica, Finegoldia magna, Flavobacterium daejeonense, Flavonifractor plautii,* Fusicatenibacter saccharivorans, *Fusobacterium gonidiaformans, Fusobacterium mortiferum, Fusobacterium necrophorum, Fusobacterium nucleatum, Fusobacterium periodonticum, Fusobacterium sp., Fusobacterium ulcerans, Fusobacterium varium, Gallibacterium anatis, Gemmiger formicilis, Gordonibacter pamelaeae, Hafnia alvei, Helicobacter bilis, Helicobacter bills, Helicobacter canadensis, Helicobacter canis, Helicobacter cinaedi, Helicobacter macacae, Helicobacter pametensis, Helicobacter pullorum, Helicobacter pylori, Helicobacter rodentium, Helicobacter winghamensis, Herbaspirillum massiliense, Holdemania biformis, Holdemania foliformis, Holdemania filiformis, Holdemania massiliensis, Holdemania filiformis,* Hungatella hathewayi, Intestinibacter bartlettii, Intestinimonas butyriciproducens, *Klebsiella oxytoca, Klebsiella pneumoniae,* Kurthia massiliensis, *Lachnospira pectinoschiza, Lactobacillus acidophilus, Lactobacillus amylolyticus, Lactobacillus animalis, Lactobacillus antri, Lactobacillus brevis, Lactobacillus buchneri, Lactobacillus casei, Lactobacillus curvatus, Lactobacillus delbrueckii, Lactobacillus fermentum, Lactobacillus gasseri, Lactobacillus helveticus, Lactobacillus hilgardii, Lactobacillus iners, Lactobacillus intestinalis, Lactobacillus johnsonii, Lactobacillus murinus, Lactobacillus paracasei, Lactobacillus plantarum, Lactobacillus reuteri, Lactobacillus rhamnosus, Lactobacillus ruminis, Lactobacillus sakei, Lactobacillus salivarius, Lactobacillus ultunensis, Lactobacillus vaginalis, Lactobacillus plantarum* subsp., *Leuconostoc mesenteroides, Leuconostoc pseudomesenteroides, Listeria grayi, Listeria innocua, Mannheimia granulomatis, Marvinbryantia formatexigens, Megamonas funiformis, Megamonas hypermegale, Methanobrevibacter smithii, Methanobrevibacter smithii* F1, *Micrococcus luteus, Microvirgula aerodenitrificans, Mitsuokella jalaludinii, Mitsuokella multacida,* Mollicutes bacterium, Murimonas intestini, *Neisseria macacae, Nitriliruptor alkaliphilus, Oceanobacillus massiliensis, Odoribacter laneus, Odoribacter splanchnicus, Ornithobacterium rhinotracheale, Oxalobacter formigenes, Paenibacillus barengoltzii, Paenibacillus chitinolyticus, Paenibacillus lautus, Paenibacillus motobuensis, Paenibacillus senegalensis, Paenisporosarcina quisquiliarum, Parabacteroides distasonis, Parabacteroides goldsteinii, Parabacteroides gordonii, Parabacteroides johnsonii, Parabacteroides merdae, Paraprevotella xylaniphila, Parasutterella excrementihominis, Parvimonas micra, Pediococcus acidilactici, Peptoclostridium difficile, Peptoniphilus harei, Peptoniphilus obesi, Peptoniphilus senegalensis, Peptoniphilus timonensis, Phascolarctobacterium succinatutens, Porphyromonas asaccharolytica, Porphyromonas uenonis, Prevotella baroniae, Prevotella bivia, Prevotella copri, Prevotella dentalis, Prevotella micans, Prevotella multisaccharivorax, Prevotella oralis, Prevotella salivae, Prevotella stercorea, Prevotella veroralis, Propionibacterium acnes, Propionibacterium avidum, Propionibacterium freudenreichii, Propionimicrobium lymphophilum, Proteus mirabilis, Proteus penneri* ATCC, *Providencia alcalifaciens, Providencia rettgeri, Providencia rustigianii, Providencia stuartii, Pseudoflavonifractor capillosus, Pseudomonas aeruginosa, Pseudomonas luteola, Ralstonia pickettii, Rheinheimera perlucida, Rheinheimera texasensis, Riemerella columbina,* Romboutsia lituseburensis, *Roseburia faecis, Roseburia intestinalis, Roseburia inulinivorans, Ruminococcus bicirculans, Ruminococcus bromii, Ruminococcus callidus, Ruminococcus champanellensis, Ruminococcus faecis, Ruminococcus gnavus, Ruminococcus lactaris, Ruminococcus obeum, Ruminococcus sp, Ruminococcus sp., Ruminococcus torques, Sarcina ventriculi,* Sellimonas intestinalis, Senegalimassilia anaerobia, *Shigella sonnei, Slackia piriformis, Staphylococcus epidermidis, Staphylococcus lentus, Staphylococcus nepalensis, Staphylococcus pseudintermedius, Staphylococcus xylosus, Stenotrophomonas maltophilia, Streptococcus agalactiae, Streptococcus anginosus, Streptococcus australis, Streptococcus caballi, Streptococcus castoreus, Streptococcus didelphis, Streptococcus equinus, Streptococcus gordonii, Streptococcus henryi, Streptococcus hyovaginalis, Streptococcus infantarius, Streptococcus infantis, Streptococcus lutetiensis, Streptococcus merionis, Streptococcus mitis, Streptococcus mutans, Streptococcus oralis, Streptococcus ovis, Streptococcus parasanguinis, Streptococcus plurextorum, Streptococcus porci, Streptococcus pyogenes, Streptococcus salivarius, Streptococcus sobrinus, Streptococcus thermophilus, Streptococcus thoraltensis, Streptomyces albus,* Subdoligranulum variabile, Succinatimonas hippei, Sutterella parvirubra, *Sutterella wadsworthensis,* Terrisporobacter glycolicus, Terrisporobacter mayombei, Thalassobacillus devorans, Timonella senegalensis, *Turicibacter sanguinis,* unknown sp, unknown sp., *Varibaculum cambriense, Veillonella*

*atypica, Veillonella dispar, Veillonella parvula, Vibrio cincinnatiensis, Virgibacillus salexigens* and/or *Weissella paramesenteroides*.

In other embodiments, the targeted bacteria cells are those commonly found on the skin microbiota and are without limitation *Acetobacter farinalis, Acetobacter malorum, Acetobacter orleanensis, Acetobacter sicerae, Achromobacter anxifer, Achromobacter denitrificans, Achromobacter marplatensis, Achromobacter spanius, Achromobacter xylosoxidans* subsp. *xylosoxidans, Acidovorax konjaci, Acidovorax radicis, Acinetobacter johnsonii, Actinomadura citrea, Actinomadura coerulea, Actinomadura fibrosa, Actinomadura fulvescens, Actinomadura jiaoheensis, Actinomadura luteofluorescens, Actinomadura mexicana, Actinomadura nitritigenes, Actinomadura verrucosospora, Actinomadura yumaensis, Actinomyces odontolyticus, Actinomycetospora* atypica, *Actinomycetospora corticicola, Actinomycetospora* rhizophila, *Actinomycetospora* rishiriensis, *Aeromonas australiensis, Aeromonas bestiarum, Aeromonas bivalvium, Aeromonas encheleia, Aeromonas eucrenophila, Aeromonas hydrophila* subsp. *hydrophila, Aeromonas piscicola, Aeromonas popoffii, Aeromonas rivuli, Aeromonas salmonicida* subsp. *pectinolytica, Aeromonas salmonicida* subsp. *smithia, Amaricoccus kaplicensis, Amaricoccus veronensis, Aminobacter aganoensis, Aminobacter ciceronei, Aminobacter lissarensis, Aminobacter niigataensis, Ancylobacter polymorphus, Anoxybacillus flavithermus* subsp. *yunnanensis, Aquamicrobium aerolatum,* Archangium gephyra, Archangium gephyra, Archangium minus, Archangium violaceum, *Arthrobacter* viscosus, *Bacillus anthracis, Bacillus* australimaris, *Bacillus drentensis, Bacillus* mycoides, *Bacillus* pseudomycoides, *Bacillus pumilus, Bacillus* safensis, *Bacillus* vallismortis, Bosea thiooxidans, *Bradyrhizobium* huanghuaihaiense, *Bradyrhizobium japonicum*, Brevundimonas aurantiaca, Brevundimonas intermedia, Burkholderia aspalathi, Burkholderia choica, Burkholderia cordobensis, Burkholderia diffusa, Burkholderia insulsa, Burkholderia rhynchosiae, Burkholderia terrestris, Burkholderia udeis, Buttiauxella gaviniae, Caenimonas terrae, Capnocytophaga gingivalis, Chitinophaga dinghuensis, Chryseobacterium gleum, *Chryseobacterium greenlandense*, Chryseobacterium jejuense, *Chryseobacterium piscium*, Chryseobacterium sediminis, Chryseobacterium tructae, *Chryseobacterium ureilyticum*, Chryseobacterium vietnamense, *Corynebacterium accolens, Corynebacterium afermentans* subsp. *lipophilum, Corynebacterium minutissimum, Corynebacterium sundsvallense, Cupriavidus metallidurans, Cupriavidus nantongensis, Cupriavidus necator, Cupriavidus pampae, Cupriavidus yeoncheonensis, Curtobacterium flaccumfaciens,* Devosia epidermidihirudinis, Devosia riboflavina, Devosia riboflavina, Diaphorobacter oryzae, Dietzia psychralcaliphila, Ensifer adhaerens, Ensifer americanus, Enterococcus malodoratus, Enterococcus pseudoavium, Enterococcus viikkiensis, Enterococcus xiangfangensis, Erwinia rhapontici, Falsirhodobacter halotolerans, Flavobacterium araucananum, Flavobacterium frigidimaris, Gluconobacter frateurii, Gluconobacter thailandicus, Gordonia alkanivorans, Halomonas aquamarina, Halomonas axialensis, Halomonas meridiana, Halomonas olivaria, Halomonas songnenensis, Halomonas variabilis, Herbaspirillum chlorophenolicum, Herbaspirillum frisingense, Herbaspirillum hiltneri, Herbaspirillum huttiense* subsp. *putei, Herbaspirillum lusitanum,* Herminiimonas fonticola, Hydrogenophaga intermedia, Hydrogenophaga pseudoflava, *Klebsiella oxytoca,* Kosakonia sacchari, *Lactobacillus delbrueckii* subsp. *bulgaricus, Lactobacillus modestisalitolerans, Lactobacillus plantarum* subsp. *argentoratensis, Lactobacillus xiangfangensis, Lechevalieria roselyniae, Lentzea albida, Lentzea californiensis, Leuconostoc carnosum, Leuconostoc citreum, Leuconostoc gelidum* subsp. *gasicomitatum, Leuconostoc mesenteroides* subsp. *suionicum, Luteimonas aestuarii, Lysobacter antibioticus, Lysobacter koreensis, Lysobacter oryzae, Magnetospirillum* moscoviense, *Marinomonas alcarazii, Marinomonas primoryensis, Massilia aurea, Massilia jejuensis, Massilia kyonggiensis, Massilia timonae, Mesorhizobium acaciae, Mesorhizobium qingshengii, Mesorhizobium shonense, Methylobacterium haplocladii, Methylobacterium platani, Methylobacterium pseudosasicola, Methylobacterium zatmanii, Microbacterium oxydan, Micromonospora chaiyaphumensis, Micromonospora chalcea, Micromonospora citrea, Micromonospora coxensis, Micromonospora echinofusca, Micromonospora halophytica, Micromonospora kangleipakensis, Micromonospora maritima, Micromonospora nigra, Micromonospora purpureochromogene, Micromonospora rhizosphaerae, Micromonospora saelicesensis, Microvirga subterranea, Microvirga zambiensis, Mycobacterium alvei, Mycobacterium avium* subsp. *silvaticum, Mycobacterium colombiense, Mycobacterium conceptionense, Mycobacterium conceptionense, Mycobacterium farcinogenes, Mycobacterium fortuitum* subsp. *fortuitum, Mycobacterium goodii, Mycobacterium insubricum, Mycobacterium llatzerense, Mycobacterium neoaurum, Mycobacterium neworleansense, Mycobacterium obuense, Mycobacterium peregrinum, Mycobacterium saopaulense, Mycobacterium septicum, Mycobacterium setense, Mycobacterium smegmatis, Neisseria subflava, Nocardia lijiangensis, Nocardia thailandica, Novosphingobium* barchaimii, *Novosphingobium* lindaniclasticum, *Novosphingobium* lindaniclasticum, *Novosphingobium mathurense, Ochrobactrum pseudogrignonense, Oxalicibacterium solurbis,* Paraburkholderia glathei, *Paraburkholderia humi, Paraburkholderia phenazinium, Paraburkholderia phytofirmans, Paraburkholderia sordidicola, Paraburkholderia terricola, Paraburkholderia xenovorans, Paracoccus* laeviglucosivorans, *Patulibacter ginsengiterrae, Polymorphospora rubra, Porphyrobacter colymbi, Prevotella jejuni, Prevotella melaninogenica, Propionibacterium acnes* subsp. *elongatum, Proteus vulgaris, Providencia rustigianii, Pseudoalteromonas agarivorans, Pseudoalteromonas atlantica, Pseudoalteromonas paragorgicola, Pseudomonas asplenii, Pseudomonas asuensis, Pseudomonas benzenivorans, Pseudomonas cannabina, Pseudomonas cissicola, Pseudomonas congelans, Pseudomonas costantinii, Pseudomonas ficuserectae, Pseudomonas frederiksbergensis, Pseudomonas graminis, Pseudomonas jessenii, Pseudomonas koreensis, Pseudomonas koreensis, Pseudomonas kunmingensis, Pseudomonas marginalis, Pseudomonas mucidolens, Pseudomonas panacis, Pseudomonas plecoglossicida, Pseudomonas poae, Pseudomonas pseudoalcaligenes, Pseudomonas putida, Pseudomonas reinekei, Pseudomonas rhizosphaerae, Pseudomonas seleniipraecipitans, Pseudomonas umsongensis, Pseudomonas zhaodongensis, Pseudonocardia alaniniphila, Pseudonocardia ammonioxydans, Pseudonocardia autotrophica, Pseudonocardia kongjuensis, Pseudonocardia yunnanensis, Pseudorhodoferax soli, Pseudoxanthomonas daejeonensis, Pseudoxanthomonas indica, Pseudoxanthomonas kaohsiungensis, Psychrobacter aquaticus, Psychrobacter arcticus, Psychrobacter celer, Psychrobacter marincola, Psychrobacter nivimaris, Psychrobacter okhotskensis, Psychrobacter okhotskensis, Psychrobacter piscatorii, Psychrobacter pulmonis, Ramlibacter ginsenosidimutans, Rheinheimera japonica, Rheinheimera* muenzenbergensis, *Rheinheimera soli, Rheinheimera tangshanensis, Rheinheimera texasensis, Rheinheimera tilapiae, Rhizobium alamii, Rhizobium azibense, Rhizobium binae, Rhizobium daejeonense, Rhizobium endophyticum, Rhizobium etli, Rhizobium fabae, Rhizobium freirei, Rhizobium gallicum, Rhizobium loessense, Rhizobium sophoriradicis, Rhizobium taibaishanense, Rhizobium vallis, Rhizobium vignae, Rhizobium vignae, Rhizobium yanglingense, Rhodococcus baikonurensis, Rhodococcus enclensis, Rhodoferax saidenbachensis, Rickettsia canadensis, Rickettsia heilongjiangensis, Rickettsia honei, Rickettsia raoultii, Roseateles aquatilis, Roseateles aquatilis, Salmonella enterica* subsp. *salamae, Serratia ficaria, Serratia myotis, Serratia vespertilionis, Shewanella aestuarii, Shewanella decolorationis, Sphingobium amiense, Sphingobium baderi, Sphingobium barthaii, Sphingobium chlorophenolicum, Sphingobium cupriresistens, Sphingobium czechense, Sphingobium fuliginis, Sphingobium indicum, Sphingobium indicum, Sphingobium japonicum, Sphingobium lactosutens, Sphingomonas dokdonensis, Sphingomonas pseudosanguinis, Sphingopyxis chilensis,* Sphingopyxis fribergensis, Sphingopyxis granuli, *Sphingopyxis indica,* Sphingopyxis witflariensis, Staphylococcus agnetis, *Staphylococcus aureus* subsp. *aureus, Staphylococcus epidermidis, Staphylococcus hominis* subsp. *novobiosepticus, Staphylococcus nepalensis, Staphylococcus saprophyticus* subsp. *bovis, Staphylococcus sciuri* subsp. *carnaticus, Streptomyces caeruleatus, Streptomyces canarius, Streptomyces capoamus, Streptomyces ciscaucasicus, Streptomyces griseorubiginosus, Streptomyces olivaceoviridis, Streptomyces panaciradicis, Streptomyces phaeopurpureus, Streptomyces pseudovenezuelae, Streptomyces resistomycificus, Tianweitania sediminis, Tsukamurella paurometabola, Variovorax guangxiensis, Vogesella alkaliphila, Xanthomonas arboricola, Xanthomonas axonopodis, Xanthomonas cassavae, Xanthomonas cucurbitae, Xanthomonas cynarae, Xanthomonas euvesicatoria, Xanthomonas fragariae, Xanthomonas gardneri, Xanthomonas perforans, Xanthomonas pisi, Xanthomonas populi, Xanthomonas vasicola, Xenophilus aerolatus, Yersinia nurmii, Abiotrophia defectiva, Acidocella aminolytica, Acinetobacter guangdongensis, Acinetobacter parvus, Acinetobacter radioresistens, Acinetobacter soli, Acinetobacter variabilis, Actinomyces cardiffensis, Actinomyces dentalis, Actinomyces europaeus, Actinomyces gerencseriae, Actinomyces graevenitzii, Actinomyces haliotis, Actinomyces johnsonii, Actinomyces massiliensis, Actinomyces meyeri, Actinomyces meyeri, Actinomyces naeslundii, Actinomyces* neuii subsp. *anitratus, Actinomyces odontolyticus, Actinomyces oris, Actinomyces turicensis, Actinomycetospora corticicola, Actinotignum schaalii, Aerococcus christensenii, Aerococcus urinae, Aeromicrobium flavum, Aeromicrobium massiliense, Aeromicrobium tamlense, Aeromonas sharmana, Aggregatibacter aphrophilus, Aggregatibacter segnis, Agrococcus baldri, Albibacter methylovorans, Alcaligenes faecalis* subsp. *faecalis, Algoriphagus ratkowskyi, Alkalibacterium olivapovliticus, Alkalibacterium pelagium, Alkalibacterium pelagium,* Alloprevotella rava, Alsobacter metallidurans, *Amaricoccus kaplicensis, Amaricoccus veronensis, Anaerococcus hydrogenalis, Anaerococcus lactolyticus, Anaerococcus murdochii, Anaerococcus octavius, Anaerococcus prevotii, Anaerococcus vaginalis, Aquabacterium citratiphilum, Aquabacterium olei, Aquabacterium olei, Aquabacterium parvum, Aquincola tertiaricarbonis, Arcobacter* venerupis, *Arsenicicoccus bolidensis, Arthrobacter russicus, Asticcacaulis excentricus, Atopobium deltae, Atopobium parvulum, Atopobium rimae, Atopobium vaginae, Aureimonas altamirensis, Aureimonas rubiginis, Azospira oryzae, Azospirillum oryzae, Bacillus circulans, Bacillus drentensis, Bacillus fastidiosus, Bacillus lehensis, Bacillus oceanisediminis, Bacillus rhizosphaerae, Bacteriovorax stolpii, Bacteroides coagulans, Bacteroides dorei, Bacteroides fragilis, Bacteroides ovatus, Bacteroides stercoris, Bacteroides uniformis, Bacteroides vulgatus, Bdellovibrio bacteriovorus, Bdellovibrio* exovorus, Belnapia moabensis, Belnapia soli, *Blautia hansenii, Blautia obeum, Blautia wexlerae,* Bosea lathyri, *Brachybacterium* fresconis, *Brachybacterium* muris, *Brevibacterium* ammoniilyticum, *Brevibacterium* casei, *Brevibacterium* epidermidis, *Brevibacterium* iodinum, *Brevibacterium* luteolum, *Brevibacterium* paucivorans, *Brevibacterium* pityocampae, *Brevibacterium* sanguinis, Brevundimonas albigilva, Brevundimonas diminuta, Brevundimonas vancanneytii, Caenimonas terrae, Calidifontibacter indicus, *Campylobacter concisus, Campylobacter gracilis, Campylobacter hominis,* Campylobacter rectus, Campylobacter showae, *Campylobacter ureolyticus,* Capnocytophaga gingivalis, *Capnocytophaga leadbetteri, Capnocytophaga ochracea, Capnocytophaga sputigena, Cardiobacterium* hominis, *Cardiobacterium valvarum, Carnobacterium divergens, Catonella morbi, Caulobacter henricii, Cavicella subterranea, Cellulomonas xylanilytica, Cellvibrio vulgaris, Chitinimonas taiwanensis, Chryseobacterium arachidis, Chryseobacterium daecheongense, Chryseobacterium formosense, Chryseobacterium formosense, Chryseobacterium greenlandense, Chryseobacterium indologenes, Chryseobacterium piscium, Chryseobacterium rigui, Chryseobacterium solani, Chryseobacterium taklimakanense, Chryseobacterium ureilyticum, Chryseobacterium ureilyticum, Chryseobacterium zeae, Chryseomicrobium aureum, Cloacibacterium haliotis, Cloacibacterium normanense, Cloacibacterium normanense, Collinsella aerofaciens, Comamonas denitrificans, Comamonas terrigena, Corynebacterium accolens, Corynebacterium afermentans* subsp. *lipophilum, Corynebacterium ammoniagenes, Corynebacterium amycolatum, Corynebacterium aurimucosum, Corynebacterium aurimucosum, Corynebacterium coyleae, Corynebacterium durum, Corynebacterium freiburgense, Corynebacterium glaucum, Corynebacterium glyciniphilum, Corynebacterium imitans, Corynebacterium jeikeium, Corynebacterium jeikeium, Corynebacterium kroppenstedtii, Corynebacterium lipophiloflavum, Corynebacterium massiliense, Corynebacterium mastitidis, Corynebacterium matruchotii, Corynebacterium minutissimum, Corynebacterium mucifaciens, Corynebacterium mustelae, Corynebacterium mycetoides, Corynebacterium pyruviciproducens, Corynebacterium simulans, Corynebacterium singulare, Corynebacterium sputi, Corynebacterium suicordis, Corynebacterium tuberculostearicum, Corynebacterium tuberculostearicum, Corynebacterium ureicelerivorans, Corynebacterium variabile, Couchioplanes caeruleus* subsp. *caeruleus, Cupriavidus metallidurans, Curtobacterium herbarum, Dechloromonas agitata, Deinococcus actinosclerus, Deinococcus antarcticus, Deinococcus caeni, Deinococcus ficus, Deinococcus geothermalis, Deinococcus radiodurans, Deinococcus wulumuqiensis, Deinococcus xinjiangensis, Dermabacter hominis, Dermabacter vaginalis, Dermacoccus nishinomiyaensis, Desemzia incerta, Desertibacter roseus, Dialister invisus, Dialister micraerophilus, Dialister propionicifaciens, Dietzia aurantiaca, Dietzia cercidiphylli, Dietzia timorensis, Dietzia timorensis, Dokdonella koreensis, Dokdonella koreensis, Dolosigranulum pigrum, Eikenella corrodens, Elizabethkingia miricola,* Elstera litoralis, *Empedobacter brevis, Enhydrobacter aerosaccus, Enterobacter* xiangfangensis, Enterococcus aquimarinus, Enterococcus faecalis, Enterococcus olivae, Erwinia rhapontici, Eubacterium eligens, Eubacterium infirmum, Eubacterium rectale, Eubacterium saphenum, Eubacterium sulci, Exiguobacterium mexicanum, Facklamia tabacinasalis, Falsirhodobacter halotolerans, Finegoldia magna, Flavobacterium cutihirudinis, Flavobacterium lindanitolerans, Flavobacterium resistens, Friedmanniella capsulata, Fusobacterium nucleatum subsp. polymorphum, Gemella haemolysans, Gemella morbillorum, Gemella palaticanis, Gemella sanguinis, Gemmobacter aquaticus, Gemmobacter caeni, Gordonia jinhuaensis, Gordonia kroppenstedtii, Gordonia polyisoprenivorans, Gordonia polyisoprenivorans, Granulicatella adiacens, Granulicatella elegans, Haemophilus parainfluenzae, Haemophilus sputorum, Halomonas sulfidaeris, Herpetosiphon aurantiacus, Hydrocarboniphaga effusa, Idiomarina maris, Janibacter anophelis, Janibacter hoylei, Janibacter indicus, Janibacter limosus, Janibacter melonis, Jeotgalicoccus halophilus, Jonquetella anthropi, Kaistia geumhonensis, Kingella denitrificans, Kingella oralis, Klebsiella oxytoca, Knoellia aerolata, Knoellia locipacati, Kocuria atrinae, Kocuria carniphila, Kocuria kristinae, Kocuria palustris, Kocuria turfanensis, Lachnoanaerobaculum saburreum, Lachnoanaerobaculum saburreum, Lactobacillus crispatus, Lactobacillus iners, Lactococcus lactis subsp. lactis, Lactococcus lactis subsp. lactis, Lactococcus piscium, Lapillicoccus jejuensis, Lautropia mirabilis, Legionella beliardensis, Leptotrichia buccalis, Leptotrichia goodfellowii, Leptotrichia hofstadii, Leptotrichia hongkongensis, Leptotrichia shahii, Leptotrichia trevisanii, Leptotrichia wadei, Luteimonas terricola, Lysinibacillus fusiformis, Lysobacter spongiicola, Lysobacter xinjiangensis, Macrococcus caseolyticus, Marmoricola pocheonensis, Marmoricola scoriae, Massilia alkalitolerans, Massilia alkalitolerans, Massilia aurea, Massilia plicata, Massilia timonae, Megamonas rupellensis, Meiothermus silvanus, Methylobacterium dankookense, Methylobacterium goesingense, Methylobacterium goesingense, Methylobacterium isbiliense, Methylobacterium jeotgali, Methylobacterium oxalidis, Methylobacterium platani, Methylobacterium pseudosasicola, Methyloversatilis universalis, Microbacterium foliorum, Microbacterium hydrothermale, Microbacterium hydrothermale, Microbacterium lacticum, Microbacterium lacticum, Microbacterium laevaniformans, Microbacterium paludicola, Microbacterium petrolearium, Microbacterium phyllosphaerae, Microbacterium resistens, Micrococcus antarcticus, Micrococcus cohnii, Micrococcus flavus, Micrococcus lylae, Micrococcus terreus, Microlunatus aurantiacus, Micropruina glycogenica, Microvirga aerilata, Microvirga aerilata, Microvirga subterranea, Microvirga vignae, Microvirga zambiensis, Microvirgula aerodenitrificans, Mogibacterium timidum, Moraxella atlantae, Moraxella catarrhalis, Morganella morganii subsp. morganii, Morganella psychrotolerans, Murdochiella asaccharolytica, Mycobacterium asiaticum, Mycobacterium chubuense, Mycobacterium crocinum, Mycobacterium gadium, Mycobacterium holsaticum, Mycobacterium iranicum, Mycobacterium longobardum, Mycobacterium neoaurum, Mycobacterium neoaurum, Mycobacterium obuense, Negativicoccus succinicivorans, Neisseria bacilliformis, Neisseria oralis, Neisseria sicca, Neisseria subflava, Nesterenkonia lacusekhoensis, Nesterenkonia rhizosphaerae, Nevskia persephonica, Nevskia ramosa, Niabella yanshanensis, Niveibacterium umoris, Nocardia niwae, Nocardia thailandica, Nocardioides agriphilus, Nocardioides dilutus, Nocardioides ganghwensis, Nocardioides hwasunensis, Nocardioides nanhaiensis, Nocardioides sediminis, Nosocomiicoccus ampullae, Noviherbaspirillum malthae, Novosphingobium lindaniclasticum, Novosphingobium rosa, Ochrobactrum rhizosphaerae, Olsenella uli, Ornithinimicrobium murale, Ornithinimicrobium tianjinense, Oryzobacter terrae, Ottowia beijingensis, Paenalcaligenes suwonensis, Paenibacillus agaridevorans, Paenibacillus phoenicis, Paenibacillus xylanexedens, Paludibacterium yongneupense, Pantoea cypripedii, Parabacteroides distasonis, Paraburkholderia andropogonis, Paracoccus alcaliphilus, Paracoccus angustae, Paracoccus kocurii, Paracoccus laeviglucosivorans, Paracoccus sediminis, Paracoccus sphaerophysae, Paracoccus yeei, Parvimonas micra, Parviterribacter multiflagellatus, Patulibacter ginsengiterrae, Pedobacter aquatilis, Pedobacter ginsengisoli, Pedobacter xixiisoli, Peptococcus niger, Peptoniphilus coxii, Peptoniphilus gorbachii, Peptoniphilus harei, Peptoniphilus koenoeneniae, Peptoniphilus lacrimalis, Peptostreptococcus anaerobius, Peptostreptococcus stomatis, Phascolarctobacterium faecium, Phenylobacterium haematophilum, Phenylobacterium kunshanense, Pluralibacter gergoviae, Polymorphobacter multimanifer, Porphyromonas bennonis, Porphyromonas endodontalis, Porphyromonas gingivalis, Porphyromonas gingivicanis, Porphyromonas pasteri, Porphyromonas pogonae, Porphyromonas somerae, Povalibacter uvarum, Prevotella aurantiaca, Prevotella baroniae, Prevotella bivia, Prevotella buccae, Prevotella buccalis, Prevotella copri, Prevotella corporis, Prevotella denticola, Prevotella enoeca, Prevotella histicola, Prevotella intermedia, Prevotella jejuni, Prevotella jejuni, Prevotella maculosa, Prevotella melaninogenica, Prevotella melaninogenica, Prevotella micans, Prevotella multiformis, Prevotella nanceiensis, Prevotella nigrescens, Prevotella oris, Prevotella oulorum, Prevotella pallens, Prevotella pleuritidis, Prevotella saccharolytica, Prevotella salivae, Prevotella shahii, Prevotella timonensis, Prevotella veroralis, Propionibacterium acidifaciens, Propionibacterium acnes subsp. acnes, Propionibacterium acnes subsp. acnes, Propionibacterium acnes subsp. elongatum, Propionibacterium granulosum, Propionimicrobium lymphophilum, Propionispira arcuata, Pseudokineococcus lusitanus, Pseudomonas aeruginosa, Pseudomonas chengduensis, Pseudonocardia benzenivorans, Pseudorhodoplanes sinuspersici, Psychrobacter sanguinis, Ramlibacter ginsenosidimutans, Rheinheimera aquimaris, Rhizobium alvei, Rhizobium daejeonense, Rhizobium larrymoorei, Rhizobium rhizoryzae, Rhizobium soli, Rhizobium taibaishanense, Rhizobium vignae, Rhodanobacter glycinis, Rhodobacter veldkampii, Rhodococcus enclensis, Rhodococcus fascians, Rhodococcus fascians, Rhodovarius lipocyclicus, Rivicola pingtungensis, Roseburia inulinivorans, Rosenbergiella nectarea, Roseomonas aerilata, Roseomonas aquatica, Roseomonas mucosa, Roseomonas rosea, Roseomonas vinacea, Rothia aeria, Rothia amarae, Rothia dentocariosa, Rothia endophytica, Rothia mucilaginosa, Rothia nasimurium, Rubellimicrobium mesophilum, Rubellimicrobium roseum, Rubrobacter bracarensis, Rudaea cellulosilytica, Ruminococcus gnavus, Runella zeae, Saccharopolyspora rectivirgula, Salinicoccus qingdaonensis, Scardovia wiggsiae, Sediminibacterium ginsengisoli, Selenomonas artemidis, Selenomonas infelix, Selenomonas noxia, Selenomonas sputigena, Shewanella aestuarii, Shuttleworthia satelles, Simonsiella muelleri, Skermanella aerolata, Skermanella stibiiresistens, Slackia exigua, Smaragdicoccus niigatensis, Sneathia sanguinegens, Solirubrobacter soli, Sphingobacterium caeni, Sphingobacterium daejeonense, Sphingobacterium hotanense, Sphingobacterium kyonggiense, Sphingobacterium multivorum, Sphingobacterium nematocida,

*Sphingobacterium spiritivorum, Sphingobium amiense, Sphingobium indicum, Sphingobium lactosutens, Sphingobium subterraneum, Sphingomonas abaci, Sphingomonas aestuarii, Sphingomonas canadensis, Sphingomonas daechungensis, Sphingomonas dokdonensis, Sphingomonas echinoides, Sphingomonas fonticola, Sphingomonas fonticola, Sphingomonas formosensis, Sphingomonas gei, Sphingomonas hankookensis, Sphingomonas hankookensis, Sphingomonas koreensis, Sphingomonas kyeonggiensis, Sphingomonas laterariae, Sphingomonas mucosissima, Sphingomonas oligophenolica, Sphingomonas pseudosanguinis, Sphingomonas sediminicola, Sphingomonas yantingensis, Sphingomonas yunnanensis, Sphingopyxis indica, Spirosoma rigui, Sporacetigenium mesophilum, Sporocytophaga myxococcoides, Staphylococcus auricularis, Staphylococcus epidermidis, Staphylococcus epidermidis, Staphylococcus hominis subsp. novobiosepticus, Staphylococcus lugdunensis, Staphylococcus pettenkoferi, Stenotrophomonas koreensis, Stenotrophomonas rhizophila, Stenotrophomonas rhizophila, Streptococcus agalactiae, Streptococcus canis, Streptococcus cristatus, Streptococcus gordonii, Streptococcus infantis, Streptococcus intermedius, Streptococcus mutans, Streptococcus oligofermentans, Streptococcus oralis, Streptococcus sanguinis, Streptomyces iconiensis, Streptomyces yanglinensis,* Tabrizicola aquatica, *Tahibacter caeni, Tannerella forsythia, Tepidicella xavieri, Tepidimonas fonticuli, Terracoccus luteus, Tessaracoccus flavescens, Thermus thermophilus, Tianweitania sediminis, Tianweitania sediminis, Treponema amylovorum, Treponema denticola, Treponema lecithinolyticum, Treponema medium, Turicella otitidis, Turicibacter sanguinis, Undibacterium oligocarboniphilum, Undibacterium squillarum, Vagococcus salmoninarum, Varibaculum cambriense, Vibrio metschnikovii, Xanthobacter tagetidis, Xenophilus aerolatus, Xenophilus* arseniciresistens, *Yimella lutea, Zimmermannella alba, Zimmermannella bifida* and/or *Zoogloea caeni.*

In other embodiments, the targeted bacteria cells are those commonly found in the vaginal microbiota and are, without limitation, *Acinetobacter antiviralis, Acinetobacter baumannii, Acinetobacter calcoaceticus, Acinetobacter johnsonii, Actinobaculum massiliense, Actinobaculum schaalii, Actinomyces europaeus, Actinomyces graevenitzii, Actinomyces israelii, Actinomyces meyeri, Actinomyces naeslundii, Actinomyces neuii, Actinomyces odontolyticus, Actinomyces turicensis, Actinomyces urogenitalis, Actinomyces viscosus, Aerococcus christensenii, Aerococcus urinae, Aerococcus viridans, Aeromonas encheleia, Aeromonas salmonicida, Afipia massiliensis, Agrobacterium tumefaciens, Algoriphagus aquatilis, Aliivibrio wodanis, Alistipes finegoldii, Alloiococcus otitis, Alloprevotella tannerae, Alloscardovia omnicolens, Altererythrobacter epoxidivorans, Ammoniphilus oxalaticus, Amnibacterium kyonggiense, Anaerococcus hydrogenalis, Anaerococcus lactolyticus, Anaerococcus murdochii, Anaerococcus obesiensis, Anaerococcus prevotii, Anaerococcus tetradius, Anaerococcus vaginalis, Anaeroglobus geminatus, Anoxybacillus pushchinoensis, Aquabacterium parvum, Arcanobacterium phocae, Arthrobacter aurescens, Asticcacaulis excentricus, Atopobium minutum, Atopobium parvulum, Atopobium rimae, Atopobium vaginae, Avibacterium gallinarum, Bacillus acidicola, Bacillus atrophaeus, Bacillus cereus, Bacillus cibi, Bacillus coahuilensis, Bacillus gaemokensis, Bacillus methanolicus, Bacillus oleronius, Bacillus pumilus, Bacillus shackletonii, Bacillus sporothermodurans, Bacillus subtilis, Bacillus wakoensis, Bacillus weihenstephanensis, Bacteroides barnesiae, Bacteroides coagulans, Bacteroides dorei, Bacteroides faecis, Bacteroides forsythus, Bacteroides fragilis, Bacteroides nordii, Bacteroides ovatus, Bacteroides salyersiae, Bacteroides stercoris, Bacteroides uniformis, Bacteroides vulgatus, Bacteroides xylanisolvens, Bacteroides zoogleoformans, Barnesiella viscericola, Bhargavaea cecembensis, Bifidobacterium adolescentis, Bifidobacterium bifidum, Bifidobacterium breve, Bifidobacterium dentium, Bifidobacterium logum subsp. infantis, Bifidobacterium longum, Bifidobacterium pseudocatenulatum, Bifidobacterium scardovii, Bilophila wadsworthia, Blautia hydrogenotrophica, Blautia obeum, Blautia producta, Brachybacterium faecium, Bradyrhizobium japonicum, Brevibacterium mcbrellneri, Brevibacterium otitidis, Brevibacterium paucivorans, Bulleidia extructa, Burkholderia fungorum, Burkholderia phenoliruptix, Caldicellulosiruptor saccharolyticus, Caldimonas taiwanensis, Campylobacter gracilis, Campylobacter hominis, Campylobacter sputorum, Campylobacter ureolyticus, Capnocytophaga ochracea, Cardiobacterium hominis, Catonella morbi, Chlamydia trachomatis, Chlamydophila abortus, Chondromyces robustus, Chryseobacterium aquaticum, Citrobacter youngae, Cloacibacterium normanense, Clostridium cavendishii, Clostridium colicanis, Clostridium jejuense, Clostridium perfringens, Clostridium ramosum, Clostridium sordellii, Clostridium viride, Comamonas terrigena, Corynebacterium accolens, Corynebacterium appendicis, Corynebacterium coyleae, Corynebacterium glucuronolyticum, Corynebacterium glutamicum, Corynebacterium jeikeium, Corynebacterium kroppenstedtii, Corynebacterium lipophiloflavum, Corynebacterium minutissimum, Corynebacterium mucifaciens, Corynebacterium nuruki, Corynebacterium pseudogenitalium, Corynebacterium pyruviciproducens, Corynebacterium singulare, Corynebacterium striatum, Corynebacterium tuberculostearicum, Corynebacterium xerosis, Cryobacterium psychrophilum, Curtobacterium flaccumfaciens, Cutibacterium acnes, Cutibacterium avidum, Cytophaga xylanolytica, Deinococcus radiophilus, Delftia tsuruhatensis, Desulfovibrio desulfuricans, Dialister invisus, Dialister micraerophilus, Dialister pneumosintes, Dialister propionicifaciens, Dickeya chrysanthemi, Dorea longicatena, Eggerthella lenta, Eggerthia catenaformis, Eikenella corrodens, Enhydrobacter aerosaccus, Enterobacter asburiae, Enterobacter cloacae, Enterococcus avium, Enterococcus durans, Enterococcus faecalis, Enterococcus faecium, Enterococcus hirae, Erwinia persicina, Erwinia rhapontici, Erwinia toletana, Escherichia coli, Escherichia fergusonii, Eubacterium brachy, Eubacterium eligens, Eubacterium nodatum, Eubacterium rectale, Eubacterium saphenum, Eubacterium siraeum, Eubacterium sulci, Eubacterium yurii, Exiguobacterium acetylicum, Facklamia ignava, Faecalibacterium prausnitzii, Filifactor alocis, Finegoldia magna, Fusobacterium gonidiaformans, Fusobacterium nucleatum, Fusobacterium periodonticum, Gardnerella vaginalis, Gemella asaccharolytica, Gemella bergeri, Gemella haemolysans, Gemella sanguinis, Geobacillus stearothermophilus, Geobacillus thermocatenulatus, Geobacillus thermoglucosidasius, Geobacter grbiciae, Granulicatella elegans, Haemophilus ducreyi, Haemophilus haemolyticus, Haemophilus parahaemolyticus, Haemophilus parainfluenzae, Hafnia alvei, Halomonas meridiana, Halomonas phoceae, Halomonas venusta, Herbaspirillum seropedicae, Janthinobacterium lividum, Jonquetella anthropi, Klebsiella granulomatis, Klebsiella oxytoca, Klebsiella pneumoniae, Lactobacillus acidophilus, Lactobacillus amylovorus, Lactobacillus brevis, Lactobacillus coleohominis, Lactobacillus crispatus, Lactobacillus curvatus, Lactobacillus delbrueckii, Lactobacillus fermentum, Lactobacil-* lus gasseri, Lactobacillus helveticus, Lactobacillus iners, Lactobacillus jensenii, Lactobacillus johnsonii, Lactobacillus kalixensis, Lactobacillus kefiranofaciens, Lactobacillus kimchicus, Lactobacillus kitasatonis, Lactobacillus mucosae, Lactobacillus panis, Lactobacillus paracasei, Lactobacillus plantarum, Lactobacillus pontis, Lactobacillus reuteri, Lactobacillus rhamnosus, Lactobacillus salivarius, Lactobacillus ultunensis, Lactobacillus vaginalis, Lactococcus lactis, Leptotrichia buccalis, Leuconostoc carnosum, Leuconostoc citreum, Leuconostoc garlicum, Leuconostoc lactis, Leuconostoc mesenteroides, Lysinimonas kribbensis, Mageeibacillus indolicus, Maribacter orientalis, Marinomonas protea, Marinospirillum insulare, Massilia timonae, Megasphaera elsdenii, Megasphaera micronuciformis, Mesorhizobium amorphae, Methylobacterium radiotolerans, Methylotenera versatilis, Microbacterium halophilum, Micrococcus luteus, Microterricola viridarii, Mobiluncus curtisii, Mobiluncus mulieris, Mogibacterium timidum, Moorella glycerini, Moraxella osloensis, Morganella morganii, Moryella indoligenes, Murdochiella asaccharolytica, Mycoplasma alvi, Mycoplasma genitalium, Mycoplasma hominis, Mycoplasma muris, Mycoplasma salivarium, Negativicoccus succinicivorans, Neisseria flava, Neisseria gonorrhoeae, Neisseria mucosa, Neisseria subflava, Nevskia ramosa, Nevskia soli, Nitriliruptor alkaliphilus, Odoribacter splanchnicus, Oligella urethralis, Olsenella uli, Paenibacillus amylolyticus, Paenibacillus humicus, Paenibacillus pabuli, Paenibacillus pasadenensis, Paenibacillus pini, Paenibacillus validus, Pantoea agglomerans, Parabacteroides merdae, Paraburkholderia caryophylli, Paracoccus yeei, Parastreptomyces abscessus, Parvimonas micra, Pectobacterium betavasculorum, Pectobacterium carotovorum, Pediococcus acidilactici, Pediococcus ethanolidurans, Pedobacter alluvionis, Pedobacter wanjuense, Pelomonas aquatica, Peptococcus niger, Peptoniphilus asaccharolyticus, Peptoniphilus gorbachii, Peptoniphilus harei, Peptoniphilus indolicus, Peptoniphilus lacrimalis, Peptoniphilus massiliensis, Peptostreptococcus anaerobius, Peptostreptococcus massiliae, Peptostreptococcus stomatis, Photobacterium angustum, Photobacterium frigidiphilum, Photobacterium phosphoreum, Porphyromonas asaccharolytica, Porphyromonas bennonis, Porphyromonas catoniae, Porphyromonas endodontalis, Porphyromonas gingivalis, Porphyromonas somerae, Porphyromonas uenonis, Prevotella amnii, Prevotella baroniae, Prevotella bergensis, Prevotella bivia, Prevotella buccae, Prevotella buccalis, Prevotella colorans, Prevotella copri, Prevotella corporis, Prevotella dentalis, Prevotella denticola, Prevotella disiens, Prevotella intermedia, Prevotella loescheii, Prevotella marshii, Prevotella melaninogenica, Prevotella micans, Prevotella nigrescens, Prevotella oris, Prevotella pleuritidis, Prevotella ruminicola, Prevotella shahii, Prevotella stercorea, Prevotella timonensis, Prevotella veroralis, Propionimicrobium lymphophilum, Proteus mirabilis, Pseudomonas abietaniphila, Pseudomonas aeruginosa, Pseudomonas amygdali, Pseudomonas azotoformans, Pseudomonas chlororaphis, Pseudomonas cuatrocienegasensis, Pseudomonas fluorescens, Pseudomonas fulva, Pseudomonas lutea, Pseudomonas mucidolens, Pseudomonas oleovorans, Pseudomonas orientalis, Pseudomonas pseudoalcaligenes, Pseudomonas psychrophila, Pseudomonas putida, Pseudomonas synxantha, Pseudomonas syringae, Pseudomonas tolaasii, Pseudopropionibacterium propionicum, Rahnella aquatilis, Ralstonia pickettii, Ralstonia solanacearum, Raoultella planticola, Rhizobacter dauci, Rhizobium etli, Rhodococcus fascians, Rhodopseudomonas palustris, Roseburia intestinalis, Roseburia inulinivorans, Rothia mucilaginosa, Ruminococcus bromii, Ruminococcus gnavus, Ruminococcus torques, Sanguibacter keddieii, Sediminibacterium salmoneum, Selenomonas bovis, Serratia fonticola, Serratia liquefaciens, Serratia marcescens, Shewanella algae, Shewanella amazonensis, Shigella boydii, Shigella sonnei, Slackia exigua, Sneathia amnii, Sneathia sanguinegens, Solobacterium moorei, Sorangium cellulosum, Sphingobium amiense, Sphingobium japonicum, Sphingobium yanoikuyae, Sphingomonas wittichii, Sporosarcina aquimarina, Staphylococcus aureus, Staphylococcus auricularis, Staphylococcus capitis, Staphylococcus epidermidis, Staphylococcus haemolyticus, Staphylococcus hominis, Staphylococcus lugdunensis, Staphylococcus saprophyticus, Staphylococcus schleiferi, Staphylococcus simiae, Staphylococcus simulans, Staphylococcus warneri, Stenotrophomonas maltophilia, Stenoxybacter acetivorans, Streptococcus agalactiae, Streptococcus anginosus, Streptococcus australis, Streptococcus equinus, Streptococcus gallolyticus, Streptococcus infantis, Streptococcus intermedius, Streptococcus lutetiensis, Streptococcus marimammalium, Streptococcus mitis, Streptococcus mutans, Streptococcus oralis, Streptococcus parasanguinis, Streptococcus phocae, Streptococcus pseudopneumoniae, Streptococcus salivarius, Streptococcus sanguinis, Streptococcus thermophilus, Sutterella wadsworthensis, Tannerella forsythia, Terrahaemophilus aromaticivorans, Treponema denticola, Treponema maltophilum, Treponema parvum, Treponema vincentii, Trueperella bernardiae, Turicella otitidis, Ureaplasma parvum, Ureaplasma urealyticum, Varibaculum cambriense, Variovorax paradoxus, Veillonella atypica, Veillonella dispar, Veillonella montpellierensis, Veillonella parvula, Virgibacillus proomii, Viridibacillus arenosi, Viridibacillus arvi, Weissella cibaria, Weissella soli, Xanthomonas campestris, Xanthomonas vesicatoria, Zobellia laminariae and/or Zoogloea ramigera.

In one embodiment, the targeted bacteria are *Escherichia coli*.

In one embodiment, the targeted bacteria are *Cutibacterium acnes* more specifically the acne related *Cutibacterium acnes* from the phylogroup IA1 or RT4, RT5, RT8, RT9, RT10 or Clonal Complex(CC) CC1, CC3, CC4, more specifically the ST1, ST3, ST4.

Thus, the first type of bacteriophage disclosed herein, and therefore the phage particles or phage-derived delivery particles of the invention, may target (e.g., specifically target) a bacterial cell from any one or more of the foregoing genus and/or species of bacteria in particular to specifically deliver the payload.

In one embodiment, the targeted bacteria are pathogenic bacteria. The targeted bacteria can be virulent bacteria.

The targeted bacteria can be antibacterial resistance bacteria, preferably selected from the group consisting of extended-spectrum beta-lactamase-producing (ESBL) *Escherichia coli*, ESBL *Klebsiella pneumoniae*, vancomycin-resistant *Enterococcus* (VRE), methicillin-resistant *Staphylococcus aureus* (MRSA), multidrug-resistant (MDR) *Acinetobacter baumannii*, MDR *Enterobacter* spp., and a combination thereof. Preferably, the targeted bacteria can be selected from the group consisting of extended-spectrum beta-lactamase-producing (ESBL) *Escherichia coli* strains.

Alternatively, the targeted bacterium can be a bacterium of the microbiome of a given species, preferably a bacterium of the human microbiota.

In a particular embodiment, said targeted bacterial cells are from a species or strain different from the production bacterial cell.

Hybrid Helper Phage System and Hybrid Helper Phage

The present invention also concerns a hybrid helper phage system comprising:
- (i) at least one phage DNA packaging gene(s), as defined in the section "Production bacterial cell" above, derived from a first type of bacteriophage, as defined in the section "Bacteriophage and gene derived from a bacteriophage" above,
- (i') at least one phage structural gene(s), as defined in the section "Production bacterial cell" above, derived from said first type of bacteriophage, and
- (ii) at least one gene, derived from a second type of bacteriophage, as defined in the section "Bacteriophage and gene derived from a bacteriophage" above, involved in phage excision/insertion, phage DNA replication, and/or phage regulation, as defined in the section "Production bacterial cell" above, wherein said genes (i), (i') and (ii) are comprised in a unique nucleic acid molecule or in separate nucleic acid molecules, wherein said first type of bacteriophage comes from and/or target bacterial species or strain different from the bacterial species or strain from which said second type of bacteriophage comes and/or that said second type of bacteriophage targets, and wherein said hybrid helper phage system does not comprise any expressed phage structural gene, as defined in the section "Production bacterial cell" above, derived from said second type of bacteriophage.

In the context of the invention, the term "hybrid helper phage system" is meant a group of at least one nucleic acid molecule, preferably of at least two separate nucleic acid molecules, comprising the genes (i), (i') and (ii) defined above, which enables the production of phage particles and/or phage-derived delivery vehicles by the production bacterial cell comprising said system, wherein when the system comprises at least two separate nucleic acid molecules, said genes (i), (i') and (ii) are distributed on said at least two separate nucleic acid molecules.

As used herein, the term "nucleic acid" refers to a sequence of at least two nucleotides covalently linked together which can be single-stranded or double-stranded or contains portion of both single-stranded and double-stranded sequence. Nucleic acids of the present invention can be naturally occurring, recombinant or synthetic. The nucleic acid can be in the form of a circular sequence or a linear sequence or a combination of both forms. The nucleic acid can be DNA, both genomic or cDNA, or RNA or a combination of both. The nucleic acid may contain any combination of deoxyribonucleotides and ribonucleotides, and any combination of bases, including uracil, adenine, thymine, cytosine, guanine, inosine, xanthine, hypoxanthine, isocytosine, 5-hydroxymethylcytosine and isoguanine. Other examples of modified bases that can be used in the present invention are detailed in Weigele et al. Chem Rev. 2016 Oct. 26; 116(20):12655-12687. The term "nucleic acid" also encompasses any nucleic acid analogs which may contain other backbones comprising, without limitation, phosphoramide, phosphorothioate, phosphorodithioate, O-methylphophoroamidite linkage and/or deoxyribonucleotides and ribonucleotides nucleic acids. Any combination of the above features of a nucleic acid is also encompassed by the present invention.

In a particular embodiment, said genes (i), (i') and (ii) are comprised in a bacterial chromosome, in particular in a production bacterial cell chromosome. In a more particular embodiment, said genes (i), (i') and (ii) are comprised in a bacterial chromosome in a same region. In an alternative embodiment, said genes (i), (i') and (ii) are comprised in a bacterial chromosome in distinct regions.

In an alternative embodiment, said genes (i), (i') and (ii) are comprised in separate plasmids. In another particular embodiment, said genes (i), (i') and (ii) are all comprised in a same plasmid.

In another particular embodiment, said genes (i), (i') and (ii) are each independently comprised in a bacterial chromosome or in a plasmid.

In a more particular embodiment, said genes (i), (i') and (ii) are comprised in a hybrid helper phage.

Therefore, in a particular embodiment, said hybrid helper phage system consists of a hybrid helper phage comprising:
- (i) at least one phage DNA packaging gene(s) and at least one phage structural gene(s), as defined in the section "Production bacterial cell" above, derived from a first type of bacteriophage, as defined in the section "Bacteriophage and gene derived from a bacteriophage" above, and
- (ii) at least one gene, derived from a second type of bacteriophage, as defined in the section "Bacteriophage and gene derived from a bacteriophage" above, involved in phage excision/insertion, phage DNA replication, and/or phage regulation, as defined in the section "Production bacterial cell" above, wherein said first type of bacteriophage comes from and/or target bacterial species or strain different from the bacterial species or strain from which said second type of bacteriophage comes and/or that said second type of bacteriophage targets, and wherein said hybrid helper phage does not comprise any phage structural gene, as defined in the section "Production bacterial cell" above, derived from said second type of bacteriophage.

By "helper phage" is meant herein an engineered phage providing all the necessary gene products for particle formation when using phagemid vectors. Helper phages typically have a defective origin of replication or packaging signal, and hence, are inefficient in self-packaging.

By "hybrid helper phage" is meant herein an engineered helper phage which is constituted of elements derived from at least two different types of bacteriophage.

In a particular embodiment, the hybrid helper phage of the invention is integrated in the genome of the production bacterial cell as a prophage.

Production Method

The present invention further concerns a method for producing phage particles or phage-derived delivery vehicles, comprising:
- (a) providing the production bacterial cell of the invention, and
- (b) inducing, in said production bacterial cell, expression of said at least one of said phage structural gene(s) and at least one of said phage DNA packaging gene(s), and assembly of the products expressed by said at least one phage structural gene(s) and said at least one phage DNA packaging gene(s), thereby producing phage particles or phage-derived delivery vehicles.

The inducing step (b) can be carried out by any technique well-known from the skilled person. In particular, as will be understood by the skilled person, said inducing step will depend on the particular induction mechanism controlling the expression of said at least one of said phage structural genes and phage DNA packaging genes, in said production bacterial cell.

More particularly, it will be understood by the skilled person that, when said induction mechanism comprises at least one gene, derived from a second type of bacteriophage, involved in phage excision/insertion, phage DNA replication, and/or phage regulation, said inducing step will depend on the bacteriophage from which said sequences are derived. Typically, said inducing step can be a thermal induction (for phages that are naturally triggered by this signal or engineered repressors such as lambda cl), small molecule inducers (depending on the phage), any signal triggering SOS response (for instance addition of mitomycin), etc.

Production of Tailocin and/or Pyocin

The approach disclosed above can also be applied to the production of tailocins and/or pyocins, enabling the safe and efficient production of such bacteriocins in manipulable production cells.

The present invention thus also concerns a production bacterial cell for producing tailocin and/or pyocin, said production bacterial cell stably comprising at least one tailocin and/or pyocin structural gene(s) derived from a bacterial species or strain containing tailocin and/or pyocin genes, wherein the expression of at least one of said tailocin and/or pyocin structural gene(s) in said production bacterial cell is controlled by at least one induction mechanism, and wherein said production bacterial cell is from a bacterial species or strain different from the bacterial species or strain containing tailocin and/or pyocin genes from which said tailocin and/or pyocin structural gene(s) is derived.

By "tailocin" is meant herein a multisubunit bacteriocin that resembles bacteriophage tails. There are two classes of tailocin particles, the flexible noncontractile F-tailocins and the rigid contractile R-tailocins, which resemble and are evolutionarily related to Siphoviridae and Myoviridae phage tails, respectively. Examples of tailocins typically include F-type and R-type pyocins, carotovoricin, xenorhabdicin, and maltocin.

By "pyocin" is meant herein a bacteriocin formed by Pseudomonas aeruginosa. They can be produced spontaneously or induced by certain chemicals, such as mitomycin C. Three different types of pyocins have been identified: R-type, S-type, and F-type (Nakayama et al., (2000) Mol. Microbiol. 38:213-231). They differ by their morphology and mode of killing. Their bactericidal activities are strain specific. R-type pyocins resemble inflexible and contractile tails of bacteriophages, belong to the tailocins disclosed above, and are further classified into five groups: R1, R2, R3, R4, and R5. F-type pyocins also resemble phage tails, flexible but noncontractile rod-like structure, with distal filaments, and also belong to the tailocins disclosed above. They are similar in structure and serological properties, but they are different in receptor specificities. Three subtypes of F-type pyocins were reported: F1, F2, and F3. In a particular embodiment, said pyocin is a R-type or F-type pyocin.

By "tailocin and/or pyocin structural gene" is meant herein genes from a tailocin and/or pyocin producing bacteria which are involved in the building of the tailocin and/or pyocin. Tailocin and/or pyocin structural genes include genes encoding the subunits and/or components of said tailocin and/or pyocin, as disclosed above, and genes encoding bacterial proteins involved in the assembly of the tailocin and/or pyocin subunits and/or components.

In a particular embodiment, said tailocin and/or pyocin structural genes are pyocin structural genes as defined above. In that embodiment, said bacterial species or strain containing tailocin and/or pyocin genes from which said pyocin structural genes are derived, is preferably a Pseudomonas aeruginosa bacteria.

In a particular embodiment, said tailocin and/or pyocin structural genes are tailocin structural genes as defined above. In that embodiment, said bacterial species or strain containing tailocin and/or pyocin genes from which said tailocin structural genes are derived, is preferably selected from the bacteria, defined in the section "Targeted bacteria" above, which naturally contain said tailocin structural genes, and preferably produce tailocins.

In a particular embodiment, said tailocin and/or pyocin structural gene(s) are comprised in at least one plasmid, chromosome, and/or helper phage.

In the context of the invention, said induction mechanism is as defined in the section "Production bacterial cell" above.

More particularly, in an embodiment, the at least one induction mechanism controls the expression of all said tailocin and/or pyocin structural gene(s).

In a particular embodiment, said at least one induction mechanism further controls the copy number of said at least one of said tailocin and/or pyocin structural gene(s).

In a particular embodiment, said at least one induction mechanism comprises at least one gene involved in tailocin and/or pyocin regulation, said gene involved in tailocin and/or pyocin regulation being derived from a bacterial species or strain containing tailocin and/or pyocin genes which are different from those from which said tailocin and/or pyocin structural genes are derived.

Therefore in a particular embodiment, said production bacterial cell further comprises at least one gene involved in tailocin and/or pyocin regulation, said gene involved in tailocin and/or pyocin regulation being derived from a bacterial species or strain containing tailocin and/or pyocin genes which are different from those from which said tailocin and/or pyocin structural genes are derived.

By "gene involved in tailocin and/or pyocin regulation" is meant herein genes encoding regulatory elements controlling induction and/or expression of tailocin and/or pyocin in a natural tailocin and/or producing bacterial cell.

Alternatively, said at least one induction mechanism comprises at least one gene, derived from a bacteriophage, as defined in the section "Bacteriophage and gene derived from a bacteriophage" above, involved in phage excision/insertion, phage DNA replication, and/or phage regulation, as defined in the section "Production bacterial cell" above, said bacteriophage coming from and/or targeting bacterial species or strain different from the bacterial species or strain from which said tailocin and/or pyocin structural gene(s) is derived.

Therefore, in a particular embodiment, said production bacterial cell further comprises at least one gene, derived from a bacteriophage, as defined in the section "Bacteriophage and gene derived from a bacteriophage" above, involved in phage excision/insertion, phage DNA replication, and/or phage regulation, as defined in the section "Production bacterial cell" above, said bacteriophage coming from and/or targeting bacterial species or strain different from the bacterial species or strain from which said tailocin and/or pyocin structural gene(s) is derived.

In a particular embodiment, said tailocin and/or pyocin is intended to lyse targeted bacterial cells, as defined in the section "Targeted bacterial cells" above.

In a particular embodiment, said targeted bacterial cells are from a species or strain different from the production bacterial cell.

In a particular embodiment, said production bacterial cell is from the same bacterial species or strain as the bacterial species or strain from which said bacteriophage comes and/or that said bacteriophage targets.

In a particular embodiment, said production bacterial cell is an *E. coli* bacterial cell.

The present invention further concerns a method for producing tailocin and/or pyocin, comprising:
- (a) providing the tailocin and/or pyocin production bacterial cell defined above, and
- (b) inducing, as defined in the section "Producing method" above, in said production bacterial cell, expression of said at least one of said tailocin and/or pyocin structural gene(s), as defined above, and assembly of the products expressed by said at least one tailocin and/or pyocin structural gene(s), thereby producing tailocin and/or pyocin.

The present invention also concerns a hybrid production system comprising:
- (i') at least one tailocin and/or pyocin structural gene(s), as defined above, derived from a bacterial species or strain containing tailocin and/or pyocin genes, as defined above, and
- (ii) at least one gene, derived from a bacteriophage, as defined in the section "Bacteriophage and gene derived from a bacteriophage" above, involved in phage excision/insertion, phage DNA replication, and/or phage regulation, as defined in the section "Production bacterial cell" above; or at least one gene involved in tailocin and/or pyocin regulation, said gene involved in tailocin and/or pyocin regulation being derived from a bacterial species or strain containing tailocin and/or pyocin genes which are different from those from which said tailocin and/or pyocin structural genes are derived, wherein said genes (i') and (ii) are comprised in a unique nucleic acid molecule or in separate nucleic acid molecules, as defined in the section "Hybrid helper phage system and hybrid helper phage" above, wherein said bacteriophage comes from and/or targets bacterial species or strain different from the bacterial species or strain from which said tailocin and/or pyocin structural gene(s) is derived, and wherein said hybrid production system does not comprise any expressed phage structural gene, as defined in the section "Production bacterial cell" above, derived from said bacteriophage.

By "hybrid production system" is meant herein a group of at least one nucleic acid molecule, preferably of at least two separate nucleic acid molecules, comprising the genes (i') and (ii) defined above, which enables the production of tailocins and/or pyocins by the production bacterial cell comprising said system, wherein when the system comprises at least two separate nucleic acid molecules, said genes (i') and (ii) are distributed on said at least two separate nucleic acid molecules.

In a particular embodiment, wherein said genes (i') and (ii) are comprised in a bacterial chromosome.

In an alternative embodiment, said genes (i') and (ii) are comprised in separate plasmids.

In still an alternative embodiment, said hybrid production system consists of a hybrid helper phage comprising:

- (i') at least one tailocin and/or pyocin structural gene(s), as defined above, derived from a bacterial species or strain containing tailocin and/or pyocin genes, and
- (ii) at least one gene, derived from a bacteriophage, as defined in the section "Bacteriophage and gene derived from a bacteriophage" above, involved in phage excision/insertion, phage DNA replication, and/or phage regulation, as defined in the section "Production bacterial cell" above, wherein said bacteriophage comes from and/or targets bacterial species or strain different from the bacterial species or strain from which said tailocin and/or pyocin structural gene(s) is derived, and wherein said hybrid helper phage does not comprise any expressed phage structural gene, as defined in the section "Production bacterial cell" above, derived from said bacteriophage.

Unless defined otherwise, all technical and scientific terms used herein have the same meaning as commonly understood by one of ordinary skills in the art to which this invention belongs.

It must be noted that as used herein, the singular forms "a", "an" and "the" include plural referents unless the context clearly dictates otherwise. Thus, for example, reference to "a cell" includes a plurality of such cells (e.g., a population of such cells). Similarly, reference to "a nucleic acid" includes one or more of such nucleic acids.

Although the invention has been described in conjunction with specific embodiments thereof, many alternatives, modifications and variations will be apparent to those skilled in the art. Accordingly, it is intended to embrace all such alternatives, modifications and variations to fall within the spirit and broad scope of the appended claims.

All publications, patents and patent applications mentioned in this specification are herein incorporated in their entirety by reference into the specification, to the same extent as if such individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

The following examples are given for the purpose of illustrating various embodiments of the invention and are not meant to limit the present invention in any fashion.

| | Sequences | |
|---|---|---|
| SEQ ID NO: | Description | Type |
| 1 | primase ori from the PICI of the *Escherichia coli* strain CFT073 | DNA |
| 2 | Restriction site | DNA |
| 3 | Primase ori deltaGAAABCC | DNA |
| 4 | Primase ori devoid of restriction sites | DNA |
| 5 | PICI primase-helicase | Protein |
| 6 | PICI primase-helicase | DNA |
| 7 | Kappa structural operon region | DNA |
| 8 | Sequence upstream of small terminase gene of Kappa prophage | DNA |
| 9 | p1866 payload | DNA |
| 10 | Candidate HNH protein ORF | DNA |
| 11 | Candidate HNH protein | Protein |
| 12 | p1869 plasmid | DNA |
| 13 | Larger region upstream of Kappa prophage terminase | DNA |
| 14 | p1867 plasmid | DNA |

-continued

| SEQ ID NO: | Description | Type |
|---|---|---|
| 15 | Predicted ORF | DNA |
| 16 | Predicted protein with 2 Zn fingers | Protein |
| 17 | Short cos site | DNA |
| 18 | p1868 payload | DNA |
| 19 | p1872 plasmid | DNA |
| 20 | AD1334 primer | DNA |
| 21 | AD1335 primer | DNA |
| 22 | AD1336 primer | DNA |
| 23 | AD1337 primer | DNA |
| 24 | AD1322 primer | DNA |
| 25 | AD1323 primer | DNA |
| 26 | BW4 genome | DNA |
| 27 | PAC7 genome | DNA |
| 28 | pANS514 plasmid | DNA |
| 29 | PAC7 cos of pAN594 | DNA |
| 30 | operon of gp15-gp19 + gp45 | DNA |
| 31 | pAN241 vector | DNA |

EXAMPLES

Figure 1:
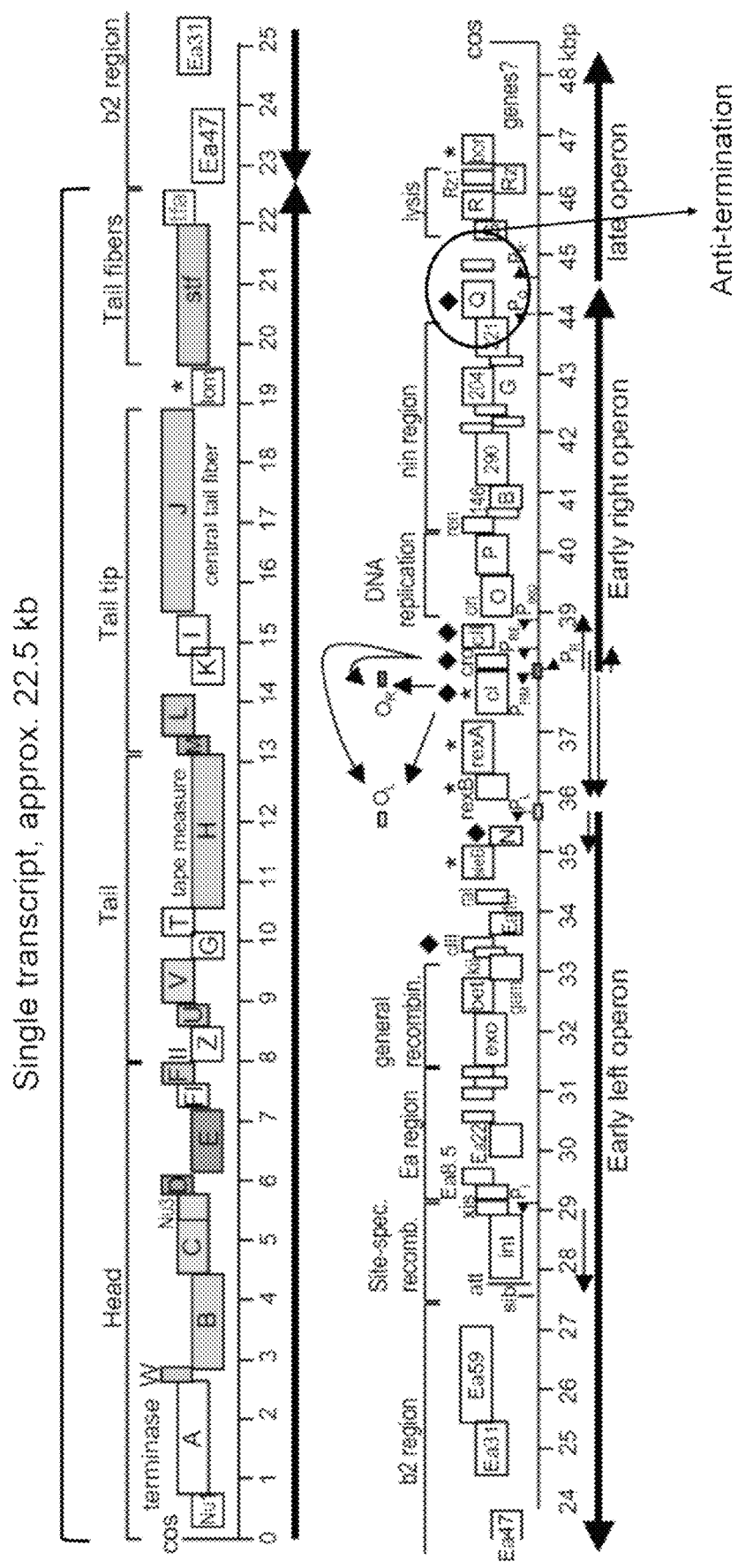
FIG. 1: Lambda genome organization (Lambda packaged phagemid variant). The structural operon is marked with a red line as well as the antitermination protein Q that allows transcription of the late structural operon. Figure adapted from Rajagopala et al. BMC Microbiol 11, 213 (2011).

Example 1: Exchange of the Structural Operon of Lambda with that of a Phage from a Different Species The inventors considered that phages can be viewed as more or less large genetic circuits whose final output is the generation of more phage particles. To do this, no matter if the phage is lytic, temperate or chronic (for instance filamentous phages such as M13), the information encoded in their genomes can be roughly categorized depending on the function it performs:

Genes devoted to insertion/excision (for temperate phages).

Genes devoted to DNA replication, RNA transcription, etc. . . . Some lytic phages encode their own RNA or DNA polymerases, for instance. Some genes modify the host's RNA polymerases to be able to work past terminators, and some other genes are involved in the segregation of the prophage sequence if it exists in a plasmid or linear plasmid form.

Genes related to defense from host's anti-phage mechanisms, degradation/modification of host's elements to complete the lytic cycle, super-exclusion mechanisms or genes that are advantageous for the host.

Genes devoted to DNA packaging: terminases and accessory proteins, ligases, etc.

Structural genes devoted to building a protein capsid for the DNA: apart from strictly structural genes, such as capsid genes, tape measure, fibers, baseplate etc, many other genes are needed to assemble the components (chaperones, proteases) as well as proteins that can be packaged inside the capsid, be it as scaffold or as pilot proteins injected into the cell (for instance, the RNA polymerase of phage N4 or some minor pilot proteins in other phages).

The last two categories (DNA packaging and structural genes) are deeply connected, since the packaging machinery recognizes the pre-assembled heads and the DNA to be packaged, initiates and terminates DNA packaging.

The inventors hypothesized that by abstracting and differentiating all the modules defined above, in principle a system could be built that contains all excision/insertion, replication and regulation elements from one phage and encodes the packaging/structural elements from another one, since, in principle, they could be viewed as independent genetic modules.

In the present example, it is referred to "structural elements" for proteins needed for DNA packaging and structural proteins needed to assemble a mature virion.

Such a system could be very advantageous for different approaches, because:
 the structural module from a phage that is not easily amplified or induced could be transferred to another one (i.e. prophages with unknown inducers; prophages found in strains with PICI/SaPI systems; phages for which the host is not known, etc.);
 a species which is more amenable for laboratory work/ large scale production/safer could be used to produce such particles where the structural genes come from another species;
 pure phagemid producing strains could be constructed using the regulatory elements of a well-characterized phage (for instance, Lambda) driving the production of capsids of a different phage, etc.

Figure 2:
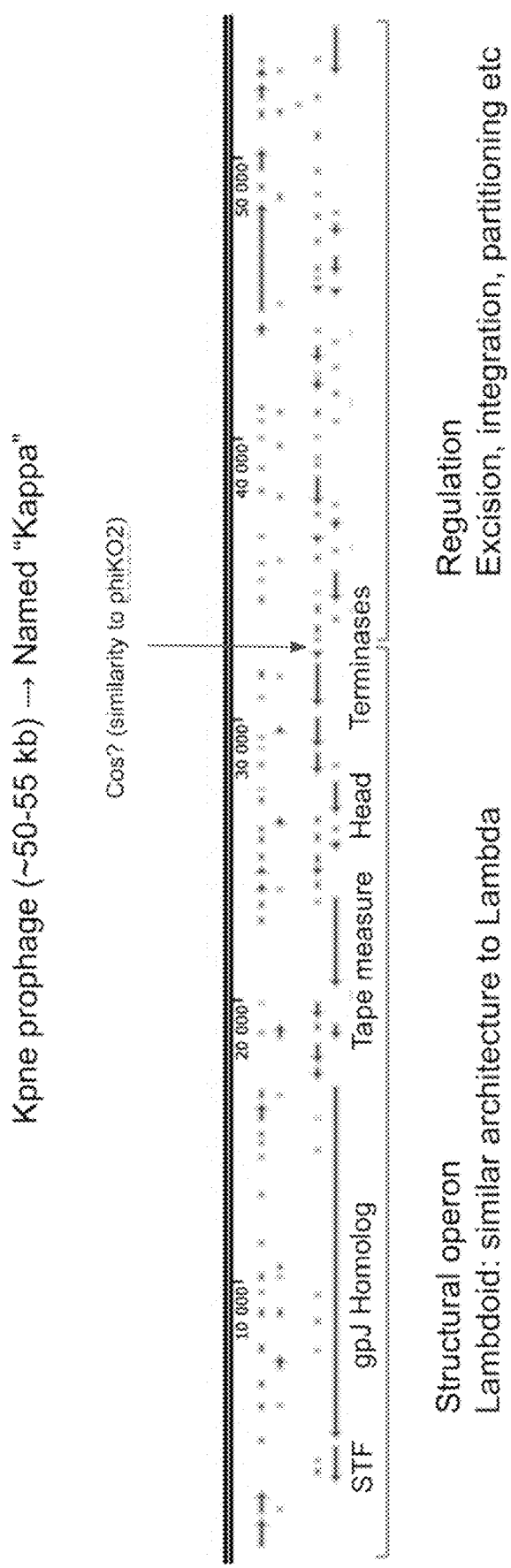
FIG. 2: *Klebsiella pneumoniae* prophage genome organization (prophage variant). The structural and regulatory operons are marked with a red line and some structural elements labeled.
Figure 3:
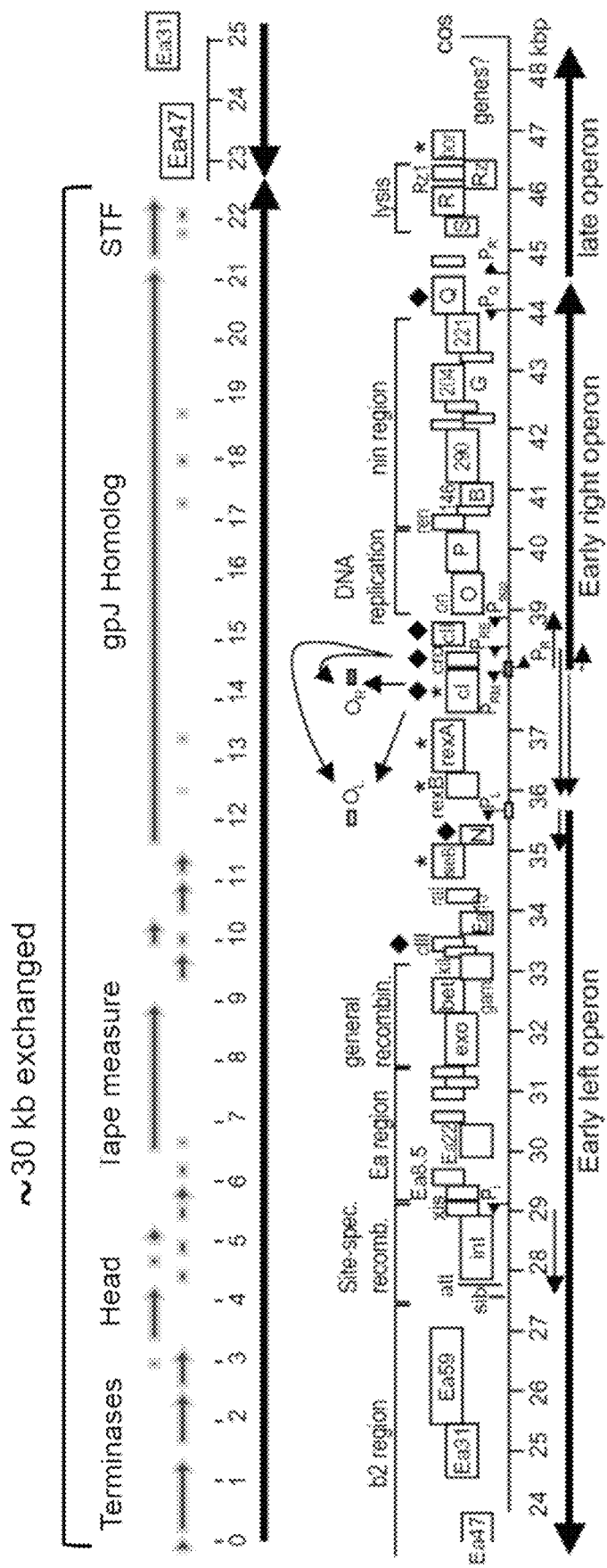
FIG. 3: Lambda-*K. pneumoniae* prophage hybrid. The complete structural operon from the *K. pneumoniae* prophage (marked with a red line) now occupies the place of the lambda late structural operon. The rest of the Lambda prophage regulating all other functions is intact.

This is the approach that was developed herein. Using a production strain encoding a system to generate pure Lambda phagemids, its structural operon has been exchanged (from the small terminase to the STF gene, about 23 kb) with the structural operon of a prophage coming from a different species (*Klebsiella pneumoniae*). A schematic diagram shows the changes made for the *Klebsiella pneumoniae* hybrid variant (FIGS. 1-3).

In this system, the thermolabile version of the prophage Lambda contains all regulatory elements needed to excise the prophage, replicate the circularized excised genome and drive the expression of the long, late operon, including the presence of the antitermination protein Q. This should drive the assembly and packaging of pure phagemid particles completely based on other phages when supplemented with a plasmid containing the correct packaging signals (cos site for the *Klebsiella pneumoniae* phage).

Analysis of the *Klebsiella pneumoniae* Prophage

The Kpne strain LMR_3612 (s17699) was analyzed with PHAST to extract prophage regions. One of them contains a predicted lambdoid prophage with some similarities to HK97. This prophage was called Kappa. Of note, a similar *Klebsiella oxytoca* prophage has been described in the literature and named phiKO2 (Casjens et al. J Bacteriol. 2004 March; 186(6):1818-32). The structural operon was found to span a continuous region encoding terminases, structural genes (capsid, tail, fibers, etc), assembly proteases and chaperones. This region is about 30 kb in length (SEQ ID NO: 7).

Construction of the Hybrid

The Lambda prophage structural operon was exchanged with the Kappa one using the lambda red recombineering system, starting from a production strain containing a Lambda prophage without the cos site (s1965). Of note, some codons were recoded to be efficiently recognized by *E. coli*.

Production and Titrations

The produced strain containing a completely exchanged structural operon was labeled Kappa. Next, a payload suitable to be packaged by this phagemid was constructed. To do this, a 350-bp long sequence (SEQ ID NO: 8) right upstream of the small terminase gene of the Kappa prophage, a candidate to encode the cos signal recognized by the Kappa terminases, was inserted in a payload containing a chloramphenicol marker and a sfGFP gene. This payload was labeled pTEST (p1866, SEQ ID NO: 9). Of note, several restriction sites found in the *Klebsiella pneumoniae* REBASE database were removed, where possible. The strain Kappa harboring the p1866 plasmid was grown overnight in LB+chloramphenicol and the next day a production following the protocol below was performed.

Overnight cultures were diluted 1:6 in a final volume of LB+5 mM $CaCl_2$ supplemented with chloramphenicol and grown for 30 min at 30° C. with shaking. After that, a 45-minute-long heat shock at 42° C. was performed. Finally the cultures were grown at 37° C. for 3 hours with shaking. After this period, cells were recovered by centrifugation and lysed using 3 mL of B-PER protein extraction reagent, 600 mg of detergent removal bio-beads were added and an incubation at room temperature with mild shaking performed for 1 hour. After that, the lysates were centrifuged for 10 min at 10,000 g and the supernatants filtered through a 0.2 micron pore-size membrane.

Two collections of *Klebsiella pneumoniae* strains belonging to different ST types (192 strains in total) were used to verify if phagemid particles were produced. Overnight cultures of *Klebsiella pneumoniae* strains were diluted 1:100 in LB+$CaCl_2$, grown for 2 hours at 37° C. and diluted 1:20 before the transductions. 10 μL of phagemid lysate was added to 90 μL of each of the *Klebsiella pneumoniae* dilutions and incubated for 30 min at 37° C. Finally, 10 μL of each transduction were plated on LB agar supplemented with chloramphenicol and incubated overnight at 37° C. Additionally, *Klebsiella pneumoniae* strain F3 (s19091), MG1655 (s003), MG1656-OmpCO157 (s14269) and MG1656-dOmpC-dLamB harboring 6 different *Klebsiella pneumoniae* OmpC variants in trans were used to verify the titers of the productions.

Figure 4:
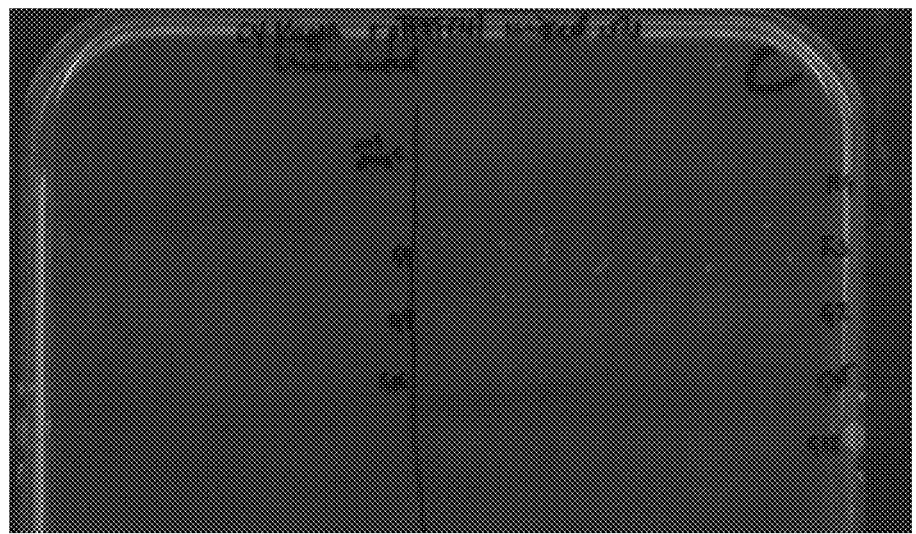
FIG. 4: Titrations of Kappa packaged phagemids with payload pTEST. From top to bottom and left to right, MG1656-OmpCO157, MG1655, MG-Kpne OmpC G1, Kpne F3, MG-Kpne OmpC 7, MG-Kpne OmpC G2, MG-Kpne OmpC G16, MG-Kpne OmpC G15, MG-Kpne OmpC G18. No hits were observed
Figure 5:
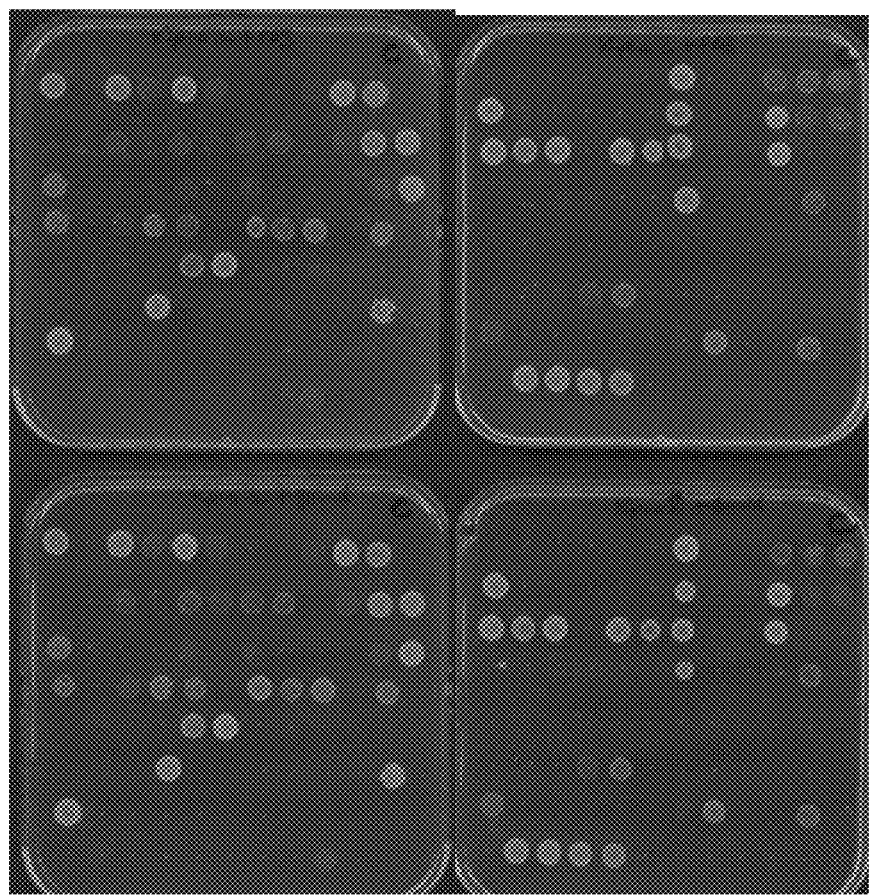
FIG. 5: Titrations of Kappa packaged phagemids on *Klebsiella pneumoniae* collections with payload pTEST. Top panels: Kpne collections treated with PBS only and plated on chloramphenicol to see background Cm resistance (left Kpne plate 1; right, Kpne plate 2). Bottom panels: Kpne collections treated with a lysate from Kappa+pTEST. No hits were observed

In this first assay, absolutely no hits were observed, either in the 192 *Klebsiella pneumoniae* strains or in any of the other 9 strains used for titrations (FIGS. 4-5).

After these results, a more detailed analysis of the Kappa prophage was performed to see if some structural or packaging element had been missed. Since this prophage seems to belong to the same family as HK97, a literature search was conducted in order to find any missing elements, and it was identified that HK97 (and in general, many other phages but not Lambda) need a small protein containing an HNH nuclease domain that assists in the processivity of the cos site cutting by the terminase complex (Moodley et al. Protein Sci. (2012) 21(6):809-818 and Kala et al. Proceedings of the National Academy of Sciences April 2014, 111 (16) 6022-6027). An analysis of the Kappa prophage region right upstream of the terminase genes (and the putative cos site) revealed the presence of an operon containing an HNH protein, some other small ORFs with unknown functions and a Zn-finger domain-containing protein right upstream of the putative cos site.

To test the hypothesis that the HNH protein was the element missing in the production strain, this ORF (SEQ ID NO: 10 and SEQ ID NO: 11) was cloned in a plasmid under the control of the inducible repressor PhIF (p1869, SEQ ID NO: 12) and used to complement the productions. Additionally, a second payload was built that contained a larger region upstream of the terminases (SEQ ID NO: 13), in case the cos site present in pTEST was not complete. This second plasmid was labeled pTEST-2 (p1867, SEQ ID NO: 14).

Phagemids were produced as for the initial experiment, but DAPG was added to the productions when the cultures were shifted to 42° C. in order to induce expression of the HNH protein. Screening of the collections was done as described above.

Figure 6:
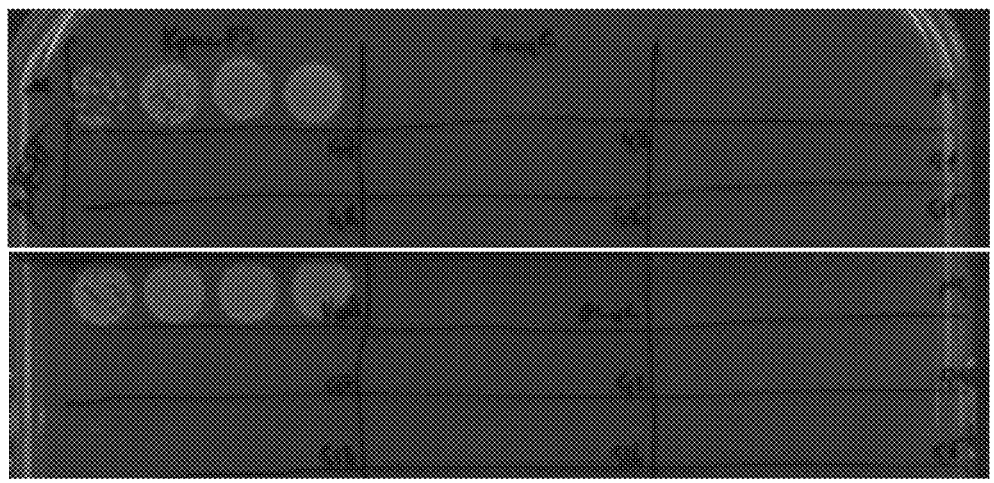
FIG. 6: Titrations of Kappa packaged phagemids with payloads pTEST or pTEST-2 in the presence of the HNH protein. Top panel, pTEST+HNH in trans. Bottom panel, pTEST-2+HNH in trans. From top to bottom and left to right, Kpne F3, MG1656-OmpCO157, MG1655, MG-Kpne OmpC G7, MG-Kpne OmpC G2, MG-Kpne OmpC G1, MG-Kpne OmpC G18, MG-Kpne OmpC G16, MG-Kpne OmpC G15.

The results showed that in the presence of the HNH protein, phagemids are readily produced (FIG. 6). In this case, the titration in single MG1655 or *Klebsiella pneumoniae* F3 strains revealed that the phagemid is specific to *Klebsiella* and that it does not recognize *E. coli* at all. This is proof that the phagemids being produced are structurally based on Kappa, but regulated and maintained in the lysogenic state by the Lambda prophage.

Figure 7:
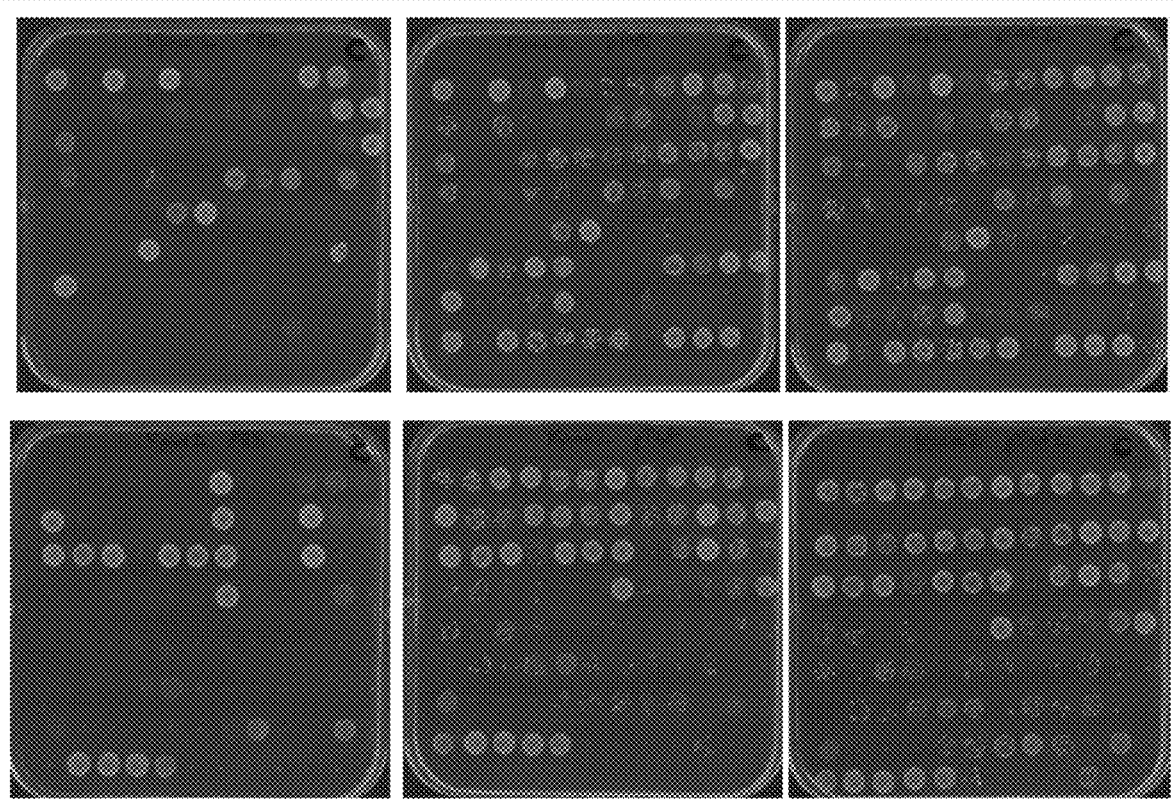
FIG. 7: Titrations of Kappa packaged phagemids with payloads pTEST or pTEST-2 in the presence of the HNH protein on *Klebsiella pneumoniae* collections. Top panels: Kpne collection 1 treated with: left) PBS; middle) pTEST+HNH in trans; right) pTEST-2+HNH in trans. Bottom panels, Kpne collection 2 treated with: left) PBS; middle) pTEST+HNH in trans; right) pTEST-2+HNH in trans.

Similarly, when titrated on both Kpne collections, this time many hits were observed (FIG. 7).

Two observations can be made from this experiment:
Titers are different when produced with pTEST or pTEST-2 payloads, both carrying the HNH protein in trans (estimated $5 \times 10^5$ TU/mL for pTEST and $5 \times 10^6$ TU/mL for pTEST-2).
Even at low titers, spots in the *Klebsiella pneumoniae* collection are dense, indicating that the delivery efficiency must be high.

Concerning the difference in titers for the payloads tested, the only change between both productions is that the putative cos site present in pTEST-2 is longer than pTEST; but also, pTEST-2 encodes a small ORF (which is part of the longer cos region) with two Zn fingers predicted (SEQ ID NO: 15 and SEQ ID NO: 16). If this protein is involved in packaging, it may be the reason why titers are higher in lysates containing pTEST-2 than in those containing pTEST, and not because of the length per se. For this reason, a third system was built in which a payload encoding a short cos site (to avoid encoding any proteins in that region) (SEQ ID NO: 17) was used, labeled pTEST-3 (p1868, SEQ ID NO: 18). To complement the putative packaging proteins in trans, the so-called "HNH-Operon" plasmid was built (p1872, SEQ ID NO: 19), encoding the HNH protein (SEQ ID NO: 10 and SEQ ID NO: 11) and the putative Zn-finger containing protein (SEQ ID NO: 15 and SEQ ID NO: 16). Productions were made the same way as described above.

Figure 8:
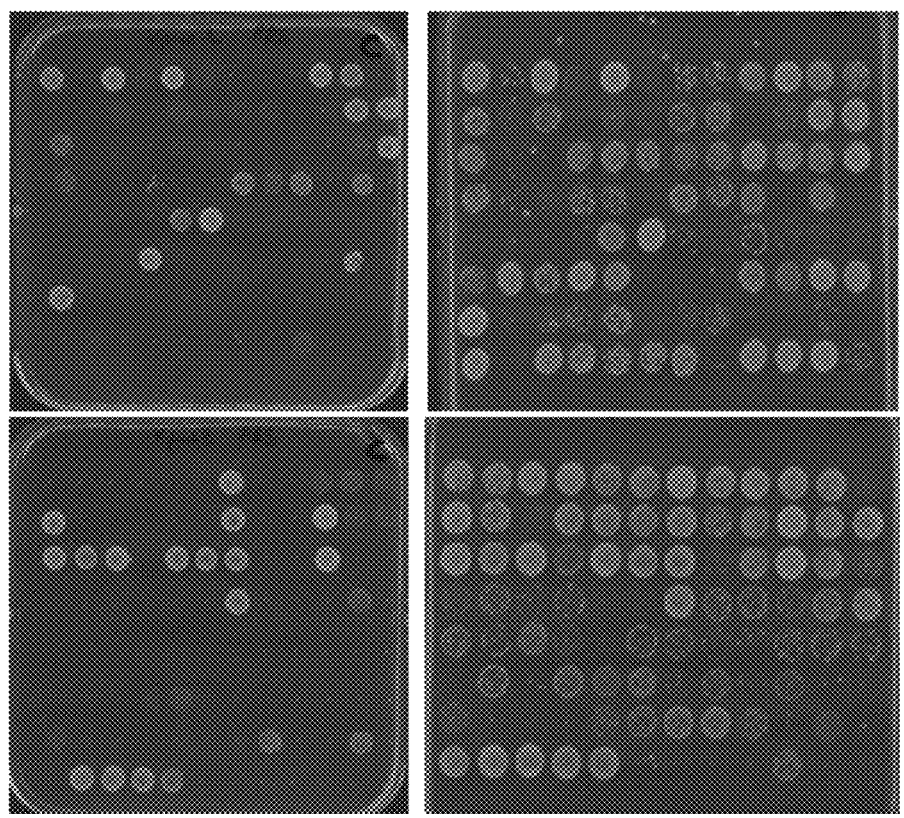
FIG. 8: Titrations of packaged phagemids on Kpne collections. Top panels: *Klebsiella pneumoniae* collection 1 treated with, left, PBS; right, pTEST-3+HNH-Operon in trans. Bottom panels, *Klebsiella pneumoniae* collection 2 treated with: left, PBS; right, pTEST-3+HNH-Operon in trans.

In this third case, a similar behavior as for pTEST-2 was observed: many hits in the Kpne collections, confirming successful productions of phagemids and titers of about $5 \times 10^6$ TU/mL (FIG. 8). The titers were obtained by analyzing dense spots on the *Klebsiella pneumoniae* plates and using those strains to titrate the lysates. These results show that the minimal cos site is encoded in a shorter region than pTEST and pTEST-2 and that the HNH-Operon machinery is necessary and improves the packaging reaction.

These results show that an *E. coli* production strain is able to produce *Klebsiella*-specific pure phagemid particles. The specificity does not come solely from the addition of a single structural element, such as a tail fiber. The complete protein composition of the phagemids produced is from *K. pneumoniae* origin, proving that phagemid particles for other species can be assembled using *E. coli* as a production strain.

Example 2: Production of *Cutibacterium Acnes* Phage-Derived Particles

*Cutibacterium acnes* is one of the most prevalent and abundant species of the skin (Kashaf et al. *Nat Microbiol* 7, 169-179 (2022)) where it colonizes the pilosebaceous unit (PSU). Unlike on the stratum corneum, bacteria present in the PSU are surrounded by living cells notably keratinocytes, sebocytes and different immune cells (Kabashima et al. *Nat Rev Immunol* 19, 19-30 (2019)). Close contact between *C. acnes* and these cells might lead to either beneficial or detrimental interactions. (Bruggemann et al. *Front Microbiol* 12, 673845 (2021)). Being able to genetically modify *C. acnes* was notoriously challenging before the applicant's new tools disclosed in US applications US2022/135986 and US2022/135987. In these patent applications, the inventors described, for the first time, the production of *C. acnes* phage-derived particles using *C. acnes* as a production strain.

In the present example, the inventors used *P. freudenreichii* strain to produce *C. acnes* phage-derived particles by swapping the structural genes from a *P. freudenreichii* prophage for the structural genes of a *C. acnes* phage.
Results
Isolation of BW4 Phage

*P. freudenreichii* and associated bacteriophages are known to be present in some dairy products (Gautier et al. (1995) Lait 75:427-434; Gautier et al. (1995) *Appl. Environ. Microbiol.* 61:2572-2576; Cheng et al. (2018) *BMC Microbiology* 18:19). The inventors therefore screened for the presence of both *Propionibacterium* phages or *P. freudenreichii* lysogens in cheese samples.

Different types of cheese samples were grinded, resuspended in Reinforced Clostridial Medium (RCM) and incubated at 30° C. in anaerobic conditions for 2 days. After incubation, a dilution of the culture was performed in lithium glycerol broth, a media selective for Propionibacteria (WO1994017201), and incubated for 6 days at 30° C. A final dilution in RCM+mitomycin C was incubated for 1 day at 30° C. in order to induce potential prophages. The induced cultures were filtered (0.2 μm) and spotted on different indicator strains. One of the samples led to turbid plaque formation on top agar of the *P. freudenreichii* strain Pf0s2841. Three individual plaques were isolated by two successive picking and streaking on Pf0s2841 and amplification was performed on top agar of Pf0s2841. For the three different plaques, amplification led to phage suspension ~$10^{1°}$ PFU/mL.

Two clusters of temperate dsDNA *P. freudenreichii* phages (BW and BV) have been previously identified (Cheng et al. (2018) *BMC Microbiology* 18:19). Using PCRs designed on BW genome from Doucette phage (KX620751) two different fragments were extracted:

ORF3 with AD1334 (SEQ ID NO: 20)/AD1335 (SEQ ID NO: 21)
ORF5 with AD1336 (SEQ ID NO: 22)/AD1337 (SEQ ID NO: 23).

Figure 9:
FIG. 9: Identification of *P. freudenreichii* phages with PCR. PCR on ORF3 and ORF5 was performed on all phage suspensions. BW4 from plaques 1-3 give a band at the expected size for both orf3 and orf5. Ladder is GeneRuler 1 kb plus.
Figure 9:
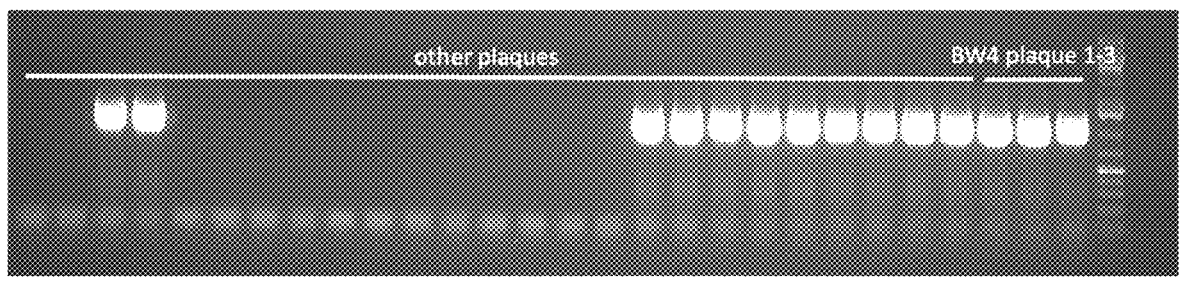

The inventors could classify the isolated phages as BW-like (FIG. 9). Sequencing of ORF5 revealed that all phages were most probably identical and therefore were coming from the same BW-like phage that was named BW4.

Isolation of Pf0s2841 Lysogen Carrying the BW4 Phage

The inventors then isolated *P. freudenreichii* lysogen carrying the BW4 phage as a prophage. For that, BW4 phage suspension was spotted on strain Pf0s2841 and incubated for 3 days. Turbid plaques were picked, resuspended and streaked. After 5 days, single colonies were obtained, several colonies were streaked and incubated a second and third time and presence of the phage genes was checked, at each streaking, by PCR, after DNAse treatment, across the cohesive ends (AD1322 (SEQ ID NO: 24)/AD1323 (SEQ ID NO: 25)) to ensure presence of the phage but absence of phage particles.

Figure 10:
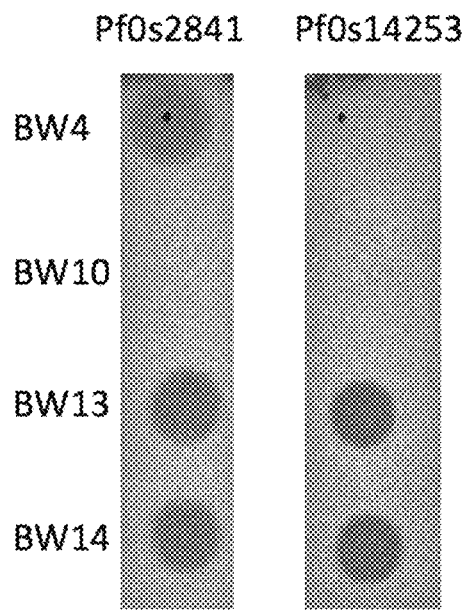
FIG. 10: Immunity to superinfection of lysogen Pf0s14253. Left panel: Top agar of Pf0s2841 with spots of 4 different BW-like phage suspensions. Right panel: Top agar of Pf0s14253 with spots of 4 different BW-like phage suspensions.

After the third streak, colonies were grown as a top agar and a spot of non diluted BW-like phages suspensions were spotted on the putative lysogene strain (Pf0s14253) and on the ancestor strain (Pf0s2841). After incubation, clearance was observed for both strains for BW13 and BW14 spots whereas clearance was only observed for Pf0s2841 in the case of BW4 spot (FIG. 10). This indicates that the strain Pf0s14253 is immune to BW4 phage superinfection and carries the BW4 prophage. The absence of immunity for BW14 and BW13 indicates that these phages have likely a different immunity repressor.

BW4 Prophage Induction

Figure 11:
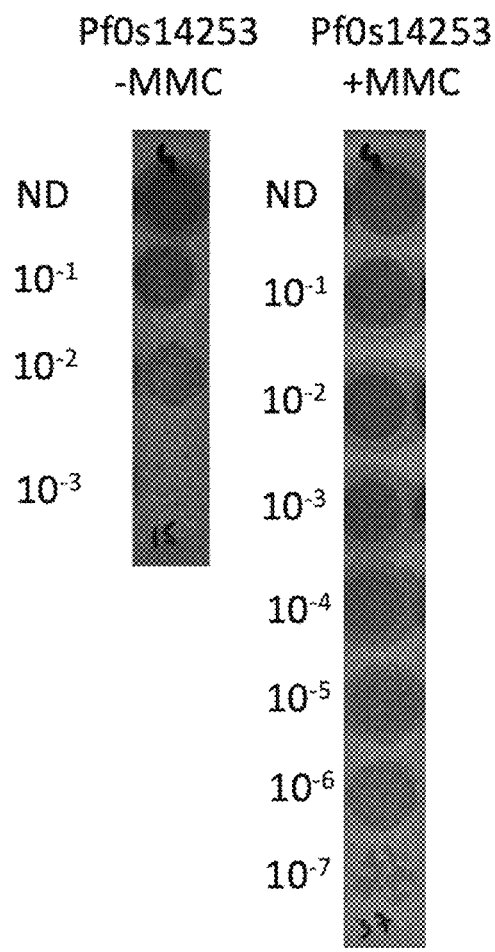
FIG. 11: High induction of BW4 phage after mitomycin C treatment. Left panel: Top agar of Pf0s2841 with spots of culture supernatant from Pf0s14253 without mitomycin C (MMC) induction (ND: non diluted to dilution $10^3$). Right panel: Top agar of Pf0s2841 with spots of culture supernatant from Pf0s14253 with 0.5 µg/ml of mitomycin C induction (ND: non diluted to dilution $10^7$).

In order to use the BW4 lysogen strain as a production strain for phage-derived particles the inventors first had to test the ability to produce high concentration of the BW4 phage upon induction of the lytic cycle. To do so, Pf0s14253 was grown in absence or presence of mitomycin C (MMC), an antibiotic known to induce prophages, and the culture supernatant was titered for the presence of BW4 phage particles on the indicator strain Pf0s2841. A high amount of BW4 phage particles was observed in the condition supplemented with mitomycin C (FIG. 11) with $7.4 \times 10^7$ PFU/µL against $3.0 \times 10^3$ PFU/µL for the condition without mitomycin C. This indicates a high dynamic range between lytic and lysogenic cycle for BW4 prophage under such conditions and confirmed the potential of BW4 for the production of phage-derived particles.

Sequencing and Annotation of BW4 Phage

To engineer the BW4 prophage towards production of *C. acnes* phage-derived particles, the BW4 phage was sequenced. DNA isolation (Promega Wizard DNA Clean-Up System) followed by Illumina sequencing was performed on BW4 phage suspension. Raw reads were assembled into a single contig using Spades and termini were corrected by sanger sequencing (SEQ ID NO: 26). Annotation was performed using Phaster and manually curated based on homologies with other BW-like phages (Cheng et al. (2018) *BMC Microbiology* 18:19).

As described in Cheng et al. (2018) *BMC Microbiology* 18:19, BW-like phages have typical genomic architecture of other temperate phages with a large putative structural operon (also called lytic operon) organized in different functional modules with, in order of transcription: packaging, head, tail, and lysis module. Surprisingly, the first gene of the putative operon (gp1) appears to be related to DNA replication based on HHpred as it contains a domain similar to bifunctional primase and polymerase proteins. Other parts of the BW4 phage genome contain the genes necessary for prophage integration/excision, DNA replication, DNA recombination, regulation of the lytic/lysogenic cycle and other accessory proteins. This modular architecture confirms the possibility to swap the genes necessary for the production of BW4 phage capsid and the packaging of the phage genome by their equivalent from a *C. acnes* phage genome.

Isolation of *C. acnes* PAC7 Phage

*C. acnes* phages were isolated from skin of healthy volunteers. Briefly a patch (Biore) was applied to the nose allowing to extract comedones that were resuspended in RCM, plated on MRS and incubated at 37° C. in anaerobic conditions. For some of the plates, plaques could be observed in the dense lawn of *C. acnes*. DPBS (Dulbecco's Phosphate Buffered Saline) was poured on the plate to resuspend potential phages and filtered to remove bacteria. This phage suspension was streaked on plate and a top agar of strain Ca0s2345 was added. Plates were incubated for 2 days and plaques were reisolated by three successive picking, streaking and top agar plating. Finally a plaque was amplified on top agar with Ca0s2345 strain and the resulting phage suspension was PEG precipitated. High titer ($>10^6$ PFU/µL) phage suspension was obtained when titered on Ca0s2345.

Sequencing and Annotation of PAC7 Phage

Figure 12:
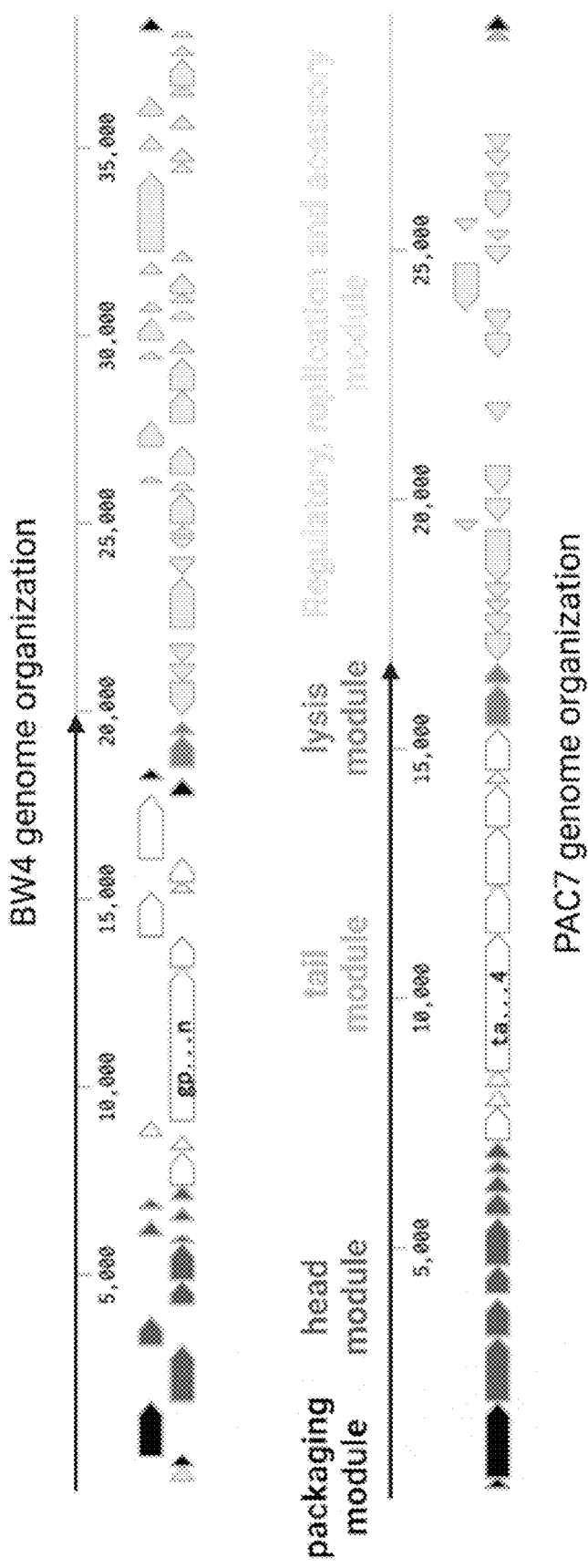
FIG. 12: Genome organization of BW4 and PAC7 bacteriophages. BW4 and PAC7 genome organization is similar with both putative structural operons (represented by the arrows) containing the packaging, head, tail and lysis modules.

DNA isolation (Promega Wizard DNA Clean-Up System) followed by Illumina sequencing was performed on PAC7 phage suspension. Raw reads were assembled into a single contig using Spades and termini were corrected by sanger sequencing (SEQ ID NO: 27). Annotation was performed using Phaster and manually curated based on homologies with other *C. acnes* phages (Marinelli et al. (2012) *mBio* 3:e00279-12). Similar to the *P. freudenreichii* BW4 phage, a structural operon comprising modules for packaging, head and tail assembly and cell lysis was identified (FIG. 12). An HNH endonuclease was identified as the last gene of the phage (gp45). Such endonuclease has already been shown to be essential for efficient packaging (Quiles-Puchalt et al. (2014) *Proc Nat. Acad. Sci.* 111:6016-6021).

Construction of Lysogen Strain with a Chimeric BW4-PAC7 Prophage

Figure 13:
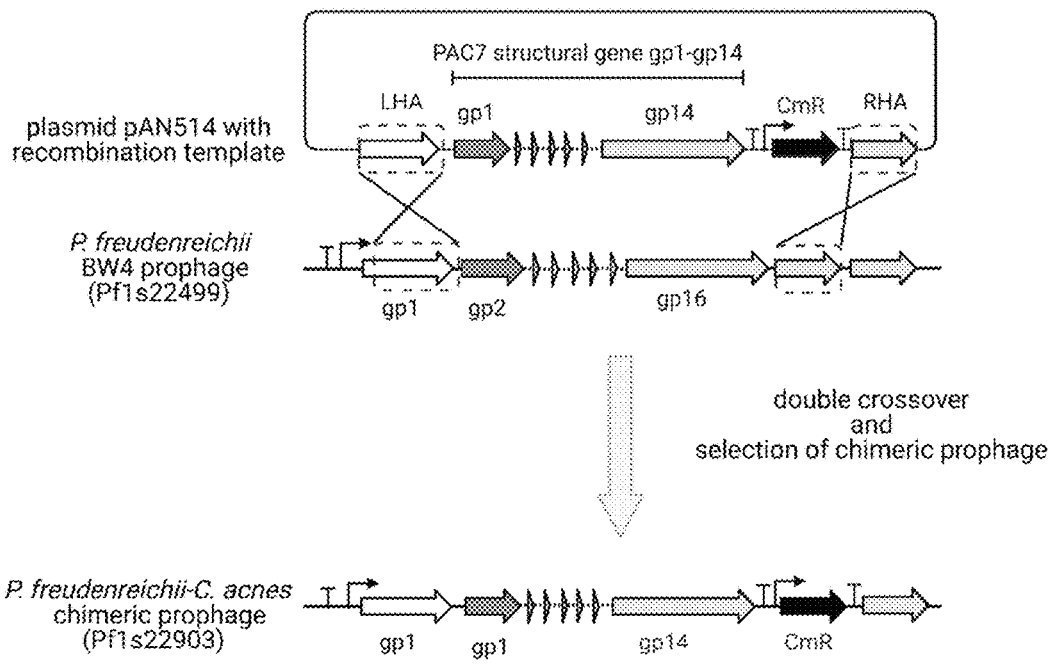
FIG. 13: Construction of chimeric BW4-PAC7 prophage. Transformation of the pAN514 suicide plasmid into strain Pf1s22499 containing the BW4 prophage. Selection on chloramphenicol was used to select for double crossover at the Left Homology Arm (LHA) and Right Homology Arm (RHA). The prophage obtained is a chimer containing a structural operon with first BW4 gp1 followed by gp1-gp14 of PAC7 and after the chloramphenicol selection cassette (CmR) the leftover of BW4 structural genes (gp15-gp25).

The genes in the structural operon of BW4 prophage, from the small terminase gp2 to the tape-measure protein gp16 included, were replaced by the structural PAC7 genes from gp1 to gp14 (FIG. 13). This was performed by homologous recombination using plasmid pAN514 (SEQ ID NO: 28), a *P. freudenreichii* suicide vector that was cloned in *E. coli* DH10B. After transformation of the vector, a double crossing over event was selected in *P. freudenreichii* (Pf1s22499) by selection on chloramphenicol. The chimeric BW4-PAC7 structural operon integrity was globally confirmed by PCR and sanger sequencing of the entire chimeric structural operon.

Figure 14:
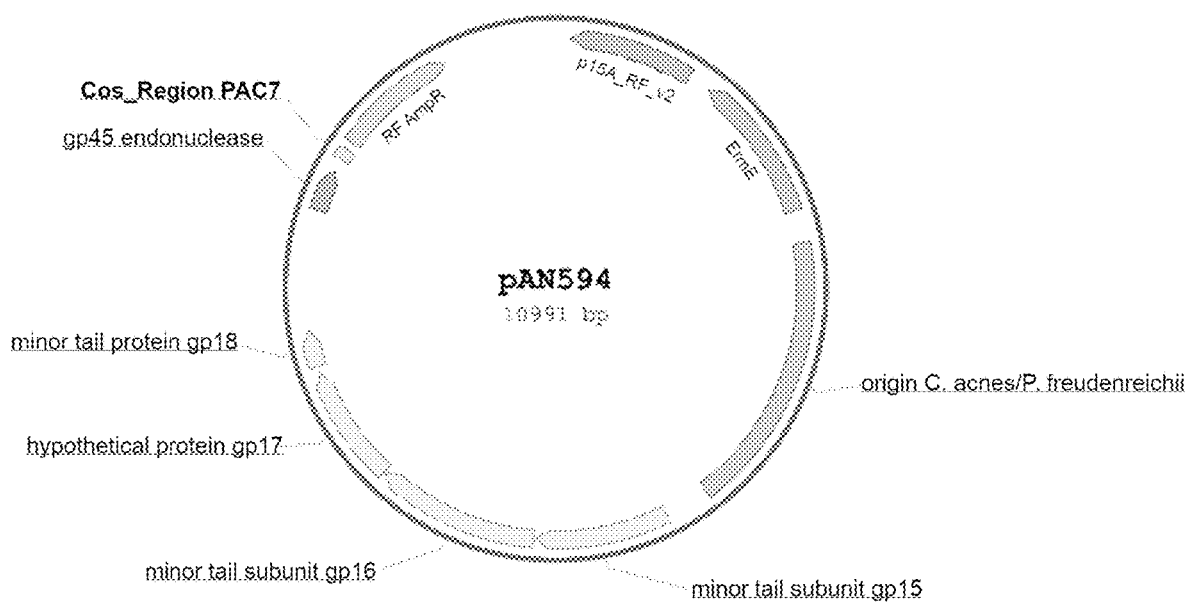
FIG. 14: Plasmid map of cosmid pAN594.

Production and Titration of PAC7 Derived Particles from a Lysogen Strain Carrying a Chimeric BW4-PAC7 Prophage In order to produce *C. acnes* phage-derived particles from a *P. freudenreichii* BW4-PAC7 chimeric lysogen, the pAN594 cosmid (FIG. 14) containing the packaging signal of the PAC7 phage (SEQ ID NO: 29), an operon expressing five genes of the PAC7 tail module (gp15-gp19) and the gp45 endonuclease (SEQ ID NO: 30) and an origin of replication functional in *P. freudenreichii* and *C. acnes* (as disclosed in US2022/135986 and US2022/135987) were transformed into Pf1s22903. Transformants were streaked and grown in presence of both chloramphenicol (1 µg/mL) to select for the presence of the prophage and erythromycin (2.5 µg/mL) to select for the presence of pAN594. At $OD_{600nm}$~0.4, culture was supplemented with 0.5 µg/ml of mitomycin C and grown overnight at 30° C. in anaerobic conditions. After incubation, cells were collected by centrifugation, lysed by bead beating (2×20 min at 30 Hz with 0.1 mm glass beads), supernatant was filtered and the presence of phage derived particles was titered on *C. acnes* Ca0s2258.

Figure 15:
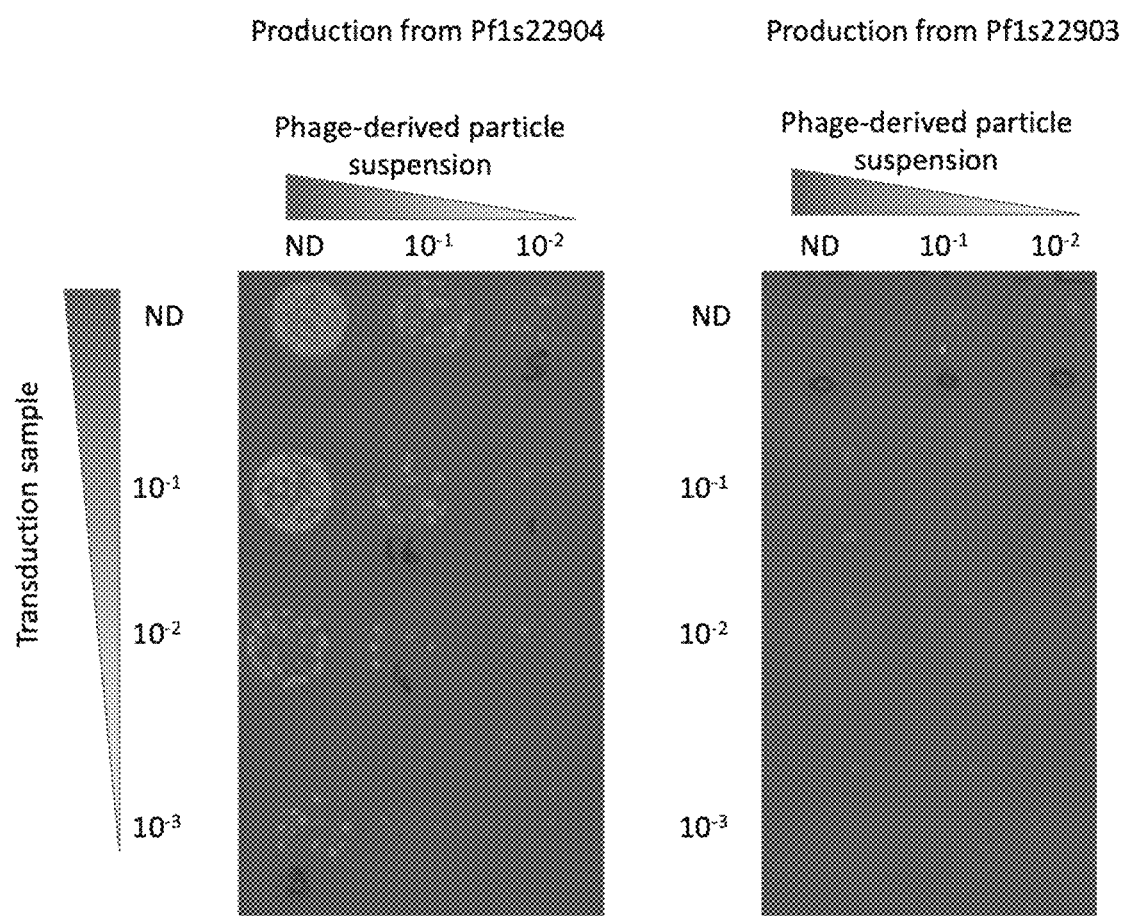
FIG. 15: Titration of PAC7 phage-derived particles. Left Panel: Titration from Pf1s22904 plated on erythromycin. Right Panel: Titration from control suspension of strain Pf1s22903 that does not carry any cosmid plated on erythromycin.
Figure 16:
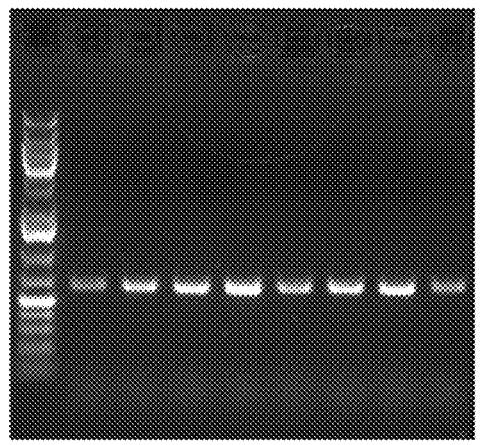
FIG. 16: Confirmation for 8 colonies streaked from phage-derived particles titration of Pf1s22904 production by PCR. Top Panel: SLTS PCR (Scholz 2014) on 8 colonies streaked from the phage derived titration assay. Expected size is 612 bp. Bottom Panel: pAN594 specific PCR on 8 colonies. Expected size is 769 bp. Ladder is generuler 1 kb plus.
Figure 16:
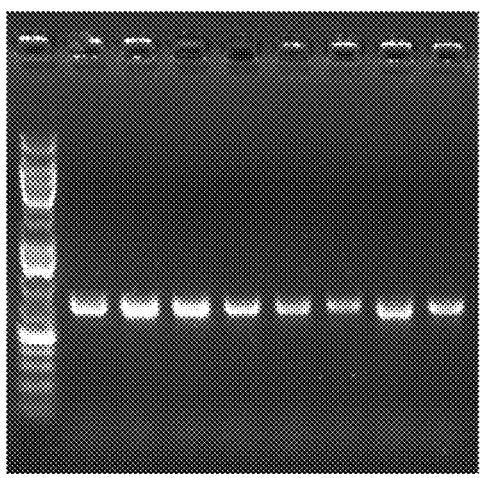

Up to ~$10^2$ potential transductants per µL were obtained (FIG. 15). 8 colonies were streaked on Brain Heart Infusion (BHI) erythromycin (5 µg/mL) and confirmed to be *C. acnes* and transductants carrying pAN594 using PCR (FIG. 16).

The inventors thus demonstrated for the first time that *C. acnes* phage-derived particles able to deliver DNA into *Cutibacterium acnes* can be produced by swapping structural genes of a *P. freudenreichii* prophage for the structural genes of a *Cutibacterium acnes* phage.

Material and Methods:
Strain Used and Generated

TABLE 1

Strains used and generated

| Eligo ID | Description |
| --- | --- |
| Pf0s2841 | Indicator strain for *P. freudenreichii* BW4 phage (CIRM-BIA 509, TL110 belonging to INRAE) |
| Pf0s14253 | Strain Pf0s2841 with a BW4 prophage |
| Pf1s22499 | Strain Pf0s14253 with the packaging signal of BW4 deleted |
| Pf1s22903 | Strain Pf1s22499 with the BW4 genes gp2-gp16 replaced by PAC7 gp1-gp14 |
| Pf1s22904 | Strain Pf1s22903 with pAN594 |
| Ca0s2345 | Indicator strain for *C. acnes* PAC7 phage |
| Ca0s2258 | *Cutibacterium acnes* ATCC 11828 |

Culture Conditions

All incubations of *P. freudenreichii* strains were performed at 30° C. in anaerobic conditions (Thermo Scientific™ Sachet Oxoid™ AnaeroGen).

All incubations of *C. acnes* strains were performed at 37° C. in anaerobic chamber.

Construction of Strain Pf1s22499

Deletion of the packaging signal from BW4 prophage was performed by homologous recombination and CRISPR-Cas selection of the recombinant using the pAN241 *P. freudenreichii* vector that was cloned in *E. coli* and then transformed into Pf0s14253 strain. The pAN241 vector contains a template for homologous recombination (SEQ ID NO: 31) and a FnCpf1 transcriptional cassette with a crRNA targeting the cos of the BW4 prophage.

Transformation Protocol for *P. freudenreichii*

Transformation of *P. freudenreichii* was adapted from Brede, D. A. et al. *Appl Environ Microb* 71, 8077-8084 (2005), replacing SLB (sodium lactate broth) media for BHI.

Phage-Derived Particles Titration

Strain Ca0s2258 was streaked on BHI agar plate. Once dense growth on plate was obtained, a liquid culture was set up in BHI. After overnight incubation, the turbid culture was concentrated 10× in BHI. 90 µl of cells were mixed with pure, diluted 1/10 and diluted 1/100 solutions of 10 µL of phage-derived particles produced from either Pf1s22904 or Pf1s22903 as negative control. Samples were incubated 2 hours at room temperature and then 1/10 serial dilutions were performed in BHI, samples were incubated 2 h at 37° C. in anaerobic conditions before spotting 4 µL on BHI+5 µg/mL erythromycin. Plates were incubated for 7 days at 37° C. in anaerobic conditions.

We claim:

1. A method for producing phage particles or phage-derived delivery vehicles, comprising:
   (a) providing a production bacterial cell stably comprising phage structural genes and phage DNA packaging genes of a first type of bacteriophage,
      wherein the expression of said phage structural genes and phage DNA packaging genes in said production bacterial cell is controlled by an induction mechanism comprising phage excision/insertion genes, phage DNA replication genes, and phage regulation genes of a second, different type of bacteriophage,
      wherein said phage excision/insertion genes, phage DNA replication genes and phage regulation genes are neither phage DNA packaging genes nor phage structural genes,
      wherein said production bacterial cell does not comprise phage excision/insertion genes and/or phage replication genes of the first type of bacteriophage,
      wherein said production bacterial cell is from a bacterial species or strain different from the bacterial species or strain from which said first type of bacteriophage comes from and/or that said first type of bacteriophage targets and wherein said production bacterial cell is from the same bacterial species or strain as the bacterial species or strain from which said second type of bacteriophage comes from and/or that said second type of bacteriophage targets,
      wherein said production bacterial cell is a *P. freudenreichii* bacterial cell,
      wherein the first type of bacteriophage is a *C. acnes* phage and
      wherein the second type of bacteriophage is a *P. freudenreichii* phage;
   and
   (b) inducing, in said production bacterial cell, expression of said phage structural genes and phage DNA packaging genes, and assembly of the products expressed by said phage structural genes and phage DNA packaging genes, thereby producing phage particles or phage-derived delivery vehicles.

2. The method according to claim 1, wherein said production bacterial cell further comprises a payload to be packaged into said phage particles or phage-derived delivery vehicles.

3. The method according to claim 2, wherein said payload is a nucleic acid payload comprising a packaging site derived from said first type of bacteriophage.

4. The method according to claim 2, wherein said payload is to be delivered into targeted bacterial cells.

5. The method according to claim 4, wherein said payload comprises a sequence of interest.

6. The method according to claim 5, wherein said sequence of interest only generates an effect in said targeted bacterial cells.

7. The method according to claim 6, wherein said targeted bacterial cells are from a species or strain different from the production bacterial cell.

8. The method according to claim 4, wherein said sequence of interest encodes a CRISPR-Cas system.

9. The method according to claim 8, wherein said sequence of interest comprises a nucleic acid sequence encoding Cas protein.

10. The method according to claim 9, wherein said Cas protein is selected from the group consisting of Cas1, Cas1B, Cas2, Cas3, Cas4, Cas5, Cas6, Cas7, Cas8, Cas9, Cas10, Cas11 (SS), Cas12a (Cpf1), Cas12b (C2c1), Cas12c (C2c3), Cas12d (CasY), Cas12e (CasX), C2c4, C2c8, C2c5, C2c10, C2c9, Cas13a (C2c2), Cas13b (C2c6), Cas13c (C2c7), Cas13d, Csa5, Csc1, Csc2, Cse1, Cse2, Csy1, Csy2, Csy3, Csf1, Csf2, Csf3, Csf4, Csm1, Csm2, Csm3, Csm4, Csm5, Csm6, Cmr1, Cmr3, Cmr4, Cmr5, Cmr6, Csn2, Csb1, Csb2, Csb3, Csx17, Csx14, Csx10, Csx16, CsaX, Csx13, Csx1, Csx15, SdCpf1, CmtCpf1, TsCpf1, CmaCpf1, PcCpf1, ErCpf1, FbCpf1, UbcCpf1, AsCpf1, LbCpf1, Mad4, Mad7, Cms1, homologues thereof, orthologues thereof, variants thereof, and modified versions thereof.

11. The method according to claim 8, wherein said sequence of interest comprises a nucleic acid sequence encoding a guide RNA or sgRNA.

12. The method according to claim 4, wherein said sequence of interest encodes a base editing system.

13. The method according to claim 2, wherein said payload is devoid of antibiotic resistance marker.

14. The method according to claim 4, wherein said payload comprises a conditional origin of replication which is inactive in the targeted bacterial cells but is active in the production bacterial cell.

15. The method according to claim 2, wherein said payload comprises a bacterial origin of replication that is functional in the production bacterial cell.

16. The method according to claim 4, wherein said payload comprises an origin of replication which is inactive in the targeted bacterial cells.

* * * * *

SEQUENCE LISTING

```
Sequence total quantity: 31
SEQ ID NO: 1            moltype = DNA  length = 282
FEATURE                 Location/Qualifiers
source                  1..282
                        mol_type = other DNA
                        note = primase ori from the PICI of the Escherichia coli
                          strain CFT073
                        organism = synthetic construct
SEQUENCE: 1
tttgttgcaa tggctgtcta ccctgtctac ctgagtaaag aaaaatacat ttaattcagt 60
acattaactt gggtagacag cctttttta ctgtctacct actatctacc ctctctacct 120
gattttacct gaatcagaca gggaggtaga tacggggtag atagtggata aaagcactct 180
accccactga aagccgcgcc attactggca tggtggccag taaggtagat aaggtagaca 240
aggggaggca caactcaaaa cttttaaac gaggggtaa aa                       282

SEQ ID NO: 2            moltype =     length =
SEQUENCE: 2
000

SEQ ID NO: 3            moltype = DNA  length = 282
FEATURE                 Location/Qualifiers
source                  1..282
                        mol_type = other DNA
                        note = Primase ori deltaGAAABCC
                        organism = synthetic construct
SEQUENCE: 3
tttgttgcaa tggctgtcta ccctgtctac ctgagtaaag aaaaatacat ttaattcagt 60
acattaactt gggtagacag cctttttta ctgtctacct actatctacc ctctctacct 120
gattttacct gaatcagaca gggaggtaga tacggggtag atagtggata aaagcactct 180
accccactga aagcagcgcc attactggca tggtggccag taaggtagat aaggtagaca 240
aggggaggca caactcaaaa cttttaaac gaggggtaa aa                       282
```

| SEQ ID NO: 4 | moltype = DNA length = 282 |
|---|---|
| FEATURE | Location/Qualifiers |
| source | 1..282 |
| | mol_type = other DNA |
| | note = Primase ori devoid of restriction sites |
| | organism = synthetic construct |

SEQUENCE: 4

```
tttgttgcaa tggctgtcta ccctgtctac ctgagtaaag aaaaatacat ttaattcagt   60
atattaactt gggtagacag ccttttttta ctgtctacct tctgtctacc ctctctacct  120
gattttacct gaatcagaca gggaggtaga cacggggtag acagtggata aaagcactct  180
accccactga aagcagtgcc attactggca tggttgccag taaggttgat aaggtagaca  240
aggggaggga caactcaaaa cttttttaaac gagggggtaa aa                    282
```

| SEQ ID NO: 5 | moltype = AA length = 584 |
|---|---|
| FEATURE | Location/Qualifiers |
| source | 1..584 |
| | mol_type = protein |
| | note = PICI primase-helicase |
| | organism = synthetic construct |

SEQUENCE: 5

```
MKLAPNVKQQ SRGIKHKETE VIIFAGSDAW SHAKQWQEHD ARMAGDNEPP VWLGEQQLSE   60
LDKLQIVPEG RKSVRIFRAG YLAPVMIKAI GQKLAAAGVQ DANFYPDGMH GQKVENWREY  120
LARERQNLSD GLVIELPVKQ KAQLSQMADS ERAQLLADRF DGVCVHPESE IVHVWCGGVW  180
CPVSTMELSR EMVAIYSEHR ATFSKRVINN AVEALKVIAE PMGEPSGDLL PFANGALDLK  240
TGEFSPHTPE NWITTHNGIE YTPPAPGENI RDNAPNFHKW LEHAAGKDPR KMMRICAALY  300
MIMANRYDWQ MFIEATGDGG SGKSTFTHIA SLLAGKQNTV SAEMTSLDDA GGRAQVVGSR  360
LIVLADQPKY TGEGTGIKKI TGGDPVEINP KYEKRFTAVI RAVVLATNNN PMIFTERAGG  420
VARRRVIFRF DNIVSEAEKD RELPEKIAAE IPVIIRRLLA NFADPEKARA LLIEQRDGDE  480
ALAIKQQTDP VIEFCQFLNF LEEARGLMMG GGGDSVKYTT RNSLYRVYLA FMAYAGRSKP  540
LNVNDFGKAM KPAAKVYGHE YITRKVKGVT QTNAITTDDC DAFL                  584
```

| SEQ ID NO: 6 | moltype = DNA length = 1752 |
|---|---|
| FEATURE | Location/Qualifiers |
| source | 1..1752 |
| | mol_type = other DNA |
| | note = PICI primase-helicase |
| | organism = synthetic construct |

SEQUENCE: 6

```
atgaaactgg caccgaacgt aaaacagcag tcacgcggca taaaacacaa agaaacagaa   60
gtcattattt ttgcgggtag tgatgcctgg tcacacgcaa aacaatggca ggaacatgac  120
gcgcgtatgg ccggagataa tgagcctcct gtgtggcttg gggagcagca gttatccgaa  180
ctggataagc tgcaaattgt gccggaaggc agaaaatccg tgcgcatatt cagggccgga  240
tatcttgcgc cagtaatgat aaaggcgatt ggtcagaagc tggcggcggc aggcgtacag  300
gatgcaaatt tttaccctga tggtatgcac ggtcagaagg tggagaactg gcgcgaatat  360
ctggcccgtg agcgccagaa tctttctgat ggtctggtca ttgagcttcc ggtaaagcaa  420
aaggcgcaac tttcgcagat ggcggacagt gagcgcgcgc agctgcttgc cgatcgcttt  480
gatggcgttt gcgtacatcc tgaaagtgaa atcgttcacg tatggtgcgg cggggtatgg  540
tgtccggtca gcacaatgga gctgagccgc gaaatggtgg cgatctattc agagcacagg  600
gccactttca gcaagcgcgt aatcaataac gccgtgaaag cgttaaaagt tattgccgaa  660
ccaatgggcg agccgtccgg cgatttgctg ccgttcgcca atggtgcgct tgacctgaaa  720
acggggaat tttccccgca cacgccgag aactggatca ccacgcacaa cggcattgga  780
tacacgccac cagcacccgg ggagaacatc cgcgataacg cgccaaactt catgaatgc  840
cttgagcacg cagccggaaa agacccgcgc aagatgatgc gtatatgtgc cgcgctgtac  900
atgattatgc cgaaccggta cgactggcag atgtttattg aggccaccgg agacggcggg  960
agcggtaaaa gtacattcac acacatagcc agccttctgg cagggaaaca aaacacggta 1020
agcgctgaaa tgacatcgct tgatgatgct ggtgggcgtg cgcaggttgt cgggagtcgt 1080
cttatcgtcc tggcagacca gccgaaatat acaggcgaag gaacgggcat caagaaaatc 1140
acgggcggc accccgtgga aattaacccg aaatatgaaa agcgttttac ggcggtaatc 1200
agggcggtgg tgctggcaac caataacaat ccgatgatat tcaccgaacg ggccggaggt 1260
gtggcacgtc gtcgggtgat attccggttc gataacatcg taagcgaggc agaaaaagac 1320
agggagctac cggaaaagat cgcggctgaa atccctgtca ttatccgccg cttgctggcg 1380
aactttgccg accctgaaaa ggcacgggct tactcattg aacagcgtga cggtgatgaa 1440
gcactggcaa taaagcaaca gacggatccg gttattgagt tttgccagtt cctgaatttt 1500
ctggaggaag cacgcggcct gatgatgggc ggcggtggga ttcagtgaa gtacacgacc 1560
agaaacagcc tttaccgcgt ctatctggcg tttatggcgt acgcaggcag gagcaaaccg 1620
ctaaacgtaa atgactttgg caaggctatg aagccagccg cgaaagttta cggacatgaa 1680
tatattacgc ggaaagttaa aggagtaacg cagactaacg caataacaac agacgattgc 1740
gacgcgtttt ta                                                    1752
```

| SEQ ID NO: 7 | moltype = DNA length = 29808 |
|---|---|
| FEATURE | Location/Qualifiers |
| source | 1..29808 |
| | mol_type = genomic DNA |
| | organism = Kappa phage |

SEQUENCE: 7

```
gctgttttgg ggtgcttttg aatgagtaca gggatgcgat cacctggtgg cggacgcaaa   60
tcgaataaca ctggaaatca ggttagttct ttaaccagag cggtttctcc gccggatgaa  120
ttactgggcg atatggctat cgatgcctgg aaacggacgt gcaaaattct tattaaccgt  180
ggcacgttcg aaatggaaga ttgttatttg ctgatggaat actgcaacac cgtgcagctg  240
```

```
ctgtacgacg ccaaccagga aattaaaagc gatggccttg gtgatgatac cgctgccggc    300
ggtcagaaac ttggtgcggc agtgaaggcg cgtagccgtt atatcagcga attaattcga    360
ctctccgttg tgttaaagct ggaccccaat agccgcatcc tgaagaaaca gcccggagat    420
aatgacaaat ccagcggtga gttcgacgag ttttaatttt ggtgcggccc taatgactta    480
aggatggagc atggccgcat atccaaacgt caatgtgcga aacaaatatg cgcgggatat    540
catagacggg aaaatagtcg cctgcagagc tattcggctg gcatgtcagc gccattttga    600
cgatttaaaa aaatcactcg ataacaatta cccttaccgg ttcgacagag atttagctga    660
gcgggcctgc cggtttgttc agaaattacc gcactccagt ggcgatttgg cggggcagaa    720
attaaaactg gaaccttggc aaagttttat tttttgttcg attttttggct gggtcacgaa    780
aaaggataaa aaacgccgat ttcgcgaagc gtatatccgg gtagccagga aaaacgggaa    840
atcgtttttt gctgccggga ttggcaccta catgtttgc gctgatgcg aaaacagcgc    900
agaagtgtat tgcggtgcga caactatggc gcaggcgaaa aaggtcttca ccccagccag    960
gcagatggcc agccgcctgc cggcacttcg ctccagattt gatatttcgg tatggaccga   1020
cagcctgaca cgcccggatg gttccgtttt cgcacctatg gcggggaaac ccggcagtga   1080
tgacagccca cattgcgcga tcattgacga gtatcacgaa cacgatacgg atcatatgta   1140
cgaggccatg acaatgggga tgggcgcccg ttcgcagccg ttaacgctca ttatcacgac   1200
agccggctcg tcactggagt ccccttgcta tgacaaggac aaggaagtca aagaggttat   1260
cgaaggcata accgtaatg atcgcctgtt tggcatgatt tacgaactgg atgctggcga   1320
tgactggacc gacccgaaaa acttaatcaa agctaaccca aatctggacg tttcggttaa   1380
gtacagcgac ctggttgagc ttctggaagt agcgaaacag gttcctcgca aggttaacgc   1440
cttcaaaacc aaacgcctca atatttgggt atccggtaaa tccgcgttct acaacatgga   1500
gcagtggaag gctgctgaag accccaacct tgagctgcgt gattttgcga atgacagctg   1560
caatatcggt ctcgatctcg ccaaaaagct ggatatgaac gccgggatac ggctatttac   1620
gcgggaaatt gaaggtaaac ggcattatta ctgcatcaaa cctaaatttt gggtcccgga   1680
agacacgatc catacaaccg atccaaaact gctgaaaact gctgacaggt atcagaagtt   1740
ttatgaaatg ggcgtgctgg aagcgacgga tggagcagag gcagactatc cggagattct   1800
ggccagtatt atcgatatgc aggacgaaaa ccgcattgac gagattgata tcgaccctgc   1860
cggcgcaaca gcacttcgcc accagttgga ggacaacgga tttaccgtag tcgatatccg   1920
gcaggattac accaatatgt caccggcgat gaaagagctt gaagcggctc tggccggtgg   1980
tcgattccac catgatggca atcccattct gacctggtgt atcagcaatg ttatcgggaa   2040
atttataccc ggtagcgatg atctcgttcg cccgacaaag ggagacaatc aaagcaaaat   2100
cgatggagct acagcgttat ttaacgccat gactcgcgca atgctgcacg aaagcagcgg   2160
cggcacatcg gtatatgatg aggaagacat agcgtgttaa tcacaattct gagtttcatt   2220
attggcctgg ccggggctgt actcatatcc gccggagcct ggttgatttt gcctgctgcc   2280
ggtcttatta cgggtgggtc aatatgtctt atctggtcat atctaactgc gcgggcggtt   2340
tcagccggtg ccaaatttaa cggggtgaa taatgtttat cccccaaatg ttcagagggc   2400
gccagcagtc gagggatggc ctctgggaag ccatgctggg cggggttcgt tcaagccaga   2460
gcaaaactgg catcataatc acgccggaaa ccgctctggg actttcagcg gtccgggcct   2520
gtgtcactct cctggctgag tccgtcgcgc agctgccgtg cgaactttac cggcgggata   2580
aaaatggcgg gcgccagcgt gcgacggacc acccggttta tgacctgatt cactcccagc   2640
ccaacaggaa agacacctca ttcgagtatt tcgagcagca gcaggggttg ctggggcttg   2700
agggaaattg ctactcgatc atcgaacggg acggaaaagg ctacccgaaa gagctgatcc   2760
ccattaaccc gaaaaaggtc atttgtgctga aagggccgga cggtatgccg tattaccaac   2820
tcccggaagt cggcgaaatt ctgccgatgc gcatgatgca ccatgtgaag gtctttttctc   2880
tggatggcta tatcggcagc tcccccattc agacgaacgc cgatgttctt ggactgaatt   2940
tggccgttga ggagcatgcg gcagcgacat tccgcgcgg gacaacgatg agcggagtga   3000
tagagcgtcc gagagaagcc gcgaccatta aaagccagga tgctattgat cgcctgctgg   3060
cgaaatggac cgagcgccat tccggtattc acaatatgtt ctctgtggca ctgctgcagg   3120
agggtatgag ctacaaacaa ctgtcgcagg ataacgaaaa ggcgcagctg ctacagtcgc   3180
ggcagtgggg cgtggaagag gtctgccggc tctataaaat cccgccacat atggtgcaga   3240
tgctgggaa agcgaccaac aacaacattg agcaccaggg cctgcagttc gtgatgtata   3300
cgctgctggc atggctgaaa cgccatgagg gtgcgctgca gcgcgatctg cttctgccca   3360
gcgaacgccg cgatttgtac atcgagttca acgtttccgg gctgctgcga ggcgatcaga   3420
aatcacgcta tgaatcttat gcgctgggcc gccagtgggg atggctatcc actaacgata   3480
tccggcgtat ggagaatctg ccgcccattg ccggcgggga taaatacctg acgccgctca   3540
atatggtcga cagtgcgaag atccttcctg gcgataaatc gccgacagca aaacagctgg   3600
ccgaaatcga aacccttctg gccagagcct gattatttcc cgccgcgcgg gatgacctgg   3660
aagacaacat gacaacgaaa ttaattaacc tgccgcacct ggcagatatg gtctttggtg   3720
tgccgcatta cgtgacgcgg caaacaatgg actccgtgaa agcggtgctc atccctcgta   3780
ttcaggggat caccgaagat accgtcattc agatggcgct aaatccggat aaatcacctg   3840
ctgctgagca ggtccagccc accggcgggg tggcggtgat ccccgttcac ggcatactcg   3900
ttccacgccg ggggcagatt acagcgatgt gctccgagct gaccagctac gagcggatac   3960
gcgggcagtt gcaggcggcg ttaaacgacc cctcaatcag cgaaatcgtt ctggatatta   4020
actccggcgg cggcgcagcg gtggggtgca aggagctggc cgattacatt tatcagtctn   4080
gcgacacgaa gcccatcacg gcgattgtga actacagcgc gtactccgcc gcgtatttca   4140
tcgcatcggc ctgcagcaaa atcatcgtca gccagaccag tggcgtgggg tcgattggtg   4200
tgatcatgga gcacctcgat acgtcgaaga tggaagaaaa aatggggctg acgttcacca   4260
ccatttaccg gggagataac aaaaataacg gtacccaaca tgaaccactg agtgaagagt   4320
cgcggggtat gttccagggc atgatcgacg aaatgtacga gacgtttacg gggtcggtgg   4380
ccgaatatcg cggcctgaag cagcaggccg tcattgatac gcaggcgggg ctgtattttg   4440
gccctggcgc tgtgtctgcc ggcctggcgg atgaagtctc tgaccccag gcggcgctca   4500
atgctatcgc ggcaaagtat cagcaacccc gtcaaaaaac ctccattcag atgcaggcag   4560
ccgcgatgga cctgcaaacc aaaatgtaac ccggcgcaaa cacaaccgc gtcacccttaa   4620
gcagccagca ggctgctttt tttatgtcta aaaagagaa aataaaatgc cacatattga   4680
agaattgcgt cgtcagcgtg cgggtatcaa cgaacagatt caggccctgg caaccattga   4740
cgccagcggc gtcacgctga ctgcggagca gatgacggag ttttcgaacc tgcagcagca   4800
gttcactgat atcagcgcca aaattgaacg cctggaagcc gccgaacgtg ctgcggcgct   4860
ggtcgcaaaa cccgtgaaag cgactcagca ggcccccggc attattgtta gcaggagcc   4920
gaaacagtac accggtgctg gcatgacccg actggttatg tctgtcgccg caggcgcagg   4980
```

```
gaatctgcag gacgcggcaa aattcgcttc agaagagctg aatgaccagt ccgtatcgat   5040
ggccatttcc accgcagcgg cgtccggtgg tgtgcttatt ccgcagaacc tccacagtga   5100
ggtgatcgag ctactgagcg accgaaccat cgtccgcaag ctgggtgccc gtcccgttcc   5160
gctgcctaac ggtaatatga cgctaccacg cgtggccggt ggagcaacgg caagctacac   5220
aggagaaaac aaagacgcca agacatcaga aacacgcttt gatgatgtaa aactgacggc   5280
gaaaactctg attgcgatgg tgcctatttc caatgcactg attggccgcg ccggattcaa   5340
cgtcgagcag ctggtcctgc aggatattct gaccgccatc tcagtgcgtg aggataaagc   5400
ctttatgcgc gatgacggta ccggcgatac accgattggt atgaaggcgc gcgcgacgca   5460
gtggaaccgc ctgctgccgt gggaagctga tgcagcgatc aacctgaaca cggttgacga   5520
gtacctggac aagatcattt tgatgcggat ggacggcaac agcaatatga tcagcagcgg   5580
ctggggcatg tcgaaccgta cctatatgaa gttgtttggg ctgcgtgacg caacggcaa    5640
caaagtctat ccggaaatgg ctcagggatt acttaaagga tatccggttc agcgtaccag   5700
cgcgatccct gcgaatctgg ggaccggggg taaggagact gagatttact ttgctgactt   5760
caatgatgtg gttatcgctg aagacgcaa tatgaaagtc gacttctcga aggaagcctc    5820
ttacatcgat gccgatggca ccctggtatc tgccgttttcc cgtaaccagt cgctaatccg   5880
cgttgttact gagcatgata ttggcttccg tcatccggaa ggcctggtgc tgggtaccgg   5940
cgtcctgttc taacccatcc ctcagtaaat acggcccgca tatgcgggct tttccttttc   6000
aggagaatgt tatggctgtg aaaaataaag cagtgggagcc ggaagaaaca ggcacacagg   6060
acaaccatgc gaccgtggtc gcacaggcag agcgtaaatc cgttgtgttc cttgggccgc   6120
accaccgtta ttcccgtgga gatatcgcgt gctttgaagg atcgcgcgcc gaagaactgg   6180
ttaagcggcg tatcgcggta tggccggagg atgccgaacg tgcgctgaaa ccgaagccgg   6240
gagacagcga ttttgatact gaaattggat gatgtgaaaa cccagctacg cctggaactg   6300
gatttcacgg agcatgacgc catgctcacg caaatggtga acgccgcgca gcggagcatc   6360
gagcgtgatt attactgcaa gctggtcacc agtgatgaag agctgcaggc actcccggag   6420
accgtccgcg gatttatcgc ggatgaagat atccggctgg ccattcagtt tctggtcagc   6480
gatgcgtatc tgaatggcca taccggacag tggctgaagc ccgtcgcggt gaggcatctt   6540
cttttccccc tgcaggagca tacgctatga gcctgaaacc gggtgatatg aactgtcgca   6600
ttgcgattag ctacgttcag tccggtcggg ggccgctggg cgaaccgcta ccggaaaagc   6660
aggttgaatc gggaaaagcg tgggcaaaac gggagctggt atcggggcgg aaagtccgca   6720
cgctggatca gcagcaggtg gtggaaacct gcctgtttac ggtctatccg ggtgtgctgg   6780
ttgatattga ctgaaaaatc acgacgaaaa atctggttta taccgtccgg aatatcgacc   6840
gcaaaacaga ccggatcatt atcacggggg aggtcgacgg gcggcatgat agagctggcg   6900
attaagggtg cgctggagcg catcaccggc atgaatgcgt atccgctttt actgccggac   6960
acggtccagg aaggtgcgac cttttcagcgt atctctgacc cggaaatggt ctcgggaatg   7020
ttgcgaacgg ggatcgtctc tgcccgtatc caggtgaatc tgtaccgtct cgatgattac   7080
acctcactgc tgcagctgga taaaaaaatc tggacgaaac tgaagtccgt cgttcatggc   7140
cagctggagg gtatcccggt tcagtatgtg gagcgaggcg gtatccatca ggataaaaac   7200
cagctgacga atcgtcgcat tcagtatcgc ctgacccgcg atttcatcat tcactacgtg   7260
gaggactcct cgtgatccga atggaaatta aagggctgag tgagctggag cggcagttga   7320
cggccctggg cgaaaagtg gcgacaaagg tattgcggga tgccgggcgc gaagcgctaa   7380
aggtcgtcga ggaagatatg aagcagcatg ccggcttga cgaaacgtct gccggaccgc   7440
acatgcggga ctcaatcaaa atccgctctt ccactcgcaa gggtaaaggg aacgcggttg   7500
taacgctccg tgttggcccc agcaagcagc accatatgaa ggcgctggcg caggagtttg   7560
gcacggttaa acaggttgca gaccccttta tccgacccgc cctggattac aacctccaga   7620
ccgttttgcg cgtgttaacc gtggaaatcc gaaacggcat tgaaaacagg tagcatccgc   7680
tgccgtataa aaagagagag aaacatggct gataaaactt cacctgaata tgcgatgttg   7740
ccagccgggca ccattgtgaa atcggggagg cctggccgtg ccacgtcagc gctgaaaccg   7800
ctgattaact gtaaagcgct gggtgcaatg gggcagacgg ggggctttgt cgactgcacc   7860
acgttactgg ataagcagaa acagtccatc agcgatctgc ctgacgggcc tgaaaagtcg   7920
ctgggcttta ttgatgatcc aggcaatacc gattttgccg cgctgctgaa cgcagcagag   7980
gcccgcaaga ccatccagtt atacgtcgaa ttacccaaca agcgaacagc gacgatgctc   8040
cttgcgctgt ccgggtggca gatgaatgaa atcgccgctc cggcgaatga ggtcatccag   8100
atcactgttc agggtaagca gaacaagatc acctggggaa ccgtcgctga taccagcggc   8160
gcctgattaa cttaacttttt aaaccgccac cttcgggtgg ctttttattt taaggacta    8220
cctgtgaaag acaaagatta cctgtccacg ctgaaatccg cgttgcttaa atcggagcca   8280
accgtcatta aaccgagtt gtttggcgcg accgtattca tccgccgcct gaccggggat   8340
tacctcatca gctacgaaga gaaaatggct gaaaccgcaa aagctggcgc agcgcgcgag   8400
gcatcggagc aagtcatcca gatcgtcatc gatgcactgg ttcagccgga tggaacggcc   8460
attccggatg agtttaaacc cacggcagcc gagctgctga aggcccatga aaacccgcaa   8520
ctgctggctg cagtggaaaa agtaagcaa cacgcaatcg gcaagctgga ggaagcggaa   8580
aaaaactgag tgactcgccc tggctggagc tgattttctg gctggccgac cgctggggcg   8640
agcctgaccc atccaaaatt gccgcattgc cggcaaacac tctgtaccac tggcgagcct   8700
acttcctgaa acagggcact ttccgccgtc ctggcgatga aaacacgcca cctaccgaaa   8760
ccacacctgc gccatcccgg gtcgatgatg aatcgcggc agtcatgagg gcattaatgt   8820
aatggcagac gtcgcatctt tagcggtcgg gctgcacctg aacgcagcca gttttaaatc   8880
ccagctgctg ggagcgtatg gcgatgcgga gaaccagtca cgacggttta accgtaatgc   8940
ccaggcggac gcgaaaaaga cggaggacgc ctataagaag gtcggtctgt cgatatccgg   9000
gatggccagc cggctggcgg ggctggcagg agccggtctt tccatcggta cgatcgtcac   9060
cacgtccaga caatatggac aggcattatc agacctgcag gccatcaccg gtgcgactgc   9120
tgctgaaatg aaaagcgctg gg atctggctgc gcaggaaatg ggacgcacga cagagtacag   9180
cgccagccag gccgccgagg cgctaaagct gatggcgtcg gctaaaccgg agcttttaaa   9240
aacgtccgat ggactgcaga aggctacgaa cagcgcgctt atcctggcgc aggccgccgg   9300
cacaacgctg cccgatgcga ccagaacgct ggcgctctcc ttaaaccagt acggggcgag   9360
cgcgcaggag gcggatcgtt atatcaacgt gctggccgcc gtgcaggaagt acggtcgtc   9420
ggagattgtg aatacagcgg ccgcattaa aaatggtggc gtcgcagccg cacaggccgg   9480
cgttggtttt gagcagctga atgccgcgat tcaggtgctg gcagagctga aaattaaagg   9540
cggtgaagcc ggcacggcgc tgcgtaacgt catcctgaat ctggaaaagg gcacggacaa   9600
gagtctcaag ccgtccgtgg ttggtctcag ccaggcgctg accaatcata ccgggaaaaa   9660
tctctccacg gcccaggccg taaaactgtt tggcgtggag aacctgaatg cggcgtctat   9720
```

```
cctggtccag aaccgttcaa ggcttgatga gctgaccgct tccctgaccg gtaccaaaac   9780
ggcgcatgag caggcatcca tcaggggtaa caacctgaac ggcgatttgc tgggtctgag   9840
cagtgcgttt gaagggatgg tcattaagat cggccagagc agtaacgggc cactccgcag   9900
cgggattcag gttgccacgg aggcactgaa cagcctggca gacaatttca acaccgtctc   9960
cagcgtggcg ctttacagtc tgatccccgt gctatccacg aaactgaccg cagggctgcg  10020
ggagaatatc gcggcctggc ggaaaagcca ggcggcggta aaagcgcggg cgcaggctga  10080
tgcggatatt gcccgcaaaa cgctggattc gacagctgcc atcctgaaac agaacgacgc  10140
tgagtttggc cactaccggc agatggagcg gacggctaaa cagtacggga tgaatatcag  10200
ttaccaagat gagtttgccc gcctcatccg acaggaaact gaacaaacca atctggccag  10260
ccaggcgaaa ctgaaactgg cggcggcaaa ccggcaattg tcgatatcag cccgcgcggc  10320
ctctgttgcg gtgggcctgg caagaggcgc cctggctttt gttggtggtc cggttggcgc  10380
ggcgacgctg gctggatctg cattactgta tttccatcaa caggcaaaag aagcccggca  10440
atcggccatt gatttaaaag atgccgtagt ggaaaccagt gaagcgctga tgcgcctctc  10500
gcttaaccag ttaaatgtga agcagttcga cctggaggat aagtacgaaa accaggtcgt  10560
gcagcgtaac cagctgatga aagagattca ggatgccgac agccgtatcg acagcctgaa  10620
agggtttgac cccttcggcc agctggaagg ggtgacaaaa ggcgaggcgc gtgcacgggc  10680
ggatctcgaa agcgttaacg agggactccg caaaactgag gaaaacatta agcgtgtcag  10740
tgatgcaaaa acactggctc agctgggttt atcgggaaaa ataacctccc ttacggacga  10800
tctgaaagga gcgttaagca cgccccccaa agagaccgga gagggaaatc cctggggcgg  10860
cgatggcggt accggcacgg ggaaaggcag taagtcccag gtcgaccagt tcaaaacgct  10920
gcggcagcaa attgaagaag cccatgcatc cagcctggcc agaattaacc tgcaggaaaa  10980
ggacagcaac agggagctgc ggaagaaaat ggcgccagtg atgctgacct  11040
gcagcgcgcg ctgttaatga atgcagagaa ctaccagaaa cagcgactgg atctggccgt  11100
gcagtattcc cccgcccggg aaactctgcg aaaagagcag gaagccagcc gggacctggc  11160
tgagcttttc aaagcccgcc ttcttgatga aaaagagtac caggccgcac gaataacgct  11220
ggccagagat accgcgaaag agctgctgca ggcaaaggct gacgaaatcg cggcgcctaa  11280
actggatatc gccggtgagg ttgatccact ggtagcactc cgcaatcagt taacgcagcg  11340
gcaggctttg ctgctgtcgt actatcgag cagcgcgatc agcaaagaac agtacgaaat  11400
gctgatgaag aaggcgacga aggattctgc agattcgcaa tatcagacgt cgctggagtt  11460
atatcgatca cagggcgaat tccagagcct ggccgtcggg ttatttgaaa cggcccatga  11520
gcgctctagc aacttcctga cgagcatgtt gacgcggacg agaagcttta aggagaacat  11580
ggctgacctg ttttcctcgc tcacgcagtc ggtcataaaa aacctcgttg atatggccgc  11640
tcaggctctt gttaccagca ctatcatgca aaccatcatg ggtgtggtgg agctggagt  11700
gagtattgca ggtggtgttt ctggagcggc tgatgtcggc gcaggaactg cgattcagaa  11760
tgcgggtaat aactttaact tcaaatacc gggttatgcc aaaggcggtg tcttcgattc  11820
tccttcatta agtgcctaca gcaaccaggt ctacgactct ccgcagttct tgctttcgc  11880
aaaaggggcc ggcgtatttg gcgaggcgg gccggaggcc atcatgccgc tgacgcgtgc  11940
cggtgatggt tcgctgggtg tacgcgcggt gggtggtggt cagaacgccg gcgcgtcgga  12000
agggccaaaa gtctatatca cgattgaagg cggaaacacc tcaacgcagg caccgtctgg  12060
ttttgagcag tttggccagc agatcggctc gtttgtggag aaaaaataca gggagctgat  12120
ggcgcaggat atgcgccctg gcgggatggt ctggaatgca gttaaagggc aacgttgatg  12180
gctattgaga tattcacctg gagtccgcgg gttaatcccc agcagaccgt taactttcgt  12240
gtccggaagg cgcagttcgg tgacgggtat gcgcaggtat ccggcgatgg tattaacacc  12300
cgatcacagg actgggagct gagttttgtc ggtacggagg actatatccg tccgattaag  12360
cagttcttcg accgtcatgc cggcacccgc gcgtttcagt ggaccccgcc tctgaagag  12420
gtggggcttt accgctgcga acaatataaa ccggtgccgc tgggcggcgg aaattactca  12480
ctttcagcca cttttattca ggcatttaaa ccatgagcct taacgcgaat tatcagaagt  12540
tagagccagg cgatgaggtt cgtctcctgg agatcgatgg ccaggcgttt ggcctggacg  12600
aggttttgta tttccacggc tataacgtcc cccatactgc agccgaaatc ctcgccgctg  12660
acggcgacct ggataagctg cctgcgaaaa gcatctggtg gcaggggcgg gagtataaag  12720
cctgccatgc tgtaatcgaa gggatcgagt catccaccac tggcagcgac gcgcagccaa  12780
cgctgcgggt agggaacatc gacgggaaaa tatccgcgct ctgtcttcat tacgacgatc  12840
tggctctggc gcgggttgtc atccacgaca cgcaaaaaca gtatctcgat gcgaagaact  12900
ttccggacgg gaatgcctca gctgatccga cgcaggagaa acggcgcctt ttcttcattg  12960
acgtaaaagca ttatgaagac gatgagaagg tggaatttac tctctccagc ccgttttgcc  13020
tgcagggat gatgatcccc actcgccagc tgcatgcgat ttgcacctgg tgtatccgca  13080
atcaataccg cagcggtaac gggtgcgact atgccggcac ccggtatttt gacaggaaca  13140
atcagccagt tgatgacccg tcgcaggatg tctgcaacgg aacgctcacg gcctgcaaat  13200
tacgtcatgg tgagaatagt gaactgccgt ttggcgggtt cccggcacc tcattaatca  13260
ggagctgata tgcgtcagaa aacgattaag gccatccagg aacatcggcg ggcagaatat  13320
ccgcgcgagg cctgcggcct cgtcgcccag aggggccgag cggagcgtta tttcccctgc  13380
cggaacctgg ccacagagtc gaaagataat tttgtgctgg cgccggagga ttatgcggag  13440
gttgaggaat ggggaacgat caccggtatt gttcacagcc atcctgatgc caccacccag  13500
ccgagcgaac tggataaagc gcaatgcgac gcgacccttc ttccctgaca tattatcagc  13560
tggccagaag gcgatctccg taccatccac ccgcgtggtg agttgccgct cctcgagcga  13620
ccattcgtgc tgggccacta cgattgctgg ggctggtga tgagctattt tcggcaaacc  13680
cacggcatcg agctgcacga ttaccgcgtc gattatccgt ggtgggaaaa ggagtatccg  13740
gacaatttt atcaggactg ctggtatgaa tgcgggtcc gtgagttga tggtccacca  13800
caaccgggtg atatggtgat catgcaggtg caggcggata agtggaacca cgccgggatt  13860
ctgctggaag aaaatatgct cctgcatcat ctgtatggcc atctcagcaa tcgcgtgccg  13920
tatggtggat actggatgga aggacgatg aaaatcgtgc gacatcattc actattttaa  13980
ggtgcctgta tattatgctc caattcaat ttacaggagc atgcgaatga atgagccaat  14040
cactgagcag ttatacaata aagttgtaaa tttcgttaat aaaatggatg ggagtgtgcg  14100
ctttgattat atttctaagt ccttgcgcat tcctcctgatg aaattgtga  14160
caggatgatt gctgatggag tcgttgttaa tacaggaacg gtaggtgaat atttaccagt  14220
aaaacatgca tcttccaaaa acactgataa agataatcga tgctgtacat ctcaaaaaaa  14280
caatgatagt agtggactaa aatttcttgt tgggagagta gcattagtta tagccataat  14340
attttttatt ataacctgct tttatgctta cagagcaccg atatcgtttg ttttttctaat  14400
cccagccata atggctgcat tgtttttac aaaccaaaat catggtggag aaggtttcct  14460
```

```
agggttgagt tcaatctctg catgtttaat cttttttgctc cttactaatg cgcagacacc  14520
aatatttgga gaagcatatg aattaagaaa gcagagggat gaaattaaaa atgaagttac  14580
taggaaatca aaggaagaag atcagcaaca gctaaatgat atccttaacg ccagagagca  14640
tataaaaggg atgctaaaag accccctcctc agctaaattt tttggtgaat tcattggaaa  14700
aaatggtgct atctgtggcc atgtcaacgc taaaaatagt tttggtggtt acactgggga  14760
gtctcgttac atattttctg tcaattttcc tgcaatagat gaaggcacca cctcctttaa  14820
taaggagtgg gagagacagt gttatcttaa ttgaatggca aggataaagc atgcaagaaa  14880
ccatgacgag aatagaactg tctggagtcc tgggtaaaac cttgggaag gttcattatc  14940
gtttaataaa gaacatcaat gaagccggag aggcattatc tgcgacgatc cctggatttg  15000
aaaggttcat gatatccagt gaggagcgtg gattgaccta tgcagtattt aaagggaata  15060
agaatatcgg gcatgatgat ttaggattcc ctgtaagtgg cgaaattatc cgcatagtcc  15120
ctgttatcat tggcagtaag aaggcaggaa ttctccaaac aatccttggt gcagttattg  15180
ttgcggcaag tgttgcctat ggttttttca cagaggattg ggctaatgcc gcgtatggta  15240
ttcaagctgg cggcgccatg atgctcggcg gcgtcgttca gatgctctcc ccacagccag  15300
ctggcctggc acgaaaagaa tccgctgaca ataaagcgtc ctacgccttt ggggggcgtga  15360
cgaacactgc ctctcaggga tacccggtcc ctttgcttta tggcaaacgg cgaattggcg  15420
gcgccattat atctgccggt atttacgtag aagaccagca ataagttta ttcagtaaac  15480
catccaattc aggccacctt gcggtggctt ttttttatgg cgtaatatgg caaataacat  15540
aattaaaggg cgcaagggtg gcggctcaaa gcagcgtaca ccgacggaac agccggatga  15600
tttacagtcc gttgcaaaag ccaaaattct gctcgcatta ggtgagggtg aatttgcagg  15660
tggtttaacc gggaaagata tttatcttga tggcaccccg cttgaaaatg ctgatggttc  15720
gcaaaacttc agtggcgtgt cctgggaatt tcgccccgc acgcaggctc agacttatat  15780
tcagggtatt cccggtactg aaaatgaaat cagtgtagga acggaagttt ccagcaaagc  15840
agcctggacc cataccttta ctaatacccca gctttctgcc gttcgtgtcc gcctgaaatg  15900
gccgtccctg atgaaacagg aagatgacgg cgacgtggtg ggcaataccg tcaagtatgc  15960
gattgacctg cagaccgacg gcggccgcctg gcagacggtg ctggaaaccg ctgtcacggg  16020
taaaaccacc tccggttatg agcggagcca tcgtattgat ctgcccccagg ccggcagtac  16080
ctggacgcta cgcctgcgta aaatctctcc ggatgcaaac agtgtcaaag ttggcgacgt  16140
gatgacgctg cagagctata ccgaagtgat tgacgcgaag ctgcgttatc ccaacaccgc  16200
gctgctttat atcgagttcg actccagcca gtttaatgc tccattccgc aaatttcctg  16260
tgagccgcgt gggcgcgtga ttcgtgtgcc ggataactac aatccggaaa cccgcgaata  16320
taccggcgtc tggaccggcg ggtttaaatg ggcctggacg ataacccgg cctggatcta  16380
ttacgacatt gttacagctg accgttttgg tctcggtaat cgtctgagca gcgccaatat  16440
ttcgaaatgg acgttgtacc agattgcaca gtactgcgat cagctggttc ctgacggggcg  16500
cggtggtgac ggcatggagc cgcgctatac ctgtaacgtc tacgtccagg aacgcaacga  16560
cgcttacacc gtgctgcgag actttgccgc cattttccgg ggcatgacct gctgaacgg  16620
tgagcagatt gttgtgcagg ctgatatgcc gcgtgatgtc gatttacct atacgcgcgc  16680
caatattgtc ggcaaacccc gttattcgag cagcagcagc caggttcggt acaccaagtg  16740
cctggtttcc tggtctgatc cggataatgc ttatgctgat gcgatggagc cggcgttat  16800
cccggaactg gtttcccgct acagttttaa ccagctcgaa ctgaccgcga ttggctgtac  16860
gcgccagagc gaagcccacc gtaagggggtt gtggggcata ctgaccaaca acaaagaccg  16920
ggtcgttgag tttgatgtgg ggctggacgg tcgcattcct caacccggtt atatcattgc  16980
cctggcggat gagttgctgg ccggacgggt caacggcggg gcaatcagcg cggtgaattgg  17040
ccgggtgatt actctggatc gtgatgtgga tgccaaacct ggcgaccgtc tccagctaaa  17100
cctgccatcc ggtatctcac agagccggac cattcaggct gttaacggac gccggcagat  17160
tacggtcaca acggcgtaca gtgagacacc agaacgggaa tgcgtctggg ccgttgaatc  17220
cgatgaccte ttcctgcagc agtaccgggt tacagggtta aaagagaaca gcgatgcaac  17280
cctcacgatc accggcgtgg cacatgaccc ggataaattc gcccgcatcg ataccggcgc  17340
tattatcgac cagcgcccgg ttagcgtatt gccggcgggc aaccagtcac ctcctgacga  17400
tattgtcatc acatcccgct cggtcgtgaa tcagggggatc agcgtcgaaa cgatgcaggt  17460
taactggatca gcggtcagcg gcgctattgc ctacgaggca cagtggcgcc gtaacgacgg  17520
gaactggatt aatgtgccgc gcagctcgac cacctcgttt gaggtcagcg gcatttatgc  17580
cggtcgttac ctggttcgcg tccgtgcgat caatcggcg gagatctcga gcggctgggc  17640
gtattccgaa gagaaaaccc tgaccggcaa ggtcggcgag ccgctggcac cgctggcgct  17700
ggcaacccgt tcgctggttc atgggggtcca ggttagctgg gagttcccga ccggctccgg  17760
ggatacgctg cgcacggaac tgcagtacag caaaaaccag gacggcagtg cgccaatgcc  17820
gttatcagac gtgggcctatc cggggaaaag ctatcagcag atgggcctca gtatgggcgc  17880
agaattctgg taccgggcgc gccttgtgga tcgtcttggc aatgaaagcc cgtggaccgg  17940
ctgggtccag gggatggcca gcgataactt tgatgactac tacgaaaacc tgaccgacgg  18000
gatcaaggat acggctgcct gggaggaaac gcagcgcacc attagcgaaa cgcaggaagg  18060
tatccgcaat acgcagcagg aactggagca gaccgctgaa gctctgcgta aggaagccga  18120
agaccaggcg aagcaggtca gccaggatat tgatgcatcg gcgaaaagca tcactgctga  18180
tgttgacggg aagatctccg ccgtgaataa accatcacg gatgagatca cctcggtcaa  18240
tgaggctctc gattctggtc tggctcaggc aaacaaaggc gttcaggagg caaaatccgc  18300
cgtcgcagat gcgaacaagc agatcgcaac tgtgaacaag tcgttgaccg acagcatcac  18360
ccaggtaaga cagtcagtca ccgatacggc tgcggaaatc aacgccacca tcgacctgga  18420
gattgccagg gtcagcaaaa cgctggccga cggcgatgcc gcattgaatg cgcagataaa  18480
gactgccgaa aatggcctga agcagtcgct gtctcaggtt aacaccacgc tgaccaatgc  18540
agtgaagcag gagaccgcgg atcgtatcgc cgatgttaac gcgaaggcgg cacaggccgg  18600
tgatgaactg ctggcggcaa cgcaggggat tgaggcgagt atcgagagcc tgtctgaggc  18660
cgtgacctct ggtgacgaaa atcggcacg ccagatctca cagattgccg ctggcacagg  18720
ggagcagttt gactctctgg aaatctggta tttcgacaaa gatgccgaag ctgacggga  18780
agacgacaac ggctacacgc caatgagcgt caccagcgat ggctggctta aagccaacaa  18840
ttcgacttca acctgctgat cccctaacgg cctgacgatc gcgatgcccatg cttatcgttt  18900
cattaagatg cgcattaaaa aggttggtag cccaacctgg aatgccaaaa tgttctggat  18960
cggcgctgat gaaaccggct ggaatgctgg tcgctccgtg gttatcagtg agccggaata  19020
cgatgacaag ggtattgcga ttctgaccct gcacgacatt gagtggcggg attcgacaac  19080
gattcgtcgt ttccgcttcg atttcacaac gggccaggat gcggacaact atctgttatt  19140
tgactggatc gccgttggcc ggccagcacc cggcgccagt acgcggctc tgcaggatgt  19200
```

```
gcgcagtacg ctgagcaacg cgctgactgc cgaagcgcag gcacgcagca cgctggcggc   19260
gcagatgcgt ggctcctatg agggcagcga tctggataaa gtcacctccg ggctgctgta   19320
ccaggaaaaa accgcgcgcg ttaccgccat ctcggcggaa gttaaggcca gagagtccct   19380
gcagacgcag tttaacgaca acaaagctgc tgtttctggt gaactgagtt ctctgacgac   19440
agagcagagc gcgcaggcga gccgtatcgg tggcctggaa accagcctcg ggaaaaaagc   19500
cgatgcggcc gcgctgacgt ccctgacgca gaaagttgag caacagggcg ccacgctgac   19560
atcgcagggc gccgcgttaa catcgctcac taaccgggtt ggccagacgg aaacgggcct   19620
ggctggtacg aatgaggcgc tgagcgggct gcagtctgtt gttacccagc agggcgacag   19680
gataaccagc cagggtcagt ccatcaacga actgacgagc gatttgggca cgacaaatgc   19740
cgcgctggcg aagaaagccg aagcggctgc ggtcactgcc ttaacgcagc aggtagagca   19800
aaacgggcgg gatattcgca gcaatactga cagcatcacc agcctgtcga atcaactggt   19860
caatggccag ccgaatcgct ggtcccgtcg actctatccg gtgcagctgg ctaacgccgg   19920
gacagtcccg tcattcagcg atgttcgcgc cgtggcgcca acggtcgtgg atgaggtggc   19980
cgacgcggcc aaactggact ttacgtccgc cggcagctat ctgatcgcgc tgtattcctg   20040
ccaggtgaaa gtggtcgcag ataccaccat cacactggcg cccggcgcca gggtttttga   20100
tgataccggc gccatatttg tgaatggggt acaggtcgcc tggggtaacg ccagctggaa   20160
taccgtcagt tttgaactga agccggctg gaacaccgtt gagtttctgg tgaatcagtg   20220
gacgggccag gcgtatatca acctgggtct gaagctgtca gacaaggttg ctgagatgta   20280
ctccggtctc gggggtttccg cgctggcaaa cgcagccggc gtgctcagct cgaatgtcag   20340
ccagattggc aacgatgtgg tcagcaattc gcagagtatc acccagctcc ggaatgcgct   20400
gacgcagaca gacgcgaacg tggccagcaa agcggatcag acggcgatga actcgctaac   20460
cggacgagtg gagaagacga aatccagcgt gacggctgct aacgccaaca ttacctcgct   20520
gaaatccgct gtacgggccg gaaacgcatc aggcggggat ttaattccca acccgacgtt   20580
tgacccggcg tatgaccaga tgggttcag cgtggtagcc acgacggctg aggaggtccc   20640
gccgggctgc ccgtatggtt atgcggcccg aattgccagc cggatcacc atcctaactt   20700
tgccgcgttc ccggccacgc ttaacgatgt gattgagatc agcgcactgg ttgcctgcgg   20760
cgccggcacg gcgaatttta atctgtatgt tggcaccgcc gttcggccag atacgagcac   20820
cggtgcgcca ctcatggcgg ggggcgggaa atcaccctcc gcgacctggc agagaaccac   20880
ctggcgcttc aaggtcacgc aggcgatggt ggacaggggg tatatccgcc cgttcctgca   20940
gatctcgcag aacagcccgt atggcaccgt atggttcgtc aggactggc atatgcgaaa   21000
tgtgacagcg gcgcaaaaggg ttcaggatac tgcggatgcc acgcgcgcgg cggttgactc   21060
tctgaccacc accgtgacgc aacagggtaa tctgctgacc tcgaccggca accgacaac   21120
ccagctggaa aacgggctgg caaccatcaa tgccgcagtg gccaaaaagg ctgatgcgac   21180
agcagtgcag gatttgacca ataccgtcac acaactgggc aacgatctga ctgctgcgaa   21240
cagcgccatc acgaaactga ccggaaatct ggcgaataac gataaagcgc tggcgcagaa   21300
agccgatgcg actgcgctgg ccacgctcga cacgaaagtg acgcagcagg gtaaaacgct   21360
ggagagccag agcaattcgc tgacgaacct gtcgaacagt ctctcgcagg ttgcggcaga   21420
tatcgatgcc agcggtcaga taccgggtaa cctggtcgtg aatccctcgt ttgaacgtgg   21480
gctgattgac tacccgggcc ggtcaaccgc gaccagtgta gtggagggttt ccgctcctcca   21540
cagcgggacg cgggcgctga aggttgatcc ggggagcgtg tctccggggc aatacatccc   21600
gtttgttcag gggcgaacct atgaaatcgg ggtgtgggtc aaggaacccg gagcgacgac   21660
ggataatggc gcggggaaca caagttgcg gatcggtaac tctgccggcc agccggtctt   21720
tgagcgtccg tacaacagcg gcacgctggg gacaaactgg accctggttt ccgctcgtg   21780
gaaagcgacg gagacagcca gcctgccggt gacgctgagc aactatctga ttaatgcag   21840
ccgctacttc gatgattttt acgtcactga cgttaccgac cgggtggaca tcgatgccac   21900
cgccggcgcc gttaccggac tgacgagccg ggtcagcaca gcggaagggg ctatcacctc   21960
gcaaagcag cagctgacga acctgcagaa cagcctgaac acgaccaaca gcaatgtgtc   22020
gaagaaggcc gatgcaacgg cactgactcc ggtcgataac cgggtgacag aggcggaagg   22080
gaaactgacc acacagagcc agcagctgac aaatctggcg aatgtgctga cggccacccg   22140
caacgctggc gacaacctga tcccgaactt tgatttcta cagggcagca ctgcctggga   22200
tattcagtat ccagccggtg tgacttttgg cgatttcggg gacgggaag cggggcgtcg   22260
gctgaaccgg acgactaaca ccagtccggg gatcttctcc aacaacaaca agccggtgcc   22320
gctgaatggc cagcgcaagt accgcgtggt ggtgaaggcc aaaggtgttt ccggcgcgat   22380
gagtctgctg atccgtcgcc agaacaaaat cggccagacg gacagtacgt atgaggataa   22440
aacgctcacg ctgaccactg actggcaaac catcacctgg gaaaccggat tgacggctgc   22500
cggcgcggac gggcagaact tcaaacttta ttctcatccg acaaacggtg aaatctggct   22560
cgattccgtc cgggttttgg atatcaccga tgaaaccaac atcaaggcga ccagcgatgc   22620
tgtttcgtct ctgaccggga cggtgacgaa ccaggggaac accctgacat cacagggaca   22680
atccatcacg gcgctgaata acgcgctgga aggggtcaaa ggcgatgtgg cgaagaaggc   22740
tgatcgcgtg gcggttcagt cactgaccaa ccggggttacc cagactgaaa aggatatccg   22800
tagcaggcc gacagcctga ccaggctgaa tacatcgctg aagcaacagg caacacgggg   22860
agccaatgta ctgccggacg gcagtttga atcctatgcc gtcggcgatg ttctcagtaa   22920
tgcccgcgct gttatcacca gtgaagctgc gcacagcggg accaaaagcc tgcgtgttac   22980
gcgcagtacg gagtacaacc cgaacgcgac ggataataac gatacccata tcttttctgg   23040
tatgcaggtt cgcgataatg cggtctatta cgtggaggcg tgggttaagt tgccggctgg   23100
ctcgaccgcc gatccgaccg tttatatggt gctaggattt tccttccagg attctgccaa   23160
tggctggtcg tggcctggcc tgaacgtgaa agtctccgga ttgtcggtgg acaactggac   23220
aaaggtcagt ggctatctga ccaacaaccg aaccgcacg aaacaggcaa tggtgaggat   23280
ctccatcccg aatacaccaa aagttcgcct gggtgacgcc ttcctgattg atgatctgat   23340
catcactgac gtgaccgatg cgaaagcggc gctcgatgcc gccgatgcga atgcgcaggc   23400
gctttccagt ctgtccgcgt cagtcacgca gaacgggaag aatattacgt ctcagggcag   23460
cgcgatcacg aagctgcagt cggatgtgac gcaacttggt aaggatatca gcggcaaggc   23520
cgatgccagc gcgctgacga atctgacgac ccgcgtgacg gctaccgaag cagcctgaa   23580
atcgcaggga gcctgccgga tccaacctgca gaacacgacta acagcaatgt   23640
ggcgaagaag gctgatgcaa cggcgctgca gagcctgcag aacaccgttg aacagcatgg   23700
cagggatctg accacgcaaa gcagcgcgct gacgaacctg gaaaacaact tttcctcct   23760
ggccgttggc gggaccaacc ttatccgcaa tgcggacaca ctgagggat ggagcagccg   23820
ccacgccaca gagacgtatc tgggcgaccg cgtggcctac acccgctgg cgaaggtgc   23880
atccggttat atccagctgg atgaacagac gctggatgtt accgggcgta ctgaatttgt   23940
```

```
attcagcttc tatgcgaaag gtgcctataa cggacaggaa atggcgagtt attttataa   24000
cccgtcgaac actaccacca cggaaaccag ccaggggtt aaaggcgggg ccggtgacgg   24060
caaggcggtc acgaaactga ccaccgcatg ggcgcgttac tgggtgaaat gggttattcc   24120
tgccaccagt ggcaccaaac ggctgattgc cgcgcgtctg gaaagcgcga cgtctgccga   24180
caaagaagtc tggctctgtc gccctcagct ggaaaccgag accgtgatga ctgactggtc   24240
accgagtccg gatgatgcgg ccagcggtat taccgcgaac acatcggcca ttaacagcct   24300
caccagtcgg gtgacgaatg ccgaggggca actgaccgcg cagtctcaga gcatcacgaa   24360
tctgcagaac agcctgaaca ccaccaacaa caacgtggca caaaggcca gcgcgcagtc   24420
ggtgagtgat ctccaccagc gggtcaccag tgcggaaggc aaaatcacct cccaggggca   24480
ggctatcacg aagctgcagg gcgatttgag cagcaccacc gataaggtca acaccaaagc   24540
ggatcagacg gcgcttaacg cgctgactgg ccgggtggag aaaaccgagg caggcctcac   24600
ggcagccaac agcaacatcg tcagcctgac ggcggcggtg aacgccggga atgctgccgg   24660
ggatgattac atcccaaacc cgtcatttga tccggcgtat gaccgcatgg gttatgacgt   24720
ggtggagacc actgctgcag gtgtgccggc tgactgcccg ttcaggtatg ccgtccggct   24780
ggccgggcga gaccatgtgc caaaaatcaa caacatcgct gtgacgccgg gcgacgttta   24840
cgaaatgtct gctctggtag cgtgtggtac cggcagcgct gactttaatt tctacatcgg   24900
tcgggccacc actgctactg gtggtattgg ggcgagagcg tccgggggaa acaccaagac   24960
caccaccgcg tggaaacgag ccacctggcg ctttactgtg ccggcagaca cgaacttcct   25020
gcgaccgttc ctgcaggtta atcagagcag cccgttcggc actgtctggt acgctgccga   25080
ctggcatatg cgtaacgtga cggcggcgaa cagtgcgcag aaaaccgcag atgcgaccgc   25140
aaaagcggtg gattcactga ccaccacggt tagccacag ggcgatacgc tcagcagcat   25200
cggcacgcgg accacctcgc tggagaacag cctccggtcg acaaacgata cggtgagtaa   25260
aaaggctgac acgacagcgg tgacgcagct gcagggcacg gtgacgcagc aggggaatga   25320
catcgcggca gccaacagcg cgctgacaaa actcagcagc gatctggcca cgacgaatgc   25380
gaatgtgaac aaaaaagcgg acgcaagcgc gatgaacacc ctgcagaacc aggtcactga   25440
gcagggcaaa acactcagtg cgcaagggga ttctctaacg caacttagta acgcctgaca   25500
ccagacggca gcggatattg acgccagcgg gaaaatgccg ggcaacctca ttgtcaacga   25560
cagttttgag cgcggcgcgg cgggctttac cggctggagc agtaccgcga cggtggccga   25620
tttacaggtt ccgcattcgg gtaacaaggc gctgaaaatg tccgccggcc agtcgaacct   25680
ggtcgggcag gaaatcagta tcacgcaggg tcgtacctac cgcatggggg tatgggcgaa   25740
gcaggaccc ggaaccacta ttaaagatgc gggtaacacg aagtttcgtg tggccgacag   25800
cactggcctg ctggtcggct caaactacgg accgtttagt tctggctggc aactggtaac   25860
gtttgactgg aaagccacga agaccacgac ggccagtttc cagctgacga ccttcctcag   25920
cgcggggcga atgtatttcg atgatttcca tgtcctcgat gttacggatg aaaaggatat   25980
cgcagctaat gccggggcca tttctcagat gaatacccgc gtcaccgctg ctgaagggc   26040
tatcaccacc caggcgcagc agctgacgaa actcagcggc gatctggccg tcacgaatgc   26100
ggcggtcagt aagaaggccg agcaaagcgc tgtcaccggg ttgaccaccc ggatgacgtc   26160
tgccgagggt aaactggatt cgcagtcgca gcagctcacc agtctgcaga acagcctgac   26220
cacgatgaat actgagctgg gtaaaaaggc tgacacgtcc gcggtgagtt cactgaccgg   26280
tcgcgtaagc caggtggaaa acaccatcac cagccagtcg cagagcatca cgtcgctgac   26340
cagcaccatc aataccatcc gcactcaggg agctaatccg tgggttgacg gtacgtttga   26400
aagctacagc gatggccagg tgctgggcgg gaacggcaca gccgttgtgg tggcgtctca   26460
gaaattcacc ggcggtaaga gcctgaagtt gagacggag gagaacaaca gcggcaacag   26520
tgataaacag cttggcaccct ggcagtcagt ccgtgaggac gcgaagttcc ggtttgagtt   26580
ctgggccatg atgccggcgg atcaggcgcc ctcctccggg tggacaacgc tggtcggtat   26640
ccagtcgcag aatgctgccg ggcaaaatgc gtggcaggcg gcggtcactg tcagcgaagc   26700
ctctctgggc gcgcgcgata agtgggtgaa attcacgggt atcgccagta acaacggggc   26760
aggcagaaca cgcgcggtgg tctggatctc cactcgtggc gccaccggca acggtacccc   26820
tggctattca ctgtatatcg acgatctggt catcacggat gttaccgatg cgaaagcggc   26880
acaggatgcc tctgacgcga cggcgagcgc cgtgagcggc ctgacggcgc gcgtaacgga   26940
tgccgaaggg aaaatcactg cccaggcgca gcagcagaca cgactggcct cgaaagtga   27000
taacgccaac tcccgcgtcg ataacatggc gaagacgctg agcgacagcc agagcacaca   27060
ggccagcctg aatacctcgc ttcagtcgca gattgacgcg caggcggccg ccaacatcaa   27120
aaaccagacg acgctggaca acacgattaa atcggtggcc agtatcacca gtacccagca   27180
gacgcatgca acggcactgg aggcgctggc aacgcagcag acgacctga catccagtgt   27240
cggggatctc agcgcttccg ttcagaacac cgccaaaacc gtggcggatg tgaatggtac   27300
ggtgagttcg ctgtggtcga tgaaggttga gacggttaac gggaagaatg ttggcgcggg   27360
gattacgctg ggcagcaatg gtgaaacaag cgatatgatc ctctacgctg accgcttctc   27420
gctgtttaac cgtaataatg cgacgcgtgt tccggtgatg gttgccgaag gcaatgagct   27480
gtatatcgat acggcacgta ttaaaaacag ttccctgacc tcaaccaaaa tcgcggacgg   27540
ttccatcacg aacgcgaaga tcggcaacga gatccgctcg aatgactttg ttgacgggtc   27600
acgcggctgg cgtatcgcca aggatggctc ttcgcagttc aacaacgtga tcgttcgcgg   27660
tgcggtttat gcgactgacg gctggttcca gggtacggta tatgcgaacc acatcgaggg   27720
cgacatcggg tcatttgcga tcaacatcgc tcagcaccgc acgccgaaggc gacctgtaa   27780
tacatggcag tggttttgagc tggcccggtt ccggcggcag aatttcgacc aggtgatcaa   27840
tattcgcggt ggactcctcc agacggatag catcactatc gacggcggcg cgaaactcag   27900
agcgggatg tcctacgcgc cagggcgtga cggcggactg aatcctggct atctgtcgta   27960
tgcaatgctt cttcgtggca caggcgctac gtctggtggc ggcagtatgg agctaggcat   28020
tgagcttatg tatgaaacag atgggagcaac acgcctgtta acggcgcaag agtcaatgaa   28080
cgtagacaac atgtcatttg tcgtccctgc cggtactggc gacgctgttc tgcgatatgg   28140
ctgttacctg gaccgtaacg gacagatggt attaaccatc ctctcaagat tcgacgcctt   28200
cgccgcgcgc aataacaacg taattcgcgg ttcatcaacc tgataacaat atatggcccc   28260
gcaagggcc tttttctttt ccagggaaaa ccatccagga ggaactttat tatgcgcatg   28320
tatgaagtcg gtaccgtcac gggtgccgcg tcgcaggcaa gggtgacagg tgcacaaca   28380
aaatggtcac aggaggcgct ggggatactg cccgggtcga ttctagtggt ctaccgcagc   28440
ggtagtgctg acctgtatgc gatcaaatcc gtggacagcg acacgcaact gacgctgacc   28500
cggaatatca ccaccgcatt ttccggtgcc agttacggca ttattaccgc tgaaaccgcc   28560
agcacctcgt cgtttgctaa ccagctgcc agcgcgtttg cattctggcg tagtgtagtg   28620
gagggctggt cgatggccct gaccggcagc ggcaatatca ccctgacaga cccgatcaca   28680
```

```
ggaaagcagg tgatcgtgcc ggcgatagcc gggatggcga aggcatcgga tcttaacgca    28740
ctggcaaaac tcacaggagg aaacaaactc gacggctcgc aggttataac cagcgataat    28800
gccggtttta ttctcggtaa gaactcagat ctggctctgc tcaaaaaaca ggggcaaggc    28860
gggacaattg ccgttggctc gggaacaccg ttcaggggttc agcgttcaag agcgaccact   28920
gtatcaccgg cagacacctt tgatgacatc ctcgttattg atgccaacaa ccaaacgaca    28980
ctgcctggcg cgctgtctgc cggcggcaat atcgataaca cgtcgaaggg taaagtgttg    29040
acgcaggcga ttgagctctc atttagcacg ccatacatcg actttcattt taactacagc    29100
accgacgact tcaccgggcg gattatggcc actgccgccg atcaaattag tgtgcaaggt    29160
agtcattggc gagttgacag ggatcttcgt gttggtggca tggcagatat tggaggctgg    29220
acgcaatgcc gcgacgacct ttcggccaac aaaacagact ttggatcccc tgctattggt    29280
tcgttggttt caggcggaag gattcgatct cgaatgctcg ggcgcggcgg taacgttgac    29340
acctccgggg cgtggggcgg tttctatctt gaagagtacg tgggaaccga acacaggatt    29400
gtcatgtata tggacggctt cgggagaacg gacgcatggt cattccgcgc aggggggaca    29460
atctccacac ctaaaggcga cgtcctgacc actggttccg acgtgcgcct gaaaacagac    29520
ttcacacaag cgtctgaaaa cgcctcagag cgcattgagc gcttagggggt gtgtgagtac   29580
cggatgaagg gggaaacgcg ccggaggcgt ggttttatcg ctcagcaggc tgaaaaagct    29640
gatgatctgt atactttcct cggcatcgag caggagatta atggcgaaaa atttaaggtg    29700
atgaatgtgg attacacggc aatcattgct gacctggtta cggtggcgca gggtttactg    29760
gttaaaaatc aggaactgga aaggcgtata tctgtactgg aggggatc                 29808

SEQ ID NO: 8           moltype = DNA   length = 350
FEATURE                Location/Qualifiers
source                 1..350
                       mol_type = genomic DNA
                       organism = Kappa phage
SEQUENCE: 8
cgggctaact gcccgaaaac atggggcggt tcatcgcgtc gcgccaatct gcgctgcagc      60
tattgtggcc agtccgggca taactcgaat gcctgcccac ataatgcgag cagcggtcga    120
cggcgcagcc tgaatgacga ctttacccctc gactgaaccg atagcacgat ggcggcaggc   180
ggaattgatt tcaatgtgaa attattcaat gtcaagtcat tgcattcgcg gatgatgata   240
atagatatca tttgagggggg taggggggat caaatcccta accccttttcg cgcttcggga   300
ctgccgcttc aggtagattt ttgcgcgtga gaaataaaaa cttttttttg                350

SEQ ID NO: 9           moltype = DNA   length = 4469
FEATURE                Location/Qualifiers
source                 1..4469
                       mol_type = other DNA
                       note = p1866 payload
                       organism = synthetic construct
SEQUENCE: 9
tgattataag aaggcgcccc aagcacccccc attttagcta taaaaaaacc cgccgaagcg     60
ggttttttcg aaaattgtaa ggtcacatta cgccccgcct tgccactcat cgcaatattg    120
ttgaagctca ttaagcatac ggcctacatg gaagccatca cacacggcat ggtgtacctg    180
gatcgccaga ggcattaaca ccttgtcgcc ttgcgtataa tatttaccca tagtgaaaac    240
aggggcgaag aagttgtcca tatttgctac gtttaaatca aaactggtga aactcaccca    300
gggattagca ctgacgaaaa acatatttttc gataaaccct ttagggaaat atgctaaatt   360
ttcaccgtaa cacgccacat cttgtgaata aatgtgcaga aatgacggaa aatcatcatg    420
gtattctgac cataacgaac taaacgtttc agtctgttca tggaaaacgg tgtaacaagg    480
gtggacacta tcccaaatca ctaattcacc gtctttcatt gccatacgaa actccgggtg    540
tgcattcatc aggcgggcaa gaatgtgaat aaaggccgga taaaacttgt gcttattttt    600
ctttacggtt tttaaaaagg ccgtaatatc cagttgtacg gtttggttat aagtgccatc    660
cgcaactgac tggaatgcct caaaatgttc tttacgatgc cattgactaa tatcaactgt    720
agtatatccg gtaatttcct tctccatttt agattcctta ggttgcgaaa tctcgataac    780
tcaaaaaata gtagtgatct tatttcatta tggtgaaagt tgtcttacgt gcaacatttt    840
cgcaacaagt tggtttcccg aggccttaact tttgttgcaa tggctgtcta ccctgttta    900
tactagctca gcccttggta caatgctagc gttttcatta aagaggagaa aggaagccat    960
gagtaaaggt gaggaattat ttactggtgt tgttccgatc ttagttgagc tggacggcga   1020
tgttaacggg cataaattca gtgttcgtgg tgaaggtgaa ggcgatgcaa ccaacggtaa   1080
gctgaccctg aaaattcatc tgcactactgg aaaattacca gtaccctggc ctactctggt   1140
gacttcttc aaatctgcaa tgccggaagg ttatgtacag agcgcacca tttctttcaa     1260
agacgatggc acgtataaaa cccgtgcaga ggttaaattt gaaggtgaca ctctggtgaa   1320
tcgtattgaa ctgaaaggca ttgatttcaa agaggacggc aatattttag gccataaact   1380
ggaatataac ttcaactccc ataacgttta catcaccgca gacaaacaaa agaacggtat   1440
caaagctaac tttaaaattc gacataacgt tgaagatggt agcgtccagc ttgcggatca   1500
ttaccaacaa aacactccga ttggagacgt cctgtttta ctgccggata ccactacctg    1560
gtccacccag tctaaactgt ctaaggatcc gaacgaaaag cgcgaccaca tggtgttatt   1620
agagttcgtt accgctagtg gtattacgca cggtatggat gaactctaca aataataatc   1680
agacagtttc acctgttttta cgttaaaacc cgcttgtggg tgttttttact tttgggttta   1740
gccgaacgcc cgggctaact gcccgaaaac atggggcggt tcatcgcgtc gcgccaatct   1800
gcgctgcagc tattgtggcc agtccgggca taactcgaat gcctgcccac ataatgcgag   1860
cagcggtcga cggcgcagcc tgaatgacga ctttacccctc gactgaaccg atagcacgat  1920
ggcggcaggc ggaattgatt tcaatgtgaa attattcaat gtcaagtcat tgcattcgcg    1980
gatgatgata atagatatca tttgagggggg taggggggat caaatcccta accccttttcg 2040
cgcttcggga ctgccgcttc aggtagattt ttgcgcgtga gaaataaaaa cttttttttg   2100
gcgttcggct aaacgtgcta catttgaaga gataaattgc actgaatctg agaaatattt    2160
tatctgatta taagattat cttcttgaga tcgttttcgt ctgcgcgtaa tctcttgctc    2220
tgaaaacgaa aaaccgcct tgcagggcgg ttttttcgaag gtcctctgag ctaccaactc    2280
tttggaccga ggtaactggc ttggaggagc gcagtcgcca aaacttgtcc tttcagttta    2340
```

```
gccttatccg gcgcatgact tcaagactaa ctcctctaaa tcaattacca gtggctgctg  2400
ccagtggtgc ttttgcatgt ctttccgggt tggactcaag acgatagtta ccggataagg  2460
cgcagcggtc ggactgaacg gggggtttgt gcatacagtc cagcttggag cgaactgcct  2520
acccggaact gagtgtcagg cgtggaatga gacaaactcg gcagtaacag aggaatgaca  2580
ccggcaaacc gaaaggcagg aacaggagag cgcacgaggg agccgccagg gggaaacgcc  2640
tggtatcttt atagtcctgt caggtttcgc caccactgat ttgagcgtca gatttcgtga  2700
tgcttgtcag gggggcggag cctatggaaa aacggctttg ccgcgaccct ctcacttccc  2760
tgttaagtat cttcctggca tcttccagga atctcagcc ccgttcgtaa gccatttccg  2820
ctcgccacag tcgaacgacc gagcgtagcg agtcagtgag cgaggaagcg gaatatatcc  2880
tgtatcacat attctgctga cgcaccgatg cagccttttt tctcctgcca catgaagcac  2940
ttcacttaca ccctcatcag tgccaacata gtaagccagt atacactccg ctagcgcaga  3000
tgtccggcgg tgcttttgcc gttacgcact actttagtca gttccgcagt accgtcaggc  3060
gctgacatag ctatttactt tgtattgcct gcaatcgaat ttctgaacta tcatatagtg  3120
gggataacgg gaaagttact atatttgcga actaacttag gcgtccacct cgaagctacc  3180
taatcacacc caacccgcgc ggggtaaata aggcactaat ccgagcttaa agcttgcgta  3240
gcacttagac acaagttaat taccaattgt ctggtagttt ggcggtatta gcgagatccc  3300
agacgcaagg cagagttaat tttaacctaa agccacaaat aagacaggtt gcacaagccc  3360
gccggaaatt aaatcttgct cacttcggta acggagtttc cctcccgcgt acttaattcc  3420
caataagaaa cgcgcccaag tcctatcagg caaaattcag ccccttcacg tcttagaacg  3480
agggtaaaaa tacaagccga ttgaacaagg gttgggggct tcaaatcgtc gtttaccca  3540
ctttacaacg gagggtaact agttcaccct atagtacgaa gcagaactat ttcgaggggc  3600
gtgcaataat cgaatcttct gcggttgact taacacgcta gggacgtgcc ctcgattcag  3660
tcgcaggtac tccgactcac actgcctcac acccagctag tcactgaccg ataaaattga  3720
cccgccctct aagtagcga gtacgtccta aaggcttcg gacagggcta tataggagag  3780
tttgatctcg ccccgacaac tgcaaccctc aactccctta gataatattg ttagccgaag  3840
ttgcacgacc cgccgtccac ggactgctct tagggtggtg cttcttaatc tgacaacgtg  3900
caaccccctat cgagggcgat tgtttctgcg aaaggggttg ccctaatagt cgcgacaatt  3960
ggcccttgta ggggtgaaac cacttagttt cgcgccgtag tcctaaaggc ccacctattg  4020
actttgtttc gggtagcact aggaatctta acaatttgaa tttggacttg ttttagggggc  4080
gttattcgag ggcaatcgga gctaacttca agactacttc tttgttgaat actaaatagt  4140
gcaaaggtcg tgtttcctca aggatactcc gctaacaata taggattcca atcagattca  4200
gcactggctg tacgggtgtt acggtgaggt tttcgggttt acggctggaa gctagcacgg  4260
taggaagcct ttcaatcaca aagcaaaagg gccgtcgaag gcccacaaga tacgaaagct  4320
ctcgaagcct tatccttgaa cgatccacct attttaggca ttacgcacaa aagctaccca  4380
ataatccgtg acaggcacaa tatcacggaa caaaggcgaa aactctcgta cacggttagg  4440
ttttcgctag gaagaataaa cctctatct                                   4469

SEQ ID NO: 10          moltype = DNA   length = 363
FEATURE                Location/Qualifiers
source                 1..363
                       mol_type = other DNA
                       note = Candidate HNH protein ORF
                       organism = synthetic construct
SEQUENCE: 10
atgccagccc ggtctaaacg tccatgccgc caccgggggt gtccggcgat aaccaacgac   60
cccagcggtt actgcgatgc tcaccggcag caacatgctg cgacggctg gcgcaactac  120
cagggcggga aaagcggca tgaaagggc tacggtcgcc cctggaaat ccgccgcgcgt  180
agaatcctcc agcgcgataa atatctatgc caaaactgcc ggcgtcatgg catcgccacc  240
aaagcgacca cgtcgaccac catcataccc aaagcgcgtg gcgtacaga cgacgattcc  300
aatctgagt cgttgtgctg gccctgccat agagcgaaaa cagcaacaga gagaacccga  360
tga                                                                363

SEQ ID NO: 11          moltype = AA   length = 120
FEATURE                Location/Qualifiers
source                 1..120
                       mol_type = protein
                       note = Candidate HNH protein
                       organism = synthetic construct
SEQUENCE: 11
MPARSKRPCR HRGCPAITND PSGYCDAHRQ QHAGDGWRNY QGGKSRHERG YGRPWEIRRA   60
RILQRDKYLC QNCRRHGIAT KATSVDHIIP KARGGTDDDS NLESLCWPCH RAKTATERTR  120

SEQ ID NO: 12          moltype = DNA   length = 4269
FEATURE                Location/Qualifiers
source                 1..4269
                       mol_type = other DNA
                       note = p1869 plasmid
                       organism = synthetic construct
SEQUENCE: 12
tcagatcctt ccgtatttag ccagtatgtt ctcagtgtg gttcgttgtt tttgcgtgag   60
ccatgagaac gaaccattga gatcatactt actttgcatg tcactcaaaa attttgcctc  120
aaaactggtg agctgaattt tgcagttaa agcatcgtgt agtgtttttc ttagtccgtt  180
acgtaggtag gaatctgatg taatggttgt tggtattttg tcaccattca tttttatctg  240
gttgttctca agttcggtta cgagatccat ttgtctatct agtttcaactt ggaaaatcaa  300
cgtatcagtc gggcggcctc gcttatcaac caccaattc atattgctgt aagtgtttaa  360
atctttactt attggtttca aaacccattg gttaagcctt ttaaactcat ggtagtatt  420
ttcaagcatt aacatgaact taaattcatc aaggctaatc tctatatttg ccttgtgagt  480
tttctttttg gttagttctt ttaataacca ctcataaatc ctcatagagt attttgttttc  540
aaaagactta acatgttcca gattatattt tatgaatttt tttaactgga aagataagg  600
```

```
caatatctct tcactaaaaa ctaattctaa tttttcgctt gagaacttgg catagtttgt    660
ccactggaaa atctcaaagc ctttaaccaa aggattcctg atttccacag ttctcgtcat    720
cagctctctg gttgctttag ctaatacacc ataagcattt tccctactga tgttcatcat    780
ctgagcgtat tggttataag tgaacgatac cgtccgttct ttccttgtag ggttttcaat    840
cgtgggttg agtagtgcca cacagcataa aattagcttg gtttcatgct ccgttaagtc    900
atagcgacta atcgctagtt catttgcttt gaaaacaact aattcagaca tacatctcaa    960
ttggtctagg tgattttaat cactatacca attgagatgg gctagtcaat gataattact   1020
agtcctttc ctttgagttg tgggtatctg taaattctgc tagaccttg ctggaaaact    1080
tgtaaattct gctagaccct ctgtaaattc cgctagaccc ttgtgtgttt tttttgttta   1140
tattcaagtg gttataattt atagaataaa gaaagaataa aaaaagataa aaagaataga   1200
tcccagccct gtgtataact cactacttta gtcagttccg cagtattaca aaaggatgtc   1260
gcaaacgctg tttgctcctc tacaaaacag accttaaaac cctaaaggct taagtagcac   1320
cctcgcaagc tcggttgcgg ccgcaatcgg gcaaatcgct gaatattcct tttgtctccg   1380
accatcaggc acctgagtcg ctgtcttttt cgtgacattc agttcgctgc gctcacggct   1440
ctggcagtga atggggtaa atggcactac aggcgccttt tatggattca tgcaaggaaa   1500
ctacccataa tacaagaaaa gcccgtcacg ggcttctcag ggcgtttat ggcgggtctg    1560
ctatgtggtc ctatctgact tttgctgtt cagcagttcc tgccctctga ttttccagtc    1620
tgaccacttc ggattatccc gtgacaggtc attcagactg gctaatgcac ccagtaaggc   1680
agcggtatca tcaacggggt ctgacgctca gtggaacgaa aactcacgtt aagggatttt   1740
ggtcatgaga ttatcaaaaa ggatcttcac ctagatcctt ttaaattaaa aatgaagttt   1800
taaatcaatc taaagtatat atgagtaaac ttggtctgac agttacgttt ccacaaccaa   1860
ttaaccaatt ctgatttaga aaaactcatc gagcatcaaa taaaactgca atttattcat   1920
atcaggatta tcaataccat attttgaaa aagccgtttc tgtaatgaag gagaaaactc    1980
accgaggcag ttccatagga tgcaagatc ctggtatcgg tctgcgattc cgactcgtcc    2040
aacatcaata caacctatta atttcccctc gtcaaaaata aggttatcaa gtgagaaatc   2100
accatgagtg acgactgaat ccggtgagaa tggcaaaagc ttatgcattt cttccagac    2160
ttgttcaaca ggccagccat tacgctcgtc atcaaaatca ctcgcatcaa ccaaaccgtt   2220
attcattcgt gattgcgcct gagcgagacg aaatacgcga tcgctgttaa aaggacaatt   2280
acaaacagga atcgaatgca accggcgcag gaacactgcc agcgcatcaa caatatttc    2340
acctgaatca ggatattctt ctaatacctg gaatgctgtt ttcccgggga tcgcagtggt   2400
gagtaaccat gcatcatcag gagtacggat aaaatgcttg atggtcggaa gaggcataaa   2460
ttccgtcagc cagtttagtc tgaccatctc atctgtaaca tcattggcaa cgctaccttt   2520
gccatgtttc agaaacaact ctggcgcatc gggcttccca tacaatcgat agattgtcgc   2580
acctgattgc ccgacattat cgcgagccca tttatacca tataaatcgc catccatgtt   2640
ggaatttaat cgcggcctcg agcaagacgt ttcccgttga atatggctca taacacccct   2700
tgtattactg tttatgtaag cagacagttt tattgttcat gatgatatat ttttatcttg   2760
tgcaatgtaa catcagagat tttgagacac aacgtggctt tccctgcagg atttcggagg   2820
cctgcgttat cccctgattc tgtggataac cgtattaccg ccttgagtg agctgatacc    2880
gctcgccgca gccgaacgcc gactagtgga ttttacggct agctcagtcc taggtacaat   2940
gctagcgaat tcattaaaga ggagaaaggt acccatggca cgtacccga gccgtagcag   3000
cattggtagc ctgcgtagtc cgcataccca taaagcaatt ctgaccagca ccattgaaat   3060
cctgaaagaa tgtggttata gcggtctgag cattgaaagc gttgcacgtc gtgccggtgc   3120
aagcaaaccg accatttatc gttggtggac caataaagca gcactgattg ccgaagtgta   3180
tgaaaatgaa agcgaacagg tgcgtaaatt tccggatctg ggtagcttta aagccgatct   3240
ggattttctg ctgcgtaatc tgtggaaagt ttggcgtgaa accatttgtg gtgaagcatt   3300
tcgttgtgtt attgcagaag cacagctgga ccctgcaacc ctgacccagc tgaaagatca   3360
gtttatggaa cgtcgtcgtg agatgccgaa aaaactggtt gaaaatgcca ttagcaatgg   3420
tgaactgccg aaagataccca atcgtgaact gctgctggat atgattttg gttttgttg    3480
gtatcgcctg ctgaccgaac agctgaccgt tgaacaggat attgaagaat taccttcct    3540
gctaattaat ggtgtttgtc cgggtacaca gcgttaacta gggcccatac cccaattat    3600
tgaaggccgc taacgcggcc ttttttgtt tctggtctgc ccgacgtacg gtgaatctga   3660
ttcgttacca attgacatga tacgaaacgt accgtatcgt taaggttcag aacgtatcac   3720
tggtgacgta catgccagcc cggtctaaac gtccatgccg ccaccggggg tgtccggcga   3780
taaccaacga ccccagcggt tactgcgatg ctcaccggca gcaacatgct ggcgacggct   3840
ggcgcaacta ccagggcggg aaaagccggc atgaaagggg ctacggtgc ccctgggaaa    3900
tccgccgcgc cagaatcctc cagcgcgata aatatctatg ccaaaactgc cggcgtcatg   3960
gcatcgccac caaagcgacc agcgtcgacc acatcatacc caaagcgcgt ggcggtacag   4020
acgacgattc caatctggag tcgttgtgct ggccctgcca tagagcgaaa acagcaacag   4080
agagaacccg atgatgacgc atcctcacga taatatccgg gtaggacgaa caataaggcc   4140
gcaaatcgcg gccttttta ttgataacaa aaggacagtt ttccctttga tatgtaacgg    4200
tgaacagttg ttctacttt gtttgttagt cttgatgctt cactgataga tacaagagcc    4260
ataagaacc                                                         4269
SEQ ID NO: 13          moltype = DNA   length = 1189
FEATURE                Location/Qualifiers
source                 1..1189
                       mol_type = genomic DNA
                       organism = Kappa phage
SEQUENCE: 13
ataatttcaa aattgaatac gttgatggcg ctttgaccgt tctggagacg gatggccagt     60
cacggatgaa tgaagccgta catggcatcc attttgagca tgtccagggc ggacgccccc    120
tgctgaaact gacgattgcg catgatattg ccccggcctc gaccccggcc ccggctgctg    180
cgtcggctca ggaaccttta gagggtgagc tggtacagga gcaacaatcc ccgctgcctg    240
gcggtcgccg ttcccgccat cgccgtggag gtaagcaatg atgtatcaac gcacggatcc    300
gacgctctcc atgttctatg catccagcgc tgatgcagac gggaacaaag tggctacgtt    360
gacggatgcag gtaattgcgg cagaggttgg tgccgtccag accagtcaac tgctatgcat    420
caccgatagc gcgaagaaaa aaacgtatac cgtgggcgag caatctatca gtaatggttc    480
cgatccgttg ctggtcgcga ttgagaatta ctggcgccag agtacggatg tcgtggttaa    540
aggactgatc gccgaggtga ccgatttcat cgcagggaat atcaactcag tgagcacctg    600
```

```
gatcggccag tttgggatga aggtatttga gaatcagcca ttagctgagc ggctgccaga  660
aagcgtgcta caggctgatg gtagctccgc tacagcgaca gggtcctgac agcaggcatt  720
acaacaggcg ctcacagagc gcctgtgata atggctgaat gcttcaccag cgcggcgttt  780
tatgggagat catgatgagt tacaccagct gtacttattg cggttcacgt ctccatacgc  840
gggctaactg cccgaaaaca tggggcggtt catcgcgtcg cgccaatctg cgctgcagct  900
attgtggcca gtccgggcat aactcgaatg cctgcccaca taatgcgagc agcggtcgac  960
ggcgcagcct gaatgacgac tttaccctcg actgaaccga tagcacgatg gcggcaggcg 1020
gaattgattt caatgtgaaa ttattcaatg tcaagtcatt gcattgcgcg atgatgataa 1080
tagatatcat ttgaggggt aggggggatc aaatccctaa ccccttttcgc gcttcgggac 1140
tgccgcttca ggtagatttt tgcgcgtgag aaataaaaac tttttttg           1189

SEQ ID NO: 14           moltype = DNA   length = 5308
FEATURE                 Location/Qualifiers
source                  1..5308
                        mol_type = other DNA
                        note = p1867 plasmid
                        organism = synthetic construct
SEQUENCE: 14
tgattataag aaggcgcccc aagcacccc attttagcta taaaaaaacc cgccgaagcg   60
ggttttttcg aaaattgtaa ggtcacatta cgccccgcct tgccactcat cgcaatattg  120
ttgaagctca ttaagcatac ggcctacatg gaagccatca cacacggcat ggtgtacctg  180
gatccgcaga ggcattaaca cctttgtcgcc ttgcgtataa tatttaccca tagtgaaaac  240
aggggcgaag aagttgtcca tatttgctac gtttaaatca aaactggtga aactcaccca  300
gggattagca ctgacgaaaa acatattttc gataaaccct ttagggaaat atgctaaatt  360
ttcaccgtaa cacgccacat cttgtgaata aatgtgcaga aactgacgga aatcatcatg  420
gtattctgac cataacgaac taaacgtttc agtctgttca tggaaaacgg tgtaacaagg  480
gtggacacta tcccaaatca ctaattcacc gtctttcatt gccatacgga actccgggtg  540
tgcattcatc aggcgggcaa gaatgtgaat aaaggccgga taaaactgt gcttattttt   600
ctttacggtt tttaaaaagg ccgtaatatc cagttgtacg gtttggttat aggtgcactg  660
cgcaactgac tggaatgcct caaaatgttc tttacgatgc cattgactaa tatcaactgt  720
agtatatccg gtaattttct tctccatttt agattcctta ggttgcgaaa tctcgataac  780
tcaaaaaata gtagtgatct tatttcatta tggtgaaagt tgtcttacgt gcaacatttt  840
cgcaacaagt tggtttccg aggcctaact tttgttgcaa tggctgtcta ccctgtttta  900
tactagctca gcccttggta caatgctagc gttttcatta aagaggagaa aggaagccat  960
gagtaaaggt gaggaattat tactggtgt tgttccgatc ttagttgagc tggacggcga 1020
tgttaacggt cataaattca gtgttcgtgg tgaaggtgaa ggcgatgcaa ccaacggtaa 1080
gctgaccctg aaattcatct gcactactgg aaaattacca gtaccctggc ctactctggt 1140
gactaccctg acctatggtg ttcagtgttt ttctcgttac cctgaccaca tgaagcaaca 1200
tgacttcttc aaatctgcaa tgcccgaagg ttatgtacag gagcgcacca tttctcttcaa 1260
agacgatggc acgtataaaa cccgtgcaga ggttaaattt gaaggtgaca ctctggtgaa 1320
tcgtattgaa ctgaaaggca ttgatttcaa agaggacggc aatattttag gccataaact 1380
ggaatataac ttcaactccc ataacgttta catcaccgca gacaaacaaa agaacggtat 1440
caaagctaac tttaaaattc gacataacgt tgaagatggt agcgtccagc ttgcggatca 1500
ttaccaacaa aacactccga ttggagacgc tcctgtttta ctgccggata ccactacct  1560
gtccacccag tctaaactgt ctaaggatcc gaacgaaaag cgcgaccaca tggtgttatt 1620
agagttcgtt accgctagtg gtattacgca cggtatggat gaactctaca ataataatc  1680
agacagttc acctgtttta cgttaaaacc cgcttcggg ggttttact tttgggttta  1740
gccgaacgcc ataatttcaa aattgaatac gttgatggcg ctttgaccgt tctggagacg 1800
gatgccagt cacggatgaa tgaagccgta catggcatcc attttgagca tgtccagggc 1860
ggacgccccc tgctgaaaact gacgattgcg catgatattg ccccgcctc gaccccggcc 1920
ccggctgctg cgtcggctca ggaaccttta gagggtgagc tggtacagga gcaacaatcc 1980
ccgctgcctg gcggtcgccg ttcccgccat cgccgtggag gtaagcaatg atgtatcaac 2040
gcacggatct gacgctctcc atgttctatg catccagcgc tgatgcagac gggaacaaag 2100
tggctacgtt gacgatgcag gtaattgcgg cagaggttgg tgccgtccag accagtcaac 2160
tgctatgcat caccgatagc gcgaagaaaa aaactgtatac cgtgggcgaa caatctatca 2220
gtaatggttc cgatccgttg ctggtcgcga ttgagaatta ctgcgcgcag agtacggatg 2280
tcgtggttaa aggactgatc gccgaggtga ccgatttcat cgcagggaat atcaactcag 2340
tgagcacctg gatcggccag tttgggatga aggtatttga gaatcagcca ttagctgagc 2400
ggctgccaga aagcgtgcta caggctgatg gtagctccgc tacagcgaca gggtcctgac 2460
agcaggcatt acaacaggcg ctcacagagc gcctgtgata atggctgaat gcttcaccag 2520
cgcggcgttt tatgggagat catgatgagt tacaccagct gtacttattg cggttcacgt 2580
ctccatacgc gggctaactg cccgaaaaca tggggcggtt catcgcgtcg cgccaatctg 2640
cgctgcagct attgtggcca gtccgggcat aactcgaatg cctgcccaca taatgcgagc 2700
agcggtcgac ggcgcagcct gaatgacgac tttaccctcg actgaaccga tagcacgatg 2760
gcggcaggcg gaattgattt caatgtgaaa ttattcaatg tcaagtcatt gcattgcgcg 2820
atgatgataa tagatatcat ttgaggggt aggggggatc aaatccctaa ccccttttcgc 2880
gcttcgggac tgccgcttca ggtagatttt tgcgcgtgag aaataaaaac tttttttgg 2940
cgttcggtca aacattgctac atttgaagag ataaatttga ctgaaatcta gaaatttttt 3000
atctgattaa taagattatc ttcttggagat cgtttttcgtc tgcgcgtaat ctcttgctct 3060
gaaaacgaaa aaaccgcctt gcagggcggt ttttcgaagg tcctctgagc taccaactct 3120
ttggaccgag gtaactggct tggaggagcg cagtcgccaa aacttgtcct tcagtttag  3180
ccttatccgg cgcatgactt caagactaac tcctctaaat caattaccag tggctgctgc 3240
cagtggtgct tttgcatgtc tttccgggtt ggactcaaga cgatagttac cggataaggc 3300
gcagcggtcg gactgaacgg ggggtttgtg catacagtcg gaactgccta 3360
cccggaactg agtgtcaggc gtggaatgag acaaactcgg cagtaacaga gaatgacac  3420
cggcaaaccg aaaggcagga acaggagagc gcacgaggga gccgccaggg ggaaacgcct 3480
ggtatcttta gtcctgtc aggttcgcc accactgatt tgagcgtcag atttcgtgat  3540
gcttgtcagg ggggcggagc ctatggaaaa acggcttgtgc cgcgaccctc tcacttccct 3600
gttaagtatc ttcctggcat cttccaggaa atctcagccc cgttcgtaag ccatttccgc 3660
```

```
tcgccacagt cgaacgaccg agcgtagcga gtcagtgagc gaggaagcgg aatatatcct    3720
gtatcacata ttctgctgac gcaccgatgc agccttttt  ctcctgccac atgaagcact    3780
tcacttacac cctcatcagt gccaacatag taagccagta tacactccgc tagcgcagat    3840
gtccggcggt gcttttgccg ttacgcacta ctttagtcag ttccgcagta ccgtcaggcg    3900
ctgacatagc tatttacttt gtattgcctg caatcgaatt tctgaactat catatagtgg    3960
ggataacggg aaagttacta tatttgcgaa ctaacttagg cgtccacctc gaagctacct    4020
aatcacaccc aacccgcgcg gggtaaataa ggcactaatc cgagcttaaa gcttgcgtag    4080
cacttagaca caagttaatt accaattgtc tggtagtttg gcggtattag cgagatccca    4140
gacgcaaggc agagttaatt ttaacctaaa gccacaaata agacaggttg cacaagcccg    4200
ccggaaatta aatcttgctc acttcggtaa cggagtttcc ctcccgcgta cttaattccc    4260
aataagaaac gcgcccaagt cctatcaggc aaaattcagc cccttcacgt cttagaacga    4320
gggtaaaaat acaagccgat tgaacaaggg ttggggggctt caaatcgtcg tttaccccac    4380
tttacaacgg agggtaacta gttcacccta tagtacgaag cagaactatt tcgagggggcg   4440
tgcaataatc gaatcttctg cggttgactt aacacgctag ggacgtgcc  tcgattcagt    4500
cgcaggtact ccgactcaca ctgcctcaca cccagctagt cactgaccga taaaattgac    4560
ccgccctcta aggtagcgag tacgtcctaa aaggcttcgg acagggctat ataggagagt    4620
ttgatctcgc cccgacaact gcaaccctca actcccttag ataatattgt tagccgaagt    4680
tgcacgaccc gccgtccacg gactgctctt agggtgtgc  ttcttaatct gacaacgtgc    4740
aaccccctatc gagggcgatt gtttctgcga aaggggttgc cctaatagtc gcgacaattg    4800
gcccttgtag gggtgaaacc acttagtttc gcgccgtagt cctaaaggcc cacctattga    4860
cttgtttcg  ggtagcacta ggaatcttaa caattgaat  ttggacttgt tttagggggcg   4920
ttattcgagg gcaatcggag ctaacttcaa gactactct  ttgttgaata ctaaatagtg    4980
caaaggtcgt gtttcctcaa ggatactccg ctaacaatat aggattccaa tcagattcag    5040
cactggctgt acgggtgtta cggtgaggtt tcgggttta cggctggaag ctagcacggt     5100
aggaagcctt tcaatcacaa agcaaagggg ccgtcgaagg cccacaagat acgaaagctc    5160
tcgaagcctt atccttgaac gatccaccta tttaggcagt tacgcacaaa agctacccaa    5220
taatccgtga caggcacaat atcacggaac aaaggcgaaa actctcgtac acggttaggt    5280
tttcgctagg aagaataaac ctctatct                                       5308

SEQ ID NO: 15            moltype = DNA  length = 234
FEATURE                  Location/Qualifiers
source                   1..234
                         mol_type = other DNA
                         note = predicted ORF
                         organism = synthetic construct
SEQUENCE: 15
atgcttcacc agcgcggcgt tttatgggag atcatgatga gttacaccag ctgtacttat     60
tgcggttcac gtctccatac gcgggctaac tgcccgaaaa catggggcgg ttcatcgcgt    120
cgcgccaatc tgcgctgcag ctattgtggc cagtccgggc ataactcgaa tgcctgccca    180
cataatgcga gcagcggtcg acggcgcagc ctgaatgacg actttacccct cgac         234

SEQ ID NO: 16            moltype = AA  length = 78
FEATURE                  Location/Qualifiers
source                   1..78
                         mol_type = protein
                         note = Predicted protein with 2 Zn fingers
                         organism = synthetic construct
SEQUENCE: 16
MLHQRGVLWE IMMSYTSCTY CGSRLHTRAN CPKTWGGSSR RANLRCSYCG QSGHNSNACP     60
HNASSGRRRS LNDDFTLD                                                   78

SEQ ID NO: 17            moltype = DNA  length = 209
FEATURE                  Location/Qualifiers
source                   1..209
                         mol_type = other DNA
                         note = Short cos site
                         organism = synthetic construct
SEQUENCE: 17
tttaccctcg actgaaccga tagcacgatg gcggcaggcg gaattgattt caatgtgaaa     60
ttattcaatg tcaagtcatt gcattgcgcg atgatgataa tagatatcat ttgagggggt    120
agggggggatc aaatccctaa ccccctttcgc gcttcgggac tgccgcttca ggtagatttt   180
tgcgcgtgag aaataaaaac tttttttttg                                     209

SEQ ID NO: 18            moltype = DNA  length = 4330
FEATURE                  Location/Qualifiers
source                   1..4330
                         mol_type = other DNA
                         note = p1868 payload
                         organism = synthetic construct
SEQUENCE: 18
tgattataag aaggcgcccc aagcacccca tttttagcta taaaaaaacc cgccgaagcg     60
ggttttttcg aaaattgtaa ggtcacatta cgccccgcct tgccactcat cgcaatattg    120
ttgaagctca ttaagcatac ggcctacatg gaagccatca cacggcat   ggtgtacctg    180
gatcgccaga ggcattaaca ccttgtcgcc ttgcgttataa tatttaccca tagtgaaaac    240
aggggcgaag aagttgtcca tatttgctac gtttaaatca aaactggtga aactcaccca    300
gggattagca ctgacgaaaa acatattttc gataaaccct ttagggaaat atgctaaatt    360
tcaccgtaa  cacgccacat cttgtgaata atgtgcaga  aactgacgga aatcatcatg    420
gtattctgac cataacgaac taaacgtttc agtctgttca tggaaaacgg tgtaacaagg    480
gtggacacta tcccaaatca ctaattcacc gtctttcatt gccatacgaa actccgggtg    540
```

```
tgcattcatc aggcgggcaa gaatgtgaat aaaggccgga taaaacttgt gcttattttt    600
ctttacggtt tttaaaaagg ccgtaatatc cagttgtacg gtttggttat aggtgcactg    660
cgcaactgac tggaatgcct caaaatgttc tttacgatgc cattgactaa tatcaactgt    720
agtatatccg gtaattttct tctccatttt agattcctta ggttgcgaaa tctcgataac    780
tcaaaaaata gtagtgatct tatttcatta tggtgaaagt tgtcttacgt gcaacatttt    840
cgcaacaagt tggtttcccg aggcctaact tttgttgcaa tggctgtcta ccctgtttta    900
tactagctca gcccttggta caatgctagc gttttcatta aagaggagaa aggaagccat    960
gagtaaaggt gaggaattat ttactggtgt tgttccgatc ttagttgagc tggacggcga   1020
tgttaacggt cataaattca gtgttcgtgg tgaaggtgaa ggcgatgcaa ccaacggtaa   1080
gctgaccctg aaattcatct gcactactgg aaaattacca gtaccctggc ctactctggt   1140
gactaccctg acctatgtgt tcagtgtttt tctcgttac cctgaccaca tgaagcaaca    1200
tgacttcttc aaatctgcaa tgccggaagg ttatgtacag gagcgcacca tttctttcaa   1260
agacgatggc acgtataaaa cccgtgcaga ggttaaattt gaaggtgaca ctctggtgaa   1320
tcgtattgaa ctgaaaggca ttgatttcaa agaggacggc aatatttag gccataaact   1380
ggaatataac ttcaactccc ataacgttta catcaccgca gacaaacaaa agaacgtat   1440
caaagctaac tttaaaattc gacataacgt tgaagatggt agcgtccagc ttgcggatca   1500
ttaccaacaa aacactccga ttggagacgc tcctgtttta ctgccggata accactacct   1560
gtccacccag tctaaactgt ctaaggatcc gaacgaaaag ccgaccaca tggtgttatt    1620
agagttcgtt accgctagtg gtattacgca cggtatggat gaactctaca aataataatc   1680
agacagtttc acctgtttta cgttaaaacc cgcttcggcg ggttttttact tttgggttta   1740
gccgaacgcc cgtttaccct cgactgaacc gatagcacga tggcggcagg cggaattgat   1800
ttcaatgtga aattattcaa tgtcaagtca ttgcattgcg gtgatgat aatagatatc    1860
atttgagggg gtaggggga tcaaatccct aaccccttc gcgcttcggg actgccgctt    1920
caggtagatt tttgcgcgtg agaaataaaa acttttttt ggcgttcggc taaacgtgct    1980
acatttgaag agataaattg cactgaaatc tagaaatatt ttatctgatt aataagatta   2040
tcttcttgag atcgttttcg tctgcgcgta atctcttgct ctgaaaacga aaaaccgcc    2100
ttgcagggcg gtttttcgaa ggtcctctga gctaccaact cttttggaccg aggtaactgg   2160
cttggaggag cgcagtcgcc aaaacttgtc ctttcagttt agccttatcc ggcgcatgac   2220
ttcaagacta actcctctaa atcaattacc agtggctgct gccagtggtg cttttgcatg   2280
tcttccgggg ttggactcaa gacgatagtt accggataag gcgcagcggt cggactgaac   2340
gggggggtttg tgcatacagt ccagcttgga gcgaactgcc tacccggaac tgagtgtcag   2400
gcgtggaatg agacaaactc ggcagtaaca gaggaatgac accggcaaac cgaaaggcag   2460
gaacaggaga gcgcacgagg gagccgccag ggggaaacgc ctggtatctt tatagtcctg   2520
tcaggtttcg ccaccactga tttgagcgtc agatttcgtg atgcttgtca ggggggcgga   2580
gcctatgaa aaacggcttt gccgcgaccc tctcacttcc ctgttaagta tcttcctggt   2640
atcttccagg aaatctcagc cccgttcgta agccatttcc gctcgccaca gtcgaacgac   2700
cgagcgtagc gagtcagtga gcgaggaagc ggaatatatc ctgtatcaca tattctgctg   2760
acgcaccgat gcagcctttt ttctcctgcc acatgaagca cttcacttac ccctcatca   2820
gtgccaacat agtaagccag tatacactcc gctagcgcag atgtccggcg gtgcttttgc   2880
cgttacgcac tactttagtc agttccgcag taccgtcagg cgctgacata gctatttact   2940
ttgtattgcc tgcaatcgaa tttcgaact atcatatagt ggggataacg ggaaagttac    3000
tatatttgcg aactaactta ggcgtccacc tcgaagctac ctaatcacac ccaacccgcg    3060
cggggtaaat aaggcactaa tccgagctta aagcttgcgc agcacttaga cacaagttaa   3120
ttaccaattg tctggtagtt tggcggtatt agcgagatcc cagacgcaag gcagagttaa   3180
ttttaaccta aagccacaaa taagacaggt tgcacaagcc cgccgaaat taaatcttgc   3240
tcacttcggt aacggagttt ccctcccgcg tacttaattc ccaataagaa acgcgcccaa   3300
gtcctatcag gcaaaattca gcccccttcac gtcttagaac ggaaggtaaa ataaagccg    3360
attgaacaag ggttggggc ttcaaatcgt cgtttacccc actttacaac ggagggtaac   3420
tagttcaccc tatagtacga agcagaacta tttcgagggg cgtgcaataa tcgaatcttc   3480
tgcggttgac ttaacacgct agggacgtgc cctcgattca gtcgcaggta ctccgactca   3540
cactgcctca cacccagcta gtcactgacc gataaaattg acccgcccctc taaggtagcg   3600
agtacgtcct aaaaggcttc ggacagggct atataggaga gtttgatctc gccccgacaa   3660
ctgcaaccct caactccctt agataatatt gttagccgaa gttgcacgac ccgccgtcca   3720
cggactgctc ttagggtgtg gcttcttaat ctgacaacgt gcaaccccta tcgagggcga   3780
ttgtttctgc gaaagggggtt gccctaatag tcgcgacaat tggcccttgt aggggtgaaa   3840
ccacttagtt tcgcgccgta gtcctaaagg cccaccatt gactttgttt cgggtgcac    3900
taggaatctt aacaatttga atttggactt gttttagggg cgttattcga gggcaatcgg   3960
agctaacttc aagactactt ctttgttgaa tactaaatag tgcaaaggtc gtgtttcctc   4020
aaggatactc cgctaacaat ataggattcc aatcagattc agcactggct gtacgggtgt   4080
tacggtgagg ttttcgggtt tacggctgga agctagcacg gtaggaagcc tttcaatcac   4140
aaaagcaaaag ggccgtcgaa ggccacaag atacgaaagc tctcgaagcc ttatccttga   4200
acgatccacc tatttaggca gttacgcaca aaagctaccc aataatccgt gacaggcaca   4260
atatcacgga acaaaggcga aaactctcgt acacggttag gttttcgcta ggaagaataa   4320
acctctatct                                                         4330
```

| SEQ ID NO: 19 | moltype = DNA  length = 5264 |
|---|---|
| FEATURE | Location/Qualifiers |
| source | 1..5264 |
| | mol_type = other DNA |
| | note = p1872 plasmid |
| | organism = synthetic construct |

SEQUENCE: 19

```
tcagatcctt ccgtatttag ccagtatgtt ctctagtgtg gttcgttgtt tttgcgtgag     60
ccatgagaac gaaccattga gatcatactt actttgtcag tcactcaaaa attttgcctc    120
aaaactggtg agctgaattt ttgcagttaa agcatcgtgt agtgttttc ttagtccgtt     180
acgtaggtag gaatctgatg taatggttgt tggtattttg tcaccattca tttttatctg    240
gttgttctca agttcggtta cgagatccat ttgtctatct agttcaactt ggaaaatcaa    300
cgtatcagtc gggcggcctc gcttatcaac caccaatttc atattgctgt aagtgtttaa    360
atctttactt attggtttca aaaccccattg gttaagcctt ttaaactcat ggtagttatt    420
```

```
ttcaagcatt aacatgaact taaattcatc aaggctaatc tctatatttg ccttgtgagt    480
tttcttttgt gttagttctt ttaataacca ctcataaatc ctcatagagt atttgttttc    540
aaaagactta acatgttcca gattatattt tatgaatttt tttaactgga aaagataagg    600
caatatctct tcactaaaaa ctaattctaa ttttttcgctt gagaacttgg catagtttgt    660
ccactggaaa atctcaaagc ctttaaccaa aggattccta atttccacag ttctcgtcat    720
cagctctctg gttgctttag ctaatacacc ataagcattt tccctactga tgttcatcat    780
ctgagcgtat tggttataag tgaacgatac cgtccgttct ttccttgtag ggttttcaat    840
cgtggggttg agtagtgcca cacagcataa aattagcttg gtttcatgct ccgttaagtc    900
atagcgacta atcgctagtt catttgcttt gaaaacaact aattcagaca tacatctcaa    960
ttggtctagg tgattttaat cactatacca attgagatgg gctagtcaat gataattact   1020
agtccttttc ctttgagttg tgggtatctg taaattctgc tagaccttttg ctggaaaact   1080
tgtaaattct gctagaccct ctgtaaattc cgctagacct ttgtgtgttt ttttttgttta   1140
tattcaagtg gttataattt atagaataaa gaaagaataa aaaaagataa aaagaataga   1200
tcccagccct gtgtataact cactacttta gtcagttccg cagtattaca aaaggatgtc   1260
gcaaacgctg tttgctcctc tacaaaacag accttaaaac cctaaaggct taagtagcac   1320
cctcgcaagc tcggttgcgg ccgcaatcgg gcaaatcgct gaatattcct tttgtctccg   1380
accatcaggc acctgagtcg ctgtcttttt cgtgacattc agttcgctgc gctcacggct   1440
ctggcagtga atgggggtaa atggcactac aggcgccttt tatggattca tgcaaggaaa   1500
ctacccataa tacaagaaaa gcccgtcacg ggcttctcag ggcgttttat ggcgggtctg   1560
ctatgtggtg ctatctgact ttttgctgtt cagcagttcc tgccctctga ttttccagtc   1620
tgaccacttc ggattatccc gtgacaggtc attcagactg gctaatgcac ccagtaaggc   1680
agcggtatca tcaacggggt ctgacgctca gtggaacgaa aactcacgtt aagggatttt   1740
ggtcatgaga ttatcaaaaa ggatcttcac ctagatcctt ttaaattaaa aatgaagttt   1800
taaatcaatc taaagtatat atgagtaaac ttggtctgac agttacgttt ccacaaccaa   1860
ttaaccaatt ctgatttaga aaactcatc gagcatcaaa tgaaactgca atttattcat   1920
atcaggatta tcaataccat atttttgaaa aagccgtttc tgtaatgaag gagaaaactc   1980
accgaggcag ttccatagga tggcaagatc ctggtatcgg tctgcgattc cgactcgtcc   2040
aacatcaata caacctatta atttcccctc gtcaaaaata aggttatcaa gtgagaaatc   2100
accatgagtg acgactgaat ccggtgagaa tggcaaaagc ttatgcattt ctttccagac   2160
ttgttcaaca ggccagccat tacgctcgtc atcaaaatca ctcgcatcaa ccaaaccgtt   2220
attcattcgt gattgcgcct gagcgagacg aaatacgcga tcgctgttaa aaggacaatt   2280
acaaacagga atcgaatgca accggcgcag gaacactgcc agcgcatcaa caatatttttc   2340
acctgaatca ggatattctt ctaatacctg gaatgctgtt ttcccgggga tcgcagtggt   2400
gagtaaccat gcatcatcag gagtacggat aaaatgcttg atggtcggaa gaggcataaa   2460
ttccgtcagc cagtttagtc tgaccatctc atctgtaaca tcattggcaa cgctacctttt  2520
gccatgtttc agaaacaact ctggcgcatc gggcttccca tacaatcgat agattgtcgc   2580
acctgattgc ccgacattat cgcgagccca tttataccca tataaatcag catccatgtt   2640
ggaatttaat cgcggcctcg agcaagacgt ttcccgttga atatggctca taacacccct   2700
tgtattactg tttatgtaag cagacagttt tattgttcat gatgatatat ttttatcttg   2760
tgcaatgtaa catcagagat tttgagacac aacgtggctt tccctgcagg atttcggagg   2820
cctgcgttat cccctgattc tgtggataac cgtattaccg cctttgagtg agctgatacc   2880
gctcgccgca gccgaacgcc gactagtgga ttttacggct agctcagtcc taggtacaat   2940
gctagcgaat tcattaaaga ggagaaaggt acccatggca cgtaccccga gccgtagcag   3000
cattggtagc ctgcgtagtc cgcataccca taaagcaatt ctgaccagca ccattgaaat   3060
cctgaaagaa tgtggttata gcggtctgag cattgaaagc gttgcacgtc gtgccggtgc   3120
aagcaaaccg accatttatc gttggtggac caataaagca gcactgattg ccgaagtgta   3180
tgaaaatgaa agcgaacagg tgcgtaaatt tccggatctg ggtagcttta aagccgatct   3240
ggattttctg ctgcgtaatc tgtgcgaagt ttggcgtgaa accatttgtg gtgaagcatt   3300
tcgttgtgtt attgcagaag cacagctgga ccctgcaacc ctgacccagc tgaaagatca   3360
gtttatggaa cgtcgtcgtg agatgccgaa aaaactggtt gaaatgcca ttagcaatgg   3420
tgaactgccg aaagatacca atcgtgaact gctgctgaat atgatttttg gtttttgttg   3480
gtatcgcctg ctgaccgaac agctgaccgt tgaacaggat attgaagaat taccttcct    3540
gctaattaat ggtgttgtc cgggtacaca gcgttaacta gggcccatac ccccaattat   3600
tgaaggccgc taacgcggcc ttttttttgtt tctggtctgc ccgacgtacg gtgaatctga   3660
ttcgttacca attgacatga tacgaaacgt accgtatcgt taaggttcag aacgtatcac   3720
tggtgacgta catgccagcc cggtctaaac gtccatgccg ccaccggggg tgtccggcga   3780
taaccaacga ccccagcggt tactgcgatg ctcaccggca gcaacatgct ggcgacggct   3840
ggcgcaacta ccagggcggg aaaagccggc atgaaagggg ctacggtcgc ccctgggaaa   3900
tccgccgcgc cagaatcctc cagcgcgata aatatctatg ccaaaactgc cggcgtcatg   3960
gcatcgccac caaagcgacc agcgtcgacc acatcatacc caaagcgcgt ggcggtacga   4020
acgacgattc caatctggag tcgttgtgct ggccctgcca tagagcgaaa acagcaacag   4080
agagaacccg atgaataatt tcaaaattga atacgttgat ggcgctttga ccgttctgga   4140
gacggatggc cagtcacgga tgaatgaagc cgtacatggc atccatttgt agcatgtcca   4200
gggcggacgc ccctgctga aactgacgat tgcgcatgat attgccccgg cctcgaccc    4260
ggccccggct gctgcgtcgg ctcaggaacc tttagagggt gagctggtac aggagcaaca   4320
atccccgctg cctggcggtc gccgttcccg ccatcgccgt ggaggtaagc aatgatgtat   4380
caacgcacgg atctgacgct ctccatgttc tatgcatcca gcgctgatgc agacgggaac   4440
aaagtggcta cgttgacgat gcaggtaatt gcggcagagg ttggtgccgt ccagaccagt   4500
caactgctat gcatcaccga tagcgcgaag aaaaaaacgt ataccgtggg cgagcaatct   4560
atcagtaatg gttccgatcc cgttgctggtc gcgattgaga attactgcg ccagagtacg   4620
gatgtcgtgg ttaaaggact gatcgccgag gtgaccgatt catcgcagg gaatatcaac    4680
tcagtgagca cctggatcgg ccagtttggg atgaaggtat ttgagaatca gccattagct   4740
gagcggctgc cagaaagcgt gctacaggct gatggtagct ccgctacagc gacagggtcc   4800
tgcacgcagg cattacaaca ggcgctcaca gagcgcctgt gataatggct gaatgcttca   4860
ccagcgcggc gttttatggg agatcatgat gagttacacc agctgtactt attgcggttc   4920
acgtctccat acgcgggcta actgcccgaa acatgggc ggttcatcgc gtcgcgccaa    4980
tctgcgctgc agctattgtg gccagtccgg cataactcg aatgcctgcc cacataatgc    5040
gagcagcggt cgacgcgca gcctgaatga cgactttacc ctcgactgat gacgcatcct   5100
cacgataata tccgggtagg acgaacaata aggccgcaaa tcgcggcctt ttttattgat   5160
```

```
aacaaaagga cagttttccc tttgatatgt aacggtgaac agttgttcta cttttgtttg    5220
ttagtcttga tgcttcactg atagatacaa gagccataag aacc                    5264
```

SEQ ID NO: 20    moltype = DNA  length = 20
FEATURE    Location/Qualifiers
source    1..20
    mol_type = other DNA
    note = AD1334 primer
    organism = synthetic construct
SEQUENCE: 20
```
ggacctccca ccattccaag                                                 20
```

SEQ ID NO: 21    moltype = DNA  length = 20
FEATURE    Location/Qualifiers
source    1..20
    mol_type = other DNA
    note = p1335 primer
    organism = synthetic construct
SEQUENCE: 21
```
acggcgatgt tcaggttctt                                                 20
```

SEQ ID NO: 22    moltype = DNA  length = 20
FEATURE    Location/Qualifiers
source    1..20
    mol_type = other DNA
    note = AD1336 primer
    organism = synthetic construct
SEQUENCE: 22
```
ggcgaaagaa gacctggtca                                                 20
```

SEQ ID NO: 23    moltype = DNA  length = 20
FEATURE    Location/Qualifiers
source    1..20
    mol_type = other DNA
    note = AD1337 primer
    organism = synthetic construct
SEQUENCE: 23
```
tagccggcga aatggatgtt                                                 20
```

SEQ ID NO: 24    moltype = DNA  length = 20
FEATURE    Location/Qualifiers
source    1..20
    mol_type = other DNA
    note = AD1322 primer
    organism = synthetic construct
SEQUENCE: 24
```
catcagaccg cattcgcttg                                                 20
```

SEQ ID NO: 25    moltype = DNA  length = 20
FEATURE    Location/Qualifiers
source    1..20
    mol_type = other DNA
    note = AD1323 primer
    organism = synthetic construct
SEQUENCE: 25
```
ggacgaagat gtggaagcca                                                 20
```

SEQ ID NO: 26    moltype = DNA  length = 32767
FEATURE    Location/Qualifiers
source    1..32767
    mol_type = genomic DNA
    organism = BW4 phage
SEQUENCE: 26
```
agcgatatct ccccgggttt ttccacaggg tgtccgccca gggcgtcgct gtcgagctca     60
cagcgcacgc tgaacgcccg ccagcactcg aggcgatccg aacagcctcg ctccgagtgc    120
gtcgggcctg tgtggatcgc tcatgagttt cgtaacaagc cctagccac agcccgattc    180
agatagaata ggagcatgga agggcagtgc ggatggtgcg gtcgggcatt cgatcgtgcc    240
cggacgggtc gcccgcgacg cttctgctcg cccgctgtc gggtcgccgc gtccggtgt     300
gcgatcccgc tggccatgag gtcccgcact gcgtgggtcc gctgcgacgg caagcgcccc    360
atcaccctgg ctggcgctcc ggcctcatcc acggacccgg gcacatggtc tggctggtcg    420
caggtgcgac gcgccacggc cggcgatggc ttcgggacca tgctcggtga cgggctgggg    480
tgctgggatc tcgaccactt cgacgatcag ggcgcccggg ccttcatcga ccggatcgat    540
aagccgatca tcttcgccga gcggtcggtg tcggggcatg gcttccacat cttcgtccgg    600
actgacgagg ccccgacg ccgcaccgga aacatcgagt tctactcacg ccatcggttc      660
atcagggtca caggagacca gttcgtctga agaaggggt gcgccatggc tgcacaggtc    720
agggccgtgg accccgatga gcgcccaccc gcccgcaagc gggccaagac catcacccag    780
gccgcgaagt ccggcactga ggttgaactg ttggaggcac tgcaggctcg cgtgcccgc    840
gccgtgcagg accgtgacac tccgccgcgc gatctgcag cgctgacgaa gcggctgatg    900
gacatcaccc gggagctcga ggcggccgg gtcaaggatc aggaggcggg atctgatggt    960
```

```
gccgtcaccg cagacgaaac atggcgaccg caagctctct gaggtcgcca agcacctgat   1020
ccttcctgaa gggatcgtct cgacgggctg gccggccgtg cgtgaccggt gtggcgagtg   1080
gggtgtggtc ttcgaccgtt ggcaggacgg catgggccgg gtgatcctgt cgaagcgcgg   1140
cagcggcctg ttcgccgctg gtgtgggcgg ggtcggcatg tcgatcccgc gccagaccgg   1200
caagaccttc accgtcggca tgatcatcct cgggctgtcc tcgctgagcg aggagctcac   1260
ggtgctgtgg acctcccacc attccaagac gaccaccaag actttcgagt cgctgcgggg   1320
catggcccag cgtaagaagg tcgccccgtt gatccgtcag gtccgaacag gaaacggtga   1380
ccagcagatc attttcagca acggttcgag gatctacttc ggtgcccggg aacagggctt   1440
cgggcgtggc ttcgacgacg tggacatcga gatctttgac gaggcgcaga tcctgtccga   1500
gcaggccctc tccgacatgg ttcccgcggc gaatgtgagc accaatccgc tgatcatctt   1560
catgggcacc ccgccgcgtc cctcggaccc gtcggaggcg ttcgcgaacc gccgcgccga   1620
agctctggcg ggcgacgccc cggacgccgc ctggatcgaa ttcggagcgg acgagcacgc   1680
cgacccgacc agccgcgccc aatggcgtaa ggcaaaccca tcctttcctc accgcacgtc   1740
ggagacctcc attctgcgga tgaagaagat gctcgggccg gagtccttca aacgcgaggg   1800
cttgggcatc tgggatgaga cggcatcggt ccgcgcgatc ccagccgaag ggtggcgcgt   1860
cctgaccgtc aaggaaccac ccgccgacgc gatccagtcc ttcggcatca agttcgccat   1920
cgacgggagt gcggtcgccc tggcagccgc cctgaaaccc aaggacgggc cgatctatgt   1980
cgaaggaatc gagcagcgct cggcatccga cggcatcgaa tggctcgccg actacctgac   2040
gcccctgtgg cgcaacacgg cccagatcgt catcgatggc aagtccgccg ccggtgcccct   2100
ggttgatgcg ctgcgccgtg gtggcgtggc tgcgaaggtg atcctcaccc cgagcgtcgc   2160
cgacgtgatc accgcccaca gcctgactct ggaggccatc aagaccggtg gactgtcgca   2220
cctggctgac ccggagctgg atcggcaggt ccgcatcgcc gcaaggcgaa agatcgggggc   2280
cgccgggggc ttcggctggc aggccccccga aggcgacacc gtcgcctcc tcgacgcat   2340
cacgcttgcc cactgggcgg ccctccaccac gaagcgacat cccggcagga aggcggtggc   2400
actggcatga gcctcctcgt caaccccat gcgtcgccgt ccttcttctc gtccccgtcc   2460
gtggtcggac tcggagcaga cgagcaggag ctcctggacg agctggtggc cctgtgggca   2520
cgcaagaagc cccgcaacgt gctgcgcggc ctgtaccttg acggcaagca gcagatcaag   2580
aacctgaaca tcgccgtgcc cgacgagatc gccgacagtc tccagatcgt ggtcggctgg   2640
cccgagaagg ccgtcttcgg gctatcgaac ctgtgcatgt gggatggcgt cgtcactccc   2700
acaggcgacg agaatccctt cgggcttgac gatctcctgt cggccaaccg cttcgacgtc   2760
gagatcaatg aaaacgatca ctcggccatg gcgaactccg tggccttcct gaccgtatcg   2820
gcgggcaacg tgtccatagg tgagccgccg gtggtgatca tgccgttctc cgccgaatgg   2880
gcctcagccc tgtgggaccg gcgcacccgc tcaatcaagg cgggactgac catcggcgac   2940
atcgactacc tgggccgccc caccagcctc tcgctcttcg cccgcaccgc caccatcacc   3000
tgcgtggggt cccggctggg atggatgatc gaagatcgcg ccgagcacgg gctgaaccgc   3060
gtccgatgg agccggtccc gttccgccca accttgacc gcccttcgg gcgctcgcgg   3120
atctcgcgcc aggtgatgac catcgtggac gcgccatgc gcgcggccct gcgcatggac   3180
atctcctcag agctgttcac cgcacccggc ctgctcctca acggaatcac cccggagcag   3240
tgggcagaga tccagaagtg gacatggaag ctcggccagg tgcgcggcct gactcgcgaa   3300
gaggatggcg agaccgcatc ggtcgagacg atccccagc agtcgatgga accgttcatc   3360
gcgcagctgc gcgagctggc cgaggaattc gcctcagcca catccatgcc gctgtctgca   3420
ttgggggtcg tccaagacaa cccctcctcg gctgacgcca tctacgcggc gaaagaagac   3480
ctggtcatcg aggccaccaa cgccaaccgg ataccggct acgcgctatc ccgggtcttc   3540
caagacgcgg tgatgatgcg cgacggcctg accgagatgc ccgacgagct cggcgggtgtc   3600
gccgccaagt ggcgcaaccc ggcgatgccg tcgatcgtgt cccagtccga cgcgatggtc   3660
aagcagattt cggcgatccc cgggctggcc gctaccgacg tcgccttcga acagctcggc   3720
tattcggcgg ctgacatcgt gcggattcgt acccagatgc ggcgagccga ggctggcgac   3780
ggcctgactt cgttgctggc caaaccagcc acgtcgtcaa cgcctggcgc ggagccctct   3840
cagtccgcaa gtccgacgga gccagctgca agcactccgc tgccgacct cgaaggggcc   3900
cctggtgacc gatcgtgatg acctgaacca tttccacgag gccaatgacg cgatccagcg   3960
gcgcgcaatc aacgacctga acaagttttg ggcgcggctt gccaagtcag acccgaaagc   4020
cgttcgcgca gccatggact tattcgtccc ccagctcatc gcctcctacg gagagttggc   4080
cgccgaagcc gctgcccgtt ggtatgagga actacgcccc gccgacaaga gaacttccca   4140
ggccgaactc gcggaccctg tgtccgacga catcatcgag gcagatgtgg ctgaggccct   4200
ggggaccagc ggcgcctggg acaccggagc ggtgcgaggg agcctggccg atgcgatcag   4260
gcgtcagatc ttctcatggg cgcgggcgac tgtcgcacgc aacatcgctc acgaccccgaa   4320
gcgtccaagg tttgcacgag ttcctcgggg cgccgtcacg tgcgcgttct gcaccatgct   4380
cgcctccagg ggtgggtgt actacaccgc gaagactgcc gggatcacac gaccctggca   4440
tcgcaagtgc gactgccaga tcgtgcctga gtggaaaagc ggcaacatcc atttcgccgg   4500
ctacgaccct gacaagatgt tcgagcagta tgccgaatcg tcgatgcgg tgggtcggaa   4560
cttcgacacg aaggcaatcc tcgccgacat gcgccgacgc catcccgaag cgctgaccga   4620
cggggtcgtc aacatgagtg aaggacaggg tccggtgacc agtgattaga cagtcggtga   4680
acggatgact acgccgtcgg cgctgcgccg ccgcctggaa tggctactgg agaaccgtga   4740
acggcttctc aggagccatg gcgagtcgga ctttgccgag gctggatg gccgccgtca   4800
cgagcttgat gaggcccgcg agcaggcagg cctggccgcg cagtcaaacc caatctgtag   4860
caagcccgt tccaccttcg ggtgggcggg ctttgtcat gcccgcatcc gggcatccaa   4920
ttccgtccca ccgcgagggt ggggcgtcga cctggtggcg cgatgccgcc gaactaatcc   4980
ctggaagggg aaactgctat gcacaagaag ctcatgccgt gggtccgtct catcgaggcg   5040
gtcgagactc ctgctggagc cgcccccacg cccgcgatcg atccgaagga tccggcagca   5100
aatcccacca ctgagccgaa gccggccgac gcgacgtcgg agaagcctct cggcgaggcg   5160
ggcaaggttg cgttggatcg cgagccgag gctcgccgca gcgccgacaa gcgcgccagt   5220
gagttggagg cccgtgtgca ccagctcgag gacgcgggca agaccgaggc ccagaagcag   5280
gccgacgaac tcaagcgcac ccagtccgag ctggagacgt gaggggcgca gaaggcacgg   5340
ctggaggtgg cgtccgcgac gggcgtcccg gtcgatctgc tcgctggccc cggcgacgat   5400
ctggatgcct acgcgcaggc cctgaacgcc tggcgcgaca gcagtccgaa aagccagcc   5460
gcccctgcgg tggacacccc ttcccttcg ccgtccgggg tgaccggaca gcccgtgcag   5520
ccgaaccgga cggtcgatga actcatcgcg gcgccgaga gaacggcga tctggcaacc   5580
gcgaagcaac tcaaattgat gaagctcgac gcactgcgtc ggacgtcctg atcagaaagg   5640
caccactatg ccgggcatta ccggacaggg caccacctac aaccttccga actatgtggg   5700
```

```
ggagcttttt gcggcatctc ccgaagacac cccgctgctg tcggcgatcg ggggactgac   5760
cggcggcgag tcggtcggcg cccgccagtt cgaatggcag ggctacgacc tgcgcgacgc   5820
cgacggttcg cgccagcgcc tcgagggagc caacgccccc gacggtgagg agcgcacccg   5880
ctactccgcc tccaatgtgg tcgagatcca ccaggagtcg gtggaggtgt cctacaccaa   5940
gcaggccgcg aaccgtgagc gggctaccaa cggtgccgcc acggtccagc tggcgggctc   6000
cgtgctgccg gccgatgagc tcacctggca gatcgaccag cagctcaagc aggtcgcccg   6060
cgatgtcgag aagtccttca tcgcgggcac ctaccagctg cccaccgaca cgccaagcc    6120
gcgccgcacg cgtggcctgc tggaggcgac caccacgaac gtggccgcct cgacccacac   6180
cgcaaaggaa ctcaccgtgg aggagatcct cgacctgttc cagaaggtgt gggagaaccg   6240
cggcatccag gaagccgaga cccgcaccgt cattgtcggt gccgccctga agcggaccct   6300
gacgcgcctg ttcatcaccg acgtcaagta ccaggaagaa tcccgcaacg ttggcggtgt   6360
gaacctgcaa accttcgaaa ccgacttcgg caaggcgaac atcatgctcg accgcttcat   6420
gccgagcgac accctcgtgg tcgcgtcgct ggaggacctg aagccggcct tcctcgacat   6480
ccccggcaag ggccacttct tcgccgagcc gctcgccaaa accggtgcag ccgacaaggt   6540
gcagatttac ggcgaggtcg ggctgcagta cgggaaccag cgcaagcacg gaaagctcac   6600
tgtcgcaccc gcaaccccg ccaagtaatc acggatcggt ttgaggttgc ctgatgaaag    6660
tcacctcgac catcccgaac ctgactgttc tcgacctgga catccagttc gttgacggtc   6720
aggccgatgt ggacccgcat ctcgccgaga ggctgcgtcg cctcgagcct ctcggcgtgc   6780
gggtccccac agccagccgc aagccgccca cgcggtcgcg gcgtaagcag ggggtcagcc   6840
atggtcgcac ctgatccgga actgccgttc gccaccgtct ccgatatgga gagccggtgg   6900
cgttctttgt ctaaggacga gcacacgcgg gccgaggccc ttctggacga tgcgagcggg   6960
ttgatcgttg atacctgccc gcgctgggaa caggcctcac ggccaccct gcggcgtgtg     7020
acgtgctctg tcgtgcgccg ggcgatggcc gcagacgatg aggacatcgg cgcaacctcg   7080
ctcatggaca cgacgggccc cttcaccact cagcgcgcct actcatcacc ggccggggat   7140
ctcttcttga ccaaggccga gaaggccgcg ctcggcgggg tcaccggcgc attcgagacg   7200
agccttcgtg ggctgacatg aagcgctcat ggccgacacc cgtggaacgt ctccgcgagg   7260
gtccgcccga gattgaccgt gacggtgatc cgattgccgg ctccggagtg atcaccaagg   7320
atcctctccc tgatgccctg ttcgcgccgg gcggctcgca gatcctcgtc gccccggcg    7380
tggcggcagt cgtggacgaa cccaccctct actggcgcgg atcagaagtg atcgatgtgg   7440
tggccaccga caaggtccgg atagccgacc gagtctggac ccctgaagga aatcctgcgc   7500
gatggccgaa gggcgtcgtg ctcaagctca aggcccagga ggcaaagaat cgtggctaat   7560
ttccgtttcg aacccaatac gaaggcgttc accgagtggg cgcagcgcga ctgcgacgcg   7620
cacctgatcg ccggcatcac ggcctcgatg ggggccaagg cgggcgaggg tttctcgacg   7680
atggtctcca acaatggcga ccgcaccgc ggttatctcg cgacggcctc cacgaagggc     7740
cgtatgcggc aggcgcaggg gcatgtcatc gagcgggtca tcggatcgag cggcgtgtga   7800
aaccgcccga cctccacacg ctcgtcgccc accatctggc tgagctcctc gacgtgccga   7860
tcgtctccac ccgccccgag ggagagacgg cgccgtccaa gttcgttcgg atcatctcga   7920
ccggcggagc gggccgctat ggccgggtct tccagggcat ccagctgacg atcggctcct   7980
acgcgggatc ggcggcgacc gccgcgtgatc tcgcgatgca ggtggacgag gccatgaatg   8040
ggctgccggt ctcgccgttg ccggtctcca aggtcaccgg caacaccccg tcggacgacc   8100
ccgatcccga cactcagcag gccgccaca cggccaccta ccaactcacc acccttatct     8160
cttaggagtc attcatggct gtcaattccg tcaacgtgca cgtcttcggg tccgatgacg   8220
acgtgctcta cctgggcccg tcaggtctga atctgggcaa catttcgctg gaaaccgcga   8280
tcccgaagga gatgatcgac accggctggc tcactgatga cggtgtgacc ctcggcatga   8340
aggactctgt caaggccatc cagggccacc agggccacgc gaatgtgctt cagttcatgg   8400
actcgtcgga taccaccctc gaggcgaccc tcatggagtc tcagctgcag accttcctgt   8460
ggaacctcga cgcggacgct gaggacatcg acgggtcac caagatcacc gcggccagct    8520
cccgcaaggt cctcaacctg tgcgcgatct gggacacctt cgacacccag cacagcggca   8580
tccattggcg ctacgtcttc ccctcgctca ccctgggcga gcgcgatgac atcccctcca   8640
aggtgggcga agccagcgct tacaagtatt cgctgggtgt gctggagaag ttcttcgtct   8700
tcaccaagcg ggcagcgatg aaggccggtg gagcatccgc caagacggtg accggtgtga   8760
agatcaccac caccgacggt gcgaccgtgg gcctccgtc gtcgctgaag gtgggggaga    8820
aggtgtccct cgccgccgag atctcctaca gcgacgggac gaaggcgtcc aagcagacca   8880
atgccgtggg cctcacctgg acgtcctcgg acaaggccaa ggccaccatc gatggcggcc   8940
tggtcaccgg agtctcggca ggcaaggccg acatcaccgc ctcgatcgac ggcaagactt   9000
ccgaagcgct gtcgctgacc atcaacaccg ccgcctgacc aaccctcaaa ccctccgccc   9060
cggtcgtcct ctcgcgccgg gcggagcct tgccacaccc gcgagaggtc aacttttctg    9120
cgagaggaaa ccatcatggc cgaggccaag aagatcagcg ccgccgagaa ggcgcgccgc   9180
gagacccagt ccgcgaagga caccgcacg atcaccgaca ccaccgtgca gatcggcgat    9240
atcgagttga ccgtcgcccgc cgccgtcttc gaagacgact gggaattcca ggaggcgctc   9300
ctgatggcca cgatcccga tgccaccgac gaggatcggg ccagggcaag catgacgctg    9360
ttccgtcgtc tggtcggaaa ccgccaccgc gaagtgcttg accagctgcg cgacgagtcg   9420
gggcgtgtgc cggtgtctaa ggtcaccgag accgtcaaga aggtcatgga cgcggtcaac   9480
ccaaactgat gagcctcttc cagctcctcg ccacacattg ggaggagctg caggtggagt   9540
tccaagaggc ctaccgcgtc gacctgcggg acttgtggcg tggtcggctg agcccggcgc   9600
gctgctgggt gctgctgaca caactgccac ccgggtctcg gctctggcgg atgctcggcg   9660
gccccatggc gtgggggcatg tcgagcgcg ccgtccgtga agagggctgg cgactcgcct     9720
cccagaacgc tggtaaggaa ctgcctcggc cggagccgcc tgcgccggga tggcgcgaca   9780
agcaggacga cctgcgacgc cgcgaagagc gccgtcttgc ccgcttcatg caacgccacg   9840
cagaacgcaa caactgaaca gtgcaccgtc ccggggaggtt tccatggctc tagatctcgg   9900
taccgcctgg gtgcaggtgt ctccgtcctt caggggcttc gcctcacgg tgaacaaaga    9960
ggtcggttcg gcagtgggcg gggccttcaa gtctgcggcc aaggtcggca ccaccgcgat  10020
cgccacgatc ggtgcggccg tcggtgggct ggcgctcaag gcggcatcg accgcgccct   10080
gtcgatcgag caggcgcagg ccaagctgaa gggcgcgcag cacgacgcag ggtcgatcac  10140
cgagatcatg aacgacgccc tcgcctcggt gaagggcacc gccttcggtc tgggcgatgc  10200
cgcgacggtt gccgcgtcga tgtcggctgc cggcgtcaag tcgggcgagc agatgaccgg  10260
tgtgctgaag acgttgccg acaccgccca gatttcgggg cgctcgctca ccgatatcgg   10320
tgcgatcttc gggtcggtgg cggccgcgcg caagctgcag ggcgacgaca tgctgcagct  10380
catgagctcc ggcgtgccgg tgctccaatt cctttccgac cagctcggcg tcaccaccgc  10440
```

```
cgacgtgtcg gacatggtgt ccaaggggca gatcgacttc gccactttct ccgccgccat   10500
gcagaagggt cttggtggtg cggcactggc tggcggcgaa accttcaccg gtgccatggc   10560
caacgtccgc gccgccctgt cccggctggg tgaggctgcc gccaagcctg ccctggacgg   10620
gctgcgcaat gtcttcaacg cgctgatccc ggcgattgat gccgccacaa atgcgctcaa   10680
gcccatcgcc agcgccctgc cgaaccgaat ttcgcaagca gcagaggcgg cttccgcctc   10740
gatcgggcgc ctcaccggct ccctcacgag catcacgaat ctcaatacag ggatgctcgg   10800
cgcggccttc tcatcgatgc tgccgatcat cggagcactg tcggggcagc ttggctcctt   10860
gcttggcggg atcccggtcg tcgggcaggc cttcgcaggg atcactgggc cggtgggatt   10920
ggctgccggc gtgctggtcg agatcgtggc ggcttcatcg tcgctgcgtc aggccctggg   10980
cacgctggtc ggggtcgtcg ggtctcagtt gtccggtgtg atgacgggca tcgtcgcggt   11040
gtttgccggc ttcaggtccg tgcttggtgc cgtcggtgac gttctggccc cgttcgtgga   11100
ccgtgcggcg gacgccgcca atgtggtcct gcccttgctg gggggtgcgc tgtcggctgc   11160
cggtggcatc ctgcagtctt ttgcgggttt catcgagcgc aaccatgtgg cgctctccat   11220
tcttgcgggt gcggtggttg cggccgcgac gagttgaaag atctataccg gcgcgcaaga   11280
tcttgcgcgg ctggcaacga cgaagctcgg gctcgcgaca acggtcctga agggcaagct   11340
gtcatcgatg ggggcggcgt tcaagacgaa tccgttcggt gtcatcctca tggcgatctc   11400
ggcgctggtg ggggcgttct cgattgccta ccagtcctct gagacgttcc gcaacggtgt   11460
gcagggggatt ctcggctcgc tggcgccggt gttttcctcc ctgatggggga cgctgtcggg   11520
gctattccag caggtcgcgg gcgctgtcgg gccggtgctg tcgtcgatcg tctcgacgcg   11580
ggcgtcggtg ttctcggcga tcggtcccgt cctgtcgcag ctggccggca ccatcggatc   11640
tgtcttctcg gcgatcggtc ccgtcctggc gtcggtcttc gggtcgatcg ggtcggttct   11700
ggcgagtgtc ttctccgggg tgatgagtgt cgtggccgcg atgctcaccg cgttgcagcc   11760
gctgttcacg cagctgtcgg cttcggcggg gcagatcggt gcgcgttcg gtcctgttgg   11820
tcaggcgctg tcgtcgtcct tccagcaggt cggtgccgcg ctggccgcc tgctgccgat   11880
gcttggtcag cagttcgggg cgatcctgtc tcagctggct gcggccctgg ctccggtcat   11940
gggtcagttg ctggctcgcg ctgctcagtt gttgccgacg ttggcgcagg ccttcggaca   12000
ggtcgccggc gtgctgatcg ggtcgctggg tcaggctctg acccagatcg ctccgctgat   12060
aggccagctg gtggggtgc tgatcgggtc gctgggtcag gctctgacgc agattgcccc   12120
gctggtgggc accctggtcg gggtggtcgc gcagctgttc gcccagctgg cccctttggt   12180
gggtcagctg ctggtgcagc ttgttccggt tgtcgcggga atccttgtgg cgatcgtgcc   12240
gatcgtcggg atgctgatta gtcagctcgt tccggtgatc gtcacgctgc tccaggtgat   12300
caccccgatt atcaccatgc taatcagcgc gctggtgccg gtgatccagg tcgtgaccca   12360
gctggtgctg gcgatcatcc aggcggtgat cccgttgatc tcggcgatcc tgccggcgat   12420
ctcggcactc atctcggcgc tgctgccggt gatcgtcatg atcatccagg tggtggcgca   12480
ggtgctgcag tggctggcgc cgctgatctc caccctgatc acggcactga ttccggtgat   12540
caccacgatc atccaggtgg tcatcacggt cgtgtcgaca atttggtcgg tggtcggggc   12600
ggtcattggc tggttccagt ccacggttgt gcccatcatc ggcaccgttg ttggtgcgat   12660
cgcgaacgct ttcggtttggg tgcgcgaccg tatttcgat gcctggaact ggattaagga   12720
ccgcattgtc gccccggttg tcgagtggtt ccagtccacg gtggtgcga agttcgaggc   12780
ggtgcgcgac tccgtggtgc gggccttcga gacgctgaag gatggcgttg tcgcgcctg   12840
ggatgcgttg aaggatctcg caaagaagcc ggtcgaattc gtcgtgaaca cggtggctgc   12900
cgggttggtg cgggcctaca actgggtggc gacgaagttc ggtgccgacg aggtcaagga   12960
gcctcatgtc gagttcgcca acggcgggtct cgcgggacgc gaggtcgcggt tcgtcgagcc   13020
gccgatcctg tgggccgagg ccggcccgga agcctatatc ccgttggatc cggcaagcg   13080
gacacgctcg ctggggatct gggccaagac cgggcagatg ctcggcgctc tacccatggc   13140
tgacggcggg atcatcggga acatcattgg cgggatcggc aacgccgctg cggcgatcgg   13200
caatttcatc aagtcaccga tcgagtggct catgggcggc tcgggaccc tgatcgatga   13260
tgtgggcagc tcaccgttcg cccagatcgc cgcgaagatc cccggcaaga tcgccgacga   13320
tatcggcgcc tgggtcaagg aacacatggc ctccatattc ggcggcggcg gttccggatc   13380
ggaagcgttc gacggctggt ggaacgcggc tgtcgccatc aatcctgata tggccccctt   13440
caagcagatc gccgccacgg tcgccagaa cgaatccgga ttcaacccga acgtcatgaa   13500
caactgggat tcgaacgctg cggcgggcac gccgtcgggt gggctgatgc agttcatcca   13560
gcccaccttc gaggcctaca gtgcccggg attgacaat tggatggggtg cggtcgatca   13620
gatcctcgcc tggtgaagt acgtgaatgc ccgctatggc gggccgttca atattcccgg   13680
aattgcctcg ctggcggggtg gcggcggata tgtcggctac gccggagggca ccctgaaccg   13740
ggctgccggc acggcatggg tggggagaa cggccccgag ctggtcgatt tcggtggccg   13800
cgagtcggtc tacaaccgct cccagattga cggtctggag gatcggatcg ctgaccggac   13860
gatttcccgg ctgcagcagc tgagggtggc gctgatcgtg gacggacatc agatgggtca   13920
ggtcatcgac ggccgcatct ccatgctggg cgctgctgca cacggatcga ggtggtgaca   13980
tggcgatcat tgcgacgcgc cgcgactggc ctgaggctcc gcaacgcttc cagtccgccg   14040
atgggcggct ggtggcggag ctggaccctg accggtgcgg agtgcgactg cgcggcaccg   14100
acctggaggc gtggagcgtc accctcaccc gtgatgccga ggtgatccac accggcgacc   14160
ccatggtcac accgggagga acaggaatcg cctacgacct gtctgcaccg ttggatgctg   14220
atgtcgtcta cgaggcgcac gcgggtgggg cggtgctcac ggcgctggac gtccacaccg   14280
gcggcttgcc tttcgagtgg gggatggtga cccgctcggc cgaccccgac aagggcctga   14340
tgctacggac cgtcgccgac accccacgc tgggcaggtc ggcacgccag aagctgtctg   14400
cggtgccctc atcgaggctg caggcaggtg gctgggacgt cccaccgac gcggcacagg   14460
gatgacgtg gctcgcggga ttccccgacg cctccaaagc gctccgcgag cgcgacgcgga   14520
tcatgaggc cctatcctg gggccgtct acttccggcc cgaaacctcc atcggcttcc   14580
cgcccatgtg ggcactgccc ggcgacgtgt cagcgaccaa gcagggcgac gcctggacgg   14640
tgtcgtcac gctgacgccg atcaccgctc ccgcaccgc cgacctgccc gctgggcgc   14700
ccggcaacag ctatgcgcgt gtggcggcca cccggggggag cctcgccgag ctcgcccgca   14760
catccaagac attcctcgag ctagtggggt tctgatgatt gaagtatcca agcgatgggc   14820
ctcctcagta ggggccggtg cacgctggtc ggtgatggtc tcctggtcct ccgacggagg   14880
ccagacctgg catgacgtgg tgccaccgc ctgctcggtg gacgagtcta ccggccagca   14940
ggtgcggtgg aagctgtcct gcaccctgcg caaggcgac gccgagggcc tgaccgtctt   15000
cggttgcagg gcgcgcgtct tcgtgtcgat gcatcacacc gacagctggg aggagacgat   15060
ccagctcggc gaattccgca ttgacaccac ctctgacacc ccctcgccg ggccgtccgg   15120
tgcgcaggtc gcggcagttc aggtgagcgg ttcgagctgg gagcagcagc tgatggactc   15180
```

```
gcggctggtt gagccgcgtg aggtgtcggg tgccgcgatc gatgtgctcg gcggcctgat   15240
ccgggaggtg ctccctgacg cagagatcgt cttcgacggc gggatcgatc cgggccgcaa   15300
cattccggcg acggtggtgg agcgtgaccg gtgggccttc attgacggct cgaattcgtc   15360
ggagacgtcg gtgtgcgcgga tgctcggcgc ccaggtctcg accgacgcac ggggcgtgtg   15420
gcatgtggcc ccgcctccgg tgctgacgg gacggcgggt tggacgatcg aggccggcaa   15480
gggcggtgcg ctcctgtcgg cggtggccaa cgaggaccgc tccacgatcc gtaacgccgt   15540
catcgcgcgc ggcgagtcaa ccgataagag cgtgccggtg tttgggtccgg tgaccgtggc   15600
tgatcacaat gcgtggtcac caaccaacgt ggacactccg gtctccaggg gcggcttcgg   15660
cacagtcccg atcttctaca cttcgagcct tttcaccgac acgacgcagg tggaggcggc   15720
agcgaaggcg atgctgcagc cgcgcctggg cgtcaaacgc accctggacc tgacaacgct   15780
cttcgaccct gccaaacgcg ccggggatgt gggtgtggtg cagaccactg atggtccggt   15840
caccgtcgtg ctcgaatcag tgtcgtgcga cctggtggcg cgtcgatga cctgccagac   15900
gcgcggcacg accggcaccg agctgatcac gaccgaaacc acgacaacca ctggggagaa   15960
gatctcatga gtgcaccaga cattgccctg caaggactga tcggggaaga caccgagcag   16020
gtggcgcttg cccaggtgct cggcgtgggc gtcgacgggc ggtcggtgcg tgtccagccg   16080
ggcactctca cccacgaggt ccgccggctc gatagctaca agccttcagc gggagaccgg   16140
gcgctgctgt tacggctatc tggcggcaaa tgggtgctga tcggcgccct cgcctgacct   16200
tgacgaccta acctctgaca acctgaaaag gagccctcca tggcaaccgt ctatggccct   16260
gacaaattca ccgtcccgac tggtccggac gcaccggacg tgccggcgac gatcatcacg   16320
ctgctggact cgatgcgtcc ctcgctgatc gggcatgcgt cttcgatcgc tgaccgcacc   16380
gcgaaatatg ggcgggcatc cgcgtcgagc attcaggcgc cgaagggcac agtggtggtg   16440
tctgccgagc tgaacgcaat ttgggtgaaa acatcggaca cgctggatga gtggggcacg   16500
atcattcagc actcggatga ggtggcgacc gtgtcggtgg tgtccaccca gtccgaccag   16560
gtgaccacgg tccagaagtt cacgattccc gagtcgggca tctatgcgct gtatgcatcg   16620
atgaatgacc agaacggctt ggatgtcgat gggtcgatcc gtgagataca tgttctggtg   16680
aacggacct ggaagttcgg tgggatcttc ccggcgacga agttctggct ctggtcggt   16740
tcgcggacga cctttctcaa taagggcgac acctatcaga tcgactttat gcaacgctca   16800
ggcggggaga ggtccctgaa ggtaacgctg tcttatcaaa ggattttgta atggcgacgt   16860
gggattacgg gtatgcgccg gctgatgtgg tgaccgatgc ggccggggat gtgctggccg   16920
gcatcgaact gcgggtgtgg gacgccgagg tggcagggaa agccgtcgcc gtccagcagg   16980
accgtggcga cggatggaaa cccgcgtcaa gagtcctcac cgacgacgtg ggccgctacc   17040
gatttcgtgc cgaagcgggc cccacggtgt gggtggagga cgtgtcaggg cggcgctggc   17100
ggatggatgc ctggcagacg ctcggcacga tgatcgactc cgcacagagc gccaccgccg   17160
cggccgagtc ggccaactca atcgcccacg aagccatgcc agtcgccacc caagccagca   17220
cgtcggcgaa ggccgccgcc gactccgccg ccgccgtcga gaagactgc tgaggcggtg cggaaggcgg   17340
cgctggctgc tttcccgacg accgggccga cgatcttcac gcacttcttg acgcgcgacg   17400
aggccctgca tgtggcgatc tccaccgacg gtgtgacggt ggaggacacc ggcctgcggt   17460
ggaagccgaa gaacgacacc accctggggg agtgcttcgt gcgcgaccca tcggtgtgtt   17520
tctggaaggg tgcctattgg gtcgccttca cccggcccac gaaggggcgg ggtgacgctt   17580
tcgggacgac caagtcgttc ggactgatga agaccacgga ctggcggacc ttccaggagc   17640
tcccgccggt cgtgatgccg agtcaatttc agcagacgtg ggcgccgcag tggttcatcg   17700
gctccacggg ggtgccgcat atctttgtgg ccctcggcac caccaccacg ccaacgcgt   17760
acttcaccca gtatgagctg cggccgctcg atgacgcgat gacgtcctgg tcggacccgg   17820
tggtcatgtc tggactgcca gcgaattgca tcgatgtcgc ggtgatcgag gacgccggta   17880
ccttccacgc ctttccgtcc aaccagaaga cgtcaacggt cgagcagtgg acgtcaaccg   17940
ggctcaccgg ccctacacg aagctggcgg ccagcgactt tcccggtgcc ggtgtcgaag   18000
gaccccagcc agtgccgctg aagacgggcg gctggcggat ctacgtcgac aattacgcgg   18060
agaccgactc gatctattc gccgagagca cggacttgct gcattggtcg gcgctcaggc   18120
cggtcaccct gccgatgcgt cacgtcgcg cggtcgcggt ggactccttc ggtgcgctac   18180
gcaccccgga gctgtggcag ccgaacatcc cgggcatgag gggatgggg gcaccctct   18240
ggggcgtacc cttcgccgcg gggaacgtgc tgaaggaatt cgcgcagatc gtgtccatgc   18300
gcaccgacgg cggcggcgaa atcgatctgg caaaggcggc cacgctgggc ttcaccggca   18360
tcgattacat ctcggcgacg gctgtcgcga acgtcgagat tctgcagatc gagcccgaca   18420
ttcgcgctgt cgacagcatg atccacgcg tcgccctgcg aggaccgact acgccgcaga   18480
tcgatacaga cgtgaaggtc gcctggcggg tgctcggctg gggcgatccg agcacgccat   18540
gagcagggac gctgacgtga ccaagcaggg atccttgcct cggcgggtct gggacatgct   18600
ggcagagccg aagtcggtga cggtcctcat gacgattgcc tacgcggcgc tcgtcgcgct   18660
cggcttctgg gcgatcgacg acgcctccac gatggggtc cgcgacatga tgggcggcct   18720
gctcatcgct ggtggcgtgt gcgggctgat cggatgcccg tggggccagt ggtggatcga   18780
gcgcgccggt ctggtggcga tcggtgccgc tttcgcggta cacctgtctt tcgtcgtggc   18840
gatctccccg cccgacggac cgtgggaagt ggcctcggcg ctgggctgc tgcttctcgt   18900
ggcgacacgc tggatcagga tcaggacgct gccagccgac ccgacgctgc ctcggcccgg   18960
gcctccagag gcggggatg aatgaatgac ttccagacat ggatcacagt gctgggcgac   19020
gccggattcc ttggcgcgct cgtcacgctc atcaagggg tggttgggtg gcgcaccggc   19080
aagtccggcc gcaaaatgag ggccgcccac gacgccatcg actcgctgaa tctggcgggc   19140
ttgtgggctg aagcctactg gcacgctcgc ggctattgcc gcagccacca tgaatggacc   19200
agcgattacg ccgacgcta tccaccccca cccgacgaca ccaacacccc tgactgacc   19260
ccgccttgtg cggggctttc tcattcctca aagacttgga gacattcatg gactggacca   19320
atctgaacgc tgacgtgacg aagctgatgg gcgtgcactt caccccccgga cgtgaaggca   19380
ggacgatcga caagatcgtg atccaccaca acggcggcaa cctgagcatc gaccagatct   19440
ggaatgtgtg gcagacccgt gaagcctccg cgcattatca ggtggaggcg ggtggccgta   19500
tcggccagct cgtcaacgat ttggacaccg cgtggcatgc cggcgactgg gacgccaacc   19560
tgacctcgat cggcatcgag catgccgacg actccgcga ctgtctgatg   19620
ctgccgtcga tgccggcgcg cacctggtgg ctgcactgtg tcgcggctac aaccttggcc   19680
ggccggagtg gatgcgcaac gtcttcccgc actctcagtt cacgtccacg tcgtgcccgg   19740
cgtcgctggc ccgggaccag ctcggcgact acatgggggcg cgcacaagcc tacttcgatg   19800
gcgcgccggt ggctgcggtc catcagtcgg tccctgcccc cgcccagcg cccagccgtc   19860
atgtggacct gcccgcgtgg aatctccccg agggcaactt ctacgcctc gtcagcggcg   19920
```

```
gaaacgactc ccacggcggc ttctatcccg ccgagcgtcc cgctgtgagg gccatccagc  19980
tgtggctcat ccgtcacggc tacgccggcg cggtgcctga cagttgggcg gacggcatct  20040
acgagcagcc gaccgccgac gccgtgaccg ctttccagca cgccgagcgc cccaacagca  20100
cggaccggtg gggcgaggtc tgggccgacg acctggccac catggccgcc aacaactgac  20160
aaggagctga tgccaagtga tctgtgactct cgcattctgg aagggcgcag gcgagcgcgc  20220
catcaaaacc gccgcgcaga ccgccgtcgg cctcatgggt acctcgacgc tcatcgaaca  20280
ggtgccgtgg actgtcgtcg cctccggcac cgccatggct gtggtgctgt cgctgatcac  20340
ctcgatcggc aacgccgact tcaccgccgg cgtccccact accgcaaagg ggctcgaggc  20400
gacgaccgtg ggcaagacgg acaccacgcc cgtcacgcca ccggcgcgcg tcgccgaaga  20460
ggtcccagcc ggcttcgtcc cggacacggc cccggatccc gtgccgaccg tctgacctga  20520
gggggtgacg gcgaccctgc gccggatagc cactcaagca acctgagcga cacaagaccg  20580
cccactctga ccttcgcggg tcggagtggg cggccttttt gcgtctcagg ggcgcagatg  20640
atgactcgtc gtctttaatt ctagcagtac gcgttcagcg tcgccagacc atgactttct  20700
cggctgcctg gagcggcgca ccttcggggc ctttgaggta ggggcgcatg tagatgagct  20760
tgcgcagtcc atgcttgggg ccgtgcgcct ggtgggtcca gtgcccgcgg accatgaacc  20820
gcacggtgag cttgtgcccg gttccgtcgt cgcggtcggt gaccacggtg cgcacgggac  20880
gcagatcgac cagggtgacg tgacggtcgg ggcgtggcgt gcggggcctg tgctcggtgc  20940
ccggggcctt gccggtgcgg gagtcgatcg tgcgccgctc ggcgacggtg ggggtgtcca  21000
tgagcacgct catcgccatc agcagcgacg cggacatgcg ggcctcgggg ctcagcgtgg  21060
catccagatc ggattcgggg cggatgagaa tcgacaggat ctcgacaagg ggaccgtcca  21120
cgtcagcgaa gccgggcgga tagtcgccca gccgcccag cagctggatc atggtgcccc  21180
caccggggca gggaagccag gcgatggcc acacggggagg attccctgc caggtgcggc  21240
cgccgggcag gtcgaaggtg gcgcggcttgg gccccggcag gggtttggcg aagcaggcca  21300
gtccggtcgg ggtgatcagc tggctcgggc tccactcggg cacgtccagg gcagcatcca  21360
gagcgagcgc cgccatctcg ccactcaccc agaacagcga cgcattaccg agccgctcgg  21420
cactccaccc gaagccggac atcggcagtg ccttgtcgac catggcttca gccaccgcat  21480
cagggtgggt ggcggccagt tgctccaggc gctcgtcgag gtggcgggag tcccgcacaa  21540
agcggcgacg cagcccggc actccgcggg gtgtccacgt ccagctctcc ggggctgcca  21600
tgtcaggcga cgactcgaat gcccaggctc cgccacgcct cggcggtgtg gtcgagcccc  21660
agatcccacc actgggtcag cgcgtgttcc atggcgaggc tggcgcaggc cgacagctgc  21720
gaggccttgt cgcgagccga cagcaggtcg gcgctgtcgg tgccgtcggg cgtgaagtcc  21780
tgcagggcga tagtgatgtc tccgccggga agctgggaga ccgtgtccgc ggtcatgcct  21840
gcctgggtgg cgtcggcgat gatgcccagc tcgaccagcg tccagccggt gcgggccagg  21900
tcgatgcgct gggcctcgcg ccacaggtcc atctcggtgc gggtgcgtgc cgacaggctc  21960
ggggggtgcgg ccacatcggc tccgcgtcgg gccatccatg cggccatgtc gtccggtgggc  22020
cgccaggtga ttgtgctggc catgaagatc ctccctcggag tggaaagtgg aaaggggagg  22080
ggccggagcc cctcccctga tggttgatgt ggtcagcgga tccaggtgaa gggctggtcg  22140
ccgatgatcg agcggaccgc gaggtcgtag ggggcctcgt cctcgctgga ctcgacatcg  22200
accgcgtcga gctcgacacc gtcgcggtg atggtgatgg tgtcggtcgt ggtggcccga  22260
ccgtcgatca ccgtcggagt gttgatgctg gtgaactctg cggtcgatgcc gaccagctcg  22320
tggtcggcga ccgcttccca gaaggcgtcc tcgtcggctt cgatgagaa gtgcacgctg  22380
gaggcgatcg tcgcaccctc ggaggtctcc tcgctgtgga gcgtgaccag ctcgtcggcg  22440
atggcgtcga ggtcatactc ggcgcggggcg tcggcgactg cacctccggc tcgatgggca  22500
tcgatgatag aggcgatggc ctcgccgcgg gtggagaagg tagtgtcggt agaatcggtc  22560
atgatcctgt cccttttcagg gtcttggcct catcggggtg cttcccggtg gggcctcttg  22620
ctttgtcctt gtgacaccca ctgtcgtcac agtgttggaa catgtcaagc cagtgggcca  22680
cctttcttta aagagatttc agcgggcgac cgcgccgcct cggacacctg ggcccagtag  22740
ccctggaggg cgcactgaat caattggttg tcaattggtt gtcaaacctg acccgtcgac  22800
ggggagtgag gaggtggtac cggctgatct acgcctgaaa cagatggagc gggcgacggg  22860
aatcgaaccc gcgtgtctag cttgggaaac gggcatcgtg ctagtctggg gaccgccgaa  22920
atgacgattt caggcgtaaa ccggcctccg gtgtcttacc ctgatagctg ggtgataggca  22980
ccgaattggt tgtcagattg gttgtcagat cgccccagga ggatggtcgc attgtcacgc  23040
gcaagctacg gggacggcac ccagccgacc cggcgttccg acgggcgctg ggcagcatcg  23100
gcctatgacg gctggcaggc gaacgggaac cgccggcgcc gatgggtgta cggccgcacc  23160
caggccgaat gcaagcggaa gctgccgac ctgaagcggga agatctggtc agacaccag  23220
cagatgaatg tgaaccccag ggagaccgtc aagagctgga cggcatcatg gctggacgac  23280
taccgatcga ttgccagacc aacaaccttc gccaccgacg agtccatggt gcgcaactgg  23340
atcgtcccag ccatcggtgc ccggcgcctg tccgaactga cagcgcgcga cgcctcgaag  23400
ctgcaacggg tctgccgaga cggggacctg tcggcgacaa cgtctcacta tgccgggctg  23460
ctcctgcggc gcatcctgaa ggctgcccgc gcgaacggct accgcatccc cgactccgtc  23520
atgctggccc ggatcccggg catcggcgca tccaacaggt ccgccctgag cgccatccag  23580
gcggccaacc tgctctcgac ggcaaacgca cgcgacacct ggccggagcc gcccagcctt  23640
cccgacctgc cctacgggc catctcgaag ctcgcaccag cagaagcgca gaagcgtgaa  23700
caactcaaga tggagcggtt ggaatggact gccgcccaaa acacggaccg ctccaggtgg  23760
gctgccgcac tcatgcaggg acttcggtca ggagaggctc gaggcctcac gtgggatcgt  23820
gtcgatctcg ataaggggac gatcaccatt gatcgtcaac tccagcgcat caagcccgac  23880
gcggcgcttc caccgggata caaggtcacc cggctgaaag cagccactg cctcgtggca  23940
ccgaaatctc gatcagggat ccgccgcgtc ccgatcgtcc cctggatggg ccaggctctc  24000
acccgctggc gcgacataca gggcgacagc cccttcggtc tcgtgtggcc gctgcccacc  24060
ggggcgccgc ccacgcgggt ccatgacctg cgggcatggc gtggactcca gcgcgtcgcc  24120
ggggtccaca aggaggatgg aaacctctac gtcctccacg aagcacgaca ctccaccgtg  24180
tcgctgctgc ttgctgccgg gtcccggaa tcagtggtca tcgcgatcgt cgggcatgca  24240
agcttcgcgg cgaccgagca ctacgcccac accgacctcg aagcagcacg cgccgccctc  24300
atgaaggtgc aggaccgcct cgggctggag gtcgagagct gagcatgcaa agagccgcgg  24360
accggaccaa tcgcggtctg gtgggcggct cttttgcgcc ttagagcacg tccgtcacca  24420
cgcctgaaag ttgctgacga cgggtgcctg tcggtgccg gtcacgtcgc agtgaaccgt  24480
gtatttggcg gagccgacgt cggcgccgat gttgacgttc cacagatcgt cggtcttatt  24540
gagggcggcg accgaatcga cggttgagtg gaccttgatc ttaagcgatg ggtattgctt  24600
gcccaaggca tccctcgcat aggtgccaca gccagaggtt gcgccggtca tggtgagtcc  24660
```

-continued

```
agtggtcgtt gcctcgacgg gtgtgggcgt ggcggacgca gtgggcgtct tcgtggccgt   24720
cggcgtcttc gccgctttcg gagtcttgga ggctgatgat gacgatcctg atgtctgggg   24780
atcgcacgcg gtcagcgcgc cggcgaggca gagtgacgca agcagggcga tgggacgag   24840
cgccttgcgg cgcatggtgt gggtcattcg ggttccttgg ttggttggtt cacatgctgt   24900
ccacagcaac ctagccgcgg aacctgcccg cctggggtg atgagggaca gtggcaagaa   24960
ttacatcgat gggattctcg ccaccccctg aagagcgtgg gtggcgaggt ctacattcgt   25020
acgcatgtac gaaacatgga agcctctcgg acacggctcg atctctggtg gatcggcccg   25080
cacaatggag tgcactgaag tagcggagtg ggcagagcgt cgtgcgcgtg ggtgggcctc   25140
agcgctggta tcgcgcctgc gcggcgtcca tgaagacgcc gggttcaaag tcgagcacgc   25200
gagcaagctc aaagaggagt gcgacaggga gatcccgctt gccctgctcg atcctgatga   25260
tggtggattc gctgactcca gcgagtcgag cggtctcgac ctgggttaag cccttggcgg   25320
ctcgctcggc tcgaagctgg gcggcgatcg cggcgcgaat tgcatcacgc ttgctggcct   25380
ggttctggtc catgctgtca gcatagccgc cacattggac agttttccgg tccgattggg   25440
atgctcggca cttgcatctg gccatatggc atggcaagct gtccatatgg ccagttcaga   25500
catcaacctg gaggctgcgg acatgatctc cgccgccatc gagcgaagcg acaccagtcg   25560
ggctgaagtc gccacgctga cgggaatccc gttgaccact ctgcgtcgga agctcatggg   25620
ccgatcgccc gtcaacatcg aggacatctt cctgatcgcc ggcgcgctcg ggataccgcc   25680
tgtgagtatc acgcccgacg ttctcacgag tgaagccgcc gcctagcccc caaacagaag   25740
aagcccccgc ctgctgtcac agacgggagc caaccaaagg agtttccaat gagcattcta   25800
cccttcgact accacggtca ggaagtccgg ttcatcaccg atgagtccgg cgagcctcag   25860
gtcgtcgcgt cagatctcgc gaaggccctc aactatcgga acgcacccga catgatgcgt   25920
tccatcgacc tagaggaaag gggtacgcgt ccggtgacgt cctgggctcc tgagcaggag   25980
atgctcacgc tgaccgaggc cggcatgtac caagccatcc tgcaacgcca gacaggccga   26040
atggtcgacg tcgcccaacg agccgctgtg aagcgattcc agcattgggt tacccacgag   26100
gtgattccct cgatccgcaa gcgcggcatg tatgccactc cggatgcagt cgaggcgatg   26160
ctggccgatc cggacgttat gatccggacg ctcaccgagc tgaaggccca gcgggccagg   26220
gtgcccagc tgcagcccaa ggccgactac gttgacggcct tcgtggccga cgaggatctg   26280
cggctcctgc gcaatgtggc caagtcgatc ggagtgcagg agggcgccat tcgcgacgcc   26340
ttgctcgcac acgagtggat ctacgcggag gagtcctcgc gctggtcgaa ctctcagggc   26400
tgcaaggtca tcgagcaccg ctattcaccg cgctctgaca aggcccgata ctttcgcccg   26460
gtcccgaatc accaggcacc ccgatttaag ggcgaggtaa tgcacaccct gaaggtcact   26520
ccggcagggg ctgaggcgat ctccaagatg gcaaagcgct ggggcctcgt cgtccaggag   26580
gtggcggcat gacctcgact ctcaccggca acatcatcgc cctgctgatc gtggccggcg   26640
tgatcgtcct cgcgatgggg gtgcgccgtg aaggtcgatg acttcgacga tgtgcgcccc   26700
gcgcagaga aggacgtcgc cgagctactc cacgcaagcg tcggttacgt gcgctcctgc   26760
cgcctggcga cgaagccgaa aggccgggtc ttcccgatcg ccggctggaa gaccgacgga   26820
aagcgctatc tgcttcccgc ttggcggttc cgcgagtggg tcgaaagctt gcccgatgcc   26880
tagcccgcgc cgcttcctaa tcctgatcgc cctgggtgcc gccgccgtcg gtttcgcgcc   26940
ctcctcaatt caatttctct tcatggccgc gcttgtgctc acgtcacca tcacatgcct   27000
caaggagtcc aaccatgcct gacacacagc cccgtcgtgc gcgtcgtcgc acgtcgtccg   27060
agatcctcgc ccccgcgccg gcgccccgca gagcggaggc aacggcatga ggccaccagc   27120
cgttgaaacc cctgatgtga aggcgccggc cacgcctgct ggttccggc tcttcaaggc   27180
tgtccgtcct gacggcttcg acttccacag cgggactgtc cggtggctcc ctgctgatgg   27240
cgcaccgatc ccggaggggcg ggtggcttgt cgagcatccg catcctggtg aggttggcag   27300
ctgggatgca gctttttatc tgtcggcgtc gtcggtggag acggactgca caggtttcca   27360
gtggcctgct ctcctcctgt ccgtggagcc cgtaggtgcc atgtggaccc ctcgcccga   27420
caaatttcct cgcaagcggg ccgcgaccgc gtggcgcgtc atagaagagc tccccgcatg   27480
gcggcttttc ggtccccagg ggcggacggt cctggacatc atcgagcaaa ccgctcatct   27540
gaccaaacgc cagatcgcgg ccctgaacag ggctctggac gccgcacggg acaccgttg   27600
ggacgttgct tggaacgccg cgtggcacgc cgctcgggtc gctgctcggg tcgctgctcg   27660
gggcgctgct cggggacgctg ctcggtacgc cgcttgggac gctgctcggg gcgctgttcg   27720
gtacgccact tgggtcgctg ctcggggcgc tgctctcgga tggctcgtca aggacctgat   27780
ctccgtcgag gacttccgca ccctgacggg ccgtgggag caggtcatgg gtccgatcga   27840
ggtggcggca tgaaccgcac ctatttcaag gccgttaggg cggacggcac tgacttctac   27900
accggcaagg tccgctggct gcccgatgat ggcgcaccga tccctgccgg gggttgggtc   27960
gttgagcatc cgacgagcga acgcgtgggg gacgacgccc gcaccatctt ctcggtttcg   28020
acggtggaaa ccgactgcgc cgggatgggc tggccgtgcc gtctcctgcg ggtcgtcccc   28080
gacggcagac aggtgagcat ccctgaaccc gtggggctgc ccagcacgag ggcctcgatc   28140
aggtggcgcg tcatcgaaga gctccccgca tggcaggcgc ttggaccca ggggcgcgag   28200
attgaggcgc tgctcggaca ggttgagagt ctcacggagg accagaccct cgaaatgtct   28260
gccgctcggg gcttcgctcg gggcttcgct cgggacgtcg cgcggttcgc cgctctggtc   28320
gcctctcggg gcggtgctct gaacgctgcc cagggcggtg ctttgggcac tgctctgaac   28380
gctgttcggg acgctgttct cggatggctc gtcaaagatt ttatctctga tgaggaattc   28440
cgcaccctcg tgggcccgtg ggagcaggtc atgggtcgatg atgccgatca   28500
ccaagccgtg cgcggttaag gacatgccgg agggcgagta tcactcggat ccctgcgtcg   28560
agccgtccct gtcgtccacg atggcgaaaa ccattgtttc gggtgaggct ggcccggccc   28620
gtctgcgaga gatcatgtct cacgggcagg aacataaggc cgtcttcgat ttcggcagcg   28680
ccgcgcacga gaaggtgctg gacgcggcg ccggtgtcga ggtgctggat ttccctgcct   28740
gaccacgaa ggcttcgcgt gaggcgcgtc aggccgtggc ggatgccggc ggaactcgtc   28800
tgctggcgaa ggattccgcc caggtggatg cgatggctga ggcgatcctg tccaatcctg   28860
tggcaggtga gctgttcacg cgcggggctg gttctcctga attgtcgatg ttcaccattg   28920
acgaggagac gggacgctgg cagcggggac ggctcgactt cctggcggac cgcaagacca   28980
tcgtcgactt caagacatct ggacagtccg tcgagctgcc cgactggatc aagcacagct   29040
tcggcagttcgg ctaccacatc caagccgcg cctatatgga caggcgatc tcgctggatc   29100
tggtcgatga ggacgccatc ttcctgcatg tcgtgcagga gacgaagccg cccttccttgc   29160
tcgcgatcta tcaggtttca gctgaccagc tggccgaggg caggcgtcag atgcgtcgtg   29220
ccctggacct gtgggaccgc tgcctgaccc tcgacgaatg gccgcgatc cctgcggtga   29280
tccaactatc caagctgccc gattgggtgc acaccactga tgacgaaaag gactcctgac   29340
atgaccgaaa ccacacctag caccgacatt gaaaccaccg ccccccacccc gtcggggtcg   29400
```

```
atcgcggcgg tcggctccga gacggcaggc ctgacgcttc agcagaagct cgactatgcc  29460
tctgccctgg ccgactccga gctcctgccc gccgcctaca agggcaagcc cgcgaatgtg  29520
ttggtggcga tggagtacgg cggcgagctg ggcatcggca cgctcgtcgc ggtgaaccag  29580
atcacgcgtga tcaacggcgg cgtctccatg gaggcgaagc tcatgatgac gctcgcccgc  29640
cgagccgggc acatcgtgcg cctgtccggc gacgacaagc aggccacctg catcatcatc  29700
cgcgccgacg atcccgggca cgaatccggtc gtcacttggg acgaggccaa ggccgaagacc  29760
gccggactgt ggggcaaggg ccactggcag aagaacccgg gcttgatgtt gaagtaccgg  29820
gcggcctcgg agaacatccg gctcacctgc cctgaggtgc tggcggggat tgtctacaca  29880
cccgaagagc tcgatgagcg caccgagcgt gcaggccggt ccacgatgcg tgtccatcga  29940
gtcgtggccg agccggagaa gaccgctgcc tacttcatga aggccctcca cctgaacggc  30000
ggccagttca aggagtttgc ccagcgcgtg ctgggacatc cgttgaagag ctggaatcg   30060
ctggccaagg cagacaagca gcgtgtcctg ggcgctctcg ccagctggga gaacagcggg  30120
gccgatccca ccactggcga ggtcctcgac gccgagccgg tcgagggcgg tgcggcatga  30180
gcaccttgcc tgcggatgct gccgagaggt ggcagcaggt ggatggcctg gcccgcacga  30240
tcctcgccct tcatctcggc ctgactgatc ttgagatggt cgagctggtg ggcgggctca  30300
tcggtgccgg ctggcatcag gatgggccgg tggagtcatg agctggcccg aggagcacca  30360
cgacgtgtgg gcgggtgtcg aggacgccat cccctgagtgg gtgagcgaca aggtggcctg  30420
ctcggtgcgg tcggatgccg attggaatgc cgacgaggac agccgcaagg ccgtggcggc  30480
ggtgaggatc tgcgagcggt gcgccttaac cgagcagtgc ctggattggg cgctggccca  30540
ccacgaggcc ggcatctggg gtgggctcac cgcctccgac cgcgagcgca tcgagcgtgg  30600
cgcgccggtc cggcgggtcc gcgagattcg tcggcgtcgc acgcgggtta ggcaggtgca  30660
ggagtcatga gcgcaccact gaccaaggcc cagaaggtcg cgcgggtcgt cgagcagctg  30720
ttgcgtggcg gcgccgacac cagcacgctc ctggaggcga cggggccga ccggcccgga  30780
cgattgcggg acacccttcg ccgcgctggc cgtgacgacc tcgccgcccg gatcatcacc  30840
accgaccggg cagcccagcg cagacgggaa gtcatcgagg cggtcgagaa gctggtctgg  30900
gtggacaggg ccgacgagat cgccgccgaa ctcggctaca gctcgcgcta cggcctgcaa  30960
cagtccttgc gcggctgggg gcgtcgggac cttgccgatc agatcgtgct gaccgcgag   31020
acgcaccgcg acagggtcat cgctgacgtg gaatggatcg ccggtacacg ggcccgag    31080
gatgtcgccc gggcgaccgg ataccgcaac gcggcggcgc tgcaggccgc cctgaccggg  31140
tggggccgca aggacctcgc cgaccggatc gtcggagcat cacgcaacga cacgggccgc  31200
ttccgcttca catggagggc cgcatgagcg ccaaccgctc ccgccgcgcc acgtacaacc  31260
acacggggat cttcgtccat ctgcgcgaag ccgccgagcc gtccgaacag ccaccctccg  31320
accagacatg cccagccctg catgtcatcg ccggactgac accctgggcc gaccaccagc  31380
cccgccacgc cctcggccgtc gacgggcgat gccggcactg ccacaccacc atcaaaggaa  31440
acccatgatc ttcaaagaca ccacgatcgg gccgctcgaa acacggttca cctggtcgat  31500
gaggtgcgac cgctgcggga cgccgctcga ctggctcgtc gccgcttcgt gcaagaccga  31560
gcgtagtgag gtaatcgccg tcaagttcct gagggagcgt gcccgcgatg gcgggggcct  31620
cagagagtgg ggggagctgg acctttgccc ttcatgcttc tcggtgatgg acgcatgatt  31680
accaccacac aactcggaga agcagcaccg tggggccgtc gcctccaagt ccgctcgatc  31740
ctgtgcaacg gctgcggcat agctctggcg accgacatcg gccttcgtgg agacgccacc  31800
gccctccaag tgcaatccga cctgcacgcc cgagcacgca ccgccggctg gacacacccc  31860
gcctggcgcg tcgacctctg cccgcaatgc accaccacaa ccaaaggagc atgaccatga  31920
aggccaccca gtacgccaaa tcgaccgacc ctgaagtcat cgccaccatc gaagagaacg  31980
agctgtcacg acgggcatgg atcgacgaca ccaaggcgtg gttcggcaag acgatccgga  32040
caggaatccc gggcgccaaa ttgttcctct tttccacccg gaccgctatc aggctgttgg  32100
ggatcgtgac gtcggacgag aagaagcctg ccgggtggaa gttctgctgg cgttcacgct  32160
ctcggttcga gccacgaaag aacaatccct tgccgcgcac atgggacgca cgccggtggc  32220
aagcagcgtc gatcccaggt ctgccccgtgg ttctcacgtc ctccgtgtcg ggagagttac  32280
agagctggtt gaggatgtat ccctgcccct tcatctctag tggtgccgca tggctggacc  32340
tggagcacat gcctgaccct gacagtccgc acttcggacc gcagtggact gaagtccgtg  32400
catccaggc aatggcagcc aaggaagcat tgaaggacgc gtcatgagca ctccaggatc  32460
actgcgcgcc gcgctcgacc agctggacga gatcggcatc gccgaccatg tgcagtcctt  32520
ggaatgggat cgggccggcg cccgcaccac agccctggctc gagacctgcg gcgacttcgc  32580
tgcggcctgc cagtgggggcg atgccgcggg cgaatgggtc acgtgggaca tcaccgacgt  32640
ggccgaggcg gacgtcagcc cccggctgcg cgtcaagcac atgcacctgc gagccaggcc  32700
ctgtgctgat gcgcccgcga aggcggtggc ggcatgagca aggcccttga cccactggat  32760
caccttc                                                           32767

SEQ ID NO: 27         moltype = DNA  length = 29768
FEATURE               Location/Qualifiers
source                1..29768
                      mol_type = genomic DNA
                      organism = PAC7 phage
SEQUENCE: 27
tcgtacggct tagtgaaata cctcccttt gttgttttat cgttttgtcg acttttgtt   60
tggtggtgtg tgtggtgcag cctgagcttc ctgatagtcg tgattggtgt ggggagacgc  120
gtcggtggtg gtgtgtgtgg ggcgaggatc cgcgtgccgg gtttgtgtct gatgaggagt  180
ggttgttttct catggatgct gcggtgattc atgatgtggt gtggcgtgag ggtcgcgcgg  240
attttggtgtg ttcgttgcgt gctcatgtga aggctttat gtgtatgttg gataggtatt  300
cggttgatgt ggcgtctggt ggcgtggtg gggttctgc ggtagcgatg attgaccggt   360
ataggaagcg taggggggct tgagtaggtg tctggtgttg ttgggtctca ggttcctcgt   420
caccgggtgt ctgtggcgta ttcggtgtct gctggcgggg atgctgggga gcttggtagg  480
gcttatgggt tgacgcctga tccgtggcag cagcaggtgt tggatgattg gcttgctgtg  540
ggtggtaatg gcaggcttgc ttcgggtgtg tgtggggtgt ttgttccgcg gcagaatggc  600
aagaatgcta tttttggaga ttgtggagtt gtttaaggcg ctattcaggg tcgccgtatt  660
ttgcatacgc ctcacgagtt gaagtcggct cgtaaggcgt ttatgcggtt gcggtcgttt  720
tttgagaatg agcggcagtt tcctgacttg tatcgtatgg tgaagtcgat tcgtgcgacg  780
aatgccagg aggctattgt gttgcatcat ccggattgtg ccacgtttga gaagaagtgt  840
ggttgtccgg gttgggggttc ggttgagttt gtggctcgta gccggggttc tgctcgcggg  900
```

```
tttacggttg atgatttggt gtgtgatgag gctcaggagt tgtcggatga gcagttggag  960
gctttgcttc ctaccgtgag cgctgccccg tctggtgatc ctcagcagat tttttttggt  1020
acgccgccgg ggccgttggc tgacgggtct gtggtgttgc gtcttcgcgg gcaggctttg  1080
tcgggtggta aacggtttgc gtggacgag ttttcgattc ctgacgagtc tgatccggat  1140
gatgtgtcgc ggcagtggcg gaagttggcg ggtgacacta atccggcgtt ggggcgccgc  1200
ctgaatttcg ggacagtctc ggatgagcat gagtcgatgt ctgctgccgg gtttgctcgg  1260
gagcggcttg gctggtggga tcgtggccag tctgcttcgt ctgtgattcc ggcggataag  1320
tgggttcagt cggctgtggt tgaggcggct ctggttggcg ggaaggtttt tggtgtctcg  1380
ttttctcgct cggggggatcg tgtcgcgttg gctggtgctg gtaaaacgga ttctggtgtg  1440
catgttgagg ttattgatgg cctgtctggg acgattgttg atggtgtggg ccagctgact  1500
gattggttgg cgttgcgttg gggtgacact gaaaaggtta tggttgcagg gtctggtgcg  1560
gtgttgttgc agaaggcttt gacgatcgt ggtgttccgg gtcgtggcgt gattgtggct  1620
gatactgggg tgtatgtgga ggcgtgtcaa gccttcctgg agggtgtcag gtctgggagc  1680
gtgtctcatc ctcgtgccga ttcgaggcgt gacatgttgg atattgctgt gaggtcggct  1740
gtgcagaaga agaagggttc tgcgtggggt tggggttcct cgtttaagga tggttctgag  1800
gttcctttgg aggctgtgtc tttggcgtat cttggtgcga agatgcgaa agcgaagcgg  1860
cgtgaacggt ctggtaggaa gcgggtgtct gtggtatgaa ctcggatgag ttggctctga  1920
ttgaggggcat gtacgatcgt attcaagggt tgtcttcgtg gcattgccgt attgagggct  1980
actatgaggg ctctaatcgg gtgcgtgatt tgggggttgc tattccttcg gagttgcagc  2040
gggtgcagac ggtggtgtca tggcctggga ttgcggtgga tgctttggag gagcgtctgg  2100
attggcttgg ctggactaat ggtgacggct acggtttgga tggtgtgtat gctgcgaatc  2160
ggcttgctac ggcgtcgtgt gatgttcacc ttgatgcact gattttttggg ttgtcgtttg  2220
tggcgatcat tccccaagag gatgggtcgg tgttggttcg tcctcagtcg ccgaagaatt  2280
gtactggccg gttttctgcc gatgggtctt gtttggatgc tggccttgtg gtgcagcaga  2340
cgtgtgatcc tgaggttgtt gaggcggagt tgttgcttcc tgatgtgatt gttcaggtgg  2400
agcggggggg ttcgcgtgag tggggttgaga cgggccgtat cgagaatgtg ttgggtcggt  2460
ttccgttggt gcctgttgtg aatcgtcgcc gtacttctag gattgatggc cgttcggaga  2520
ttacgaggtc tattagggct tacacgatg aggctgttcg cacactgttg gggcagtctg  2580
tgaatcgtga tttttatgcg tatcctcagc gttgggtgac tggcgtgagc gcggatgagt  2640
tttcgcagcc gggttgggtt ctgtcgatgg ctttctgtgtg ggcgtggat aaggatgatg  2700
atggtgacac tccgaatgtg gggtcgtttc ctgtgaattc tcctacaccg tattctgatc  2760
agatgcgttt gttggcgcag ttgactgcgg gtgaggcggc tgttccggaa cgctatttcg  2820
ggtttatcac ttctaaccgc ccttctgggg aggctttggc tgcggaggag tctcggcttg  2880
tgaagcgtgc tgaacgcagg cagacgtcgt ttggtcaggg ctggctgtcg gttggtttcc  2940
tggctgcccg ggcgttggat tcgagtgttg atgaggcggc gtttttttggt gatgttggtt  3000
tgcgttggcg tgatgcgtcg acgccgactc gggcggctac ggctgatgct gtgacgaagc  3060
ttgtgggtgc tggtattttg cctgctgatt ctcggacggt gttggagatg ttgggtttgg  3120
atgatgtgca ggttgaggct gtgatgcgtc atcgtgccga gtcttcggat ccgttggcgg  3180
cactggctgg gctattcc cgtcaaacta acgaggtttg ataggcgatg gcttcgggtg  3240
ctgtgtcgag gcttgctgcg actgagtatc agcgtgaggc tgtcaggttt ctgggggaagt  3300
atgcgggcta ttatgccgag ttgggtcgtt tgtggcgtgc cggcaggatg agtgacacgc  3360
agtatgtgcg ttttgtgtgtg gagttggagc gtgccggcca tgacggttca gcagctatgg  3420
cgggcaaatt cgtttcagat tttcgccggt tgaatgctgt cgtgcctgga ttgatcgtgt  3480
atgacgagtt tgatgctgcg gcggctttgg ctaggtcgtt ttcgactatg aagattatga  3540
ataagtgaccc ggatagggcg aatgatacga ttgatgcgat ggctgcgggt gttaatcggg  3600
ctgttatgaa tgctggtcgt gacacggttg agtggtcggc gggtgcgcag ggtaggtcgt  3660
ggcgtcgggt gactgatggt gatccgtgtg cttttttgtc catgttggct acgaggtcgg  3720
attatacgac taaagagcgg gcgcttacta ctggtcatac gcggcgtcat aagcgtgccg  3780
gtaggcgtcc gtttggttcg aagtatcatg atcattgtgg ttgtacggtg gttgaggttg  3840
ttggtccttg gaaccgaat agggctgatg ccgagtatca gaggacgtat gagaaggctc  3900
gtgagtgggt tgatgatcat gggttgcagc agtcgtctgg caatatttttg aaggctatgc  3960
gtactgttgg tggcatgaga taatttgatg tggtttccgg ttgtgtgccg ccggttatcg  4020
gtgcacaggg ttgtctcccg cacggggggtc aacaatgttg tgttgttttc cgcaaggagt  4080
gtagggttag gctatggccg atcagagtat tgaggaacag aatgttgaca atgatgttga  4140
ggagtccgga aaggataacg gcattgttga tacagtaaaa gacgatggcg ggcaggaggt  4200
agccgacaat cagttgaaga atgaaggcga gggtaaatcg ccggggactg attggaaggc  4260
ggaggcccgt aagtgggagt ctcgtgctaa aagtaatttc gccgagttgg agaagcttcg  4320
tacatcgagt gacgattctg gatctactat tgatgagctt cgccgcaaga atgaggaact  4380
cgaagaccgg attaacgggt ttgttcttga gggtgtgaaa cgcgaggtgg ctgccgagtg  4440
tggcctgtcg ggtgatgcga tcgcttttct tcacgtagc gataaggagt cgcttgccga  4500
gtctgctaag gctttgaagg gtttgatcga ccatagtagt ggtggtggcg cgggtgtgcg  4560
ccgtcttgcg gggagtgccc ccgttgatga tgttaaacga cgtgagggtg tcgcgtttgt  4620
ggatgctctt gtcaataatt ctaggagatg atttatcatg gctgacgatt ttctttctgc  4680
agggaagctt gagcttcctg gttctatgat tggtgcgatt cgtgaccgtg ctatcgattc  4740
tggtgttctt gctaaactgt caccggagca gccgactatt ttcgggcctg ttaagggcgc  4800
cgtttttagt ggtgttccgc gcgctaagat tgttggcgag ggcgatgtta agccttccgc  4860
tagcgttgat gtttctgcgt ttactgcgca gcctatcaag gttgtgactc agcagcgtgt  4920
ctcggacgag tttatgtggg ctgacgccga ttaccgtctg ggtgtgcttc aggatctgat  4980
ttccccgagc ctgggtgctt ctattggtcg cgccgttgat cttattgctt tccatgctga  5040
tgatcctgct acgggtaagc ctgctggcgc tgtcaaggtc tcgctggata agacgaataa  5100
gacggttgat gccaccgatt ccgctacggc tgatcttgtt aaggctgttg gtctgattgc  5160
tggtgctggt ttgcaggttc ctaacggtgt tgctttggat ccggcgttct cgtttgctct  5220
gtcaactgag gtgtatccga agggtcgcc gcttgccggt cagccaatgt atcctgccgc  5280
ccgggttgcc ggcctggata attgcgcgg cctaaatgtt ggttcttctt cgactgtttc  5340
tggtgccccg gagatgtcgc ctgcttctgg tgttaaggct attgttggtg atttctctcg  5400
tgtccattgg gggttccagc gtaacttccc gattgagctg atcgagtatg gtgacccgga  5460
tcagacgggg cgtgacttga agggccataa tgaggttatg gttcgtgccg aggctgtgct  5520
gtatgttgcg attgagtcgc ttgattcgtt tgctgtcgtg aaggagaagg ctgccccgaa  5580
gcctaatccg ccggccggta actgattcat ttgttgcgat aatgtttatg ctgtgtgcag  5640
```

```
ggggtggtgt tgatgggtat cattttgaag cctgaggata ttgagccttt cgccgatatt    5700
cctagagaga agcttgaggc gatgattgcc gatgtggagg ctgtggctgt cagtgtcgcc    5760
ccctgtatcg ctaaaccgga tttcaaatat agggatgccg ctaaggctat tctgcgtagg    5820
gctttgttgc gctggaatga tactggcgtg tcgggtcagg tgcagtatga gtctgcgggc    5880
ccgttgctc agactacacg gtcgaatact cctacgaatt tgttgtggcc ttctgagatt    5940
gccgcgttga agaagttgtg tgagggtgat agtgggggctg gtaaggcgtt cactattaca    6000
ccgaccatga ggagtagtgt gaatcattct gaggtgtgtt ccacggtgtg gggtgagggt    6060
tgctcgtgcg ggtcgaatat taacggctat gctggcccgt tgtgggagat atgatatgac    6120
cggttttcct tacggtgaaa cggttgtgat gcttcagccg actgttcgtg tcgatgatct    6180
tggtgacaag gtggaggatt ggtctaagcc tgtcgagact gtgtaccata acgtggccat    6240
ctatgcttcc gtttcgcagg aggatgaggc cgcggggcgt gactcggatt atgagcattg    6300
gacactgctg ttcaagcagc ctgtcaaggc tgctggttat cggtgtcgtt ggcgtattcg    6360
gggtgttgtg tgggaggctg acgggtctcc tatggtgtgg catcatccga tgtctggctg    6420
ggatgctggt acgcaggtta atgtgaagcg taagaaggc gtgggttg tggcacgtga    6480
tgttgatgtg aagctgaact tgccgggtat tcgtgaggtg ttgaagtctt ctggggtgca    6540
gggcatgttg gctgagcgtg gtgagcgtgt caagcgtgcg gcctcggcga atgtgggcgg    6600
taacgcttac gatagggccc agtatcgtgc cgggttgtcg tctgaggtgc aggttcaccg    6660
tgttgaggct gtggcgcgta ttggcaccac ctataaggga ggtaaaagga ttgaggctaa    6720
gcatggcacg ttggcgaggt cgattggggc tgcgtcgtga tcgtttacgg tgatcctcga    6780
atatgggcta aacgtgtgtt ggcggatgat ggttggctgt ctgatgtacc gtgcacgggt    6840
actgtgccga atacatttga gggtgatctg atttggttgg cgttggatgg tggcccggag    6900
ttgcatgttc gtgagcgtgt ttttttgcgt gtgaatgtgt ttcggatac gccggatcgt    6960
gctatgtctt tggctcgccg ggttgaggct gtgctggctg atggtgtgga tggtgatccg    7020
gtggtgtttt gcaggcgttc gactgggcct gatttgctgg tggatggtgc acgttttgat    7080
gtgtattcgc tttttgagct gatatgtagg cctgcgagt ctgaataagc ttattgtttt    7140
tgttttaatg taattgtttg atatttaatg ggggttgta tgctgctac acgtaaagcg    7200
tctaatgttc gttcagcggt tactggcgac gtttatattg gtgacgcgca cgcgggtgat    7260
tctattaagg gtgtgaggc ggttccttcc gggcttacag cttgggta tctgtctgat    7320
gacggggttta agattaagcc tgagcgtaaa acgatgatt tgaaggcttg gcagaatgcg    7380
gatgttgtc gcactgtggc tacggagtcg tctatcgaga tttctttcca gctgattgag    7440
tcgaagaagg aggttatcga actgttttgg cagtcgaagg ttactgccgg atctgattcg    7500
ggttcgttcg atatttctcc tggtgccaca acaggtgttc acgccctgtt gatggatatt    7560
gttgatggcg atcaggttat tcgctactat ttccctgagg ttgagctcat tgatcgtgac    7620
gagattaagg gcaagaatgg cgaagtgtac gggtatggtg tgacgttgaa ggcgtatcct    7680
gcccagatta ataagactgg taatgcggtg tcgggtcggg ggtggatgac ggctttaaaa    7740
gctgatactc ctccgactcc tccgccggcc ccggttcctc cgaagcctca gccgatccg    7800
aatccgccgt ccggtaactg atacacgatt ttaggggatt gttaatagat gagtgacact    7860
ggtttcacgt tgaagattgg tgatcgtagc tgggtgttgg cggatgcgga ggagacggct    7920
caggcgttc ctgcccgcgt tttccgtcgt gccgccagtc ggggagtct    7980
gcggatttcg cccaggttga ggtgatgttt tctatgttgg aggctgccgc cccagctgac    8040
gcggtggagg cccctgaggg gcttcctatg gttcgtgtgg cggaggtttt ccgtgagtgg    8100
atggaataca agcctgacgg taaggtgcc tcgctggggg aatagtttgg ctccacggcc    8160
tgattgatga ttatcgtggg gccatcgaat acgatttccg caccaagttt ggtgtttctg    8220
tttatagtgt tggtggcccg cagatgtgtt ggggtgaggc tgtccggctg gctggctgtg    8280
tgtgtaccga tacgtctagc cagttggcgg cccaccttaa tggttggcag cgcccgtttg    8340
agtggtgcga gtgggctgtg ttggacatgt tggatcatta caggtctgct aatagtgagg    8400
ggcagccgga gcctgtggcg aggccagactg atgagcgtgg ggcaaggttt acgtctgggc    8460
aggtggacga tattttggcg cgtgttcgtg ccggtggcgg ggtgtctcgc gagattgata    8520
ttatggggtg aatagtgtat gtctggtgag attgcttccg catatgtgtc gttgtatacg    8580
aagatgcctg gccttaaaag tgatgttggt aaacagttgt cgggtgttat gcctgctgag    8640
gggcagccgt cgggtagcct gttgctaaa ggcatgaagt tggcgcttgg tggtgcggcg    8700
atgatgggtg ccatcaatgt tgctaagaag ggcctcaagt ctatctatga tgtgactatt    8760
ggtggcggta ttgctcgcgc tatgctatt gatgaggctc aggctaaact gactggtttg    8820
ggtcacacgt cttctgatac gtcttcgatt atgaattcgg ctattgaggc tgtgactggt    8880
acgtcgtatg cgttggggga tcgggcgtct acggcgcgcg cgttgtcgtgc ttcgggtgtg    8940
aagtctggcg gtcagatgac ggatgtgttg aagactgtcg cggatgtgtc ttatatttcg    9000
ggtaagtcgt ttcaggatac gggcgctatt tttacgtctg tgatggctcg cggtaagttg    9060
cagggcgatg acatgttgca gcttacgatg gctggtgttc ctgtgctgtc tttgcttgcc    9120
aggcagacgg gtaaaacctc ggctgaggtt tcgcagatgg tgtccaaggg gcagattgat    9180
tttgccacgt ttgcggctgc gatgaagctt ggcatgggtg gtgctgcga gtgctctggt    9240
aagacgtttg agggcgctat gaagaatgtt aagggcgctt tgggctattt gggtgctacg    9300
gctatggcgc cgtttcttaa cggcctgcgg cagattttg ttgcgttgaa tccgttatt    9360
aagtctatca cggattctgt gaagccgatg tttgctgccg tcgatgctgg tatccagcgg    9420
atgatgccgt ctattttggc gtggattaac gctatgatcac gagaatgaat    9480
gcacagatgc gcgccaaggt ggagcagttg aagggcattt ttgcgagaat gcatttgcct    9540
gttcctaaag tgaatttggg tgccatgttt gctggcggca ccgcagtgtt tggtattgtt    9600
gctgcgggtg tggggaagct tgttcagggg tttgctccgt tggcggttgc gttgaagaat    9660
ctgttgccgt cgtttggtgc tttgaggggt ccgccgggg gcttggtgg cgtgtttcgc    9720
gccctgggtg gccctgtcgg gattgtgatc ggcttgttt tgccacgaac    9780
gcccagttcc gtgccgctgt tatgcagctg gtggctgtgg ttggtcaggc gttgggccag    9840
attatgcgag ctgtgcagcc gctgtttggt ttggttgctg gcgtggttgc caggttggcg    9900
ccggtgttcg gccagattat cggtatggtt gctggtttgg ctgccggct ggtgcctgtt    9960
attggtatgc ttattgcccg gctggttcct gttatcaccc agattattgg tatggtaacc   10020
caggttgtc ccatgtgtt gcctatgctg atgccggtta tcaggctgt tgttgctgtg   10080
atacggcagg ttattggtgt cattatgcag ttgatacctg ttttgatgcc ggttgtgcag   10140
cagatttggg gtgctgtcat gtctgttttg ccgccgattg tggtttgat acggtcgctg   10200
ataccggtga tcatgtcgat tatgcgtgtg gtggtgcagg tgttggtgc tgtgctacag   10260
gtggtggccc gtattattcc ggttgttatg ccgatttatg tttcggtgat tggattcatt   10320
gccaagagtt atgctgcggt tatcgttttt gaggctaagg ttattggcgc tattcttcgt   10380
```

```
actattacgt ggattgtgaa tcattcagtg tctggcgtga ggtctatggg cacggccatc   10440
cagaatggct ggaatcatat taaatcgttt acgtctgcgt ttattaacgg ttttaagtcg   10500
atcatttctg gcggcgtgaa cgcggttgtg gggttttta cgcggcttgg tttgtcggtt    10560
gcttcccatg tgaggtccgg ttttaacgct gcgaggggtg ctgtttcttc cgccatgaat   10620
gctattcgga gtgttgtgtc ttcggtggcg tctgctgttg gcggttttt cagttcgatg    10680
gcgtctcgtg ttcggaatgg tgctgtgcgc gggtttaatg gtgcccggag tgcggcttct   10740
tctgctatgc atgctatggg gtccgctgtg tctagtggtg tgcatggtgt gctgggtttt   10800
ttccggaatt tgcctgacaa tattcggcgt gcgcttggta atatgggggtc cctgttggtg   10860
tcggctggcc gtgatgtggt gtccggttta ggtaatggta tcaagaatgc tttgagtggc   10920
ctgttggata cggtgcgtaa tatgggttct caggttgcta atgcggcgaa gtcggtgttg   10980
ggtattcatt ccccgtctcg ggtgtttcgt gacgagggttg gccggcaggt tgttgccggt   11040
ttggctgagg gtattactgg taatgctggt ttggcgttgg atgcgatgtc gggtgtggct   11100
gggaggctgc ctgatgcggt tgatgcccgg tttggtgtgc gatcgtctgt gggttcgttt   11160
accccgtatg gcaggtatca gcgcatgaat gataagagtg ttgtggtgaa tgtgaatggg   11220
cctacttatg gggatcctgc cgagtttgcg aagcggattg agcggcagca gcgtgacgct   11280
ttgaacgcgt tggcttacgt gtgattttgg gggtgtggtg catgtttatt cctgacccgt   11340
ctgatcgttc tggttttgact gtgacttggt ctatgttgcc gttgattggt aatgatccgg   11400
agcgtgtgct tcattttgacg gattatacgg ggtcgtctcc gataatgttg ttgaatgatt   11460
cgttgcgcgg tttgggtgtt cctgaggtgg agcatttttc tcaaactcat gttggggtgc   11520
atggctcgga gtgtcgcggg tttaatgtga agcctcgcga ggtgacgcta ccggtgttgg   11580
tgtcgggtgt tggcccggat ccggtgggcg ttttcgtga cggttttttg aaggcgtatg    11640
acgagttgtg gtctgcttt cctcctggcg aggtggggga gtttgtctgtg aagactcctg    11700
ccggtcgtga gcgtgtgttg aagtgccggt ttgattcggt ggatgacacg tttacggtgg   11760
atccggtgaa caggggttat gcgcgttatc tgttgcattt gacggcttat gacccgtttt   11820
ggtatgggga tgagcagaag tttcgttttca gtaacgctaa gttgcaggat tggttggggtg   11880
gcggccctgt cgacggtaag ggtaccgcgt ttccggtggt gttgacgcct ggtgttggtt   11940
cgggttggga taatctgtct aataaggggtg atgtggcctgc gtggcctgtg attcgttgtg   12000
aggggccgtt gtcgtcgtgg tctgtgcaga ttgatggttt gcgtgtgtcc tcggattggc   12060
cggtggagga gtatgattgg atcactattg atacggatcc tcgtaagcag tctgcgttgt   12120
tggacggggt tgaggatgtg atggatcgtt tgaaggaggtg ggagtttgcg cctatcccgc   12180
ctggcggttc tcggagtgtg aatattgaga tggttggttt gggtgccatt gttgtgtcgg   12240
tgcagtacag gttttgagg gcttggtgaa tagttgatgg ctggttttgt tccgcatgta    12300
acattgttta caccggatta tcgccgtgtg gcgcctatca attttttga gtcgttgaag   12360
ttgtcgttga agtggaatgg tttgtccact ttggagttgg tggtgtctgg tgatcattct   12420
aggcttgacg ggttgactag gccgggtgcg cggcttgtgg ttgattatgg tggtggccag   12480
atttttttctg ggcctgtgcg tcgggtgcat ggtgtgggtc cgtggcgttc ttcgcgtgtg   12540
actatcacgt gtgaggatga tattcgtctg ttgtggcgta tgttgatgtg gcctgtgaat   12600
tatcgtcctg gtatggttgg tatggagtgg cgtgcggatc gggattatgc ccattattcg   12660
ggtgcggcga gtcggtggc taagcgggtg ttgggggata atgcttggcg ttttccgtct    12720
ggtttgttta tgaacgatga tgagagtcgt ggccgctata ttaaggattt tcaggtgcgg   12780
tttcacgtgt ttgccgataa gttgttgccg gtgttgtcgt gggctcggat gactgtcacg   12840
gtgaaccagt ttgagaatgc gaagtttgat cagcgtggtt tggtgtttga ttgtgtgcct   12900
gctgtgaccc ggaaacatgt gttgactgcc gagtcgggtct cgattgtgtc gtgggagtat   12960
gtgcgtgacg ccccgaaggc gacatctgtg gtggttggtg gccgtggcga gggtaaggat    13020
cggctgttt gtgaggatgt tgattcggcg gccgaggat attggtttga tcgtgtcgag   13080
gtgtttaagg atgcccgtaa cacgattcc gagaaggtgt ctctcttcga tgaggctgag   13140
cgggtgttgt ccgagtcggg ggctacgtcg gggtttaaga ttgagttggc tgagtcggat   13200
gtgttgcggt ttggtccggg caatctgatg cctgggggatt tgatctatgt ggatgtgggt   13260
tctgggccta ttgcggagat tgtgcggcag attgatgtgg agtgtgtatc gcctggtgat   13320
ggttggacga aggtgactcc ggttgcgggg gattatgagg ataatccgtc ggccctgttg   13380
gctcgccgtg tggctggttt ggctcgcgtg gtgcgggatt tgcaaaagtt ttagtaagtg   13440
attggggttt gttgtgggta ttgtgtgtaa agggtttgat ggtgtgttga ccgagtgatga    13500
ttgggctcaa atgtctggtc tgatgggtaa tatgccgtct gtgaagggc ctgacgattt     13560
tcgtgtcggc acgacgattc agggttctac ggtgttgtgt gagatcctgc cggggcaggc   13620
ttgggctcac gggggtgatgt gcacgtcgaa tagtgttgag acggtgacgg gtcagcttcc   13680
gggcccgggt gagactcgat acgactatgt ggtgttgtct cgggattggc aggagaatac   13740
ggccaagttg gagattgttc ccggtgggcg tgcggagcgt gccagggatg tgttgagggc   13800
tgagcctggc gtgtttcatc agcagctact ggcgactttg gtgttgtcgt ctaacgggtt   13860
gcagcagcag ttggataggc gtgctgtggc ggctaggggt gcgtttgggg agtctgctgc   13920
gtgtgatcct accccgtggg agggtgaccg tgtgatggtt cctttcgggg ctgtgtgggg    13980
taaccatgcc ggcgagtgga tgttgttgtc tcccaggatt gagacgggtt cgaagtcgat   14040
catgtttggt ggttctgctg tgtatgctta cacgatcccg tttgagcgcc agttcagtag   14100
tccgcctgtt gtggtggcgt ctatggctac ggcggctggg ggcacggcac agattgatgt   14160
gaaagcctac aatgtgactg cccaaaattt tagtttggcg tttattacga atgatgggtc   14220
gaagccgaat ggtgtgcctg cggtggcgaa ttggattcgt gtccgcgtgt gactgcacgg   14280
tgttgtggc ggatggtgtg atgttggggg gctgtggtgt cgtggtttac tcctgcactg     14340
gtggcctcta tttgtaccgc gttggccacg gttttgggtt ctgttcaggc tgtcacatcc   14400
cggtctagga agcgtttacg caggctgtcg gctcaggtgg atgcgatgga agagtatacg   14460
tggggtgtgc ggcgcgaggt gcgaaaggttt aacgccggtc ttcctgatga tgtggagccg   14520
atgcatcttc ctgatttgcc cgagtttttg aaagatactg ttgatggtgg aggtgagtag   14580
ggttgaggga gttggaggag gagaagcggc agcgccgcaa ttttgagaag gcttcactgg   14640
tgttgttgtt tttgtcgctt gtgttgttgg cggtggttgc tgcgggtgct ttgcgtttcg   14700
gggctgtatc ctctgagcgg gattcggagc aggcgagggc ccagtcgaat ggtacgcgtg   14760
ccagggggttt ggctgcccgt gtgaagcagg cgtgtcgtgg gagtctgtcg                14820
gtcttcaccg ttctggtttg tgtgtggatg ctgtgcgtgt tgagcagcgt gttcagggtg   14880
tgccgggtcc tgccggtgag cgcggcccgc aagcccttc aggtcctgcc ggccgggatg    14940
gtgttaatgc ttcggctggg ctggttgcc ctgttggtcc gcaaggttct ccgggtttga    15000
atggtgtgaa aggtcctgac ggcttgcctg gcgctaacgg ttcggatggc cgtgatggtg   15060
ttccaggtcg tgcaggtgct gacggtgtga acggcgttga cggcgctgat ggtcgggatg   15120
```

```
gttctgccgg tgagcgcggc ccgcaaggcc cttcaggtcc tgccggcccg caaggtgcac    15180
agggtgaacg gggtgagcgt ggtcccgccg gtgcgaatgg atcggatggc catgatggta    15240
aggatgggcg ctcggtggtg tctgtgtact gttccggggg ccgcctggtt gtgaaatata    15300
gtgacggtgt ggcttccacg atatcgggtt cggcggcctg ccagggtgtg aaaccgtcgc    15360
ctctagtgac tatatcatcc cacaaataga aaggagtggc tgtgatggtg gtgtttggtg    15420
gtggtgtgtt gtgagatata ttcctgcggc gcatcattct gccggctcga atagtccggt    15480
gaataggggtt gtgattcatg cgacgtgccc ggatgtgggg tttccgtccg cctcgcgtaa    15540
aggacgggcg tgtccacgg caaactattt cgcttcccca tcgtctggtg gttcggcgca    15600
ttatgtgtgt gatattgggg agacggtgca atgcttgtcg gagtctacga ttgggtggca    15660
tgccccgccg aatccgcata gtttgggtat agagatttgc gcggatgggg gttcgcacgc    15720
ctcgttccgg gtgccgggggc atgcttacac tcgtgagcag tggctggatc ctcgcgtgtg    15780
gcctgccgtt gagcgtgccg ccatcctgtg tagacgtttg tgtgacaagc atggtgttcc    15840
gaaaaggaaa ctgtctgtgg ccgatttgaa ggccggtaaa cggggtgttt gcgggcatgt    15900
ggatgttacg gatgcgtggc atcagtcgga tcatgacgat ccggggccgt ggtttccgtg    15960
ggacaaattt atggctgtgg ttaatggcca cggcggcggt tcaagtagtg aggagttgag    16020
tatggctgat gtacaagcgt tacataatca gattaaacag ttgtcggcac aggtggccca    16080
gtcggtgaat aagctgcatc acgatgttgg tgtggttcag gttcagaatg gtgatttggg    16140
taaacgtgtt gatgccttgt cgtggggtgaa gaatcctgcta acggggaagc tgtggccgac    16200
taaggatgct ttgtggagtg tctggtatta cgtgttggag tgtcgtagcc gtcttgacag    16260
gctcgagtct gctgtcaacg atttgaaaaa gtgatggtgg tttgttgtgg gtaaacagtt    16320
ttggttaggt ttgctggagc gtgccctgaa aactttttgtt caaacgtttg ttgccgtgtt    16380
gggggttact gcgggtgtca cctatactgc ggagtcgttt cgtggtttgc cgtgggaatc    16440
cgcgctgatc acgcaacggg ttgctgctgt cctgtcggtt gctacctcgt ttggtagccc    16500
gtcgtttgtg gccggcaagc ccggcaagca gccccaggtg gatgcggggtt tggttccacc    16560
ggatgatggg ggcttggttg agccgcatat ggtggatgtg tcggatcctg gcatgatcga    16620
gccgacggat gatgcggatc ttgccggcta tgagcctgcg cgtgcagccg agtcggaggt    16680
tggcacggta gagtctactg ttgcataatt gaatatagat gtgtgcccca gcggtgctgc    16740
cacgattgtg tggtggcggc tgctggggca ctatttttgt atatgcggtg tggctatgat    16800
tcgttgctgt cgatggtgtc ttcgagcatc tgatacaggt ggaggcaggt agagatagtt    16860
tcgctggcct gatcgagaac gttccggccg ataacgtttt tgtggttgtc gcggtggcgg    16920
atgatagccc acatgatctc gtcggctgcc gcctgtaata gtttggcctg gtatcgatt    16980
ccggcgagcc agtctagtgc ttcctggctt gtataggggc tctggtcctc gctgttgccg    17040
cgggtgttgc tgttgttgt ggggtgtcct gcactgtcgc atagccacag gatttcgctg    17100
cactcgtcta gcgtgtcttg gtcgatagcg agatcgtcga ggctgacatt gttgacggta    17160
aggttcacgt tgtcgaggga gatgggtaca ccgtactggt tttcgacact gtcaacaatg    17220
ttttccagct gttgcatgtt ggtgggctgt tgttggacga tacggtgtat cgctgtgttg    17280
agggtggtgt aggtgatgtt gtgtgtgttg tccatggttt ttatgccatt ccttcgttat    17340
cgtctggcat gtagtatgtg ctgtttgcgt actcggttaa cgtcatcagt gtttggtctg    17400
cccactgttt cacggtttgc cggggtgactc cgagtcgttg ggcggctgtg gcgtaggttt    17460
gatcataccc gtatacttcc cggaatgctg ccaacctagc taggtgtttc ctctgtttgg    17520
atggttcaca ggtgagggtg tagtcgtcga tggctagctg tagatcgatc atggagacga    17580
tgttgttgcc gtggtgttgt ggcgcggttg gtggggggtgg cattcctggc tccacggagg    17640
gtttccaggg gccgccgttc cagatccatt gggcagcttg gatgatgtcg gcggtgggtgt    17700
aggttcggtt cactggtcac ccctgaaca ggtcgttggt gttgttggtg tcgaatcgtc    17760
cgacgcagtg gcagtagtcg tacatgagtt taataatgtg ttggtggtct cccaaatagg    17820
tgtttccgct gatgctgtat gtggctgtgc cgtctttcgc gatggtgtat ttggcggtga    17880
tggtttcggg gttttcggtg tcggtgatga ttgctgtggt ggtggcgcct actgtttgga    17940
gtatggtggt ttgggttccg tcgtcgatgg tggttttaac catggtgtgt gttttccctt    18000
ttgttagttg cttgtttggt tgtcggctag atgaataata tcgggtaaag gtttcggctg    18060
gtctaggtgt tgtatggttt tgttggctag ccgtttggct accctgtaac acattttggt    18120
gtagtgttta ttgtctaggt tgtggtattg ttcccgcacc gcaatatata gcagggagtc    18180
ttggtacagg tcgtctgcac tgattgcggg gtagtgtgcg gctgttttgg tgcatgcccg    18240
gttgagtgtg cgaagatgat ggtctgtggc ccacacccac gatgcggtgg tggccaggtc    18300
ggcttttgtt ggtcgtctgc tcatggcact atttcatctc gctatctgat agttgtttgg    18360
tgttttgttg tggatagtgt agcacactag tcctgggtgg ccggtggtgc ctgtgcggtg    18420
acggaaccat gtggattcgc cttccatgga tgggcattgg atgaaggtgc gttgtccttg    18480
ctcggagatt tctaggtggt gccggtgccc ggccatgaga atattagata cggtgccgtt    18540
gtggaattct tggccgcgcc accaatcata gtgtttaccg gtgcgccatt ggtgcccgtg    18600
ggcgtgcagt atccgtgtgc ctgccacatc aacggtggtg gtcatttcgt ctcggctggg    18660
gaagtggaag tgtaggttgg ggtattggtt attgagctgg taggcttctg cgatggcccg    18720
gcagcagtcc acgtcgaatg agtcatcgta ggtggtgact cctttaccga agcgcacggc    18780
ttcaccatgt tgccgggga tggatgtgat ggtcacattt ttgcagtggt cgaattggtg    18840
gatgagttgc atcatggcca tgcgggtgag cctgatttgt tcggtgaggg gtgtttgtgt    18900
tcgccaggcg ttgttgcctc cttgtgacac gtatccttcg atcatgtcgc cgaggaaggc    18960
gatgtggact cgttcgggtt tgcctgcttg ttgccagcag tgtttgcga ctatgaggga    19020
gtgtaggtag ttgtcggcga agtgtgctgt ttctccgccg gggatgcctt tgccgatttg    19080
gaagtctcct gccccgatga cgaaggctgc ggtgctgtag tcggtgtggg tgtcttgttc    19140
gggttttggg ggtgtccatt cggctagttt atcgacgagt tcgtctaccg ggtagggggtt    19200
tgttgcgggt tggtgtcga tgatttttttg tatgatcgg cctgtttctc cgttggggag    19260
tgtccattcg gagatgcgtg tgcggcgcac ggtgccgttg gctagattgt cgtcgatggt    19320
gtcgatggcc ttgtcgtggt tggctagctg tgtgagtagc cggtcaatat tgtctatcac    19380
tgggtatcct cctcttgcgg ggtggtgctg gcttgtttgc ggcgtagtc tttaataacg    19440
gtggcggaga tgggggtatcc tgcctgggtg agctgttttg ctagccatga ggcggggata    19500
gacctgtcgg cgagcacgtc ggcggcttttg ttgccgtacg gttgaataag ggtttcagtt    19560
ttggttgcca tgatgtccta tcggttgtgt ggtgggctgc catcctgtgc ggcagtcgcc    19620
gtcgtgtcct ggtttgcgtg tgcaccacga tacggttccg tctgtgtggt tgagtgtttt    19680
accgcacatg acgtttcgga gatgctccgg cagctggtca tcctggttgc tggtttgtgt    19740
gtcgaagagt gttttctggt tggtgaaatg ttctgacacg gtgccgttat gcacgggtag    19800
tatccatgtt ttccattgtt gttgtagcct ggtgttccag tggaattgtt tggcggcgtt    19860
```

```
ttcggcctgt tttaaggttt tgtggtagcc gactagtatg cgttgatgct gctggtctgg   19920
agggtttggg cctcgccagt attgtgccgc cacggcgtag cggttgctgt ctgtgaaggc   19980
gtcccagcag tattcgataa tgtgttgcaa catactgtct ggcaggctgt cagggttgat   20040
gttgatgttt tgggtgataa tgtcacggat ggcttgccgg tttttggtgg tgggtttgaa   20100
cgagatcgtc acgatagtac cggctggtcg tcttgcatga actggttgaa ggtgttgttc   20160
ccggcgtgtt gggcttgtgt tatttgttgg tcggtccagt ctgggtgttg ctgtttcaga   20220
tagtgccagt ggcacgcatt gtaggtttcg tcttgtagcc gtgtgagatg gttttcggtg   20280
atgatttgtt tccacatggc ccatgacacg tcgagccggt cgaggatttc gagggctggg   20340
atgttgaatt ggttcaggaa gaggatttcg tgggtgtagt agttttttctc gtaggcgtcc   20400
catccgcttc ggtgcctgtt gggctggttt ttgggggtagg cttcccggca tactttgtgt   20460
aaacgcttgg ccatgtcgtc gggtagttta atgtcggggt tggcgcggat catggatcgc   20520
atcccatcat aggtggtgcc ccaggtgtgc atgatgtagg tggggtcttc tccgtcggcc   20580
cattttttctg cacagatggc gaggcggata cgcctcctgg cagcttggct ggtgttgcgc   20640
cggttgggga ttgggcacgt gtcgagggga tccatgatgt tttagtgtac cttttctggtt   20700
tcgtgttgtt gacaggtttt actgtagcac agtgtctagt gcgtgtgtca acctgttttt   20760
tccggcttga aggtaggtgt ctgtgacatc ccctaggggtg aggggcacgt gcacagcttg   20820
ggggagtgcc gcctggaggg tttgggccat ctggtcgcct gcggggtctg ggtctgacca   20880
gatgtagatg tggtcgtagc cttcaaaaaaa tttggtccaa aaaatttgcc acgaggttgc   20940
gccgggtagg gcgacggccg accatccgca ttgttcgagg atcatggagt cgaattcgcc   21000
ttcgcaaatg tgcatttcgg ctgccgggtt ggccatggcg gccatgttgt agatggagcc   21060
tgtgtctcct gccggggtta ggtatttggg gtggttgtgg gttttgcagt cgtgcgggag   21120
tgagcagcgg aaacgcattt ttcttatttc ggctgggccg ccccaaacgg ggtacatgta   21180
tgggatggtg atgcactggt tgtagttttc gtggcctggg atgggtcat tgtcgatgta   21240
tccaaggtgg tggtagcggg ctgtttcttc gctgatgcct cttgctgaga gcaggtcgag   21300
tatgttttcg aggtgggttt cgtagcgggc tgaggctttc tggattcggc ggcgttccgc   21360
aatgttgtat gggcgtatgc tgtcgtacat ttgggttttc ttcttctaat cgttgttgta   21420
gcttggcgag tccgcctccg acaccgcatg tgtggcagta ccagacgccc ttgtcgaggt   21480
tgatgctcat ggagggctgg tggtcgtcgt ggaacgggca gagtatgtgt tgctcgttcc   21540
tggacggatt gtaccgtatc tgataatggt cgaggaggcg gcaggtgtca gaggtgtggg   21600
aggagctcgt tgagggttga taccacatag gcttcactcc atggcttgtt gcgctgtttc   21660
atcactacga gtccgatggt ggaattgttt tgtttgtttc ggtgtgtttc gtagttgcgt   21720
gcctccggc tggcttgttt cacgaattgg gctaggtgtg gttgcccggc tttcgcctcg   21780
ataatgtagg ttttatggcc ggttgtgagg atgaggtcgc cttcgtcttc gcggccgttg   21840
aggtggaggc gttcgatatt gtgtccggtg tcgcgtagct ggtgggaggag tcttcgtttcc   21900
cattcgatcc cggcccgccg gttcgctgcc tgctgtgtgg ccatagtttt ttagagtcct   21960
ttgtgtgttg tggtcatgtt ccagggctgt ttttcggcga gtggcccgaa gaatgtgtat   22020
tcggggtatg ctctgagtcg ttcgtatcgg gtgccgtcgg ggctggattt gcctgtgcgc   22080
tgtttgagta cggcgatgcg tgcctctgcc ggtatcgata gcccgttgcc gttatcctcg   22140
ccaccataca atgagactcc gaggatgagt tgtggttttt gcgagaggcc gtttttgatt   22200
tctcgccgtg ctggcgggtg ttcgatgtcg gttccggttt tgtcggttgc tgggtgtgtg   22260
acaataatgg tggagccagt atccctgccc aatgctgtga tccattgcat ggcttcttgc   22320
tgtgcctggt agtcggattc gcagtcttga atgtccatca ggttgtcgat aacaatgagt   22380
ggtgggaagg tgttccacat ttccatgtag gcttgtaact ccatgatgct gtctgccat   22440
gtgatgggtg actggaatga gaatgtgatg tgttggccgt ggtggatgct gtctcgatag   22500
tattctggcc cgtagtcgtc gatgtttttgt tgtatttgtt gggtggtgtg ttgtgtgttg   22560
agggagatga ttcgtgtgga ggcctccag ggtgtcatgt cccctgatat gtagagggcg   22620
ggctggttga gcatcgctgt gatgaacatg gctagccctg atttttggct gccggaccgc   22680
cccgcgatca tcaccaagtc gcccttatgg atgtgcaaat cttggttatc atatagtggt   22740
gcgagttgtg gtatgcgggg tagttcggct gcggtttggg aggctctctc gaaggatcgt   22800
tgtagagaga gcatcgggac cttaatctat ctgtctgttg gttgtgtggc tggtcagatg   22860
gagtcgatat cgatatcagc atcagcagag gctgaagtgt catctagctg accattatcg   22920
cgcttgtcta cgtattcggc aaccttatcg tagatggcgt cgtccaatgt tttgagcacg   22980
accgcgttga aaccgttttt ggtgcgcacg tggctagtt tgaaggcctg ctcctcgcca   23040
aggtatgcct ctagttcgcg gatcatggag tgtgggcggt cgttattgcc gcgggctttc   23100
tcaataatag cgttgggat ggtttctggg gtgccgtctc tagggtgtgg                23160
aagatggtga catcagcgta gatgcggtct gcgaccgtc caccgtagcc ttcagtgttg   23220
tgctggacgt cgtgcacttt gaaggcgatg gccgtgggcg tcctggtttcg ggaggggttg   23280
aagaaggtgc tgttgctgtt gttgcggtag tttgcgagtc ccataactat tgtttccttt   23340
tactgtttgtg tctgtttttg ttggcttata ttggtttatc gggtgaggct gtttcgctta   23400
gtgcggaaag cgtcggaaac atcactgtta ctggtgatga tcttcttgta ctgttttaga   23460
aggtctgcta gctgtgcctt gcttgttgca ttgttgattt tgttgatgac gatggtgttt   23520
tctttggatg cgattttgtt gacgtagtct ttggctgcct ggttgtatcg gtcttggagg   23580
atgattgatg cgctcgctac gagtgttgct agatcccagt ctttgacac gtcatcgttt   23640
ttgagtccgc ctagcaggtc gatgatgcc tgttttgtc gctctgctgt gtctcctcgg   23700
atgaccgccc atggtgcagc atagtctcca ccatatttga gtgtgatcgt gagtcgatca   23760
ttgtcgatct tgtctttatc tgtcatttgg tgtccttttc tttattgtct gtttctggtg   23820
gctgtacggg ggattctacc gggtatctgt acgagttttt gccgttgacg gcccagcagg   23880
cgtctcgtac ggggcatcct ttacagagtg ttgtgacgtg ggggacgaag atgccttcgc   23940
tgattcctttt cattgcttga ctgtacatgg atgatacatg ttgttgtcaa                24000
ggtcgtagag ttcggtggat gtgccttgtg tcggggactt gtcgtcgttg cggctggtga   24060
ctggcgtcca aaacatgcct ttcgtgacat ggatgtcgtg ttggttgagc atgtaccggt   24120
atgtgtgcag ctgcatactg tcggcgggta ggcgtccggt tttgaggtcg aggatgaagg   24180
tttcgccggt gtcggtgtcg gtgaaaaacac ggtcgatgta gccgactatt tttgtgtcat   24240
cgtcgaggat ggtttctacc gggtattcga tgcctgtgtt accgtccagg attgcggtga   24300
tgtattctgg gtggttgcgc ctccatgttt tccagcggtc cacaaaggtg gggccgtaaa   24360
ccatccacca gtcgtagtct ttcttgtgtg gtccgcctga ctcgcacatg ttttttgcata   24420
ttctgccgga gggtttgatt tctgtgcctt cggattcggc gagggctacc tgggtgtcga   24480
aaatgttttt gaaggatgag agtttgtctg gcagtcagg gtattcggcg ggattgtaca   24540
ggtgtaggtc gtattgttcg gtgatgtggt gtatggcgct tccggcgatg gtggcgtacc   24600
```

```
aggtgtggtg ttgggcgtga tagccgtggg ataggcgcca ttttctccg cattcggccc   24660
actgggtgag tgaactgtag gagatgtgtc ctggggtggct gatggttttc gggtattgtg  24720
ctagaggcat tacttgtcgc ttgtgttcca tgtgttgcgg gtgtcttggc cggcgtggtg   24780
ttgctggtag gcgaggagtg cgaggcagtg ccaggctgcg tgtgctagat gggtagccc    24840
ggattcgtgg tcgaggttgt tgccttgctg ccatgatagt agatgcctgt agagggcgtc   24900
gacactgtgg ctccacgggt atcctccggt ccagttgttg tcgccatatt tggtggcacc   24960
gtatccggct acttcgccta gggcgtgaag ggatgctggg tcgatgaggg agagcctgca   25020
gagtttcaat tcttttcggg caccgctgtt ggggtcggtg tacatgcggg tgggctcatc   25080
catggggtgt gtgctcctta agggtgggtt actggttgtt gttgtgggct agggcggcgg   25140
cgagaataat gatggcgagg gtttcggcta tcagtatggg tgttgtgatc atttggtgtc   25200
tcggggattg ttggtgagtg ttgaggcacc caggagggtg gcgagggcgc atgcggcaat   25260
aatggcgagg gctgccttgt gtggggtgcc ggttgcgtac atccatgtga tgatggcacc   25320
ttggatccag gctaggctgg tgaagaaggt ttcgtagctg tgcagctcaa tgttgttgtt   25380
gggtgtgttc atgcttgctc ctgaagaatg gtgttgatgg ttttataaat gttgtacagg   25440
tcggtttcga tagataacag ttggttgatt tggtggtcga gatcaatgtc tgggttgagt   25500
gtgttgatgc gggaggcaat atcggtggct gtgcgtagtg tgccgccggt gtggtgaata   25560
atgtgtgccg tgtcggcgag tccggtggtg acggcgtagt gggataggag aggcatagcg   25620
gggatgctcc ttggcggggtt actgttgcgg gttgatgttg aggtcggtga cgtgcggtga   25680
gttttctgtt ccggtgacga ggcagtggac ggtgacgggt agtttggatg ctcccggctg   25740
gcggacggtg gcgccgtaga cgatgctgaa tgtgtctttta ccgatggttt tgtggagttg   25800
gaggtcgatg tcggggttgc cgttccagtt gacaccttgc gctgcggcct gttgttcggc   25860
tttgtgggtg caggtgtgtg tgccgtgat catggtagt ccggtggcgg tttcttcacc    25920
ccttgcttgg gcttgcttgt gggctttggc ctgctcggct tgtagggatc gggtggcggc   25980
tgcctgccgt gccgctttct cggctttgcg ctgttgggta gtcttggggg tccatgtggt   26040
gttggctgtg gttgcctgtg gggctggctg tgaggtgagt ggcgggttgt cgtctggtgc   26100
tggcatgaat gaggcggcgg caatgatggc ggctgtgatg cctgcgatgg tgtagccgtt   26160
tttcttgttc atgttttgtg tccccttttcc ggggtgttgt tcgttgctga catggttaat   26220
actttcagcg gctgggccca ctgtcaaggc tgcgctcagt ttgtgtgagc gtttggtgtg   26280
tggctagggg ttttgtcatg taagcgtgac atgtcactac cttgcgtcca gtatccatgg   26340
cggttgcgag ccatcccttt ggcgagcatc tcgtccacag tgaggcacct ccgcggattg   26400
gggccttcct tgaccccgtg atcgcctatg cggtgcatgt ccccggcata agtgccatta   26460
aatgtttcgt ggcagactgt gcagtgttct ggtcggtatc cgatgattgt gctatcgcac   26520
ttgtggcatg tccattgcat gattggtcct tctttcgtgt tttaagcttg tgctctgagg   26580
attagagcga ctttcagccc ttgggggtag gattatatag gtcaggtatt tctaggcgat   26640
tctaggctca ttgtgtgtgg ttgggggtttt atcgggcgca tagggttagc aggtggccca   26700
cattggtgcg gctcacattc cagtagagtt gcgtggcttc cttactggtg agcggcttcc   26760
actcgtcatg gctgaacacg gtgccatcgg atgcgatgaa cgtgttgggg cgtagccttgt  26820
gaagctcggc ttccacatgc tgccggtagg cttcggcgag gctctcaaaa tccatgtggt   26880
cgcaggagag gttttcgagg cgtgtcaggt cgaaaggctc cgggcagtcg tagctggctg   26940
gagtgtagag ctgggtgaag tggtcggcga tcttctgcat ggcgggttcc tttctggtgt   27000
gtggatggtt tttatcgtgt ggatgcgaca aggatgcgt ctacgtcgat catgtcgatc    27060
atgtcgttga gttcctcggc ctcattctcg gagaggtggc gccagtcggg tggcccgtat   27120
acggcgccgt cgagggtgac agtccacagg ggccggtgta gtcgtatgcc ttcttcgact   27180
ttggcgtggt acatgcggcg caccatatcc agatcgatgt cgtctgaatg gtttccggtg   27240
aggctgtgga ggctgagcgg gtcgatttct gtctgcctgt agaggctggt gaatgatggt   27300
gtgatgagtg tgccatccat gagtgtgctc ctttctaggg gttgttgtgg tttctagagt   27360
gtgtgggctg tgaccccaca gtcaaggcta cgctcatttg gattgagcgt ttcatatggg   27420
tgtggcatgg aatctacacc ctcatactgt gtgagatgta tcacatcccc ctggcttggt   27480
gtgcacccct caagactact ctgccgacct ggcgtggagg gtgtagccca gaaatgccgt   27540
ttaaagcttc aggggtacgc ctaggagcgc cttacgggt gggggctagg tatttatacc    27600
cccagcatat tctgatcgat tctagacgac tcccagaagcc cgatacacga tcaaccatct   27660
cgacatagac catcagcccc tatcctggtt agctaagcct caactatgtg gacagtgtgg   27720
gacactgtgg gggaagaagg acacggtaca agaaagaggg gggagcatca gcttaaagc    27780
cttaagatct tagcgcttag caccgatggt cttagcagtt agcaccgagc ccttgagggg   27840
gctcggcatc agcctcatcg ggctcagtc atcaggcaca gccctgaaaa gggtacacgc    27900
catcagggaa ggcttgagag tacgaggagc cctagcgacg agtactcgaa agcctgaggg   27960
aacaccctca gtactgatga gcctagcgta ttcggaaagg acgcaagagt aaagtgtgac   28020
agctatccgg gagtgaaacc cgttccgact agggggtttca gccttaacca ccctcaaagg   28080
ttacaagact ctaagaaaat ttaagaaact tcttaggaag aaagttgtgt tcatatcccc   28140
ctaaaaacac ccaaaatagt cctcaaaccc gcctatagag ccaaacagtc aagtttgact   28200
cgtctagacg gcgtatgata ggctggacag gtagccagct ggacgcaagg ccagaaagtg   28260
ctgacgcact tcccgacctc gcttaccatc agtctaccaa acactttaaa gcttcaaggc   28320
ttagcgctaa gcccttaaga tcttaacgct tagcaccgag ccccccctcaa gggctcgaca   28380
tcagtcttaa agtcttaaac actttaagta actttaaggg agccccttaag agcccctaag   28440
gatctaagtt actataaaag ctttaaacac ttaaagtaac tataaagctt taagagctta   28500
acatttaagg atataaataa acattaaagc tttaagtct taaagtaaat atataccttt    28560
aacacttaag ttaagtataa aaccttaaag gcttagcact taaggatata aacttaacat   28620
cagtgtttaa gacttaaaga gttaagtaa ctattaagac ttaaaggctt ataagcttta     28680
atactttaag tagctataag acttttaaaaa cctgaagtac ttaaagttaa ccatcagtct   28740
taaactttaa tattataagt attaaagctt ataagttata aaagttttta gaagagttaa   28800
agggttaact tctttacttc tcttctctct ttggttcttt ctctcttctc ttcttttctt   28860
catcagggga gaagaggaac ctttaaccgt caacgctgat ggacttttca ccgtgtgact   28920
cgtgtgcttc tggtcgcaag ctcccatcgc acactcccca cactctttca cccgtgcccc   28980
tttacggctt agcgtgttcg tcggaaggcg tacggcgtgt cacgcttaaa ccttaacac    29040
caggtaagac ttaaagtgca tattataagt agaagactcc aaaacctata aggtgttccc   29100
gcttagcccg tgttccttta acgctaggcg ctcagcgcta agatgtgaaa cgtgaacacc   29160
catccacccc catttttctt ccgtgtcctt tccttttga caccgctggg gggcgatgtg   29220
atatttctca catgccaggg ggtagtggag aaaacaacca ccccgaacg tttaagacac    29280
cccctcaaac gaacaaaaca gggcctagaa tcgatcagca gggcaccggt agggtattcc   29340
```

```
tacccccaga cgattcaagg ccattacagg agcaatgaga ggctcacagg ggccatggga   29400
gattggggggg cgtgatggca cacaccaacc gcacagccag ccaagcccac cggcgctggc  29460
gggcaaggct catcacccaa gcccgacaac aaggccaaac cgaatgccca ctctgcggag   29520
tcaccatcac ctggaacacc cacgacctgc caaccagccc cgaagccgac cacatccac   29580
ccgtcagccg gggaggactc aacaccctcg acaacgggca aatcatctcg agaacatgca   29640
acagaagcaa aggcaacaga acacaaccaa acatcaaatt ccaacaacaa accacaaaaa   29700
cattgattcc atggtgaaaa acccgccaac ccccaccggg cacacccccct gcacacccgt   29760
gcaagacc                                                             29768

SEQ ID NO: 28           moltype = DNA  length = 11979
FEATURE                 Location/Qualifiers
source                  1..11979
                        mol_type = other DNA
                        note = pANS514 plasmid
                        organism = synthetic construct
SEQUENCE: 28
catggttgcg ccatgcagca caggccaagc gtgaggccca agcacgagga ctcgcccgct   60
gcccactgtg cggcgtctgg atggactacg aggtcggcaa gcgacccaac tcggccgaag   120
cagaccacat cagaccgcat tcgcttggtg gttcagacga catcgacaac attcgcgtca   180
tttgtcgtcg ttgcaatcaa tcgcgcggaa acggcctgaa gcgaccaggg cgccaacgtc   240
agcgtccaat caagcgcatc gagctggccc aaccggcccg cagtggggca tttcctgccc   300
cgccggcatg aatggaaggg cagtgcggat ggtgcggtcg tgcgcccgga                360
cgggtcgccc gcgacgcttc tgctcggccc gctgtcgggt cgccgcgtcc cggtgtgcga   420
tcccgctggc catgaggtcc cgcactgcgt gggtccgctg cgacggcaag cgccccatca   480
ccctggctgg cgctccggcc tcatccacgg acccgggcac atggtctggc tggtcgcagg   540
tgcgacgcgc cacggccggc gatgcttcg ggaccatgcc cggtgacgg ctggggtgct   600
gggatctcga ccacttcgac gatcagggcg cccgggcctt catcgaccgg atcgataagc   660
cgatcatctt cgccgagcgg tcggtgtcgg ggcatggctt ccacatcttc gtccggactg   720
acgaggcccc cggacgccgc accggaaaca tcgagttcta ctcacgccat cggttcatca   780
gggtcacagg agaccagttc gtctgaaggt cgtgccgggt ttgtgtctga tgaggagtgg   840
ttgtttctca tggatgctgc ggtgattcat gatgtggtgt ggcgtgaggg tcgcgcggat   900
ttggtggctt cgttgcgtgc tcatgtgaag gcttttatgg gtatgttgga taggtattcg   960
gttgatgtgc cgtctggtgg ccgtggtggg ggttctgcgg tagcgatgat tgaccggtat   1020
aggaagcgta gggggggcttg agtaggtgtc tggtgttgtt gggtgggggac ttcctcgtca   1080
ccgggtggct gtgcgtatt cggtgtctgc tggcggggat gctggggcga ttggtagggc   1140
ttatgggttg acgcctgatc cgtggcagca gcaggtgttg gatgattggc ttgctgtggg   1200
tggtaatggc aggcttgctt cgggtgtgtg tggggtgttt gttccgcggc agaatggcaa   1260
gaatgctatt ttggagattg tggagttgtt taaggcgact attcagggtc gccgtatttt   1320
gcatacggct cacgagttga agtcggctcg taaggcgttt atgcggttgc ggtcgttttt   1380
tgagaatgag cggcagttct ctgacttgta tcgtatggtg aagtcgattc gtgcgacgaa   1440
tggccaggag gctattgtgt tgcatcatcc ggattgtgcc acgtttgaga agaagtgtgg   1500
ttgtccgggt tggggttcgg ttgagtttgt ggctcgtagc cggggttctg ctcgcgggtt   1560
tacggttgat gatttggtgt gtgatgaggc tcaggagttg tcggatgagc agttggaggc   1620
tttgcttcct accgtgagcg ctgccccgtc tggtgatcct cagcagattt tttttgggtac   1680
gccgccgggg ccgttggctg acgggtctgt ggtgttgcgt cttcgcgggc aggctttgtc   1740
gggtggtaaa cggtttgcgt ggacggagtt ttcgattcct gacgagtctg atccggatga   1800
tgtgtcgcgg cagtggcgga agttgccggg tgacactgat ccggcgttgg ggccgcgcct   1860
gaatttcggg acagtctcgg atgagcatga gtcgatgtct gctgccgggt ttgctcggga   1920
gcggcttggc tggtgggatc gtggccagtc tgcttcgtct gtgattccgg cggataagtg   1980
ggttcagtcg gctgtggttg aggcggctct ggttggcggg aaggtttttg gtgtctcgtt   2040
ttctcgtccg gggatcgtg tcgcgttggc tggtgctgat aaaacggatt ctggtgtgca   2100
tgttgaggtt attgatgcc tgtctggac gattgttgat ggtgtgggcc agctggctga   2160
ttggttggcg ttgcgttggg gtgacactga aaaggttatg gttgcagggt ctggtgcggt   2220
gttgttgcag aaggctttga cggatcgtgg tgttccgggt cgtggcgtga ttgtggctga   2280
tactgggggtg tatgtggagg cgtgtcaagc cttcctggga ggtgtcaggt ctgggagcgt   2340
gtctcatcct cgtgccgatt cgaggcgtga catgttggat attgctgtga ggtcggctgt   2400
gcagaagaag aaggggttctg cgtgggggttg gggttcctcg tttaaggatg gttctgaggt   2460
tcctttggag gctgtgtctt tggcgtatct tggtgcgaag atggcgaaag cgaagcggcg   2520
tgaacggtct ggtaggaagc gggtgtctgt ggtatgaact cggatgagtt ggctctgatt   2580
gagggcatgt acgatcgtat tcaaggggtt g tcttcgtgg attgccgtat tgagggctac   2640
tatgagggct ctaatcgggt gcgtgatttg gggttgcta ttccttcgga gttgcagcgg   2700
gtgcagacgt tggtgtcatg gcctgggatt gcggtggatg cttttggagga gcgtctggat   2760
tggcttggct ggactaatgg tgacggctac ggtttgatg gtgtgtatgc tgcgaatcgg   2820
cttgctacgg cgtcgtgtga tgttcaccctt gatgcactga tttttgggtt gtcgtttgtg   2880
gcgatcattc cccaagagga tgggtcggtg ttggttcgtc ctcagtgccc gaagaattgt   2940
actgccggt tttctgccga tgggtcttgt ttggatgctg gccttgtggt gcagcagacg   3000
tgtgatcctg aggttgttga ggcggagttg ttgcttcctg atgtgattgt tcaggtggag   3060
cggcggggtt cgcgtgagtg ggttgagacg ggccgtatcg agaatgtgtt gggtgcggtt   3120
ccgttggtgc ctcttgtgaa tcgtcgccgt acttctagga ttgatgccga ttcggagatt   3180
acgaggtcta ttagggctta cacgatgag gctgttcgca cactgttggg gcagtctgtg   3240
aatcgtgatt tttatgcgta tcctcagcgt tgggtgactg gcgtgagcgc ggatgagttt   3300
tcgcagccgg gttgggttct gtcgatggct tctgtgtggg ctgtggataa ggatgatgat   3360
ggtgacactc cgaatgtggg gtcgtttcct gtgaattctc ctacaccgta ttctgatcag   3420
atgcgtttgt tggcgcagtt gactgcgggt gaggcggtcg cggcagg ctatttcggg   3480
tttatcactt ctaacccgcc ttctggggag gctttggctc cggaggagtc tcggcttgtg   3540
aagcgtgctg aacgcaggca gacgtcgttt ggtcagggct ggctgtcggt tggtttcctg   3600
gctgcccggg cgttggattc gagtgttgat gaggccgcgt ttttttggtga tgttggtttg   3660
cgttggcgtg atgcgtcgac gccgactcgg cggctacgg ctgatgctgt gacgaagctt   3720
gtgggtgctg gtattttgcc tgctgattct cggacggtgt tggagatgtt gggttttggat  3780
```

```
gatgtgcagg ttgaggctgt gatgcgtcat cgtgccgagt cttcggatcc gttggcggca 3840
ctggctgggg ctatttcccg tcaaactaac gaggtttgat aggcgatggc ttcgggtgct 3900
gtgtcgaggc ttgctgcgac tgagtatcag cgtgaggctg tcaggtttgc tgggaagtat 3960
gcgggctatt atgccgagtt gggtcgtttg tggcgtgccg gcaggatgag tgacacgcag 4020
tatgtcgctt tgtgtgtgga gttggagcgt gccggccatg acggttcagc agctatggcg 4080
ggcaaattcg tttcagattt tcgccggttg aatggtgtcg atcctggttt gatcgtgtat 4140
gacgagtttg atgctgcggc ggctttggct aggtcgtttt cgactatgaa gattatgaat 4200
agtgacccgg ataggcgaaa tgatacgatt gatgcgatgg ctgcgggtgt taatcgggct 4260
gttatgaatg ctggtcgtga cacggttgag tggtcggcgg gtgcgcaggg taggtcgtgg 4320
cgtcgggtga ctgatggtga tccgtgtgct ttttgtgcca tgttggctac gaggtcggat 4380
tatacgacta aagagcgggc gcttactact ggtcatacgc ggcgtcataa gcgtgccggt 4440
aggcgtccgt ttggttcgaa gtatcatgat cattgtggtt gtacggtggt tgaggttgtt 4500
ggtccttggg aaccgaatag ggctgatgcc gagtatcaga ggacgtatga gaaggctcgt 4560
gagtgggttg atgatcatgg gttgcagcag tcgtctgcca atattttgaa ggctatgcgt 4620
actgttggtg gcatgagata atttgatgtg gtttccggtt gtgtgccgcc ggttatcggt 4680
gcacagggtt gtctcccgca cggggtcaa caatgttgtg ttgttttccg caaggagtgt 4740
agggttaggc tatggccgat cagagtattg aggaacagaa tgttgacaat gatgttgtgg 4800
agtccggaaa ggataacggc attgttgata cagtaaaaga cgatggcggg caggaggtag 4860
ccgacaatca gttgaagaat gaaggcgagg gtaaatcgcc ggggactgat tggaaggcgg 4920
aggcccgtaa gtgggagtct cgtgctaaaa gtaatttcgc cgagttggag aagcttcgta 4980
catcgagtga cgattctgga tctactattg atgagcttcg ccgcaagaat gaggaactcg 5040
aagaccggat taacgggttt gttcttgagg gtgtgaagcg cggagtcgcc gccgagtgtg 5100
gcctgtcggg tgatgcgatc gcttttcttc acgtagcga taaggagtcg cttgccgagt 5160
ctgctaaggc tttgaagggt ttgatcgacc atagtagtgg tggtggcgcg ggtgtgcgcc 5220
gtcttgcggg gagtgccccc gttgatgatg ttaaacgacg tgagggtgtc gcgtttgtgg 5280
atgctcttgt caataattct aggagatgat ttatcatggc tgacgattt ctttctgcag 5340
ggaagcttga gcttcctggt tctatgattg gtgcggttcg tgaccgtgct atcgattctg 5400
gtgttcttgc taaactgtca ccggagcagc cgactatttt cgggcctgtt aagggcgccg 5460
ttttttagtgg tgttccgcgc gctaagattg ttggcgaggg cgatgttaag ccttccgcta 5520
gcgttgatgt ttctgcgttt actgcgcagc ctatcaaggt tgtgactcag cagcgtgtct 5580
cggacgagtt tatgtgggct gacgccgatt accgtctggg tgtgcttcag gatctgattt 5640
ccccggccct gggtgcttct attggtcgcg ccgttgatct tattgctttc catggtattg 5700
atcctgctac gggtaagcct gctgcggctg tcaaggtgtc gctggataag acgaataaga 5760
cggttgatgc caccgattcc gctacggctg atcttgttaa ggctgttggt ctgattgctg 5820
gtgctggttt gcaggttcct aacggtgttg ctttggatcc ggcgttctcg tttgctctgt 5880
caactgaggt gtatccgaag ggttcgccgc ttgccggtca gccaatgtat cctgccgccg 5940
ggttcgccgg cctggataat tggcgcggcc taaatgttgg ttcttcttcg actgtttctg 6000
gtgccccgga gatgtcgcct gcttctggtg ttaaggctat tgttggtgat ttctctcgtg 6060
tccattgggg gttccagcgt aacttcccga ttgagctgat cgagtatgct gacccggatc 6120
agacggggcg tgacttgaag ggccataatg aggttatggt tcgtgccgag gctgtgctgt 6180
atgttgcgat tgagtcgctt gattcgtttg ctgtcgtgaa ggagaaggct gccccgaagc 6240
ctaatccgcc ggccggtaac tgattcattt gttgcgataa tgtttatgct gtgtgcaggg 6300
ggtggtgttg atgggtatca ttttgaagcc tgaggatatt gagccttccg ccgatattcc 6360
tagagagaag cttgaggcga tgattgccga tgtggaggcg gtggctgtca gtgtcgcccc 6420
ctgtatcgct aaaccggatt tcaaatatag ggatgccgct aaggctattc tgcgtagggc 6480
tttgttgcgc tggaatgata ctggcgtgtc gggtcaggtg cagtatgagt ctgcgggccc 6540
gtttgctcag actacacggt cgaatactcc tacgaatttg ttgtggcctt ctgagattgc 6600
cgcgttgaag aagttgtgtg aggggtgatag tgggcgtggt aaggcgttca ctattacacc 6660
gaccatgagg agtagtgtga atcattctga ggtgtgttcc acggtgtggg gtgagggttg 6720
ctcgtgcggg tcgaatatta acggctatgc tggcccgttg tgggagatat gatatgaccg 6780
gttttcctta cggtgaaacg gttgtgatgc ttcagccgac tgttcgtgtc gatgatcttg 6840
gtgacaaggt ggaggattgg tctaagcctg tcgagactgt gtaccataac gtggccatct 6900
atgcttccgt ttcgcaggag gatgaggccg cggggcgtga ctcggattat gagcattgga 6960
cactgctgtt caagcagcct gtcaaggctg ctggttatcg gtgtcgttgg cgtattcggg 7020
gtgttgtgtg ggaggctgac gggtctccta tggtgtggca tcatccgatg tctggctggg 7080
atgctggtac gcaggttaat gtgaagcgta agaaggctg atgggttgtg gcacgtgatg 7140
ttgatgtgaa gctgaacttg ccgggtattc gtgaggtgtt gaagtcttct ggggtgcagg 7200
gcatgttggc tgagcgtggt gagcgtgtca agcgtgcggc ctcggcgaat gtgggcggta 7260
acgcttacga tagggcccag tatccgtccg ggttgtcgtc tgaggtgcag gttcaccgtg 7320
ttgaggctgt ggcgcgtatt ggcaccacct ataagggtgg taaaaggatt gaggctaagc 7380
atggcacgtt ggcgaggtcg attggggctg cgtcgtgatc gtttacggtg atcctcgaat 7440
atgggctaaa cgtgtgttgg cggatgatgg ttggctgtct gatgtaccgt gcacgggtac 7500
tgtgccggat acatttgagg gtgatctgat ttggttggcg ttggatggtg cccggagttt 7560
gcatgttcgt gagcgtgttt ttttgcgtgt gaatgtgttt gacgtacgc tctggctggg 7620
tatgtctttg gctcgccggg ttgaggctgt gctggctgat ggtgtggatg gtgatccggt 7680
ggtgttttgc aggcgttcga ctgggcctga tttgctggtg gatggtcac gttttgatgt 7740
gtattcgctt tttgagctga tatgtaggcc tgcggagtct gaataagctt attgttttg 7800
ttttaatgta attgtttgat atttaatggg ggttgtgatg gctgctacac gtaaagcgtc 7860
taatttcgt tcagcggtta ctgcgacgt ttatattggt gacgcgcacg cgggtgattc 7920
tattaagggt gtgaggcgg ttccttccgg gcttacagct ttgggtatc tgtctgatga 7980
cgggtttaag attaagcctg agcgtaaaac ggatgatttg aaggcttggc agaatgcgga 8040
tgttgttcgc actgtggcta cggagtcgtc tatcgagatt tctttccagc tgattgagtc 8100
gaagaaggag gttatcgaac tgttttggca gtcgaaggtt actgccggat ctgattcggg 8160
ttcgttcgat attctcctg gtgccacaac aggtgttcac gccctgttga tggatattgt 8220
tgatggcgat caggttattc gctactattt ccctgaggtt gagctcattg atcgtgacga 8280
gattaagggc aagaatggcg aagtgtacgg tatggtgtg acgttgaagg cgtatcctgc 8340
ccagattaat aagactggta atgcggtgtc gggtcggggg tggatgacgg ctttaaaagc 8400
tgatactcct ccgactcctc cgccggcccc ggttcctccg aagcctcagc cggatccgaa 8460
tccgccgtcc ggtaactgat acacgatttt aggggattgt taatagatga gtgacactgg 8520
```

```
tttcacgttg aagattggtg atcgtagctg ggtgttggcg gatgcggagg agacggctca  8580
ggctgttcct gccgcgcttt tccgtcgtgc cgccaggatt gcccagtcgg gggagtctgc  8640
ggatttcgcc caggttgagg tgatgttttc tatgttggag gctgccgccc cagctgacgc  8700
ggtggaggcc ctgagggggc ttcctatggt tcgtgtggcg gaggttttcc gtgagtggat  8760
ggaatacaag cctgacggta agggtgcctc gctgggggaa tagtttggct ccacggcctg  8820
attgatgatt atcgtggggc catcgaatac gatttccgca ccaagtttgg tgtttctgtt  8880
tatagtgttg gtgccccgca gatgtgttgg ggtgaggctg tccggctggc tggcgtgttg  8940
tgtaccgata cgtctagcca gttggcggcc caccttaatg gttggcagcg cccgtttgag  9000
tggtgcgagt gggctgtgtt ggacatgttg gatcattaca ggtctgctaa tagtgagggg  9060
cagccggagc ctgtggcgag gccgactgat gagcgtcggg caaggtttac gtctgggcag  9120
gtggacgata ttttggcgcg tgttcgtgcc ggtggcgggg tgtctcgcga gattgatatt  9180
atggggtgaa tagtgtatgt ctggtgagat tgcttccgca tatgtgtcgt tgtatacgaa  9240
gatgcctggc cttaaaagtg atgttggtaa acagttgtcg ggtgttatgc ctgctgaggg  9300
gcagcgttcg ggtagcctgt ttgctaaagg catgaagttg gcgcttggtg gtgcggcgat  9360
gatgggtgcc atcaatgttg ctaagaaggg cctcaagtct atctatgatg tgactattgg  9420
tggcggtatt gctcgcgcta tggctattga tgaggctcag gctaaactga ctggtttggg  9480
tcacacgtct tctgatacgt cttcgattat gaattcggct attgaggctg tgactggtac  9540
gtcgtatgcg ttgggggatg cggcgtctac ggcggccggg ttgtctcgct cgggtgtgaa  9600
gtctggcggt cagatgacgg atgtgttgaa gactgtcgcg gatgtgtctt atatttcggg  9660
taagtcgttt caggatacgg gcgctatttt tacgtctgtg atggctcgcg gtaagttgca  9720
gggcgatgac atgttgcagc ttacgatggc tggtgttcct gtgctgtctt tgcttgccag  9780
gcagacgggt aaaacctcgg tcgaggtttc gcagatggta tcgaagggc agattgattt  9840
tgccacgttt gcggctgcga tgaagctggg catgggtggt gctgcgcagg cgtctggtaa  9900
gacgtttgag ggcgctatga agaatgttaa gggcgctttg ggctatttgg gtgctacggc  9960
tatgcgcgcc tttcttaacg gcctgcggca gattttttgtt gcgttgaatc cggttattaa 10020
gtctatcacg gattctgtga agccgatgtt tgctgccgtc gatgctggta tccagcggat 10080
gatgccgtct attttggcgt ggattaaccg tatgccggct atgatcacga gaatgaatgc 10140
acagatgcgc gccaaggtgg agcagttgaa gggcattttt gcgagaatgc atttgcctgt 10200
tcctaaagtg aatttgggtg ccatgtttgc tggcggcacc gcagtgtttg gtattgttgc 10260
tgcgggtgtg gggaagcttg ttgcagggtt tgctccgttg gcgggttgcgt tgaagaatct 10320
gttgccgtcg tttggtgctt tgaggggtgc cgccggggg cttggtgcgg tgtttcgcgc 10380
cctgggtggc cctgtcggga ttgtgatcgg cttgtttgcg gcaatgtttg ccacgaacgc 10440
ccagttccgt gccgctgtta tgcagctggt ggctgtggtt ggtcaggcgt gggccagat  10500
tatgcagct gtgcagccgc tgttggtttt ggttgctggc gtggttgcca ggttggcgcc 10560
ggtgttcggc cagattatcg gtatggttgc tggtttggct gcccggctgg tgcctgttat 10620
tggtatgctt attgcccggc tggttcctgt tatcacccag attattggta tggtaaccca 10680
ggttgctgcc atgttgttgc ctatgctgat gccggttatt caggctgttg ttgctgtgat 10740
acggcaggtt attggtgtca ttatgcagtt gatacctgtt tgatgccgg ttgtgcagca 10800
gattttggt gttgtcatgt ctgtttttgcc gccgattgtt ggtttgatac ggctgctgat 10860
accggtgatc atgtcgatta tgcgtgtggt ggtgcaggtt gttggtgctg tgctacaggt 10920
ggtggccgt attattccgg ttgttatgcc gatttatgtt tcggtgattg gattcattgc 10980
caagatttat gctgcggtta tcgttttttga ggctaaggtt attggcgcta ttcttcgtac 11040
tattacgtgg attgtgaatc attcagtgtc tggcgtgagt tctatgggca cggccatcca 11100
gaatggctgg aatcatatta aatcgtttac gtctgcgttt attaacggtt ttaagtcgat 11160
catttctggc ggcgtgaacg cggttgtggg gttttttacg cggcttggtt tgtcggttgc 11220
ttccccatgtg aggtccggtt taacgctgc gagggggtgct gtttcttccg ccatgaatgc 11280
tattcggagt gttgtgtctt cggtgcgtgc tgctgttggc ggttttttca gttcgatggc 11340
gtctcgtgtt cggaatggtg ctgtgcgcgg gtttaatggt gcccggagtg cggcttcttc 11400
tgctatgcat gctatggggt ccgctgtgtc tagtggtgtg catggtgtgc tgggtttttt 11460
ccggaatttg cctgacaata ttcggcgtgc gcttggtaat atgggtgccc tgttggtgtc 11520
ggctggccgt gatgtgggtg tccggtttagg taatggtatc aagaatgctt tgagtggcct 11580
gttggatacg gtgcgtaata tgggttctca ggttgctaat gcggcgaagt cggtgttggg 11640
tattcattcc ccgtctcggg tgtttcgtga cgaggttggc cggcaggttg ttgccggttt 11700
ggctgagggt attactggta atgctggttt ggcgttggat gcgatgtcgg gtgtggctgg 11760
gaggctgcct gatgcggttg atgcccggtt tggtgtgcga tcgtctgtgg gttcgtttac 11820
cccgtatggc aggtatcagc gcatgaatga taagagtgtt gtggtgaatg tgaatgggcc 11880
tacttatggg gatcctgccg agtttgcgaa gcgattgag cggcagcagc gtgacgcttt 11940
gaacgcgttg gcttacgtgt gattttgggg gtgtggtgc                       11979
```

```
SEQ ID NO: 29          moltype = DNA  length = 83
FEATURE                Location/Qualifiers
source                 1..83
                       mol_type = other DNA
                       note = PAC7 cos of pAN594
                       organism = synthetic construct
SEQUENCE: 29
acaaaaggga ggtatttcac taagccgtac gaggtcttgc acgggtgtgc aggggtgtg    60
cccggtgggg gttggcgggt ttt                                          83

SEQ ID NO: 30          moltype = DNA  length = 4670
FEATURE                Location/Qualifiers
source                 1..4670
                       mol_type = other DNA
                       note = operon of gp15-gp19+gp45
                       organism = synthetic construct
SEQUENCE: 30
cgacgcggcg gtctgccgac ccggcaacga ccaactcccc gacgggcgct gacaccggcc    60
cggcagcgtg catgcgtgca tttccaccct caagaaccat tgactggcga cgcgcaggtg   120
ggagaattga actgaacgct ttgaacgcgt tggcttacgt gtgattttgg gggtgtggtg   180
```

-continued

```
catgtttatt cctgacccgt ctgatcgttc tggtttgact gtgacttggt ctatgttgcc    240
gttgattggt aatgatccgg agcgtgtgct tcatttgacg gattatacgg ggtcgtctcc    300
gataatgttg ttgaatgatt cgttgcgcgg tttgggtgtt cctgaggtgg agcattttc    360
tcaaactcat gttggggtgc atggctcgga gtggcgcggg tttaatgtga agcctcgcga    420
ggtgacgcta ccggtgttgg tgtcgggtgt tggcccggat ccggtgggcg gttttcgtga    480
cggttttttg aaggcgtatg acgagttgtg gtctgctttt cctcctggcg aggtggggga    540
gttgtctgtg aagactcctg ccggtcgtga gcgtgtgttg aagtgccggt ttgattcggt    600
ggatgacacg tttacggttg gatccggtga cagggggttat gcgcgttatc tgttgcattt    660
gacggcttat gacccgtttt ggtatgggga tgagcagaag tttcgtttca gtaacgctaa    720
gttgcaggat tggttgggtg gcggccctgt cgacggtaag ggtaccgcgt ttccggtggt    780
gttgacgcct ggtgttggtt cgggttggga taatctgtct aataagggtg atgtgcctgc    840
gtggcctgtg attcgtgttg aggggccgtt gtcgtcgtgg tctgtgcaga ttgatggttt    900
gcgtgtgtcc tcggattggc cggtggagga gtatgattgg atcactattg atacggatcc    960
tcgtaagcag tctgcgttgt tggacggggtt tgaggatgtg atggatcgtt tgaaggagtg   1020
ggagtttgcg cctatcccgc ctggcggttc tcggagtgtg aatattgaga tggttggttt   1080
gggtgccatt gttgtgtcgg tgcagtacag gttttttgagg gcttggtgaa tagttgatgg   1140
ctggtttttgt tccgcatgta acattgttta caccggatta tcgccgtgtg gcgcctatca   1200
attttttttga gtcgttgaag ttgtcgttga agtggaatgg tttgtccact ttggagttgg   1260
tggtgtctgg tgatcattct aggcttgacg ggttgactag gccgggtgcg cggcttgtgg   1320
ttgattatgg tggtggccag attttttctg ggcctgtgcg tcgggtgcat ggtgtgggtc   1380
cgtggcgttc ttcgcgtgtg actatcacgt gtgaggatga tattcgtctg ttgtggcgta   1440
tgttgatgtg gcctgtgaat tatcgtcctg gtatgattgg tatggagtgg cgtgcggatc   1500
gggattatgc ccattattcg ggtgcgcgcg agtcggtggc taagcgggtg ttgggggata   1560
atgcttggcg ttttccgtct ggtttgttta tgaacgatga tgagagtcgt ggccgctata   1620
ttaaggattt tcaggtgcgg tttcacgtgt ttgccgataa gttgttgccg gtgttgtcgt   1680
gggctcggat gactgtcacg gtgaaccagt ttgagaatgc gaagtttgat cagcgtggtt   1740
tggtgtttga ttgtgtgcct gctgtgaccc ggaaacatgt gttgactgcc gagtcgggtt   1800
cgattgtgtc gtgggagtat gtgcgtgacg ccccgaaggc gacatctgtg gtggttggtg   1860
gccgtggcga gggtaaggat cggctgtttt gtgaggatgt tgattcggcg ccgaggatg   1920
attggtttga tcgtgtcgag gtgtttaagg atgcccgtaa cacggattcc gagaaggtgt   1980
ctctcttcga tgaggctgag cgggtgttgt ccgagtcggg ggctacgtcg ggtttaaga   2040
ttgagttggc tgagtcggat gtgttgcggt ttggtcccgg caatctgatg cctggggatt   2100
tgatctatgt ggatgtgggt tctgggccta ttgcggacag tgtgcggcag attgatgtgg   2160
agtgtgtatc gcctggtgat ggttggacga aggtgactcc ggttgcgggg gattatgagg   2220
ataatccgtc ggccctgttg gctcgccgtg tggctggttt ggctgcgggt gtgcgggatt   2280
tgcaaaagtt ttagtaagtg attggggttt gttgtgggta ttgtgtgtaa agggtttgat   2340
ggtgtgttga ccgagtatga ttgggctcaa atgtctggtc tgatgggtaa tatgccgtct   2400
gtgaagggcc ctgacgattt tcgtgtcggc acgacgattc agggtctac ggtgttgtgt   2460
gagatcctgc cggggcaggc ttgggctcac ggggtgatgt gcacgtcgaa tagtgttgag   2520
acggtgacgg gtcagcttcc gggcccgggt gagactcgat acgactatgt ggtgttgtct   2580
cgggattggc aggagaatac ggccaagttg gagattgttc ccggtgggcg tgcggagcgt   2640
gccagggatg tgttgagggc tgagcctggc gtgtttcatc agcagctact ggcgactttg   2700
gtgttgtcgt ctaacgggtt gcagcagcag ttggataggc gtctgtggc ggctagggtt   2760
gcgtttgggg agtctgctgc gtgtgatcct accccctgtgg agggtgaccg tgtgatggtt   2820
ccttcggggg ctgtgtgggc taaccatgcc ggcgagtgga tgttgttgtc tcccaggatt   2880
gagacgggtt cgaagtcgat catgtttggt ggttctgctg tgtatgctta cacgatcccg   2940
tttgagcgcc agttcagtag tccgcctgtt gtggtggcgt ctatggctac ggcggctggg   3000
ggcacggcac agattgatgt gaaagcctac aatgtgactg cccaaaattt tagttttgcg   3060
tttattacga atgatggttc gaagccgaat ggtgtgcctg cggtggcgaa ttggattgct   3120
gtcggcgtgt gactgcacgg tgttgtggc ggatggtgtg atgttgggggg gctgtggtgt   3180
cgtggtttac tcctgcactg gtggcctcta tttgtaccgc gttggccacg gttttgggtt   3240
ctgttcaggc tgtcacatcc cggtctagga agcgtttacg caggctgtcg gctcaggtgg   3300
atgcgatgga agagtatacg tggggtgtgc ggcgcgaggt gcgaaggttt aacgccggtc   3360
ttcctgatga tgtggagccg atgcatcttc ctgattttgcc cgagtttttg aaagatactg   3420
ttgatggtgg aggtgagtag ggttgaggga gttggaggag gagaagcggc agcgccgcaa   3480
ttttgagaag gcttcactgg tgttgttgtt tttgtcgctt gtgttgttgg cggtggttgc   3540
tgcgggtgct ttgcgtttcg gggctgtatc ctctgagcgg gattcggagc aggcgagggc   3600
ccagtcgaat ggtacggctg ccaggggttt ggctgcccgt gtgaagcagg cgtctgcttc   3660
gggtgggttg gagtctgtgc gtcttcaccg ttctggtttg tgtgtggatg ctgtgcgtgt   3720
tgagcagcgt gttcagggtg tgccgggtcc tgccggtgag cgcggccgc aaggcccttc   3780
aggtcctgcc ggcggggatg tgttaatgg ttccgctggg ctggttggcc ctgttggtcc   3840
gcaaggttct ccgggtttga atggtgtgaa aggtcctgac ggcttgcctg gcgctaacgg   3900
ttcggatggc cgtgatggtg ttccaggtcg tgcaggtgct gacggtgtga acggcgttga   3960
cggcgtcgat ggtcgggatg gttctgccgg tgagcgcggc ccgcaaggcc cttcaggtcc   4020
tgccggcccg caaggtgcac agggtgaacg gggtgagcgt ggtcccgccg gtgcgaatgc   4080
atcggatggc catgatggta aggatgggcg tccgtggtgg tctgtgtact gttccgggg   4140
ccgcctggtt gtgaaatata gtgacggtgt ggcttccacg atatcggggtt cggcggcctg   4200
ccagggtgtg aaaccgtcgc ctctagtgac tatatcatcc cacaaataga ggctcacagg   4260
ggccatggga gattggggggg cgtgatggca caccaaacc gcacagccag ccaaggccac   4320
cggcgctggc gggcaaggct catcacccaa gcccgacaac aaggccaaac cgaatgccca   4380
ctctgcggag tcaccatcac ctggaacacc cacgacctgc caaccagccc cgaagccgac   4440
cacatcacac ccgtcagccg ggaggactc aacaccctcg acaacgggca aatcatctgc   4500
agaacatgca acagaagcaa aggcaacaga acacaaccaa acatcaaatt ccaacaacaa   4560
accacaaaaa cattgattcc atggtgagga tatccacgag ctgcgttcgg ctaaacccaa   4620
aagtaaaaac ccgccgaagc gggttttaac gtaaaacagg tgaaactgac                4670
```

-continued

```
SEQ ID NO: 31          moltype = DNA  length = 1910
FEATURE                Location/Qualifiers
source                 1..1910
                       mol_type = other DNA
                       note = pAN241 vector
                       organism = synthetic construct
SEQUENCE: 31
caagtggccc atcgaagagg acggcaccac catctcgccg ggcaagctca aggacgtgtc   60
caggctgacg ctcacggtgc tgctgcaccc ctcgtgcgcc atcatcgtgg atcccaaga  120
ttgtccggac ggcggttgag cgcggcctga taggcgccgc agctcctgct cccgggccgc  180
cccggtcggc ggtttactcc tttcctgccg gccggggcac tcaagacaac cgggggcccc  240
cgcgaaattg aggggccccg cctgattgca aggggggtgcc catgaagcaa cccgggcccc  300
accaaagaat gcgggctacc ttcaaggccg acaggggctg gcgagtggca tgcccacggt  360
gcgcctggca tgccaccagc acccaccttg catggctcat ggatcaggcc agcacacaca  420
cctgtgcacc cctgctgttg tcgcccacgc cacccgacgt ggagctggca ccggcaggcg  480
acgggctgtc cgtcctgtgg cccgaggtgg acggtgacgt gcagttcacc tgcatccaca  540
ccagcaccgc cacgtgcagg caggacgcac catgagcacc agtcgcaccg gcacggccac  600
atggttgcgc catgcagcac aggccaagcg tgaggcccaa gcacgaggac tcgcccgctg  660
cccactgtgc ggcgtctgga tggactacga ggtcggcaag cgacccaact cggccgaagc  720
agaccacatc agaccgcatt cgcttggtgg ttcagacgac atcgacaaca ttcgcgtcat  780
ttgtcgtcgt tgcaatcaat cgcgcggaaa cggcctgaag cgaccagggc gccaacgtca  840
gcgtccaatc aagcgcatcg agctggccca accggcccgc agtggggcat ttcctgcccc  900
gccggcatga atgggaaggg agtgcggatg gtgcggtcgg gcattcgatc gtgcccggac  960
gggtcgcccg cgacgcttct gctcggcccg ctgtcgggtc gccgcgtccc ggtgtgcgat 1020
cccgctggcc atgaggtccc gcactgcgtg ggtccgctgc gacggcaagc gccccatcac 1080
cctggctggc gctccggcct catccacgga cccgggcaca tggtctggct ggtcgcaggt 1140
gcgacgcgcc acggccggcg atggcttcgg gaccatgctc ggtgacgggc tggggtgctg 1200
ggatctcgac cacttcgacg atcagggcgc ccgggccttc atcgaccgga tcgataagcc 1260
gatcatcttc gccgagcggt cggtgtcggg gcatggcttc cacatcttcg tccggactga 1320
cgaggccccc ggacgccgca ccggaaacat cgagttctac tcacgccatc ggttcatcag 1380
ggtcacagga gaccagttcg tctgaagaag ggggtgcgcc atggctgcac aggtcagggc 1440
cgtggacccc gatgagcgcc cacccgcccg caagcgggcc aagaccatca cccaggccgc 1500
gaagtccggc actgaggttg aactgttgga ggcactgcag gctcgcgtgg cccgcgccgt 1560
gcaggaccgt gacactccgc cgcgcgatct ggcagcgctg acgaagcggc tgatggacat 1620
cacccgggag ctcgaggcgg cccgggtcaa ggatcaggag gcgggatctg atggtgccgt 1680
caccgcagac gaaacatggc gaccgcaagc tctctgaggt cgccaagcac ctgatccttc 1740
ctgaagggat cgtctcgacg ggctggccgg ccgtgcgtga ccggtgtggc gagtggggtg 1800
tggtcttcga ccgttggcag gacggcatgg gccgggtgat cctgtcgaag cgcggcagcg 1860
gcctgttcgc cgctggtgtg ggcggggtcg gcatgtcgat cccgcgccag             1910
```